(12) United States Patent
Roth et al.

(10) Patent No.: US 6,762,180 B1
(45) Date of Patent: Jul. 13, 2004

(54) SUBSTITUTED INDOLINES WHICH INHIBIT RECEPTOR TYROSINE KINASES

(75) Inventors: Gerald Juergen Roth, Biberach (DE); Armin Heckel, Biberach (DE); Rainer Walter, Biberach (DE); Jacobus Van Meel, Moedling (AT); Norbert Redemann, Biberach (DE); Ulrike Tontsch-Grunt, Baden (AT); Walter Spevak, Oberrohrbach (AT); Frank Hilberg, Vienna (AT)

(73) Assignee: Boehringer Ingelheim Pharma KG, Ingelheim (DE)

( * ) Notice: Subject to any disclaimer, the term of this patent is extended or adjusted under 35 U.S.C. 154(b) by 68 days.

(21) Appl. No.: 09/678,682

(22) Filed: Oct. 3, 2000

Related U.S. Application Data
(60) Provisional application No. 60/160,547, filed on Oct. 20, 1999.

(30) Foreign Application Priority Data

| Oct. 13, 1999 | (DE) | ............................. 199 49 208 |
| Aug. 31, 2000 | (DE) | ............................. 100 42 696 |

(51) Int. Cl.$^7$ ............ C07D 209/34; C07D 401/12; C07D 403/12; C07D 405/12; A61K 31/404
(52) U.S. Cl. .............. 514/228.2; 544/373; 544/144; 544/58.2; 514/254.09; 514/323; 514/418; 514/235.2; 514/414; 546/201; 548/486; 548/467
(58) Field of Search ................... 544/373, 144, 544/58.2; 514/254.09, 418, 235.2, 228.2, 414, 323; 546/201; 548/486, 467

(56) References Cited

U.S. PATENT DOCUMENTS 5,886,020 A  3/1999  Tang et al.
6,043,254 A  * 3/2000  Grell et al. ................. 514/310

FOREIGN PATENT DOCUMENTS

| DE | WO 99/15500 | * 4/1999 |
| DE | 198 15 020 A | 10/1999 |
| WO | WO 99 15500 A | 4/1999 |
| WO | WO 99 52869 A | 10/1999 |
| WO | WO 99 62882 A | 10/1999 |
| WO | WO 00 56710 A | 9/2000 |

* cited by examiner

*Primary Examiner*—Richard L. Raymond
*Assistant Examiner*—Hong Liu
(74) *Attorney, Agent, or Firm*—Robert P. Raymond; Alan R. Stempel; Mary-Ellen M. Devlin

(57) ABSTRACT

Indolinones of the formula (I)

having an inhibitory effect on receptor tyrosine kinases and cyclin/CDK complexes, as well as on the proliferation of endothelial cells and various tumor cells. Exemplary are:

(a) 3-Z-[1-(4-(piperidin-1-yl-methyl)-anilino)-1-phenyl-methylene]-6-ethoxycarbonyl-2-indolinone, (b) 3-Z-[(1-(4-(piperidin-1-yl-methyl)-anilino)-1-phenyl-methylene]-6-carbamoyl-2-indolinone, and (c) 3-Z-[1-(4-(piperidin-1-yl-methyl)-anilino)-1-phenyl-methylene]-6-metboxycarbonyl-2-indolinone.

8 Claims, No Drawings

SUBSTITUTED INDOLINES WHICH INHIBIT RECEPTOR TYROSINE KINASES

RELATED APPLICATIONS

Benefit of U.S. Provisional Application Serial No. 60/160,547, filed on Oct. 20, 1999, is hereby claimed.

FIELD OF THE INVENTION

The present invention relates to novel indolinones that inhibit receptor tyrosine kinases, their use as pharmaceuticals, particularly in the treatment of proliferative diseases, and pharmaceutical compositions comprising these compounds.

DESCRIPTION OF THE INVENTION

The present invention provides new indolinones of general formula

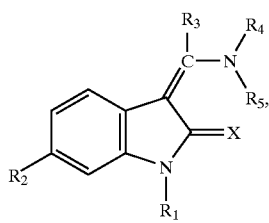

(I)

substituted in the 6 position, the tautomers, the diastereomers, the enantiomers, the mixtures thereof and the salts thereof, particularly the physiologically acceptable salts thereof which have valuable properties.

The above compounds of general formula I wherein $R_1$ denotes a hydrogen atom or a prodrug group have valuable pharmacological properties, in particular an inhibiting effect on various kinases, especially receptor tyrosine kinases such as VEGFR2, PDGFRα, PDGFRβ, FGFR1, FGFR3, EGFR, HER2, IGF1R and HGFR, as well as complexes of CDK's (Cyclin Dependent Kinases) such as CDK1, CDK2, CDK3, CDK4, CDK5, CDK6, CDK7, CDK8 and CDK9 with their specific cyclins (A, B1, B2, C, D1, D2, D3, E, F, G1, G2, H, I and K) and to viral cyclin (cf. L. Mengtao in J. Virology 71(3), 1984–1991 (1997)), and on the proliferation of cultivated human cells, in particular endothelial cells, e.g. in angiogenesis, but also on the proliferation of other cells, in particular tumour cells.

The other compounds of the above general formula I wherein $R_1$ does not denote a hydrogen atom or a prodrug group are valuable intermediate products for preparing the abovementioned compounds.

The present invention thus relates to the above compounds of general formula I, whereby those compounds wherein $R_1$ denotes a hydrogen atom or a prodrug group have valuable pharmacological properties, pharmaceutical compositions containing the pharmacologically active compounds, the use thereof and processes for preparing them.

In the above general formula I

X denotes an oxygen or sulphur atom, $R_1$ denotes a hydrogen atom or a prodrug group such as a $C_{1-4}$-alkoxycarbonyl or $C_{2-4}$-alkanoyl group, $R_2$ denotes a carboxy group, a straight-chain or branched $C_{1-6}$-alkoxy-carbonyl group, a $C_{4-7}$-cycloalkoxy-carbonyl or an aryloxycarbonyl group, a straight-chain or branched $C_{1-6}$-alkoxy-carbonyl group, which is terminally substituted in the alkyl moiety by a phenyl, heteroaryl, carboxy, $C_{1-3}$-alkoxy-carbonyl, aminocarbonyl, $C_{1-3}$-alkylamino-carbonyl or di-($C_{1-3}$-alkyl)-aminocarbonyl group, a straight-chain or branched $C_{2-6}$-alkoxy-carbonyl group, which is terminally substituted in the alkyl moiety by a chlorine atom or a hydroxy, $C_{1-3}$-alkoxy, amino, $C_{1-3}$-alkylamino or di-($C_{1-3}$-alkyl)-amino group, an aminocarbonyl or methylaminocarbonyl group, an ethylaminocarbonyl group optionally substituted in the 2 position of the ethyl group by a hydroxy or $C_{1-3}$-alkoxy group or, if $R_4$ does not denote an aminosulphonyl-phenyl or N—($C_{1-5}$-alkyl)-$C_{1-3}$-alkylaminocarbonyl-phenyl group, it may also denote a di-($C_{1-2}$-alkyl)-aminocarbonyl group, $R_3$ denotes a hydrogen atom, a $C_{1-6}$-alkyl, $C_{3-7}$-cycloalkyl, trifluoromethyl or heteroaryl group, a phenyl or naphthyl group, a phenyl or naphthyl group mono- or disubstituted by a fluorine, chlorine, bromine or iodine atom, by a trifluoromethyl, $C_{1-3}$-alkyl or $C_{1-3}$-alkoxy group, whilst in the event of disubstitution the substituents may be identical or different and wherein the abovementioned unsubstituted as well as the mono- and disubstituted phenyl and naphthyl groups may additionally be substituted by a hydroxy, hydroxy-$C_{1-3}$-alkyl or $C_{1-3}$-alkoxy-$C_{1-3}$-alkyl group, by a cyano, carboxy, carboxy-$C_{1-3}$-alkyl, $C_{1-3}$-alkoxycarbonyl, aminocarbonyl, $C_{1-3}$-alkylaminocarbonyl or di-($C_{1-3}$-alkyl)-aminocarbonyl group, by a nitro group, by an amino, $C_{1-3}$-alkylamino, di-($C_{1-3}$-alkyl)-amino or amino-$C_{1-3}$-alkyl group, by a $C_{1-3}$-alkylcarbonylamino, N—($C_{1-3}$-alkyl)-$C_{1-3}$-alkyl-carbonylamino, $C_{1-3}$-alkylcarbonylamino-$C_{1-3}$-alkyl, N—($C_{1-3}$-alkyl)-$C_{1-3}$-alkylcarbonylamino-$C_{1-3}$-alkyl, $C_{1-3}$-alkyl-sulphonylamino, $C_{1-3}$-alkylsulphonylamino-$C_{1-3}$-alkyl, N—($C_{1-3}$-alkyl)-$C_{1-3}$-alkylsulphonylamino-$C_{1-3}$-alkyl or aryl-$C_{1-3}$-alkylsulphonylamino group, by a cycloalkylamino, cycloalkyleneimino, cycloalkyleneiminocarbonyl, cycloalkyleneimino-$C_{1-3}$-alkyl, cycloalkyleneiminocarbonyl-$C_{1-3}$-alkyl or cycloalkyleneiminosulphonyl-$C_{1-3}$-alkyl group having 4 to 7 ring members in each case, whilst in each case the methylene group in position 4 of a 6- or 7-membered cycloalkyleneimino group may be replaced by an oxygen or sulphur atom, by a sulphinyl, sulphonyl, —NH or —N($C_{1-3}$-alkyl) group, or by a heteroaryl or heteroaryl-$C_{1-3}$-alkyl group, $R_4$ denotes a $C_{3-7}$-cycloalkyl group, whilst the methylene group in the 4 position of a 6- or 7-membered cycloalkyl group may be substituted by an amino, $C_{1-3}$-alkylamino or di-($C_{1-3}$-alkyl)-amino group or replaced by an —NH or —N($C_{1-3}$-alkyl) group, or a phenyl group substituted by the group $R_6$, which may additionally be mono- or disubstituted by fluorine, chlorine, bromine or iodine atoms, by $C_{1-5}$-alkyl, trifluoromethyl, hydroxy, $C_{1-3}$-alkoxy, carboxy, $C_{1-3}$-alkoxycarbonyl, amino, acetylamino, $C_{1-3}$-alkyl-sulphonylamnino, aminocarbonyl, $C_{1-3}$-alkyl-aminocarbonyl, di-($C_{1-3}$-alkyl)-aminocarbonyl, aminosulphonyl, $C_{1-3}$-alkyl-aminosulphonyl, di-($C_{1-3}$-alkyl)-aminosulphonyl, nitro or cyano groups, wherein the substituents may be identical or different and wherein $R_6$ denotes a hydrogen, fluorine, chlorine, bromine or iodine atom, a cyano, nitro, amino, $C_{1-5}$-alkyl, $C_{3-7}$-cycloalkyl, trifluoromethyl, phenyl, tetrazolyl or heteroaryl group, the group of formula

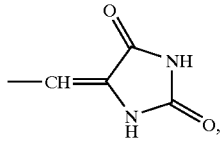

wherein the hydrogen atoms bound to a nitrogen atom may in each case be replaced independently of one another by a $C_{1-3}$-alkyl group, a $C_{1-3}$-alkoxy group, a $C_{1-3}$-alkoxy-$C_{1-3}$-alkoxy, phenyl-$C_{1-3}$-alkoxy, amino-$C_{2-3}$-alkoxy, $C_{1-3}$-alkylamino-$C_{2-3}$-alkoxy, di-($C_{1-3}$-alkyl)-amino-$C_{2-3}$-alkoxy, phenyl-$C_{1-3}$-alkylamino-$C_{2-3}$-alkoxy, N—($C_{1-3}$-alkyl)-phenyl-$C_{1-3}$-alkylamino-$C_{2-3}$-alkoxy, $C_{5-7}$-cycloalkyleneimino-$C_{2-3}$-alkoxy or $C_{1-3}$-alkylmercapto group, a carboxy, $C_{1-4}$-alkoxycarbonyl, aminocarbonyl, $C_{1-3}$-alkylamino-carbonyl, N—($C_{1-5}$-alkyl)-$C_{1-3}$-alkylaminocarbonyl, phenyl-$C_{1-3}$-alkylaminocarbonyl, N—($C_{1-3}$-alkyl)-phenyl-$C_{1-3}$-alkylaminocarbonyl, piperazinocarbonyl or N—($C_{1-3}$-alkyl)-piperazinocarbonyl group, a $C_{1-3}$-alkylaminocarbonyl or N—($C_{1-5}$-alkyl)-$C_{1-3}$-alkylaminocarbonyl group wherein an alkyl moiety is substituted by a carboxy or $C_{1-3}$-alkoxycarbonyl group or in the 2 or 3 position by a di-($C_{1-3}$-alkyl)amino, piperazino, N—($C_{1-3}$-alkyl)-piperazino or a 4- to 7-membered cycloalkyleneimino group, a $C_{3-7}$-cycloalkyl-carbonyl group, wherein the methylene group in the 4 position of the 6- or 7-membered cycloalkyl moiety may be substituted by an amino, $C_{1-3}$-alkylamino or di-($C_{1-3}$-alkyl)-amino group or replaced by an —NH or —N($C_{1-3}$-alkyl) group, a 4- to 7-membered cycloalkyleneimino group wherein a methylene group linked to the imino group may be replaced by a carbonyl or sulphonyl group or the cycloalkylene moiety may be fused to a phenyl ring or one or two hydrogen atoms may each be replaced by a $C_{1-3}$-alkyl group and/or in each case the methylene group in the 4 position of a 6- or 7-membered cycloalkyleneimino group may be substituted by a carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, a $C_{1-4}$-alkyl group substituted by the group $R_7$, wherein $R_7$ denotes a $C_{3-7}$-cycloalkyl group, whilst the methylene group in the 4 position of a 6- or 7-membered cycloalkyl group may be substituted by an amino, $C_{1-3}$-alkylamino or di-($C_{1-3}$-alkyl)-amino group or replaced by an —NH or —N($C_{1-3}$-alkyl) group or in a 5- to 7-membered cycloalkyl group a —$(CH_2)_2$ group may be replaced by a —CO—NH group, a —$(CH_2)_3$ group may be replaced by a —NH—CO—NH or —CO—NH—CO group or a —$(CH_2)_4$ group may be replaced by a —NH—CO—NH—CO group, whilst in each case a hydrogen atom bound to a nitrogen atom may be replaced by a $C_{1-3}$-alkyl group, an aryl or heteroaryl group, a hydroxy or $C_{1-3}$-alkoxy group, an amino, $C_{1-7}$-alkylamino, di-($C_{1-7}$-alkyl)-amino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group, an ω-hydroxy-$C_{2-3}$-alkyl-amino, N—($C_{1-3}$-alkyl)-ω-hydroxy-$C_{2-3}$-alkyl-amino, di-(ω-hydroxy-$C_{2-3}$-alkyl)-amino, di-(ω-($C_{1-3}$-alkoxy)-$C_{2-3}$-alkyl)-amino or N-(dioxolan-2-yl)-$C_{1-3}$-alkyl-amino group, a $C_{1-3}$-alkylcarbonylamino-$C_{2-3}$-alkyl-amino or $C_{1-3}$-alkylcarbonylamino-$C_{2-3}$-alkyl-N—($C_{1-3}$-alkyl)-amino group, a $C_{1-3}$-alkylsulphonylamino, N—($C_{1-3}$-alkyl)-$C_{1-3}$-alkylsulphonylamino, $C_{1-3}$-alkylsulphonylamino-$C_{2-3}$-alkyl-amino or $C_{1-3}$-alkylsulphonylamino-$C_{2-3}$-alkyl-N—($C_{1-3}$-alkyl)-amino group, a hydroxycarbonyl-$C_{1-3}$-alkylamino or N—($C_{1-3}$-alkyl)-hydroxycarbonyl-$C_{1-3}$-alkyl-amino group, a guanidino group wherein one or two hydrogen atoms may each be replaced by a $C_{1-3}$-alkyl group, a group of formula

wherein $R_8$ denotes a hydrogen atom or a $C_{1-3}$-alkyl group, n denotes one of the numbers 0, 1, 2 or 3 and $R_9$ denotes an amino, $C_{1-4}$-alkylamino, di-($C_{1-4}$-alkyl)-amino, phenylamino, N—($C_{1-4}$-alkyl)-phenylamino, benzylamino, N—($C_{1-4}$-alkyl)-benzylamino or $C_{1-4}$-alkoxy group, a 4- to 7-membered cycloalkyleneimino group, whilst in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, or, if n denotes one of the numbers 1, 2 or 3, it may also denote a hydrogen atom, a group of formula

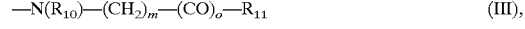

wherein $R^{10}$ denotes a hydrogen atom, a $C_{1-3}$-alkyl group, a $C_{1-3}$-alkylcarbonyl, arylcarbonyl, phenyl-$C_{1-3}$-alkyl-carbonyl, $C_{1-3}$-alkylsulphonyl, arylsulphonyl or phenyl-$C_{1-3}$-alkylsulphonyl group, m denotes one of the numbers 1, 2, 3 or 4, o denotes the number 1 or, if m denotes one of the numbers 2, 3 or 4, o may also denote the number 0 and $R_{11}$ denotes an amino, $C_{1-4}$-alkylamino, di-($C_{1-4}$-alkyl)-amino, phenylamino, N—($C_{1-4}$-alkyl)-phenylamino, benzylamino, N—($C_{1-4}$-alkyl)-benzylamino, $C_{1-4}$-alkoxy or $C_{1-3}$-alkoxy-$C_{1-3}$-alkoxy group, a di-($C_{1-4}$-alkyl)-amino-$C_{1-3}$-alkylamino group optionally substituted in the 1 position by a $C_{1-3}$-alkyl group or a 4- to 7-membered cycloalkyleneimino group, wherein the cycloalkylene moiety may be fused to a phenyl ring or in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, a $C_{4-7}$-cycloalkylamino, $C_{4-7}$-cycloalkyl-$C_{1-3}$-alkylamino or $C_{4-7}$-cycloalkenylamino group wherein position 1 of the ring is not involved in the double bond and wherein the abovementioned groups may each additionally be substituted at the amino-nitrogen atom by a $C_{5-7}$-cycloalkyl, $C_{2-4}$-alkenyl or $C_{1-4}$-alkyl group, a 4- to 7-membered cycloalkyleneimino group, wherein the cycloalkylene moiety may be fused to a phenyl group or to an oxazolo, imidazolo, thiazolo, pyridino, pyrazino or pyrimidino group optionally substituted by a fluorine, chlorine, bromine or iodine atom, by a nitro, $C_{1-3}$-alkyl, $C_{1-3}$-alkoxy or amino group, and/or one or two hydrogen atoms may each be replaced by a $C_{1-3}$-alkyl, $C_{5-7}$-cycloalkyl or phenyl group and/or the methylene group in the 3 position of a 5-membered cycloalkyleneimino group may be substituted by a hydroxy, hydroxy-$C_{1-3}$-alkyl, $C_{1-3}$-alkoxy or $C_{1-3}$-alkoxy-$C_{1-3}$-alkyl group, the methylene group in the 3 or 4 position of a 6- or 7-membered cycloalkyleneimino group may in each case be substituted by a hydroxy, hydroxy-$C_{1-3}$-alkyl, $C_{1-3}$-alkoxy, $C_{1-3}$-alkoxy-$C_{1-3}$-alkyl, carboxy, $C_{1-4}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkyl-amino group or may be replaced by an oxygen or sulphur atom, by a sulphinyl, sulphonyl, —NH, —N($C_{1-3}$-alkyl-), —N(phenyl), —N(phenyl-$C_{1-3}$-alkyl-), —N($C_{1-3}$-alkyl-carbonyl-), —N($C_{1-4}$-hydroxy-carbonyl-), —N($C_{1-4}$-alkoxy-carbonyl-), —N(benzoyl-) or —N(phenyl-$C_{1-3}$-alkyl-carbonyl-) group, wherein a methylene group linked to an imino-nitrogen atom of the cycloalkyleneimino group may be replaced by a carbonyl or sulphonyl group or in a 5- to 7-membered monocyclic cycloalkyleneimino group or a cycloalkyleneimino group fused to a phenyl group the two methylene groups linked to the imino-nitrogen atom may each be replaced by a carbonyl group, or $R_6$ denotes a $C_{1-4}$-alkyl group which is substituted by a carboxy, $C_{1-3}$-alkoxycarbonyl, aminocarbonyl, $C_{1-3}$-alkylaminocarbonyl or di-($C_{1-3}$-alkyl)-aminocarbonyl group or by a 4- to 7-membered cycloalkyleneiminocarbonyl group, an N—($C_{1-3}$-alkyl)-$C_{2-4}$-alkanoylamino group) which is additionally substituted in the alkyl moiety by a carboxy or $C_{1-3}$-alkoxycarbonyl group, a group of formula

—N($R_{12}$)—CO—$(CH_2)_p$—$R_{13}$ (IV), wherein $R_{12}$ denotes a hydrogen atom, a $C_{1-6}$-alkyl or $C_{3-7}$-cycloalkyl group or a $C_{1-3}$-alkyl group terminally substituted by a phenyl, heteroaryl, trifluoromethyl, hydroxy, $C_{1-3}$-alkoxy, aminocarbonyl, $C_{1-4}$-alkylamino-carbonyl, di-($C_{1-4}$-alkyl)-aminocarbonyl, $C_{1-3}$-alkyl-carbonyl, $C_{1-3}$-alkyl-sulphonylamino, N—($C_{1-3}$-alkyl)-$C_{1-3}$-alkyl-sulphonylamino, $C_{1-3}$-alkyl-aminosulphonyl or di-($C_{1-3}$-alkyl)-aminosulphonyl group and p denotes one of the numbers 0, 1, 2 or 3 and $R_{13}$ assumes the meanings of the abovementioned group $R_7$, or, if p denotes one of the numbers 1, 2 or 3, it may also denote a hydrogen atom, a group of formula

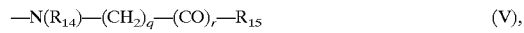
—N($R_{14}$)—$(CH_2)_q$—$(CO)_r$—$R_{15}$ (V), wherein $R_{14}$ denotes a hydrogen atom, a $C_{1-4}$-alkyl group, a $C_{1-3}$-alkylcarbonyl, arylcarbonyl, phenyl-$C_{1-3}$-alkylcarbonyl, heteroarylcarbonyl, heteroaryl-$C_{1-3}$-alkylcarbonyl, $C_{1-4}$-alkylsulphonyl, arylsulphonyl, phenyl-$C_{1-3}$-alkylsulphonyl, heteroarylsulphonyl or heteroaryl-$C_{1-3}$-alkyl-sulphonyl group, q denotes one of the numbers 1, 2, 3 or 4, r denotes the number 1 or, if q is one of the numbers 2, 3 or 4, it may also denote the number 0 and $R_{15}$ assumes the meanings of the abovementioned group $R_7$, a group of formula

—N($R_{16}$)—$SO_2$—$R_{17}$ (VI), wherein $R_{16}$ denotes a hydrogen atom or a $C_{1-4}$-alkyl group optionally terminally substituted by a cyano, trifluoromethyl-carbonylamino or N—($C_{1-3}$-alkyl)-trifluoromethyl-carbonyl-amino group and $R_{17}$ denotes a $C_{1-3}$-alkyl group, an amino group substituted by a di-($C_{1-3}$-alkyl)-amino-$C_{1-3}$-alkyl-carbonyl or di-($C_{1-3}$-alkyl)-amino-$C_{1-3}$-alkyl-sulphonyl group and a di-($C_{1-3}$-alkyl)-aminocarbonyl-$C_{1-3}$-alkyl group, or an N—($C_{1-3}$-alkyl)-$C_{1-5}$-alkylsulphonylamino or N—($C_{1-3}$-alkyl)-phenylsulphonylamino group wherein the alkyl moiety is additionally substituted by a cyano or carboxy group, wherein all the single-bonded or fused phenyl groups contained in the groups mentioned under $R_6$ may be mono- or disubstituted by fluorine, chlorine, bromine or iodine atoms, by $C_{1-5}$-alkyl, trifluoromethyl, hydroxy, $C_{1-3}$-alkoxy, carboxy, $C_{1-3}$-alkoxycarbonyl, aminocarbonyl, $C_{1-4}$-alkylamino-carbonyl, di-($C_{1-4}$-alkyl)-amino-carbonyl, aminosulphonyl, $C_{1-3}$-alkyl-aminosulphonyl, di-($C_{1-3}$-alkyl)-aminosulphonyl, $C_{1-3}$-alkyl-sulphonylamino, nitro or cyano groups, wherein the substituents may be identical or different, or two adjacent hydrogen atoms of the phenyl groups may be replaced by a methylenedioxy group, and $R_5$ denotes a hydrogen atom or a $C_{1-3}$-alkyl group, wherein by an aryl group is meant a phenyl or naphthyl group optionally mono- or disubstituted by a fluorine, chlorine, bromine or iodine atom, by a cyano, trifluoromethyl, nitro, carboxy, aminocarbonyl, $C_{1-3}$-alkyl or $C_{1-3}$-alkoxy group and by a heteroaryl group is meant a monocyclic 5- or 6-membered heteroaryl group optionally substituted by a $C_{1-3}$-alkyl group in the carbon skeleton, wherein
the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or
an imino group optionally substituted by a $C_{1-3}$-alkyl or phenyl-$C_{1-3}$-alkyl group or an oxygen or sulphur atom and additionally a nitrogen atom or
an imino group optionally substituted by a $C_{1-3}$-alkyl or phenyl-$C_{1-3}$-alkyl group and two nitrogen atoms,
and moreover a phenyl ring may be fused to the abovementioned monocyclic heterocyclic groups via two adjacent carbon atoms and the bonding takes place via a nitrogen atom or via a carbon atom of the heterocyclic moiety or a fused phenyl ring,
some or all of the hydrogen atoms in the abovementioned alkyl and alkoxy groups or in the alkyl moieties contained in the above-defined groups of formula I optionally being replaced by fluorine atoms,
the saturated alkyl and alkoxy moieties with more than 2 carbon atoms which are present in the groups defined hereinbefore also include the branched isomers thereof, such as for example the isopropyl, tert.butyl, isobutyl group, unless otherwise stated, and
additionally the hydrogen atom of any carboxy group present or a hydrogen atom bound to a nitrogen atom, e.g. a hydrogen atom of an amino, alkylamino or imino group or a saturated N-heterocycle such as the piperidinyl group, may each be replaced by a group which can be cleaved in vivo.

By a group which can be cleaved in vivo from an imino or amino group is meant, for example, a hydroxy group, an acyl group such as the benzoyl or pyridinoyl group or a $C_{1-16}$-alkanoyl group such as the formyl, acetyl, propionyl, butanoyl, pentanoyl or hexanoyl group, an allyloxycarbonyl group, a $C_{1-16}$-alkoxycarbonyl group such as the methoxycarbonyl, ethoxycarbonyl, propoxycarbonyl, isopropoxycarbonyl, butoxycarbonyl, tert.butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-$C_{1-6}$-alkoxycarbonyl group such as the benzyloxycarbonyl, phenylethoxycarbonyl or phenylpropoxycarbonyl group, a $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or $R_e$CO—O—($R_f$C$R_g$)—O—CO group wherein
$R_e$ denotes a $C_{1-8}$-alkyl, $C_{5-7}$-cycloalkyl, phenyl or phenyl-$C_{1-3}$-alkyl group,
$R_f$ denotes a hydrogen atom, a $C_{1-3}$-alkyl, $C_{5-7}$-cycloalkyl or phenyl group and
$R_g$ denotes a hydrogen atom, a $C_{1-3}$-alkyl or $R_e$CO—O—($R_f$C$R_g$)—O group wherein $R_e$ to $R_g$ are as hereinbefore defined,
wherein additionally the amino group may be a phthalimido group, whilst the abovementioned ester groups may also be used as a group which can be converted in vivo into a carboxy group.

One sub-group of compounds of general formula I which deserves special mention comprises those wherein
X, $R_1$ and $R_3$ to $R_5$ are as hereinbefore defined and
$R_2$ denotes a straight-chain or branched $C_{1-6}$-alkoxy-carbonyl group, a $C_{4-7}$-cycloalkoxycarbonyl or a aryloxycarbonyl group, a straight-chain or branched $C_{1-6}$-alkoxy-carbonyl group, which is terminally substituted in the alkyl moiety by a phenyl, heteroaryl, carboxy, $C_{1-3}$-alkoxycarbonyl, aminocarbonyl, $C_{1-3}$-alkylaminocarbonyl or di-($C_{1-3}$-alkyl)-aminocarbonyl group, a straight-chain or branched $C_{2-6}$-alkoxy-carbonyl group, which is terminally substituted in the alkyl moiety by a chlorine atom or a hydroxy, $C_{1-3}$-alkoxy, amino, $C_{1-3}$-alkylamino or di-($C_{1-3}$-alkyl)-amino group, the tautomers, the diastereomers, the enantiomers, the mixtures thereof and the salts thereof.

A second sub-group of compounds of general formula I which deserves special mention comprises those wherein
X, $R_1$ and $R_3$ to $R_5$ are as hereinbefore defined and
$R_2$ denotes an aminocarbonyl or methylaminocarbonyl group, an ethylaminocarbonyl group optionally substituted in the 2 position of the ethyl group by a hydroxy or $C_{1-3}$-alkoxy group or, if $R_4$ does not denote an aminosulphonyl-phenyl or N—($C_{1-5}$-alkyl)-$C_{1-3}$-alkylaminocarbonyl-phenyl group, $R_2$ may also denote a di-($C_{1-2}$-alkyl)-aminocarbonyl group, the tautomers, the diastereomers, the enantiomers, the mixtures thereof and the salts thereof.

A third sub-group of compounds of general formula I which deserves special mention comprises those wherein
X, $R_1$ to $R_3$ and $R_5$ are as hereinbefore defined and
$R_4$ denotes an $R_7$—($C_{1-4}$-alkyl)-phenyl group, wherein
$R_7$ denotes an amino, $C_{1-7}$-alkylamino, di-($C_{1-7}$-alkyl)-amino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group,
or a phenyl group substituted by the group of formula

$$-N(R_{12})-CO-(CH_2)_p-R_{13} \qquad (IV),$$

wherein $R_{12}$, p and $R_{13}$ are as hereinbefore defined,
the tautomers, the diastereomers, the enantiomers, the mixtures thereof and the salts thereof.

Preferred compounds of general formula I are those wherein
$R_1$ and $R_3$ are as hereinbefore defined and
X denotes an oxygen atom,
$R_2$ denotes a carboxy group, a straight-chain or branched $C_{1-6}$-alkoxy-carbonyl group, a $C_{5-7}$-cycloalkoxycarbonyl or a phenoxycarbonyl group, a straight-chain or branched $C_{1-3}$-alkoxy-carbonyl group, which is terminally substituted in the alkyl moiety by a phenyl, heteroaryl, carboxy, $C_{1-3}$-alkoxycarbonyl, aminocarbonyl, $C_{1-3}$-alkylaminocarbonyl or di-($C_{1-3}$-alkyl)-aminocarbonyl group, a straight-chain or branched $C_{2-3}$-alkoxy-carbonyl group, which is terminally substituted in the alkyl moiety by a chlorine atom, by a hydroxy, $C_{1-3}$-alkoxy, amino, $C_{1-3}$-alkylamino or di-($C_{1-3}$-alkyl)-amino group, an aminocarbonyl or methylaminocarbonyl group, an ethylaminocarbonyl group optionally substituted in the 2 position of the ethyl group by a hydroxy or $C_{1-3}$-alkoxy group or, if $R_4$ does not denote an aminosulphonyl-phenyl or N—($C_{1-5}$-alkyl)-$C_{1-3}$-alkylaminocarbonyl-phenyl group, it may also denote a di-($C_{1-2}$-alkyl)-aminocarbonyl group, $R_4$ denotes a $C_{3-7}$-cycloalkyl group,
whilst the methylene group in the 4 position of a 6 or 7-membered cycloalkyl group may be substituted by an amino, $C_{1-3}$-alkylamino or di-($C_{1-3}$-alkyl)-amino group or replaced by an —NH or —N($C_{1-3}$-alkyl) group, or a phenyl group substituted by the group $R_6$, which may additionally be mono- or disubstituted by fluorine, chlorine or bromine atoms, by $C_{1-3}$-alkyl, trifluoromethyl, hydroxy, $C_{1-3}$-alkoxy, carboxy, $C_{1-3}$-alkoxycarbonyl, amino, acetylamino, aminocarbonyl, $C_{1-3}$-alkyl-aminocarbonyl, di-($C_{1-3}$-alkyl)-aminocarbonyl, nitro or cyano groups, wherein the substituents may be identical or different and wherein $R_6$ denotes a hydrogen, fluorine, chlorine, bromine or iodine atom, a cyano, nitro, amino, $C_{1-5}$-alkyl, $C_{3-7}$-cycloalkyl, trifluoromethyl, phenyl, tetrazolyl or heteroaryl group, the group of formula

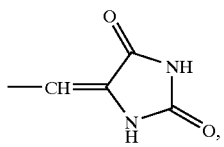

wherein a hydrogen atom bound to the nitrogen atom may be replaced by a $C_{1-3}$-alkyl group, a $C_{1-3}$-alkoxy group, an amino-$C_{2-3}$-alkoxy, $C_{1-3}$-alkylamino-$C_{2-3}$-alkoxy, di-($C_{1-3}$-alkyl)-amino-$C_{2-3}$-alkoxy, phenyl-$C_{1-3}$-alkylamino-$C_{2-3}$-alkoxy, N—($C_{1-3}$-alkyl)-phenyl-$C_{1-3}$-alkylamino-$C_{2-3}$-alkoxy, pyrrolidino-$C_{2-3}$-alkoxy, piperidino-$C_{2-3}$-alkoxy or $C_{1-3}$-alkylmercapto group, a carboxy, $C_{1-4}$-alkoxycarbonyl, aminocarbonyl, $C_{1-3}$-alkylamino-carbonyl, phenyl-$C_{1-3}$-alkylamino-carbonyl or N—($C_{1-3}$-alkyl)-phenyl-$C_{1-3}$-alkylamino-carbonyl group, a $C_{3-7}$-cycloalkyl-carbonyl group,
wherein the methylene group in the 4 position of the 6- or 7-membered cycloalkyl moiety may be replaced by an —NH or —N($C_{1-3}$-alkyl) group, a 4- to 7-membered cycloalkyleneimino group, wherein a methylene group linked to the imino group may be replaced by a carbonyl or sulphonyl group or
one or two hydrogen atoms may each be replaced by a $C_{1-3}$-alkyl group and/or
in each case the methylene group in the 4 position of a 6- or 7-membered cycloalkyleneimino group may be substituted by a carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or
may be replaced by an oxygen or sulphur atom, by a sulphinyl, sulphonyl, —NH or —N($C_{1-3}$-alkyl) group, a $C_{1-4}$-alkyl group terminally substituted by the group $R_7$, wherein
$R_7$ denotes a $C_{5-7}$-cycloalkyl group,
whilst the methylene group in the 4 position of a 6- or 7-membered cycloalkyl group may be replaced by an —NH or —N($C_{1-3}$-alkyl) group or
in a 5- to 7-membered cycloalkyl group a —(CH$_2$)$_2$ group may be replaced by a —CO—NH group, a —(CH$_2$)$_3$ group may be replaced by a —NH—CO—NH— or a —(CH$_2$)$_4$ group may be replaced by a —NH—CO—NH—CO group, whilst in each case a hydrogen atom bound to a nitrogen atom may be replaced by a $C_{1-3}$-alkyl group, a phenyl or heteroaryl group,
a hydroxy or $C_{1-3}$-alkoxy group,
an amino, $C_{1-6}$-alkylamino, di-($C_{1-6}$-alkyl)-amino, phenylamino, N-phenyl-$C_{1-3}$-alkylamino, phenyl-$C_{1-3}$-alkylamino, N—($C_{1-3}$-alkyl)-phenyl-$C_{1-3}$-alkylamino or di-(phenyl-$C_{1-3}$-alkyl)-amino group,
a ω-hydroxy-$C_{2-3}$-alkyl-amino, N—($C_{1-3}$-alkyl)-ω-hydroxy-$C_{2-3}$-alkyl-amino, di-(ω-hydroxy-$C_{2-3}$-alkyl)-amino, di-(ω-($C_{1-3}$-alkoxy)-$C_{2-3}$-alkyl)-amino or N—(dioxolan-2-yl)-$C_{1-3}$-alkyl-amino group,
a $C_{1-3}$-alkylcarbonylamino-$C_{2-3}$-alkyl-amino or $C_{1-3}$-alkylcarbonylamino-$C_{2-3}$-alkyl-N—($C_{1-3}$-alkyl)-amino group,
a $C_{1-3}$-alkylsulphonylamino, N—($C_{1-3}$-alkyl)-$C_{1-3}$-alkylsulphonylamino, $C_{1-3}$-alkylsulphonylamino-$C_{2-3}$-alkyl-amino or $C_{1-3}$-alkylsulphonylamino-$C_{2-3}$-alkyl-N—($C_{1-3}$-alkyl)amino group,
a hydroxycarbonyl-$C_{1-3}$-alkylamino or N—($C_{1-3}$-alkyl)-hydroxycarbonyl-$C_{1-3}$-alkyl-amino group
a guanidino group wherein a hydrogen atom may be replaced by a $C_{1-3}$-alkyl group,
a group of formula

wherein
$R_8$ denotes a hydrogen atom or a $C_{1-3}$-alkyl group,
n denotes one of the numbers 0, 1, 2 or 3 and
$R_9$ denotes an amino, $C_{1-3}$-alkylamino, di-($C_{1-3}$-alkyl)-amino, phenylamino, benzylamino or $C_{1-4}$-alkoxy group, a 5- to 7-membered cycloalkyleneimino group, wherein the methylene group in position 4 of the piperidino group may be replaced by an oxygen or sulphur atom, by an —NH, —N($C_{1-3}$-alkyl), —N(phenyl), —N($C_{1-3}$-alkylcarbonyl) or —N(benzoyl) group, or, if n denotes one of the numbers 1, 2 or 3, it may also denote a hydrogen atom,
a group of formula

wherein
$R_{10}$ denotes a hydrogen atom, a $C_{1-3}$-alkyl group, a $C_{1-3}$-alkylcarbonyl or $C_{1-3}$-alkylsulphonyl group,
m denotes one of the numbers 1, 2 or 3,
o denotes the number 1 or, if m is one of the numbers 2 or 3, o may also denote the number 0 and
$R_{11}$ denotes an amino, $C_{1-3}$-alkylamino, di-($C_{1-3}$-alkyl)-amino, $C_{1-4}$-alkoxy or $C_{1-3}$-alkoxy-$C_{1-3}$-alkoxy group or a 5- to 7-membered cycloalkyleneimino group, wherein the methylene group in position 4 of the piperidino group may be replaced by an oxygen or sulphur atom, by an —NH, —N($C_{1-3}$-alkyl), —N(phenyl), —N($C_{1-3}$-alkylcarbonyl) or —N(benzoyl) group,
a $C_{4-7}$-cycloalkylamino or $C_{4-7}$-cycloalkenylamino group wherein position 1 of the ring is not involved in the double bond,
a 4- to 7-membered cycloalkyleneimino group, wherein the cycloalkylene moiety may be fused to a phenyl group or
one or two hydrogen atoms may each be replaced by a $C_{1-3}$-alkyl group and/or
the methylene group in position 3 of the pyrrolidino group may be substituted by a hydroxy or $C_{1-3}$-alkoxy group, in each case the methylene group in the 4 position of a 6- or 7-membered cycloalkyleneimino group may be substituted by a hydroxy, hydroxy-$C_{1-3}$-alkyl, $C_{1-3}$-alkoxy, carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or may be replaced by an oxygen or sulphur atom, by a sulphinyl, sulphonyl, —NH, —N($C_{1-3}$-alkyl), —N(phenyl), —N(phenyl-$C_{1-3}$-alkyl), —N($C_{1-3}$-alkyl-carbonyl), —N($C_{1-4}$-alkoxy-carbonyl), —N(benzoyl) or —N(phenyl-$C_{1-3}$-alkyl-carbonyl) group, wherein a methylene group linked to an imino-nitrogen atom of the cycloalkyleneimino group may be replaced by a carbonyl or sulphonyl group or in a 5- to 6-membered monocyclic cycloalkyleneimino group or a cycloalkyleneimino group fused to a phenyl group the two methylene groups linked to the imino-nitrogen atom may each be replaced by a carbonyl group, or $R_6$ denotes a $C_{1-4}$-alkyl group which is terminally substituted by a carboxy, $C_{1-3}$-alkoxycarbonyl, aminocarbonyl, $C_{1-3}$-alkylaminocarbonyl or di-($C_{1-3}$-alkyl)-aminocarbonyl group or by a 4- to 7-membered cycloalkyleneiminocarbonyl group, a group of formula

$$-N(R_{12})-CO-(CH_2)_p-R_{13} \quad (IV),$$

wherein $R_{12}$ denotes a hydrogen atom, a $C_{1-3}$-alkyl, $C_{5-7}$-cycloalkyl, phenyl-$C_{1-3}$-alkyl or heteroaryl-$C_{1-3}$-alkyl group and p denotes one of the numbers 0, 1, 2 or 3 and $R_{13}$ assumes the meanings of the abovementioned group $R_7$, or, if p denotes one of the numbers 1, 2 or 3, it may also denote a hydrogen atom, a group of formula

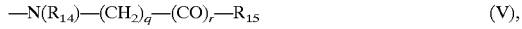

$$-N(R_{14})-(CH_2)_q-(CO)_r-R_{15} \quad (V),$$

wherein $R_{14}$ denotes a hydrogen atom, a $C_{1-4}$-alkyl group, a $C_{1-3}$-alkylcarbonyl, phenylcarbonyl, phenyl-$C_{1-3}$-alkylcarbonyl, heteroarylcarbonyl, heteroaryl-$C_{1-3}$-alkylcarbonyl, $C_{1-4}$-alkylsulphonyl, phenylsulphonyl, phenyl-$C_{1-3}$-alkylsulphonyl- heteroarylsulphonyl or heteroaryl-$C_{1-3}$-alkyl-sulphonyl group, q denotes one of the numbers 1, 2, 3 or 4, r denotes the number 1 or, if q is one of the numbers 2, 3 or 4, it may also denote the number 0 and $R_{15}$ assumes the meanings of the abovementioned group $R_7$, a group of formula

$$-N(R_{16})-SO_2-R_{17} \quad (VI),$$

wherein $R_{16}$ denotes a hydrogen atom or a $C_{1-4}$-alkyl group optionally terminally substituted by a cyano, trifluoromethyl-carbonylamino or N—($C_{1-3}$-alkyl)-trifluoromethyl-carbonyl-amino group and $R_{17}$ denotes a $C_{1-3}$-alkyl group, an amino group substituted by a di-($C_{1-3}$-alkyl)-amino-$C_{1-3}$-alkyl-carbonyl or di-($C_{1-3}$-amino-$C_{1-3}$-alkyl-sulphonyl group and a di-($C_{1-3}$-alkyl)-aminocarbonyl-$C_{1-3}$-alkyl group, wherein all the single-bonded or fused phenyl groups contained in the groups mentioned under $R_6$ may be mono- or disubstituted by fluorine, chlorine or bromine atoms, by $C_{1-3}$-alkyl, trifluoromethyl, hydroxy, $C_{1-3}$-alkoxy, carboxy, $C_{1-3}$-alkoxycarbonyl, aminocarbonyl, $C_{1-3}$-alkyl-aminocarbonyl, aminosulphonyl, $C_{1-3}$-alkyl-aminosulphonyl, nitro or cyano groups, wherein the substituents may be identical or different, or two adjacent hydrogen atoms of the phenyl groups may be replaced by a methylenedioxy group, and $R_5$ denotes a hydrogen atom or a $C_{1-3}$-alkyl group, whilst by a heteroaryl group as mentioned above is meant a pyridinyl, pyrazinyl, pyrimidinyl, pyridazinyl, pyrrolyl, furyl, thienyl, oxazolyl, thiazolyl, pyrazolyl, imidazolyl or triazolyl group optionally substituted in the carbon skeleton by a $C_{1-3}$-alkyl group wherein a hydrogen atom bound to a nitrogen atom may be replaced by a $C_{1-3}$-alkyl or phenyl-$C_{1-3}$-alkyl group and wherein the 5-membered heteroaryl groups containing at least one imino group are bound via a carbon or nitrogen atom, a hydrogen atom bound to a nitrogen atom in the abovementioned groups may be replaced by a group which can be cleaved in vivo, particularly by an acetyl or tert.butoxycarbonyl group, the carboxy groups contained in the abovementioned groups may each be substituted by a group which can be cleaved in vivo and may occur, for example, in the form of the tert.butoxycarbonyl group, some or all of the hydrogen atoms in the abovementioned alkyl and alkoxy groups or in the alkyl moieties contained in the above-defined groups of formula I optionally being replaced by fluorine atoms and the saturated alkyl and alkoxy moieties contained in the abovementioned groups, which contain more than 2 carbon atoms, may be straight-chain or branched, unless otherwise stated, the tautomers, the diastereomers, the enantiomers, the mixtures thereof and the salts thereof.

One subgroup of preferred compounds of general formula I deserving special mention comprises those wherein X, $R_1$ and $R_3$ to $R_5$ are as hereinbefore defined and $R_2$ denotes a straight-chain or branched $C_{1-6}$alkoxy-carbonyl group, a $C_{5-7}$-cycloalkoxycarbonyl or a phenoxycarbonyl group, a straight-chain or branched $C_{1-3}$-alkoxy-carbonyl group, which is terminally substituted in the alkyl moiety by a phenyl-carboxy, $C_{1-3}$-alkoxycarbonyl, aminocarbonyl, $C_{1-3}$-alkylaminocarbonyl or di-($C_{1-3}$-alkyl)-aminocarbonyl group, a straight-chain or branched $C_{2-3}$-alkoxy-carbonyl group, which is terminally substituted in the alkyl moiety by a hydroxy, $C_{1-3}$-alkoxy, amino, $C_{1-3}$-alkylamino or di-($C_{1-3}$-alkyl)-amino group, the tautomers, the diastereomers, the enantiomers, the mixtures thereof and the salts thereof.

A second sub-group of preferred compounds of general formula 1 deserving special mention comprises those wherein X, $R_1$ and $R_3$ to $R_5$ are as hereinbefore defined and $R_2$ denotes an aminocarbonyl or methylaminocarbonyl group, an ethylaminocarbonyl group optionally substituted in the 2 position of the ethyl group by a hydroxy or $C_{1-3}$-alkoxy group or, if $R_4$ does not denote an aminosulphonyl-phenyl or $N-(C_{1-5}-alkyl)-C_{1-3}$-alkylaminocarbonyl-phenyl group, $R_2$ may also denote a di-$(C_{1-2}-alkyl)$-aminocarbonyl group, the tautomers, the diastereomers, the enantiomers, the mixtures thereof and the salts thereof.

A third sub-group of preferred compounds of general formula I deserving special mention comprises those wherein X, $R_1$ to $R_3$ and $R_5$ are as hereinbefore defined and $R_4$ denotes an $R_7$-(n-$C_{1-4}$-alkyl)-phenyl group, wherein $R_7$ denotes an amino, $C_{1-6}$-alkylamino, di-$(C_{1-6}$-alkyl)-amino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group, or a phenyl group substituted by the group of formula

wherein $R_{12}$, p and $R_{13}$ are as hereinbefore defined, the tautomers, the diastereomers, the enantiomers, the mixtures thereof and the salts thereof.

Particularly preferred compounds of general formula I are those wherein

X denotes an oxygen atom, $R_1$ denotes a hydrogen atom, $R_2$ denotes a carboxy group, a straight-chain or branched $C_{1-4}$-alkoxycarbonyl group or a phenoxycarbonyl group, a straight-chain or branched $C_{1-3}$-alkoxycarbonyl group, which is terminally substituted in the alkyl moiety by a phenyl, carboxy, $C_{1-3}$-alkoxycarbonyl, aminocarbonyl, $C_{1-3}$-alkylaminocarbonyl or di-$(C_{1-3}$-alkyl)-aminocarbonyl group, a straight-chain or branched $C_{2-3}$-alkoxy-carbonyl group which is terminally substituted in the alkyl moiety by a hydroxy, $C_{1-3}$-alkoxy, amino, $C_{1-3}$-alkylamino or di-$(C_{1-3}$-alkyl)-amino group, an aminocarbonyl or methylaminocarbonyl group, an ethylaminocarbonyl group optionally substituted in the 2 position of the ethyl group by a hydroxy or $C_{1-3}$-alkoxy group or, if $R_4$ does not denote an aminosulphonyl-phenyl or $N-(C_{1-5}-alkyl)-C_{1-3}$-alkylaminocarbonyl-phenyl group, it may also denote a di-$(C_{1-2}-alkyl)$-aminocarbonyl group, $R_3$ denotes a $C_{1-4}$-alkyl group or a phenyl group which may be substituted by a fluorine, chlorine or bromine atom, by a trifluoromethyl, $C_{1-3}$-alkyl, hydroxy or $C_{1-3}$-alkoxy group, $R_4$ denotes a $C_{5-6}$cycloalkyl group,
wherein the methylene group in position 4 of the cyclohexyl group may be substituted by an amino, $C_{1-3}$-alkylamino or di-$(C_{1-3}$-alkyl)-amino group or replaced by an —NH or —N($C_{1-3}$-alkyl) group, a phenyl group, a phenyl group disubstituted by $C_{1-3}$-alkyl, $C_{1-3}$-alkoxy or nitro groups, wherein the substituents may be identical or different, or a phenyl group substituted by the group $R_6$, which may additionally be substituted by a fluorine, chlorine or bromine atom or by an amino or nitro group, wherein $R_6$ denotes a fluorine, chlorine or bromine atom, a $C_{1-3}$-alkyl, $C_{1-3}$-alkoxy, nitro, amino or $C_{5-6}$-cycloalkyl group, a pyrrolyl, pyrazolyl, imidazolyl, triazolyl or tetrazolyl group bound via a carbon atom, wherein the abovementioned heteroaromatic groups in the carbon skeleton may be substituted by a $C_{1-3}$-alkyl group or a hydrogen atom bound to a nitrogen atom may be replaced by a $C_{1-3}$-alkyl or phenyl-$C_{1-3}$-alkyl group, the group of formula

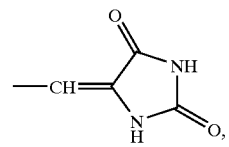

a carboxy, $C_{1-4}$-alkoxycarbonyl, phenyl-$C_{1-3}$-alkylaminocarbonyl or $C_{5-7}$-cycloalkyl-carbonyl group, a 5 or 6-membered cycloalkyleneimino group, wherein the methylene group in position 4 of the piperidino group may be replaced by an oxygen or sulphur atom, by an —NH or —N($C_{1-3}$-alkyl) group, an unbranched $C_{1-3}$-alkyl group terminally substituted by the group $R_7$, wherein $R_7$ denotes a $C_{5-7}$-cycloalkyl group,
wherein in a 5 or 6-membered cycloalkyl group a —(CH$_2$)$_2$ group may be replaced by a —CO—NH group, a CH$_2$)$_3$ group may be replaced by an —NH—CO—NH— or a —(CH$_2$)$_4$ group may be replaced by an —NH—CO—NH—CO group, whilst in each case a hydrogen atom bound to a nitrogen atom may be replaced by a $C_{1-3}$-alkyl group, a phenyl or pyridinyl group or a pyrrolyl, pyrazolyl, imidazolyl or triazolyl group bound via a carbon or nitrogen atom, wherein the abovementioned heteroaromatic groups in the carbon skeleton may be substituted by a $C_{1-3}$-alkyl group or a hydrogen atom bound to a nitrogen atom may be replaced by a $C_{1-3}$-alkyl group, a hydroxy or $C_{1-3}$-alkoxy group, an amino, $C_{1-6}$-alkylamino, di-$(C_{1-6}$-alkyl)-amino, phenylamino, N-phenyl-$C_{1-3}$-alkylamino, phenyl-$C_{1-3}$-alkylamino or N—($C_{1-3}$-alkyl)-phenyl-$C_{1-3}$-alkylamino group, a ω-hydroxy-$C_{2-3}$-alkyl-amino, N—($C_{1-3}$-alkyl)-ω-hydroxy-$C_{2-3}$-alkylamino, di-(ω-hydroxy-$C_{2-3}$-alkyl)-amino or di-(ω-($C_{1-3}$-alkoxy)-$C_{2-3}$-alkyl)-amino group, a $C_{1-3}$-alkylcarbonylamino-$C_{2-3}$-alkyl-amino or $C_{1-3}$-alkylcarbonylamino-$C_{2-3}$-alkyl-N—($C_{1-3}$-alkyl)-amino group, a $C_{1-3}$-alkylsulphonylamino, N—($C_{1-3}$-alkyl)-$C_{1-3}$-alkylsulphonylamino, $C_{1-3}$-alkylsulphonylamino-$C_{2-3}$-alkylamino or $C_{1-3}$-alkylsulphonylamino-$C_{2-3}$-alkyl-N—($C_{1-3}$-alkyl)-amino group, a hydroxycarbonyl-$C_{1-3}$-alkylamino or N—($C_{1-3}$-alkyl)-hydroxycarbonyl-$C_{1-3}$-alkyl-amino group, a guanidino group wherein a hydrogen atom may be replaced by a $C_{1-3}$-alkyl group, a group of formula

wherein $R_8$ denotes a hydrogen atom or a $C_{1-3}$-alkyl group, n denotes one of the numbers 0, 1, 2 or 3 and $R_9$ denotes an amino, $C_{1-3}$-alkylamino, di-($C_{1-3}$-alkyl)-amino or $C_{1-4}$-alkoxy group, a 5- or 6-membered cycloalkyleneimino group, wherein the methylene group in position 4 of the piperidino group may be replaced by an —NH, —N($C_{1-3}$-alkyl) or —N($C_{1-3}$-alkyl-carbonyl) group, or, if n denotes one of the numbers 1, 2 or 3, $R_9$ may also denote a hydrogen atom, a group of formula

wherein $R_{10}$ denotes a hydrogen atom or a $C_{1-3}$-alkyl group, m denotes one of the numbers 1, 2 or 3, o denotes the number 1 or, if m is one of the numbers 2 or 3, o may also denote the number 0 and $R_{11}$ denotes an amino, $C_{1-3}$-alkylamino, di-($C_{1-3}$-alkyl)-amino, $C_{1-4}$-alkoxy or methoxy-$C_{1-3}$-alkoxy group or a 5- or 6-membered cycloalkyleneimino group, wherein the methylene group in position 4 of the piperidino group may be replaced by an —NH, —N($C_{1-3}$-alkyl) or —N($C_{1-3}$-alkyl-carbonyl) group, an azetidino, pyrrolidino, piperidino, 2,6-dimethyl-piperidino, 3,5-dimethyl-piperidino or azepino group, wherein the methylene group in position 3 of the pyrrolidino group may be substituted by a hydroxy group, the methylene group in position 4 of the piperidino group may be substituted by a hydroxy, hydroxy-$C_{1-3}$-alkyl or $C_{1-3}$-alkoxy group or may be replaced by an oxygen or sulphur atom, by a sulphinyl, sulphonyl, —NH, —N($C_{1-3}$-alkyl), —N($C_{1-3}$-alkyl-carbonyl), —N(benzoyl) or —N(phenyl-$C_{1-3}$-alkyl-carbonyl) group, wherein a methylene group linked to an imino-nitrogen atom of the pyrrolidino, piperidino or piperazino group may be replaced by a carbonyl group, or $R_6$ denotes a straight-chain $C_{1-3}$-alkyl group which is terminally substituted by a carboxy or $C_{1-3}$-alkoxy-carbonyl group, a group of formula

wherein $R_{12}$ denotes a hydrogen atom, a $C_{1-3}$-alkyl or phenyl-$C_{1-3}$-alkyl group, p denotes one of the numbers 0, 1 or 2 and $R_{13}$ denotes an amino, $C_{1-4}$-alkylamino, di-($C_{1-4}$-alkyl)-amino, benzylamino, N—($C_{1-3}$-alkyl)-benzylamino, $C_{1-3}$-alkoxy-$C_{1-3}$-alkylamino, N—($C_{1-3}$-alkyl)-$C_{1-3}$-alkoxy-$C_{1-3}$-alkylamino, di-(2-methoxy-ethyl)-amino, di-(ω-hydroxy-$C_{2-3}$-alkyl)-amino or aminocarbonyl-methyl-N-(methyl)-amino group, a pyrrolyl, pyrazolyl or imidazolyl group bound via a nitrogen atom and optionally substituted by a $C_{1-3}$-alkyl group, a pyrrolidino, piperidino, morpholino, thiomorpholino or a piperazino group optionally substituted in the 4 position by a $C_{1-3}$-alkyl, phenyl-$C_{1-3}$-alkyl, $C_{1-3}$-alkylcarbonyl or $C_{1-4}$-alkoxycarbonyl group or, if n denotes the number 1 or 2, it may also denote a hydrogen atom, a group of formula

wherein $R_{14}$ denotes a hydrogen atom, a $C_{1-4}$-alkyl, $C_{1-3}$-alkyl-carbonyl, phenylcarbonyl, phenyl-$C_{1-3}$-alkylcarbonyl, furyl-carbonyl, pyridinyl-carbonyl, furyl-$C_{1-3}$-alkyl-carbonyl, pyridinyl-$C_{1-3}$-alkylcarbonyl, $C_{1-4}$-alkylsulphonyl, phenylsulphonyl or phenyl-$C_{1-3}$-alkylsulphonyl group, q denotes one of the numbers 1, 2 or 3, r denotes the number 1 or, if q is one of the numbers 2 or 3, it may also denote the number 0 and $R_{15}$ denotes an amino, $C_{1-4}$-alkylamino, di-($C_{1-4}$-alkyl)-amino, phenylamino, N—($C_{1-4}$-alkyl)-phenylamino, benzylamino or N—($C_{1-4}$-alkyl)-benzylamino group, or a group of formula

wherein $R_{16}$ denotes a hydrogen atom or a $C_{1-3}$-alkyl group optionally terminally substituted by a cyano, trifluoromethyl-carbonylamino or N—($C_{1-3}$-alkyl)-trifluoromethyl-carbonyl-amino group and $R_{17}$ denotes a $C_{1-3}$-alkyl group, wherein all the single-bonded or fused phenyl groups contained in the groups mentioned under $R_6$ may be substituted by a fluorine, chlorine or bromine atom, by a methyl, trifluoromethyl, methoxy, nitro or cyano group and $R_5$ denotes a hydrogen atom, wherein a hydrogen atom bound to a nitrogen atom in the abovementioned groups may be replaced by an acetyl or tert.butoxycarbonyl group, the carboxy groups contained in the abovementioned groups may also be present in the form of the tert.butoxycarbonyl precursor group and the saturated alkyl and alkoxy moieties contained in the abovementioned groups, which contain more than 2 carbon atoms, may be straight-chain or branched, unless otherwise stated, the tautomers, the diastereomers, the enantiomers, the mixtures thereof and the salts thereof.

One subgroup of particularly preferred compounds of general formula I deserving special mention comprises those wherein X, $R_1$, $R_3$ and $R_5$ are as hereinbefore defined, $R_2$ denotes a straight-chain or branched $C_{1-4}$-alkoxycarbonyl group or a phenoxycarbonyl group, a straight-chain or branched $C_{1-3}$-alkoxycarbonyl group, which is terminally substituted in the alkyl moiety by a phenyl-carboxy, $C_{1-3}$-alkoxycarbonyl, aminocarbonyl, $C_{1-3}$-alkylaminocarbonyl or di-($C_{1-3}$-alkyl)-aminocarbonyl group, or a straight-chain or branched $C_{2-3}$-alkoxy-carbonyl group, which is terminally substituted in the alkyl moiety by a hydroxy, $C_{1-3}$-alkoxy, amino, $C_{1-3}$-alkylamino or di-($C_{1-3}$-alkylamino group, and $R_4$ denotes an $R_7$—(n-$C_{1-3}$-alkyl)-phenyl group, wherein $R_7$ denotes an amino, $C_{1-6}$-alkylamino, di-($C_{1-4}$-alkyl)-amino, ω-hydroxy-$C_{2-3}$-alkyl-amino, N—($C_{1-3}$-alkyl)ω-hydroxy-$C_{2-3}$-alkyl-amino, di-(ω-hydroxy- $C_{2-3}$-alkyl)-amino or di-($\omega$-($C_{1-3}$-alkoxy)-$C_{2-3}$-alkyl)-amino group, or a phenyl group substituted by the group of formula $$-N(R_{12})-CO-(CH_2)_p-R_{13} \quad (IV),$$

wherein $R_{12}$, p and $R_{13}$ are as hereinbefore defined, the tautomers, the diastereomers, the enantiomers, the mixtures thereof and the salts thereof.

A second subgroup of particularly preferred compounds of general formula I deserving special mention comprises those wherein X, $R_1$, $R_3$ and $R_5$ are as hereinbefore defined, $R_2$ denotes an aminocarbonyl or methylaminocarbonyl group, an ethylaminocarbonyl group optionally substituted in the 2 position of the ethyl group by a hydroxy or $C_{1-3}$-alkoxy group or, if $R_4$ does not denote an aminosulphonyl-phenyl or N—($C_{1-5}$-alkyl)-$C_{1-3}$-alkylaminocarbonyl-phenyl group, $R_2$ may also denote a di-($C_{1-2}$-alkyl)-aminocarbonyl group and $R_4$ denotes a $R_7$—(n-$C_{1-3}$-alkyl)-phenyl group, wherein $R_7$ denotes an amino, $C_{1-6}$-alkylamino, di-($C_{1-4}$-alkyl)-amino, $\omega$-hydroxy-$C_{2-3}$-alkyl-amino, N—($C_{1-3}$-alkyl)-$\omega$-hydroxy-$C_{2-3}$-alkyl-amino, di-($\omega$-hydroxy-$C_{2-3}$-alkyl)-amino or di-($\omega$-($C_{1-3}$-alkoxy)-$C_{2-3}$-alkyl)amino group, or a phenyl group substituted by the group of formula $$-N(R_{12})-CO-(CH_2)_p-R_{13} \quad (IV),$$

wherein $R_{12}$, p and $R_{13}$ are as hereinbefore defined, the tautomers, the diastereomers, the enantiomers, the mixtures thereof and the salts thereof.

Most particularly preferred compounds of general formula I are those wherein

X denotes an oxygen atom, $R_1$ and $R_5$ each denote a hydrogen atom, $R_2$ denotes a methoxycarbonyl, ethoxycarbonyl or aminocarbonyl group, $R_3$ denotes a phenyl group and $R_4$ denotes a phenyl group monosubstituted by the group $R_6$, wherein $R_6$ denotes an N-methyl-imidazol-2-yl group, an unbranched $C_{1-3}$-alkyl group which is terminally substituted by a $C_{1-4}$-alkylamino, di-($C_{1-4}$-alkyl)-amino, piperidino or 2,6-dimethyl-piperidino group, a group of formula $$-N(R_{12})-CO-(CH_2)_p-R_{13} \quad (IV),$$

wherein $R_{12}$ denotes a $C_{1-3}$-alkyl group, p denotes one of the numbers 1 or 2 and $R_{13}$ denotes a di-($C_{1-3}$-alkyl)-amino group, or a group of formula $$-N(R_{14})-(CH_2)_q-(CO)_r-R_{15} \quad (V),$$

wherein $R_{14}$ denotes a $C_{1-3}$-alkyl-carbonyl or $C_{1-3}$-alkylsulphonyl group, q denotes one of the numbers 1, 2 or 3, r denotes the number 1 or, if q is one of the numbers 2 or 3, r may also denote the number 0 and $R_{15}$ denotes a di-($C_{1-3}$-alkyl)-amino group, wherein the saturated alkyl moieties contained in the abovementioned groups which contain more than 2 carbon atoms may be straight-chain or branched, unless otherwise stated, the tautomers, the diastereomers, the enantiomers, the mixtures thereof and the salts thereof.

A subgroup of most particularly preferred compounds of general formula I deserving special mention comprises those wherein X, $R_1$, $R_3$ and $R_5$ are as hereinbefore defined, $R_2$ denotes a methoxycarbonyl or ethoxycarbonyl group and $R_4$ denotes a di-($C_{1-3}$-alkyl)-amino-$C_{1-3}$-alkylphenyl group or a phenyl group substituted by the group of formula $$-N(R_{12})-CO-(CH_2)_p-R_{13} \quad (IV),$$

wherein $R_{12}$, p and $R_{13}$ areas hereinbefore defined, the tautomers, the diastereomers, the enantiomers, the mixtures thereof and the salts thereof.

The following are mentioned as examples of particularly preferred compounds:

(a) 3-Z-[1-(4-(piperidin-1-yl-methyl)-anilino)-1-phenyl-methylene]-6-ethoxycarbonyl-2-indolinone, (b) 3-Z-[(1-(4-(piperidin-1-yl-methyl)-anilino)-1-phenyl-methylene]-6-carbamoyl-2-indolinone, (c) 3-Z-[1-(4-(piperidin-1-yl-methyl)-anilino)-1-phenyl-methylene]-6-methoxycarbonyl-2-indolinone, (d) 3-Z-[1-(4-(dimethylaminomethyl)-anilino)-1-phenyl-methylene]-6-ethoxycarbonyl-2-indolinone, (e) 3-Z-[1-(4-((2,6dimethyl-piperidin-1-yl)-methyl)-anilino)-1-phenyl-methylene]-6-ethoxycarbonyl-2-indolinone, (f) 3-Z-[1-(4N-(2-dimethylamino-ethyl))-N-acetyl-amino)-anilino)-1-phenyl-methylene]-6-ethoxycarbonyl-2-indolinone, (g) 3-Z-[1-(4-(3-dimethylamino-propyl)-N-acetyl-amino)-anilino)-1-phenyl-methylene]-6-ethoxycarbonyl-2-indolinone, (h) 3-Z-[1-(4(N-(2-dimethylamino-ethyl)-N-methylsulphonyl-amino)anilino)-1-phenyl-methylene]-6-ethoxycarbonyl-2-indolinone, (i) 3-Z-[1-(4-(dimethylaminomethyl)-anilino)-1-phenyl-methylene]-6-methoxycarbonyl-2-indolinone, (j) 3-Z-[1-(4-(N-acetyl-N-dimethylaminocarbonylmethyl-amino)-anilino)-1-phenyl-methylene]-6-methoxycarbonyl-2-indolinone, (k) 3-Z-[1-(4-ethylaminomethyl-anilino)-1-phenyl-methylene]-6-methoxycarbonyl-2-indolinone, (l) 3-Z-[1-(4-(1-methyl-imidazol-2-yl)-anilino)-1-phenyl-methylene]-6-methoxycarbonyl-2-indolinone, (m) 3-Z-[1-(4N-dimethylaminomethylcarbonyl-N-methyl-amino)-anilino)-1-phenyl-methylene]-6-methoxycarbonyl-2-indolinone, (n) 3-Z-[1-(4-(N-(2-dimethylamino-ethyl)-N-methylsulphonyl-amino)-anilino)-1-phenyl-methylene]-6-methoxycarbonyl-2-indolinone, (o) 3-Z-[1-(4-(N-(3-dimethylamino-propyl)-N-methylsulphonyl-amino)-anilino)-1-phenyl-methylene]-6-methoxycarbonyl-2-indolinone, (p) 3-Z-[1-(4-(N-dimethylaminocarbonylmethyl-N-methylsulphonyl-amino)-anilino)-1-phenyl-methylene]-6-methoxycarbonyl-2-indolinone, (q) 3-Z-[1-(4(N-((2-dimethylamino-ethyl)carbonyl)-N-methyl-amino)-anilino)-1-phenyl-methylene]-6-methoxycarbonyl-2-indolinone, (r) 3-Z-[1-(4-(N-(2-dimethylamino-ethyl)-N-acetyl-amino)-anilino)-1-phenyl-methylene]-6-methoxycarbonyl-2-indolinone and (s) 3-Z-[1-(4-methylaminomethyl-anilino)-1-phenyl-methylene]-6-methoxycarbonyl-2-indolinone the tautomers, the mixtures and the salts thereof.

Another subgroup of compounds of general formula I comprises those wherein X denotes an oxygen or sulphur atom, $R_1$ denotes a hydrogen atom or a prodrug group such as a $C_{1-4}$-alkoxycarbonyl or $C_{2-4}$-alkanoyl group, $R_2$ denotes a carboxy group, a straight-chain or branched $C_{1-6}$-alkoxycarbonyl group, a $C_{5-7}$Cycloalkoxycarbonyl or phenyl-$C_{1-3}$-alkoxycarbonyl group, an aminocarbonyl or $C_{1-2}$-alkylaminocarbonyl group or, if $R_4$ does not denote an aminosulphonyl-phenyl or N—($C_{1-5}$-alkyl)-$C_{1-3}$-alkylaminocarbonyl-phenyl group, a di-($C_{1-2}$-alkyl)-aminocarbonyl group, $R_3$ denotes a hydrogen atom, a $C_{1-6}$-alkyl, $C_{3-7}$-cycloalkyl, trifluoromethyl or heteroaryl group, a phenyl or naphthyl group, a phenyl or naphthyl group mono- or disubstituted by a fluorine, chlorine, bromine or iodine atom, by a trifluoromethyl, $C_{1-3}$-alkyl or $C_{1-3}$-alkoxy group, whilst in the event of disubstitution the substituents may be identical or different and wherein the abovementioned unsubstituted as well as the mono- and disubstituted phenyl and naphthyl groups may additionally be substituted by a hydroxy, hydroxy-$C_{1-3}$-alkyl or $C_{1-3}$-alkoxy-$C_{1-3}$-alkyl group, by a cyano, carboxy, carboxy-$C_{1-3}$-alkyl, $C_{1-3}$-alkoxycarbonyl, aminocarbonyl, $C_{1-3}$-alkylaminocarbonyl or di-($C_{1-3}$-alkyl)-aminocarbonyl group, by a nitro group, by an amino, $C_{1-3}$-alkylamino, di-($C_{1-3}$-alkyl)-amino or amino-$C_{1-3}$-alkyl group, by a $C_{1-3}$-alkylcarbonylaamino, N—($C_{1-3}$-alkyl)-$C_{1-3}$-alkyl-carbonylamino, $C_{1-3}$-alkylcarbonylamino-$C_{1-3}$-alkyl, N—($C_{1-3}$-alkyl)-$C_{1-3}$-alkylcarbonylamino-$C_{1-3}$-alkyl, $C_{1-3}$-alkyl-sulphonylamino, $C_{1-3}$-alkylsulphonylamino-$C_{1-3}$-alkyl, N—($C_{1-3}$-alkyl)-$C_{1-3}$-alkylsulphonylamino-$C_{1-3}$-alkyl or aryl-$C_{1-3}$-alkylsulphonylamino group, by a cycloalkylamino, cycloalkyleneimino, cycloalkyleneiminocarbonyl, cycloalkyleneimino-$C_{1-3}$-alkyl, cycloalkyleneiminocarbonyl-$C_{1-3}$-alkyl or cycloalkyleneiminosulphonyl-$C_{1-3}$-alkyl group having 4 to 7 ring members in each case, whilst in each case the methylene group in position 4 of a 6 or 7-membered cycloalkyleneimino group may be replaced by an oxygen or sulphur atom, by a sulphinyl, sulphonyl, —NH or —N($C_{1-3}$-alkyl) group, or by a heteroaryl or heteroaryl-$C_{1-3}$-alkyl group, $R_4$ denotes a $C_{3-7}$-cycloalkyl group, whilst the methylene group in the 4 position of a 6- or 7-membered cycloalkyl group may be substituted by an amino, $C_{1-3}$-alkylamino or di-($C_{1-3}$-alkyl)-amino group or replaced by an —NH or —N($C_{1-3}$-alkyl) group, or a phenyl group substituted by the group $R_6$, which may additionally be substituted by a fluorine, chlorine, bromine or iodine atom, by a $C_{1-5}$-alkyl, trifluoromethyl, $C_{1-3}$-alkoxy, carboxy, $C_{1-3}$-alkoxycarbonyl, aminosulphonyl, nitro or cyano group, wherein $R_6$ denotes a hydrogen, fluorine, chlorine, bromine or iodine atom, a cyano, nitro, $C_{1-5}$-alkyl, $C_{3-7}$-cycloalkyl, trifluoromethyl, phenyl, tetrazolyl or heteroaryl group, a $C_{1-3}$-alkoxy group optionally substituted by 1 to 3 fluorine atoms, a $C_{1-3}$-alkoxy-$C_{1-3}$-alkoxy, phenyl-$C_{1-3}$-alkoxy, amino-$C_{2-3}$-alkoxy, $C_{1-3}$-alkylamino-$C_{2-3}$-alkoxy, di-($C_{1-3}$-alkyl)-amino-$C_{2-3}$-alkoxy, phenyl-$C_{1-3}$-alkylamino-$C_{2-3}$-alkoxy, N—($C_{1-3}$-alkyl)-phenyl-$C_{1-3}$-alkylamino-$C_{2-3}$-alkoxy, $C_{5-7}$-cycloalkyleneimino-$C_{2-3}$-alkoxy or $C_{1-3}$-alkylmercapto group, a carboxy, $C_{1-4}$-alkoxycarbonyl, aminocarbonyl, $C_{1-3}$-alkylamino-carbonyl, N—($C_{1-5}$-alkyl)-$C_{1-3}$-alkylaminocarbonyl, phenyl-$C_{1-3}$-alkylamino-carbonyl, N—($C_{1-3}$-alkyl)phenyl-$C_{1-3}$-alkylaminocarbonyl, piperazinocarbonyl or N—($C_{1-3}$-alkyl)-piperazinocarbonyl group, a $C_{1-3}$-alkylaminocarbonyl or N—($C_{1-5}$-alkyl)-$C_{1-3}$-alkylaminocarbonyl group wherein an alkyl moiety is substituted by a carboxy or $C_{1-3}$-alkoxycarbonyl group or is substituted in the 2 or 3 position by a di-($C_{1-3}$-alkyl)-amino, piperazino, N—($C_{1-3}$-alkyl)-piperazino or a 4- to 7-membered cycloalkyleneimino group, a 4- to 7-membered cycloalkyleneimino group, wherein a methylene group linked to the imino group may be replaced by a carbonyl or sulphonyl group or the cycloalkylene moiety may be fused to a phenyl ring or one or two hydrogen atoms may each be replaced by a $C_{1-3}$-alkyl group and/or in each case the methylene group in the 4 position of a 6 or 7-membered cycloalkyleneimino group may be substituted by a carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, a $C_{1-4}$-alkyl group which may be substituted by a hydroxy or $C_{1-3}$-alkoxy group, by an amino, $C_{1-7}$-alkylamino, di-($C_{1-7}$-alkyl)-amino, di-N—($C_{1-3}$-alkyl)-amino-$C_{2-3}$-alkylamino, tri-N,N,N'-$C_{1-3}$-alkyl)-amino-$C_{2-3}$-alkylamino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group, by a $C_{1-3}$-alkylcarbonylamino, N—($C_{1-3}$-alkyl)-$C_{1-3}$-alkylcarbonylamino, $C_{1-3}$-alkoxycarbonyl-$C_{1-3}$-alkylamino or N—($C_{1-3}$-alkyl) $C_{1-3}$-alkoxycarbonyl-$C_{1-3}$-alkylamino group, by a $C_{4-7}$-cycloalkylamino, $C_{4-7}$-cycloalkyl-$C_{1-3}$-alkylamino or $C_{4-7}$-cycloalkenylamino group wherein position 1 of the ring is not involved in the double bond and wherein the abovementioned groups may each additionally be substituted at the amino-nitrogen atom by a $C_{1-3}$-alkyl group wherein some or all of the hydrogen atoms are replaced by fluorine atoms, by a $C_{5-7}$-cycloalkyl, $C_{2-4}$-alkenyl or $C_{1-4}$-alkyl group, by a 4- to 7-membered cycloalkyleneimino group, wherein a methylene group linked to the imino group may be replaced by a carbonyl or sulphonyl group or the cycloalkylene moiety may be fused to a phenyl group or to an oxazolo, imidazolo, thiazolo, pyridino, pyrazino or pyrimidino group optionally substituted by a fluorine, chlorine, bromine or iodine atom, by a nitro, $C_{1-3}$-alkyl, $C_{1-3}$-alkoxy or amino group or one or two hydrogen atoms may each be replaced by a $C_{1-3}$-alkyl, $C_{5-7}$-cycloalkyl or phenyl group and/or in each case the methylene group in the 4 position of a 6- or 7-membered cycloalkyleneimino group may be substituted by a hydroxy, carboxy, $C_{1-4}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, by a carboxy, $C_{1-3}$-alkoxycarbonyl, aminocarbonyl, $C_{1-3}$-alkylaminocarbonyl or di-($C_{1-3}$-alkyl)-aminocarbonyl group or by a 4- to 7-membered cycloalkyleneiminocarbonyl group, an amino, pyrrolidino, piperidino, morpholino, benzoylamino or N—($C_{1-3}$-alkyl)-benzoylamino group, an N—($C_{1-3}$-alkyl)-$C_{2-4}$-alkanoylamino group which is additionally substituted in the alkyl moiety by a carboxy or $C_{1-3}$-alkoxycarbonyl group, a group of formula

—N($R_8$)—CO—($CH_2$)$_n$—$R_9$ (II), wherein $R_8$ denotes a hydrogen atom or a $C_{1-3}$-alkyl group, n denotes one of the numbers 0, 1, 2 or 3 and $R_9$ denotes an amino, $C_{1-4}$-alkylamino, phenylamino, N—($C_{1-4}$-alkyl)-phenylamino, benzylamino, N—($C_{1-4}$-alkyl)-benzylamino or di-($C_{1-4}$-alkyl)-amino group, a 4- to 7-membered cycloalkyleneimino group, whilst in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(phenyl), —N($C_{1-3}$-alkylcarbonyl) or —N(benzoyl) group, or, if n denotes one of the numbers 1, 2 or 3, it may also denote a hydrogen atom, a group of formula

—N($R_{10}$)—($CH_2$)$_m$—(CO)$_o$—$R_{11}$ (III), wherein $R_{10}$ denotes a hydrogen atom, a $C_{1-3}$-alkyl group, a $C_{1-3}$-alkylcarbonyl, arylcarbonyl, phenyl-$C_{1-3}$-alkylcarbonyl, $C_{1-3}$-alkylsulphonyl, arylsulphonyl or phenyl-$C_{1-3}$-alkylsulphonyl group, m denotes one of the numbers 1, 2, 3 or 4, o denotes one of the numbers 0 or 1 and $R_{11}$ denotes an amino, $C_{1-4}$-alkylamino, phenylamino, N—($C_{1-4}$-alkyl)-phenylamino, benzylamino, N—($C_{1-4}$-alkyl)-benzylamino or di-($C_{1-4}$-alkyl)-amino group, a 4- to 7-membered cycloalkyleneimino group, wherein the cycloalkylene moiety may be fused to a phenyl ring or in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, a $C_{1-3}$-alkoxy group or a di-($C_{1-4}$alkyl)-amino-$C_{1-3}$-alkylamino group optionally substituted in the 1 position by a $C_{1-3}$-alkyl group, or an N—($C_{1-3}$-alkyl)-$C_{1-5}$-alkylsulphonylamino or N—($C_{1-3}$-alkyl)-phenylsulphonylamino group wherein the alkyl moiety is additionally substituted by a cyano or carboxy group, wherein all the single-bonded or fused phenyl groups contained in the groups mentioned under $R_6$ may be mono- or disubstituted by fluorine, chlorine, bromine or iodine atoms, by $C_{1-5}$-alkyl, trifluoromethyl, $C_{1-3}$-alkoxy, carboxy, $C_{1-3}$-alkoxycarbonyl, aminosulphonyl, nitro or cyano groups, wherein the substituents may be identical or different, or two adjacent hydrogen atoms of the phenyl groups may be replaced by a methylenedioxy group, and $R_5$ denotes a hydrogen atom or a $C_{1-3}$-alkyl group, wherein by an aryl group is meant a phenyl or naphthyl group optionally mono- or disubstituted by a fluorine, chlorine, bromine or iodine atom, by a trifluoromethyl, $C_{1-3}$-alkyl or $C_{1-3}$-alkoxy group and by a heteroaryl group is meant a monocyclic 5- or 6-membered heteroaryl group optionally substituted by a $C_{1-3}$-alkyl group, wherein the 6-membered heteroaryl group contains one, two or three nitrogen atoms and the 5-membered heteroaryl group contains an imino group optionally substituted by a $C_{1-3}$-alkyl group, an oxygen or sulphur atom or an imino group optionally substituted by a $C_{1-3}$-alkyl group and an oxygen or sulphur atom or one or two nitrogen atoms, and moreover a phenyl ring may be fused to the abovementioned monocyclic heterocyclic groups via two adjacent carbon atoms, the saturated alkyl and alkoxy moieties present in the groups defined above which contain more than 2 carbon atoms also include the branched isomers thereof such as, for example, the isopropyl, tert.butyl or isobutyl group, unless otherwise stated, and additionally any carboxy, amino or imino group present may be substituted by a group which can be cleaved in vivo, the isomers and the salts thereof.

According to the invention the new compounds are obtained, for example, by the following methods known in principle from the literature:

a. reacting a compound of general formula

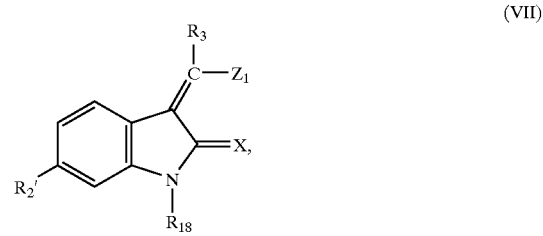

wherein

X and $R_3$ are as hereinbefore defined, $R_2'$ has the meanings given for $R_2$ hereinbefore, $R_{18}$ denotes a hydrogen atom or a protecting group for the nitrogen atom of the lactam group, wherein one of the groups $R_2'$ and $R_{18}$ may also denote a bond to a solid phase optionally formed via a spacer and the other one of the groups $R_2'0$ and $R_{18}$ has the above-mentioned meanings, and $Z_1$ denotes a halogen atom, a hydroxy, alkoxy or aryl-alkoxy group, e.g. a chlorine or bromine atom, a methoxy, ethoxy or benzyloxy group, with an amine of general formula

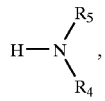
(VIII)

wherein
$R_4$ and $R_5$ are as hereinbefore defined, and if necessary subsequently cleaving any protecting group used for the nitrogen atom of the lactam group or cleaving from a solid phase.

The protecting group for the nitrogen atom of the lactam group may be, for example, an acetyl, benzoyl, ethoxycarbonyl, tert.butyloxycarbonyl or benzyloxycarbonyl group and the solid phase may be a resin such as a 4-(2',4'-dimethoxyphenylaminomethyl)-phenoxy resin, the bond preferably being formed via the amino group, or a p-benzyloxybenzyl alcohol resin, wherein the bond is conveniently formed via an intermediate member such as a 2,5-dimethoxy-4-hydroxy-benzyl derivative.

The reaction is conveniently carried out in a solvent such as dimethylformamide, toluene, acetonitrile, tetrahydrofuran, dimethylsulphoxide, methylene chloride or mixtures thereof, optionally in the presence of an inert base such as triethylamine, N-ethyl-diisopropylamine or sodium hydrogen carbonate at temperatures between 20 and 175° C., whilst any protecting group used can be cleaved at the same time by transamidation.

If $Z_1$ in a compound of general formula VII denotes a halogen atom, the reaction is preferably carried out in the presence of an inert base at temperatures of between 20 and 120° C.

If $Z_1$ in a compound of general formula VII denotes a hydroxy, alkoxy or arylalkoxy group, the reaction is preferably carried out at temperatures between 20 and 200° C.

If a protecting group used subsequently has to be cleaved, this is conveniently done either hydrolytically in an aqueous or alcoholic solvent, e.g. in methanol/water, ethanol/water, isopropanol/water, tetrahydrofuran/water, dioxan/water, dimethylformamide/water, methanol or ethanol in the presence of an alkali metal base such as lithium hydroxide, sodium hydroxide or potassium hydroxide at temperatures between 0 and 100° C., preferably at temperatures between 10 and 50° C., or advantageously by transamidation with an organic base such as ammonia, butylamine, dimethylamine or piperidine in a solvent such as methanol, ethanol, dimethylformamide and the mixtures thereof or in an excess of the amine used, at temperatures between 0 and 100° C., preferably at temperatures between 10 and 50° C.

Cleaving from any solid phase used is preferably carried out using trifluoroacetic acid and water at temperatures between 0 and 35° C., preferably at ambient temperature.

b. In order to prepare a compound of general formula I wherein $R_2$ has the meanings given hereinbefore, with the exception of the carboxy group:

reacting a compound of general formula

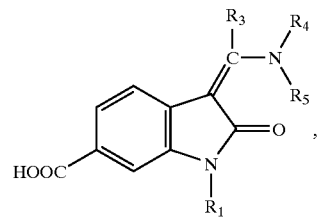
(IX)

wherein
$R_1$ and $R_3$ to $R_5$ are as hereinbefore defined, or the reactive derivatives thereof, with a compound of general formula $H-R_{19}$ (X), wherein
$R_{19}$ denotes a $C_{1-6}$-alkanol, a $C_{4-7}$-cycloalkanol or an aromatic alcohol,
a $C_{1-6}$-alkanol which is terminally substituted in the alkyl moiety by a phenyl, heteroaryl, carboxy, $C_{1-3}$-alkoxy-carbonyl, aminocarbonyl, $C_{1-3}$-alkylamino-carbonyl or di-($C_{1-3}$-alkyl)-aminocarbonyl group,
a $C_{2-6}$-alkanol which is terminally substituted in the alkyl moiety by a chlorine atom or a hydroxy, $C_{1-3}$-alkoxy, amino, $C_{1-3}$-alkylamino or di-($C_{1-3}$-alkyl)-amino group,
an amino or methylamino group, an ethylamino group optionally substituted in the 2 position of the ethyl group by a hydroxy or $C_{1-3}$-alkoxy group or a di-($C_{1-2}$-alkyl)amino group.

The esterification or amidation is preferably carried out in a solvent such as methylene chloride, diethylether, tetrahydrofuran, toluene, dioxan, acetonitrile, dimethylsulphoxide or dimethylformamide, optionally in the presence of an inorganic or a tertiary organic base, preferably at temperatures between 20° C. and the boiling temperature of the solvent used. The reaction with a corresponding acid is preferably carried out in the presence of a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexylcarbodiimide, N,N'-dicyclohexyl-carbodiimide/N-hydroxysuccinimide, N,N'-dicyclohexyl-carbodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylaminopyridine, N-methyl-morpholine or triethylamine, conveniently at temperatures between 0 and 150° C., preferably at temperatures between 0 and 100° C., and the acylation with a corresponding reactive compound such as an anhydride, ester, imidazolide or halide thereof, is optionally carried out in the presence of a tertiary organic base such as triethylamine, N-ethyl-diisopropylamine or N-methyl-morpholine at temperatures between 0 and 150° C., preferably at temperatures between 50 and 100° C.

c. In order to prepare a compound of general formula I, wherein $R_4$ denotes a $C_{1-4}$-alkyl group substituted by the group $R_7$, wherein $R_7$ denotes an amino, $C_{1-7}$-alkylamino, di-($C_{1-7}$-alkyl)-amino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group, a ω-hydroxy-$C_{2-3}$-alkyl-amino, N—($C_{1-3}$-alkyl)-ω-hydroxy-$C_{2-3}$-alkyl-amino, di-(ω-hydroxy-$C_{2-3}$-alkyl)-amino, di-(ω-($C_{1-3}$-alkoxy)-$C_{2-3}$-alkyl)-amino or N-(dioxolan-2-yl)-$C_{1-3}$-alkyl-amino group, a $C_{1-3}$-alkylcarbonylamino-$C_{2-3}$-alkyl-amino or $C_{1-3}$-alkylcarbonylamino-$C_{2-3}$-alkyl-N—($C_{1-3}$-alkyl)-amino group, a $C_{1-3}$-alkylsulphonylamino, N—($C_{1-3}$-alkyl)-$C_{1-3}$-alkylsulphonylamino, $C_{1-3}$-alkylsulphonylamino-$C_{2-3}$-alkyl-amino or $C_{1-3}$-alkylsulphonylamino-$C_{2-3}$-alkyl-N—($C_{1-3}$-alkyl)-amino group, a group of formula

$$—N(R_{10})—(CH_2)_m—(CO)_o—R_{11} \quad (III),$$

wherein $R_{10}$ denotes a hydrogen atom, a $C_{1-3}$-alkyl group, a $C_{1-3}$-alkylcarbonyl, arylcarbonyl, phenyl-$C_{1-3}$-alkylcarbonyl, $C_{1-3}$-alkylsulphonyl, arylsulphonyl or phenyl-$C_{1-3}$-alkylsulphonyl group, m denotes one of the numbers 1, 2, 3 or 4, o denotes the number 1 and $R_{11}$ denotes an amino, $C_{1-4}$-alkylamino, di-($C_{1-4}$-alkyl)-amino, phenylamino, N—($C_{1-4}$-alkyl)-phenylamino, benzylamino, N—($C_{1-4}$-alkyl)-benzylamino, $C_{1-4}$-alkoxy or $C_{1-3}$-alkoxy-$C_{1-3}$-alkoxy group, a di-($C_{1-4}$-alkyl)-amino-$C_{1-3}$-alkylamino group optionally substituted in the 1 position by a $C_{1-3}$-alkyl group, or a 4- to 7-membered cycloalkyleneimino group, wherein the cycloalkylene moiety may be fused to a phenyl ring or in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, a $C_{4-7}$-cycloalkylamino, $C_{4-7}$-cycloalkyl-$C_{1-3}$-alkylamino or $C_{4-7}$-cycloalkenylamino group wherein position 1 of the ring is not involved in the double bond and wherein the abovementioned groups may each additionally be substituted at the amino-nitrogen atom by a $C_{5-7}$-cycloalkyl, $C_{2-4}$-alkenyl or $C_{1-4}$-alkyl group, or a 4- to 7-membered cycloalkyleneimino group, wherein the cycloalkylene moiety may be fused to a phenyl group or to an oxazolo, imidazolo, thiazolo, pyridino, pyrazino or pyrimidino group optionally substituted by a fluorine, chlorine, bromine or iodine atom, by a nitro, $C_{1-3}$-alkyl, $C_{1-3}$-alkoxy or amino group, and/or one or two hydrogen atoms may each be replaced by a $C_{1-3}$-alkyl, $C_{5-7}$-cycloalkyl or phenyl group and/or the methylene group in the 3 position of a 5-membered cycloalkyleneimino group may be substituted by a hydroxy, hydroxy-$C_{1-3}$-alkyl, $C_{1-3}$-alkoxy or $C_{1-3}$-alkoxy-$C_{1-3}$-alkyl group, in each case the methylene group in the 3 or 4 position of a 6- or 7-membered cycloalkyleneimino group may be substituted by a hydroxy, hydroxy-$C_{1-3}$-alkyl, $C_{1-3}$-alkoxy, $C_{1-3}$-alkoxy-$C_{1-3}$-alkyl, $C_{1-4}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or may be replaced by an oxygen or sulphur atom, by a sulphinyl, sulphonyl, —NH, —N($C_{1-3}$-alkyl-), —N(phenyl), —N(phenyl-$C_{1-3}$-alkyl-), —N($C_{1-3}$-alkyl-carbonyl-), —N($C_{1-4}$-alkoxy-carbonyl-), —N(benzoyl-) or —N(phenyl-$C_{1-3}$-alkyl-carbonyl-) group, wherein a methylene group linked to an imino-nitrogen atom of the cycloalkyleneimino group may be replaced by a carbonyl or sulphonyl group or in a 5- to 7-membered monocyclic cycloalkyleneimino group or a cycloalkyleneimino group fused to a phenyl group the two methylene groups linked to the imino-nitrogen atom may each be replaced by a carbonyl group:

reacting a compound of general formula

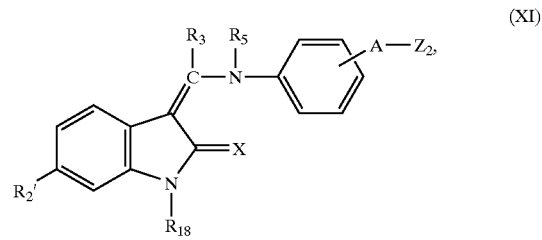

wherein $R_3$, $R_5$ and X are as hereinbefore defined, $R_2'$ has the meanings given for $R_2$ hereinbefore, $R_{18}$ denotes a hydrogen atom or a protecting group for the nitrogen atom of the lactam group, wherein one of the groups $R_2'$ and $R_{18}$ may also denote a bond to a solid phase optionally formed via a spacer and the other one of the groups $R_2'$ and $R_{18}$ has the above-mentioned meanings, A denotes a $C_{1-4}$-alkyl group and $Z_2$ denotes a leaving group, for example an alkyl or arylsulphonyloxy group such as the methylsulphonyloxy, ethylsulphonyloxy, p-toluenesulphonyloxy or trifluoromethanesulphonyloxy group, with an amine of general formula

$$H—R_7, \quad (XII),$$

wherein $R_7$, has the meanings given for $R_7$ hereinbefore, and subsequently, if necessary, cleaving any protecting group used for the nitrogen atom of the lactam group, or cleaving from a solid phase.

The reaction is conveniently carried out in a solvent such as methylene chloride, tetrahydrofuran, 1,4-dioxan, toluene, acetonitrile, dimethylsulphoxide, dimethylformamide, dimethylacetamide, N-methylpyrrolidone or the mixtures thereof, optionally with the saddition of water as a co-solvent and/or with the addition of an inert auxiliary base, e.g. sodium hydrogen carbonate, pyridine, 2,4,6-trimethylpyridine, quinoline, triethylamine, N-ethyldiisopropylamine, N-ethyl-dicyclohexylamine, 1,4-diazabicyclo[2,2,2]octane or 1,8-diazabicyclo[5,4,0]undec-7-ene, at temperatures between −50° C. and +100° C., preferably between −10° C. and +50° C., while any protecting group used may be cleaved at the same time by transamidation.

If any protecting group used for the nitrogen atom of the lactam group has to be removed or if the compound has to be cleaved from a solid phase this is carried out as described under method (a) above.

If according to the invention a compound of general formula I is obtained which contains an alkoxycarbonyl group, this may be converted by hydrolysis into a corresponding carboxy compound, or if a compound of general formula I is obtained which contains an amino or alkylamino group, this may be converted by reductive alkylation into a corresponding alkylamino or dialkylamino compound, or if a compound of general formula I is obtained which contains an amino or alkylamino group, this may be converted by acylation or sulphonation into a corresponding acyl or sulphonyl compound, or if a compound of general formula I is obtained which contains a carboxy group, this may be converted by esterification or amidation into a corresponding ester or aminocarbonyl compound, or if a compound of general formula I is obtained which contains a cycloalkyleneimino group wherein a methylene group is replaced by a sulphur atom, this may be converted by oxidation into a corresponding sulphinyl or sulphonyl compound, or if a compound of general formula I is obtained which contains a nitro group, this may be converted by reduction into a corresponding amino compound, or if a compound of general formula I is obtained wherein $R_4$ denotes a phenyl group substituted by an amino, alkylamino, aminoalkyl or N-alkyl-amino group, this may subsequently be converted, by reaction with a corresponding cyanate, isocyanate or carbamoyl halide, into a corresponding urea compound of general formula I, or if a compound of general formula I is obtained wherein $R_4$ denotes a phenyl group substituted by an amino, alkylamino, aminoalkyl or N-alkyl-amino group, this may subsequently be converted, by reaction with a corresponding compound which transfers the amidino group or by reaction with a corresponding nitrile, into a corresponding guanidino compound of general formula I.

The subsequent hydrolysis is preferably carried out in an aqueous solvent, e.g. in water, methanol/water, ethanol/water, isopropanol/water, tetrahydrofuran/water or dioxan/water, in the presence of an acid such as trifluoroacetic acid, hydrochloric acid or sulphuric acid or in the presence of an alkali metal base such as lithium hydroxide, sodium hydroxide or potassium hydroxide at temperatures between 0 and 100° C., preferably at temperatures between 10 and 50° C.

The subsequent reductive alkylation is preferably carried out in a suitable solvent such as methanol, methanol/water, methanol/water/ammonia, ethanol, ether, tetrahydrofuran, dioxan or dimethylformamide, optionally with the addition of an acid such as hydrochloric acid in the presence of catalytically activated hydrogen, e.g. hydrogen in the presence of Raney nickel, platinum or palladium/charcoal, or in the presence of a metal hydride such as sodium borohydride, lithium borohydride, sodium cyanoborohydride or lithium aluminium hydride at temperatures between 0 and 100° C., preferably at temperatures between 20 and 80° C.

The subsequent acylation or sulphonylation is preferably carried out with the corresponding free acid or a corresponding reactive compound such as the anhydride, ester, imidazolide or halide thereof, preferably in a solvent such as methylene chloride, diethylether, tetrahydrofuran, toluene, dioxan, acetonitrile, dimethylsulphoxide or dimethylformamide, optionally in the presence of an inorganic or tertiary organic base at temperatures between −20 and 200° C., preferably at temperatures between 20° C. and boiling temperature of the solvent used. The reaction with the free acid may optionally be carried out in the presence of an acid-activating agent or a dehydrating agent, e.g. in the presence of isobutyl chloroformate, tetraethyl orthocarbonate, trimethyl orthoacetate, 2,2-dimethoxypropane, tetramethoxysilane, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benzotriazole, 2-(1H-benzotriazol-1-yl)-1,1,3,3-tetramethyluronium-tetrafluoroborate, 2-(1H-benzotriazol-1-yl)-1,1,3,3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylamino-pyridine, N-methyl-morpholine or triethylamine, conveniently at temperatures between 0 and 150° C., preferably at temperatures between 0 and 100° C. The reaction with a corresponding reactive compound may optionally be carried out in the presence of a tertiary organic base such as triethylamine, N-ethyl-diisopropylamine, N-methyl-morpholine or pyridine or by using an anhydride in the presence of the corresponding acid at temperatures between 0 and 150° C., preferably at temperatures between 50 and 100° C.

The subsequent esterification or amidation is conveniently carried out by reacting a corresponding reactive carboxylic acid derivative with a corresponding alcohol or amine as described hereinbefore.

The subsequent oxidation of the sulphur atom is preferably carried out in a solvent or mixture of solvents, e.g. in water, water/pyridine, acetone, methylene chloride, acetic acid, acetic acid/acetic anhydride, dilute sulphuric acid or trifluoroacetic acid, usefully at temperatures of between −80 and 100° C. depending on the oxidising agent used.

In order to prepare a corresponding sulphinyl compound of general formula I the oxidation is expediently carried out with one equivalent of the oxidising agent used, e.g. with hydrogen peroxide in glacial acetic acid, trifluoroacetic acid or formic acid at 0 to 20° C. or in acetone at 0 to 60° C., with a peracid such as performic acid in glacial acetic acid or trifluoroacetic acid at 0 to 50° C. or with m-chloroperbenzoic acid in methylene chloride, chloroform or dioxan at −20 to 80° C., with sodium metaperiodate in aqueous methanol or ethanol at −15 to 25° C., with bromine in glacial acetic acid or aqueous acetic acid optionally in the presence of a weak base such as sodium acetate, with N-bromosuccinimide in ethanol, with tert.butyl hypochlorite in methanol at −80 to −30° C., with iodobenzodichloride in aqueous pyridine at 0 to 50° C., with nitric acid in glacial acetic acid at 0 to 20° C., with chromic acid in glacial acetic acid or in acetone at 0 to 20° C. and with sulphuryl chloride in methylene chloride at −70° C., the resulting thioether-chlorine complex is expediently hydrolysed with aqueous ethanol.

In order to prepare a sulphonyl compound of general formula I the oxidation is expediently carried out starting from a corresponding sulphinyl compound with one or more equivalents of the oxidising agent used or starting from a corresponding mercapto compound, expediently with two or more equivalents of the oxidising agent used, e.g. with hydrogen peroxide in glacial acetic acid/acetic anhydride, trifluoroacetic acid or in formic acid at 20 to 100° C. or in acetone at 0 to 60° C., with a peracid such as performic acid or m-chloroperbenzoic acid in glacial acetic acid, trifluoroacetic acid, methylene chloride or chloroform at temperatures between 0 and 60° C., with nitric acid in glacial acetic acid at 0 to 20° C., with chromic acid, sodium periodate or potassium permanganate in acetic acid, water/sulphuric acid or in acetone at 0 to 20° C.

The subsequent reduction of a nitro group is preferably carried out by hydrogenolysis, e.g. with hydrogen in the presence of a catalyst such as palladium/charcoal or Raney nickel in a solvent such as methanol, ethanol, ethyl acetate, dimethylformamide, dimethylformamide/acetone or glacial acetic acid, optionally with the addition of an acid such as hydrochloric acid or glacial acetic acid at temperatures of between 0 and 50° C., but preferably at ambient temperature, and at a hydrogen pressure of 1 to 7 bar, but preferably 3 to 5 bar.

The subsequent preparation of a corresponding urea compound of general formula I is conveniently carried out with an inorganic cyanate or a corresponding isocyanate or carbamoylchloride, preferably in a solvent such as dimethylformamide and optionally in the presence of a tertiary organic base such as triethylamine at temperatures between 0 and 50° C., preferably at ambient.

The subsequent preparation of a corresponding guanidino compound of general formula I is conveniently carried out by reacting with a compound which transfers the amidino group such as 3,5-dimethylpyrazole-1-carboxylic acid amidine, preferably in a solvent such as dimethylformamide and optionally in the presence of a tertiary organic base such as triethylamine at temperatures of between 0 and 50° C., preferably at ambient temperature.

In the reactions described hereinbefore, any reactive groups present such as carboxy, hydroxy, amino, alkylamino or imino groups may be protected during the reaction by conventional protecting groups which are cleaved again after the reaction.

For example, a protecting group for a carboxyl group may be a trimethylsilyl, methyl, ethyl, tert.butyl, benzyl or tetrahydropyranyl group and protecting groups for a hydroxy, amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, tetrahydrofuran/water or dioxan/water, in the presence of a acid such as trifluoroacetic acid, hydrochloric acid or sulphuric acid or in the presence of an alkali metal base such as lithium hydroxide, sodium hydroxide or potassium hydroxide, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid or glacial acetic acid at temperatures between 0 and 50° C., but preferably at ambient temperature, and at a hydrogen pressure of 1 to 7 bar, but preferably 3 to 5 bar.

A methoxybenzyl group may also be cleaved in the presence of an oxidising agent such as cerium(IV) anmmonium nitrate in a solvent such as methylene chloride, acetonitrile or acetonitrile/water at temperatures of between 0 and 50° C., but preferably at ambient temperature.

A 2,4dimethoxybenzyl group, however, is preferably cleaved in trifluoroacetic acid in the presence of anisole.

A tert.butyl or tert.butyloxycarbonyl group is preferably cleaved by treating with an acid such as trifluoroacetic acid or hydrochloric acid, optionally using a solvent such as methylene chloride, dioxan, ethyl acetate or ether.

A phthalyl group is preferably cleaved in the presence of hydrazine or a primary amine such as methylamine, ethylamine or n-butylamine in a solvent such as methanol, ethanol, isopropanol, toluene/water or dioxan at temperatures between 20 and 50° C.

Moreover, chiral compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the mixture of diastereomeric salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, N-acetylglutarnic acid, aspartic acid, N-acetylaspartic acid or quinic acid. An optically active alcohol may be for example (+)- or (−)-menthol and an optically active acyl group in arnides, for example, may be a (+)- or (−)-menthyloxycarbonyl group.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid, maleic acid or methanesulphonic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

The compounds of general formulae VII to XII used as starting materials are known from the literature in some cases or may be obtained by methods known from the literature or may be obtained by the methods described hereinbefore and in the Examples. For example, the compounds of general formula VI are described in German Patent Application 198 24 922.5.

Moreover, the compounds of general formula XI may be obtained from the compounds of general formula I wherein $R_4$ denotes a $C_{1-4}$-alkyl-phenyl group substituted in the alkyl moiety by a hydroxy group, for example, by reacting with alkyl- or arylsulphonyl-chlorides.

As already mentioned, the new compounds of general formula I wherein $R_1$ denotes a hydrogen atom or a prodrug group have valuable pharmacological properties, particularly inhibitory effects on various kinases, especially on receptor-tyrosine kinases such as VEGFR2, PDGFRα, PDGFRβ, FGFR1, FGFR3, EGFR, HER2, IGF1R and HGFR, as well as on complexes of CDK's (Cyclin Dependent Kinases) such as CDK1, CDK2, CDK3, CDK4, CDK5, CDK6, CDK7, CDK8 and CDK9 with their specific cyclins (A, B1, B2, C, D1, D2, D3, E, F, G1, G2, H, I and K) and on viral cyclin, on the proliferation of cultivated human cells, particularly endothelial cells, e.g. in angiogenesis, but also on the proliferation of other cells, particularly tumour cells.

The biological properties of the new compounds were tested by the following standard procedure, as follows:

Human umbilical endothelial cells (HUVEC) were cultivated in IMDM (Gibco BRL), supplemented with 10% foetal calf serum (FBS) (Sigma), 50 μM of β-mercaptoethanol (Fluka), standard antibiotics, 15 μg/ml of endothelial cell growth factor (ECGS, Collaborative Biomedical Products) and 100 μg/ml of heparin (Sigma) on gelatine-coated culture dishes (0.2% gelatine, Sigma) at 37° C., under 5% $CO_2$ in a water-saturated atmosphere.

In order to investigate the inhibitory activity of the compounds according to the invention the cells were starved for 16 hours, i.e. kept in culture medium without growth factors (ECGS+heparin). The cells were detached from the culture dishes using trypsin/EDTA and washed once in serumontaining medium. Then they were seeded out in amounts of $2.5 \times 10^3$ cells per well.

The proliferation of the cells was stimulated with 5 ng/ml of $VEGF_{165}$ (vascular endothelial growth factor; H. Weich, GBF Braunschweig) and 10 μg/ml of heparin. As a control, 6 wells in each dish were not stimulated.

The compounds according to the invention were dissolved in 100% dimethylsulphoxide and added to the cultures in various dilutions in triplicate, the maximum dimethyl sulphoxide concentration being 0.3%.

The cells were incubated for 76 hours at 37° C., then for a further 16 hours $^3$H-thymidine (0.1 μCi/well, Amersham) was added in order to determine the DNA synthesis. Then the radioactively labelled cells were immnobilised on filter mats and the radioactivity incorporated was measured in a β-counter. In order to determine the inhibitory activity of the compounds according to the invention the mean value of the non-stimulated cells was subtracted from the mean value of the factor-stimulated cells (in the presence or absence of the compounds according to the invention).

The relative cell proliferation was calculated as a percentage of the control (HUVEC without inhibitor) and the concentration of active substance which inhibits the proliferation of the cells by 50% ($IC_{50}$) was determined.

The test results of the following compounds (a) to (s) of general formula I are given by way of example:

(a) 3-Z-[1-(4-(piperidin-1-yl-methyl)-anilino)-1-phenyl-methylene]-6-ethoxycarbonyl-2-indolinone,
(b) 3-Z-[1-(4-(piperidin-1-yl-methyl)-anilino)-1-phenyl-methylene]-6-carbamoyl-2-indolinone,
(c) 3-Z-[1-(4-(piperidin-1-yl-methyl)-anilino)-1-phenyl-methylene]-6-methoxycarbonyl-2-indolinone,
(d) 3-Z-[1-(4-(dimethylaminomethyl)-anilino)-1-phenyl-methylene]-6-ethoxycarbonyl-2-indolinone,
(e) 3-Z-[1-(4-((2,6-dimethyl-piperidin-1-yl)-methyl)-anilino)-1-phenyl-methylene]-6-ethoxycarbonyl-2-indolinone,
(f) 3-Z-[1-(4-(N-(2-dimethylamino-ethyl)-N-acetyl-amino)-anilino)-1-phenyl-methylene]-6-ethoxycarbonyl-2-indolinone,
(g) 3-Z-[1-(4-(N-(3-dimethylamino-propyl)-N-acetyl-amino)-anilino)-1-phenyl-methylene]-6-ethoxycarbonyl-2-indolinone,
(h) 3-Z-[1-(4-(N-(2-dimethylamino-ethyl)-N-methylsulphonyl-amino)-anilino)-1-phenyl-methylene]-6-ethoxycarbonyl-2-indolinone,
(i) 3-Z-[1-(4-(dimethylaminomethyl)-anilino)-1-phenyl-methylene]-6-methoxycarbonyl-2-indolinone,
(j) 3-Z-[1-(4-(N-acetyl-N-dimethylaminocarbonylmethyl-amino)-anilino)-1-phenyl-methylene]-6-methoxycarbonyl-2-indolinone,
(k) 3-Z-[1-(4-ethylaminomethyl-anilino)-1-phenyl-methylene]-6methoxycarbonyl-2-indolinone,
(l) 3-Z-[1-(4-(1-methyl-imidazol-2-yl)-anilino)-1-phenyl-methylene]-6-methoxycarbonyl-2-indolinone,
(m) 3-Z-[1-(4-(N-dimethylaminomethylcarbonyl-N-methyl-amino)-anilino)-1-phenyl-methylene]-6-methoxycarbonyl-2-indolinone,
(n) 3-Z-[1-(4-(N-(2-dimethylamino-ethyl)-N-methylsulphonyl-amino)-anilino)-1-phenyl-methylene]-6-methoxycarbonyl-2-indolinone,
(o) 3-Z-[1-(4-(N-(3-dimethylamino-propyl)-N-methylsulphonyl-amino)-anilino)-1-phenyl-methylene]-6methoxycarbonyl-2-indolinone,
(p) 3-Z-[1-(4-(N-dimethylaminocarbonylmethyl-N-methylsulphonyl-amino)-anilino)-1-phenyl-methylene]-6-methoxycarbonyl-2-indolinone,
(q) 3-Z-[1-(4-(N-((2-dimethylamino-ethyl)-carbonyl)-N-methyl-amino)-anilino)-1-phenyl-methylene]-6-methoxycarbonyl-2-indolinone,
(r) 3-Z-[1-(4-(N-(2-dimethylamino-ethyl)-N-acetyl-amino)-anilino)-1-phenyl-methylene]-6-methoxycarbonyl-2-indolinone and
(s) 3-Z-[1-(4methylaminomethyl-anilino)-1-phenyl-methylene]-6-methoxycarbonyl-2-indolinone.

The following Table contains the results found:

| Compound | $IC_{50}$ [μm] |
| --- | --- |
| (a) | 0.04 |
| (b) | 0.35 |
| (c) | 0.01 |
| (d) | 0.02 |
| (e) | 0.05 |
| (f) | 0.01 |
| (g) | 0.003 |
| (h) | 0.01 |
| (i) | 0.03 |
| (j) | 0.02 |
| (k) | 0.03 |
| (l) | 0.1 |
| (m) | 0.02 |
| (n) | 0.02 |
| (o) | 0.01 |
| (p) | 0.02 |
| (q) | 0.02 |
| (r) | 0.01 |
| (s) | 0.04 |

In view of their inhibitory effect on the proliferation of cells, particularly endothelial cells and tumour cells, the compounds of general formula I are suitable for treating diseases in which the proliferation of cells, particularly endothelial cells, plays a part.

Thus, for example, the proliferation of endothelial cells and the concomitant neovascularisation constitute a crucial stage in tumour progression (Folkman J. et al., Nature 339, 58–61, (1989); Hanahan D. and Folkman J., Cell 86, 353–365, (1996)). Furthermore, the proliferation of endothelial cells is also important in haemangiomas, in metastasisation, rheumatoid arthritis, psoriasis and ocular neovascularisation (Folkman J., Nature Med. 1, 27–31, (1995)). The therapeutic usefulness of inhibitors of endothelial cell proliferation was demonstrated in the animal model for example by O'Reilly et al. and Parangi et al. (O'Reilly M. S. et al., Cell 88, 277–285, (1997); Parangi S. et al., Proc Natl Acad Sci USA 93, 2002–2007, (1996)).

The compounds of general formula I, their tautomers, their stereoisomers or the physiologically acceptable salts thereof are thus suitable, for example, for treating tumours (e.g. plate epithelial carcinoma, astrocytoma, Kaposi sarcoma, glioblastoma, lung cancer, bladder cancer, carcinoma of the neck, melanoma, ovarian cancer, prostate cancer, breast cancer, small-cell lung cancer, glioma, colorectal carcinoma, urogenital cancer and gastrointestinal carcinoma as well as haematological cancers, such as multiple myeloma), psoriasis, arthritis (e.g. rheumatoid arthritis), haemangioma, angiofibroma, eye diseases (e.g. diabetic retinopathy), neovascular glaucoma, kidney diseases (e.g. glomerulonephritis), diabetic nephropathy, malignant nephrosclerosis, thrombic microangiopathic syndrome, transplant rejections and glomerulopathy, fibrotic diseases (e.g. cirrhosis of the liver), mesangial cell proliferative diseases, arteriosclerosis and damage to the nerve tissue and also for inhibiting the reocclusion of blood vessels after treatment with a balloon catheter, in vascular prosthetics or after the insertion of mechanical devices for keeping blood vessels open (e.g. stents), or other diseases in which cell proliferation or angiogenesis are involved.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g. etoposide), mitosis inhibitors (e.g. vinblastin, taxol), compounds which interact with nucleic acids (e.g. cis-platin, cyclophosphamide, adriamycin), hormone antagonists (e.g. tamoxifen), inhibitors of metabolic processes (e.g. 5-FU etc.), cytokines (e.g. interferons), kinase inhibitors, antibodies, or in conjunction with radiotherapy, etc. These combinations may be administered either simultaneously or sequentially.

For pharmaceutical use the compounds according to the invention are generally used for warm-blooded vertebrates, particularly humans, in doses of 0.01–100 mg/kg of body weight, preferably 0.1–20 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof in conventional galenic preparations such as plain or coated tablets, capsules, powders, injectable solutions, ampoules, suspensions, solutions, sprays or suppositories.

The Examples which follow are intended to illustrate the invention:

Abbreviations used:

FMOC=9-fluorenylmethoxycarbonyl

HOBt=1-hydroxy-1H-benzotriazole

TBTU=O-benzotriazol-1-yl-N,N,N',N'-tetramethyluronium-tetrafluoroborate

DBU=1,8-diazabicyclo[5.4.0]undec-7-ene

Preparation of the starting compounds:

SOLID PHASE EXAMPLE I 2.0 g of Rink resin (MBHA resin, made by Messrs Novabiochem) are left to swell in 30 ml of dimethylformamide. Then 40 ml of 30% piperidine in dimethylformamide are added and the mixture is shaken for 7 minutes to cleave the FMOC protecting group. The resin is then washed repeatedly with dimethylformamide. Then 0.4 g of 2-indolinone-6-carboxylic acid (prepared analogously to Langenbeck et al., Justus Liebigs Ann. Chem. 499, 201–208 (1932)), 297 mg HOBt, 706 mg TBTU and 0.9 ml of Nethyl-diisopropylamine in 30 ml of dimethylformamide are added and the mixture is shaken for 1 hour. Then the solution is suction filtered and the resin is washed five times with 30 ml of dimethylformamide and three times with 30 ml of methylene chloride. To dry it, nitrogen is blown through the resin.

Yield: 1.9 g of charged resin.

SOLID PHASE EXAMPLE II 1.9 g of the resin obtained in Example I are stirred with 6 ml of acetic anhydride and 6 ml of triethyl orthobenzoate for 3 hours at 110° C. Then the mixture is left to cool and the resin is washed with dimethylformamide and subsequently with methylene chloride.

Yield: 1.9 g of moist resin.

The following charged resins are prepared analogously to Example II:

(1) resin charged with 3-Z-(1-ethoxy-methylene)-6-carbamoyl-2-indolinone

Prepared by reacting the resin obtained according to Example I with triethyl orthoformate (2) resin charged with 3-Z-(1-methoxy-1-methyl-methylene)-6-carbamoyl-2-indolinone Prepared by reacting the resin obtained according to Example I with trimethyl orthoacetate (3) resin charged with 3-Z-(1-methoxy-1-ethyl-methylene)-6-carbamoyl-2-indolinone Prepared by reacting the resin obtained according to Example I with tfimethyl orthopropionate (4) resin charged with 3-Z-(1-methoxy-1-propyl-methylene)-6-carbamoyl-2-indolinone Prepared by reacting the product of Example I and trimethyl orthobutyrate

EXAMPLE III

N-(4-nitrophenyl)-N-methyl-methanesulphonamide 3.0 g of N-methyl-4-nitroaniline are dissolved in 20 ml of pyridine and 2.4 g of methanesulphonic acid chloride added dropwise at room temperature. The mixture is stirred for 12 hours at room temperature. After this time the mixture is poured onto water, the precipitate formed is filtered off and dried at 50° C. in vacuo.

Yield: 4.0 g (87% of theory), $R_f$ value: 0.5 (silica gel, ethyl acetate/toluene=7:3).

Melting point: 107–108° C.

EXAMPLE IV

N-(2-dimethylamino-ethyl)-N-methylsulphonyl-4-nitroaniline 38.9 g of N-methylsulphonyl-4-nitroaniline are dissolved in 2.0 l of acetone, 51.9 g of 1-chloro-2-dimethylamino-ethane, 77.4 g of potassium carbonate and 5.0 g of sodium iodide are added and the mixture is stirred for a total of 4 days at 50° C., while after 12 hours a further 25.9 g of 1-chloro-2dimethylamino-ethane, 49.8 g of potassium carbonate and 5.0 g of sodium iodide in 500 ml of acetone are added and after 36 hours another 26.0 g of 1-chloro-2-dimethylamino-ethane, 50.0 g of potassium carbonate and 5.0 g of sodium iodide in 100 ml of acetone are added. After this time the mixture is filtered and the filtrate evaporated down. The residue is stirred with ether, suction filtered and dried at 40° C.

Yield: 25.3 g (49% of theory), $R_f$ value: 0.5 (silica gel, methylene chloride/methanol/ammonia=9:1:0.1) $C_{11}H_{17}N_3O_4S$.

ESI mass spectrum: m/z=288 [M+H$^+$].

The following compounds are prepared analogously to Example IV:

(1) 4-[N-(3-dimethylamino-propyl)-N-methylsulphonyl-amino]-nitrobenzene (2) N-carboxymethyl-N-methylsulphonyl-4-nitroaniline (3) N-cyanomethyl-N-methylsulphonyl-p-phenylenediamine (4) 4-[N-(2-(N-benzyl-N-methyl-amino)-ethyl)-N-methylsulphonyl-amino]-nitrobenzene (5) 4-[N-(3-phthalimido-2-yl-propyl)-N-methylsulphonyl-amino]-nitrobenzene (6) 4-[N-(3-(N-benzyl-N-methyl-amino)-propyl)-N-methylsulphonyl-amino]-nitrobenzene

EXAMPLE V

N-(dimethylaminocarbonyl-methyl)-N-methylsulphonyl-4-nitroaniline 7.0 g of N-carboxymethyl-N-methylsulphonyl-4-nitroaniline, 2.5 g of dimethylamine hydrochloride, 8.1 g of TBTU and 3.9 g of HOBT are dissolved in 125 ml of dimethylformamide and at 0° C. 17.6 ml of N-ethyl-diisopropylamine are added. The mixture is stirred for 4 hours at room temperature, diluted with 1 l l of water and the precipitate formed is suction filtered. After washing with water, ethanol and ether the residue is dried at 70° C. in vacuo.

Yield: 5.3 g (69% of theory), $R_f$ value: 0.40 (silica gel, methylene chloride/methanol=9:1) $C_{11}H_{15}N_3O_5S$.

ESI mass spectrum: m/z=300 [M–H$^-$].

The following compounds are prepared analogously to Example V:

(1) 4-[(N-dimethylaminocarbonylmethyl)-amino]-nitrobenzene prepared from 4-(N-carboxymethyl-amino)-nitrobenzene and dimethylamine hydrochloride (2) 4-(N-methylaminocarbonylmethyl-N-methylsulphonyl-amino)-nitrobenzene Prepared from N-carboxymethyl-N-methylsulphonyl-4-nitroaniline and methylamine hydrochloride (3) 4-[(N-(methylcarbamoyl-methyl)-N-methyl-amino)-methyl]-nitrobenzene Prepared from 4-[(N-carboxymethyl-N-methyl-amino)-methyl]-nitrobenzene and methylamine hydrochloride (4) 4-[(N-(dimethylcarbamoyl-methyl)-N-methyl-amino)-methyl]-nitrobenzene Prepared from 4-[(N-carboxymethyl-N-methyl-amino)-methyl]-nitrobenzene and dimethylamine hydrochloride

EXAMPLE VI

4-[N-(2-dimethylamino-ethyl)-N-acetyl-amino]-nitrobenzene 3.6 g of 4-(2-dimethylamino-ethylamino)-nitrobenzene (according to Gabbay et al., J. Am. Chem. Soc. 91, 5136 (1969)) are dissolved in 50 ml of methylene chloride and 5.0 ml of triethylamine are added. 1.3 ml of acetyl chloride are slowly added dropwise to this mixture at room temperature and the mixture is stirred for 2 hours at room temperature. After this time another 5.0 ml of triethylamine and 1.3 ml of acetylchloride are added and the mixture is refluxed for another 2 hours. The solvent is removed, the residue is taken up in ethyl acetate and the organic phase is extracted twice with water. After drying over MgSO$_4$ the solvent is removed and the residue dried in vacuo.

Yield: 2.0 g (45% of theory), $R_f$ value: 0.55 (silica gel, methylene chloride/methanol/ammonia=9:1:0.1) $C_{12}H_{17}N_3O_3$.

ESI mass spectrum: m/z=252 [M+H$^+$].

The following compounds are prepared analogously to Example VI:

(1) 4-[N-(3-dimethylamino-propyl)-N-acetyl-amino]-nitrobenzene

Prepared from 4-(3-dimethylamino-propylamino)-nitrobenzene (according to Gabbay et al., J. Am. Chem. Soc. 91, 5136 (1969) and acetyl chloride (2) 4-[N-(2-dimethylamino-ethyl)-N-propionyl-amino]-nitrobenzene Prepared from 4-(2-dimethylamino-ethylamino)-nitrobenzene and propionyl chloride (3) 4-[N-acetyl-N-(dimethylaminocarbonylmethyl)-amino]-nitrobenzene Prepared from 4-[N-(dimethylaminocarbonylmethyl)-amino]-nitrobenzene and acetyl chloride (4) 4-[N-(2-dimethylamino-ethyl)-N-butyryl-amino]-nitrobenzene Prepared from 4-(2-dimethylamino-ethylamino)-nitrobenzene and butyryl chloride (5) 4-[N-(2-dimethylamino-ethyl)-N-isobutyryl-amino]-nitrobenzene Prepared from 4-(2-dimethylamino-ethylamino)-nitrobenzene and isobutyryl chloride (6) 4-[N-(2-dimethylamino-ethyl)-N-benzoyl-amino]-nitrobenzene Prepared from 4-(2-dimethylamino-ethylamino)-nitrobenzene and benzoyl chloride (7) 4-[N-(2-dimethylamino-ethyl)-N-acetyl-amino]-1,3-dinitrobenzene Prepared from 4-(2-dimethylamino-ethyl-amino)-1,3-dinitrobenzene and acetyl chloride (8) 4-[N-(2-dimethylamino-ethyl)-N-(furan-2-carbonyl)-amino]-nitrobenzene Prepared from 4-(2-dimethylamino-ethylamino)-nitrobenzene and furan-2-carbonyl chloride (9) 4[-(2-dimethylamino-ethyl)-N-(2-methoxy-benzoyl)-amino]-nitrobenzene Prepared from 4-(2-dimethylamino-ethylamino)-nitrobenzene and 2-methoxy-benzoyl chloride

(10) 4-[N-(2-dimethylamino-ethyl)N-(pyridine-3-carbonyl)-amino]-nitrobenzene

Prepared from 4-(2-dimethylamino-ethylamino)-nitrobenzene and nicotinic acid chloride

(11) 4-[N-(2-dimethylamino-ethyl)-N-(phenyl-acetyl)-amino]-nitrobenzene

Prepared from 4-(2-dimethylamino-ethylamino)-nitrobenzene and phenylacetyl-chloride

(12) 4-[N-(2-dimethylamino-ethyl)-N-acetyl-amino]-3-bromo-nitrobenzene

Prepared from 4-[N-(2-dimethylamino-ethyl)-amino]-3-bromo-nitrobenzene and acetyl chloride

(13) N-acryloyl-N-methyl-4-nitro-aniline

Prepared from 4-methylamino-nitrobenzene and acrylic acid chloride

(14) N-acryloyl-N-isopropyl-4-nitro-aniline

Prepared from 4-isopropylamino-nitrobenzene and acrylic acid chloride

(15) N-acryloyl-N-benzyl-4-nitro-aniline

Prepared from 4-benzylamino-nitrobenzene and acrylic acid chloride

(16) N-bromoacetyl-N-methyl-4-nitro-aniline

Prepared from 4-methylamino-nitrobenzene and bromoacetyl chloride

(17) N-bromoacetyl-N-isopropyl-4-nitro-aniline

Prepared from 4-isopropylamino-nitrobenzene and bromoacetyl chloride

(18) N-bromoacetyl-N-benzyl-4-nitro-aniline

Prepared from 4-benzylamino-nitrobenzene and bromoacetyl chloride

EXAMPLE VII

N-(dimethylaminomethylcarbonyl)-N-methyl-4-nitro-aniline 1.8 g of dimethylamine hydrochloride and 5.5 g of potassium carbonate are placed in 80 ml of acetone and 4.2 g of N-bromoacetyl-N-methyl-4nitroaniline are added in three batches at room temperature. The mixture is stirred for 12 hours at room temperature. After this time the mixture is filtered and the filtrate is evaporated down. The residue is dissolved in ethyl acetate, washed twice with water, dried over sodium sulphate and finally concentrated by rotary evaporation.

Yield: 2.8 g (79% of theory), $R_f$ value: 0.5 (silica gel, ethyl acetate/methanol=7:3).

Meltingpoint: 121–122° C.

The following compounds are prepared analogously to Example VII:

(1) N-(piperidin-1-yl-methylcarbonyl)-N-methyl-4-nitroaniline (2) N-(morpholin-4-yl-methylcarbonyl)-N-methyl-4-nitroaniline (3) N-[(4-benzyl-piperazin-1-yl)-methylcarbonyl]-N-methyl-4-nitroaniline (4) N-(pyrrolidin-1-yl-methylcarbonyl)-N-methyl-4-nitroaniline (5) N-[(N-aminocarbonylmethyl-N-methyl-amino)-methylcarbonyl]-N-methyl-4-nitroaniline (6) N-[(N-benzyl-N-methyl-amino)-methylcarbonyl]-N-methyl-4-nitroaniline (7) N-[di-(2-methoxyethyl)-amino-methylcarbonyl]-N-methyl-4-nitroaniline (8) N-(dimethylaminomethylcarbonyl)-N-isopropyl-4-nitro-aniline (9) N-(piperidin-1-yl-methylcarbonyl)-N-isopropyl-4-nitro-aniline

(10) N-[(4-tert.butoxycarbonyl-piperazin-1-yl)methylcarbonyl]-N-isopropyl-4-nitro-aniline

(11) N-[(N-benzyl-N-methyl-amino)-methylcarbonyl]-N-benzyl-4-nitro-aniline

(12) N-(dimethylaminomethylcarbonyl)-N-benzyl-4-nitro-aniline

(13) N-(piperidin-1-yl-methylcarbonyl)-N-benzyl-4-nitro-aniline

(14) N-[di-(2-hydroxyethyl)-amino-methylcarbonyl]-N-methyl-4-nitroaniline

(15) N-[(N-(2-methoxyethyl)-N-methyl-amino)-methylcarbonyl]-N-methyl-4-nitroaniline

(16) N-[(N-(2-dimethylamino-ethyl)-N-methyl-amino)-methylcarbonyl]-N-methyl-4-nitroaniline

(17) N-[(4-methyl-piperazin-1-yl)-methylcarbonyl]-N-methyl-4-nitroaniline

(18) N-[(imidazol-1-yl)-methylcarbonyl]-N-methyl-4-nitroaniline

(19) N-[(phthalimido-2-yl)-methylcarbonyl]-N-methyl-4-nitroaniline

EXAMPLE VIII

N-[(2-dimethylamino-ethyl)-carbonyl]-N-benzyl-4-nitro-aniline 0.5 g of dimethylamine hydrochloride, 1.1 ml of triethylamine and 1.2 g of N-acryloyl-N-benzyl-4-nitro-aniline are dissolved in 50 ml of methanol and stirred for 24 hours at room temperature. After this time the mixture is evaporated down. The residue is purified over an aluminium oxide column (activity 2–3) with methylene chloride/ethanol 50:1 as eluant.

Yield: 1.4 g (98% of theory), $R_f$ value: 0.8 (aluminium oxide, methylene chloride/ethanol=20:1).

Melting point: 73° C.

The following compounds are prepared analogously to Example VIII:

(1) N-[(2-dimethylamino-ethyl)-carbonyl]-N-isopropyl-4-nitro-aniline

Prepared from N-acryloyl-N-isopropyl-4-nitro-aniline and dimethylamine hydrochloride (2) N-[(2-dimethylamino-ethyl)-carbonyl]-N-methyl-4-nitro-aniline Prepared from N-acryloyl-N-methyl-4-nitro-aniline and dimethylamine hydrochloride (3) N-[(2-(4-tert.butoxycarbonyl-piperazin-1-yl)-ethyl)-carbonyl]-N-methyl-4-nitro-aniline Prepared from N-acryloyl-N-methyl-4-nitro-aniline and N-tert.butoxycarbonyl-piperazine (4) N-[(2-(piperidin-1-yl)-ethyl)-carbonyl]-N-methyl-4-nitroaniline Prepared from N-acryloyl-N-methyl-4-nitro-aniline and piperidine (5) N-[(2-(N-benzyl-N-methyl-amino)-ethyl)-carbonyl]-N-methyl-4-nitro-aniline Prepared from N-acryloyl-N-methyl-4-nitro-aniline and N-benzyl-N-methyl-amine

EXAMPLE IX 4-(4-methyl-piperazine-1-yl)-nitrobenzene 31.5 g of 4-chloro-1-nitrobenzene and 44.4 ml of 1-methylpiperazine are combined and stirred for 18 hours at 90° C. Then the solution is poured onto ice water and the precipitate formed is suction filtered, washed with water and recrystallised from ethanol/water 1:1. The residue is dried in vacuo at 75° C.

Yield: 44.0 g (99% of theory), $R_f$ value: 0.5 (silica gel, methylene chloride/methanol=10:1).

Melting point: 108–112° C.

The following compounds are prepared analogously to Example IX:

(1) N-(2-dimethylaminoethyl)-N-methyl-4-nitroaniline

Prepared from 1-fluoro-4-nitrobenzene and 1-dimethylamino-2-methylamino-ethane (2) N-(3-dimethylaminopropyl)-N-methyl-4-nitroaniline Prepared from 1-fluoro-4-nitrobenzene and 1-dimethylamino-3-methylamino-propane (3) 4-(N-carboxymethyl-amino)-nitrobenzene Prepared from 1-fluoro-4-nitrobenzene and glycine (4) N-cyclohexyl-p-phenylenediamine Prepared from 1-fluoro-4-nitrobenzene and cyclohexylamine (5) 6-[N-(2-dimethylamino-ethyl)-N-methylsulphonyl-amino]-3-phthalimido-2-yl-nitrobenzene Prepared from 2-nitro-4-phthalimido-2-yl-fluorobenzene, N-(2-dimethylamino-ethyl)-methanesulphonamide and sodium hydride as base (6) 6[N-(2-dimethylamino-ethyl)-N-methylsulphonyl-amino]-1,3-dinitrobenzene Prepared from 2,4-dinitro-chlorobenzene, N-(2-dimethylamino-ethyl)-methanesulphonamide and sodium hydride as base (7) 4-[N-(2-dimethylamino-ethyl)-N-methylsulphonyl-amino]-3-chloro-nitrobenzene Prepared from 2-fluoro-5-nitro-chlorobenzene, N-(2-dimethylamino-ethyl)-methanesuiphonamide and sodium hydride as base (8) 4-(2-dimethylamino-ethyl-amino)-1,3-dinitrobenzene Prepared from 1-chloro-2,4-dinitro-benzene and N,N-dimethyl-ethylenediamine (9) 4-[N-(2-dimethylamino-ethyl)-N-(ethylsulphonyl)-amino]-nitrobenzene Prepared from 1-fluoro-4-nitro-benzene, N-(2-dimethylamino-ethyl)-ethanesulphonamide and sodium hydride as base

(10) 4-[N-(2-dimethylamino-ethyl)-N-(propylsulphonyl)-amino]-nitrobenzene

Prepared from 1-fluoro-4nitro-benzene, N-(2-dimethylamino-ethyl)-propanesulphonamide and sodium hydride as base

(11) 4-[N-(2-dimethylamino-ethyl)-N-(butylsulphonyl)-amino]-nitrobenzene

Prepared from 1-fluoro-4nitro-benzene, N-(2-dimethylamino-ethyl)-butanesulphonamide and sodium hydride as base

(12) 4-[N-(2-dimethylamino-ethyl)-N-(benzylsulphonyl)-amino]-nitrobenzene

Prepared from 1-fluoro-4nitro-benzene, N-(2-dimethylamino-ethyl)-C-phenylmethanesulphonamide and sodium hydride as base

(13) 4-[N-(2-dimethylamino-ethyl)-N-(phenylsulphonyl)-amino]-nitrobenzene

Prepared from 1-fluoro-4-nitro-benzene, N-(2-dimethylamino-ethyl)-benzenesulphonamide and sodium hydride as base

(14) 4-[N-(2-dimethylamino-ethyl)-N-(isopropylsulphonyl)-amino]-nitrobenzene

Prepared from 1-fluoro-4-nitro-benzene, N-(2-dimethylamino-ethyl)-isopropylsulphonamide and sodium hydride as base

(15) 4-[N-(2-dimethylamino-ethyl)-amino]-3-bromo-nitrobenzene

Prepared from 2-bromo-1-fluoro-4-nitro-benzene and N,N-dimethyl-ethylenediamine

(16) 4-isopropylamino-nitrobenzene

Prepared from 1-fluoro-4-nitrobenzene and isopropylamine

(17) 4-benzylamino-nitrobenzene

Prepared from 1-fluoro-4-nitrobenzene and benzylamine

EXAMPLE X 4-(imidazol-4-yl)-nitrobenzene 9.5 g of 2-phenylimidazole are carefully dissolved in 50 ml of concentrated sulphuric acid and 5.8 g of ammonium nitrate are added to this solution at 0° C. After a further 60 minutes stirring at 0° C. the mixture is poured onto ice water, made basic with ammonia water and the precipitate formed is suction filtered and recrystallised from ethanol.

Yield: 8.0 g (64% of theory), $R_f$ value: 0.6 (silica gel, ethyl acetate/ethanol=10:1) $C_9H_7N_3O_2$.

Mass spectrum: m/z=189 [M$^+$].

The following compounds are prepared analogously to Example X:

(1) 4-(imidazol-2-yl)-nitrobenzene

Prepared from 4-(imidazol-2-yl)-benzene (2) 4-(5-methyl-imidazol-4-yl)-nitrobenzene Prepared from 4-methyl-5-phenyl-imidazole (J. Heterocycl. Chem. 1983, 20, 1277–1281)

EXAMPLE XI 4-(2-(imidazol-4-yl)-ethylene)-nitrobenzene 1.5 g of 4-nitrobenzaldehyde and 7.45 g of (N-trityl-imidazol-4-yl-methyl)-triphenylphosphonium chloride are dissolved in 75 ml of tetrahydrofuran and to this solution 3.0 ml of DBU are added dropwise at room temperature. After a further 120 minutes stirring at room temperature the mixture is poured onto water and the precipitate formed is suction filtered. The product is taken up in 25 ml of 1N hydrochloric acid and refluxed for 4 hours. After this time it is neutralised with ammoniacal water, extracted with ethyl acetate and the organic phase is washed with water, dried over sodium sulphate and evaporated down. The residue is purified over a silica gel column with methylene chloride/methanol 10:1 as eluant.

Yield: 1.0 g of (47% of theory), $R_f$ value: 0.6 (silica gel, ethyl acetate/ethanol=10:1).

Melting point: 185–188° C.

EXAMPLE XII 4-(piperidin-1-yl-methyl)-nitrobenzene 40.0 g of 4-nitrobenzyl bromide are dissolved in 500 ml of methylene chloride, 51.5 ml of triethylamine are added and 18.3 ml of piperidine are carefully added dropwise. After the end of the exothermic reaction the mixture is refluxed for another 30 minutes. After cooling it is washed with water and the organic phase is dried over sodium sulphate. Finally, the organic phase is evaporated down.

Yield: 36.3 g of (89% of theory), $R_f$ value: 0.6 (silica gel, methylene chloride/methanol=9:1) $C_{12}H_{16}N_2O_2$.

Mass spectrum: m/z=221 [M$^+$].

The following compounds are prepared analogously to Example XII:

(1) 4-[(2,6-dimethyl-piperidin-1-yl)-methyl]-nitrobenzene
(2) 3-(N,N-dimethyl-aminomethyl)-nitrobenzene
(3) 4-(N,N-dimethyl-aminomethyl)-nitrobenzene
(4) 4-(2-dimethylamino-ethyl)-nitrobenzene
(5) 4-(2-diethylamino-ethyl)-nitrobenzene
(6) 4-(diethylamino-methyl)-nitrobenzene
(7) 4-(N-benzyl-N-methyl-aminomethyl)-nitrobenzene
(8) 4-(N-ethyl-N-methyl-aminomethyl)-nitrobenzene
(9) 4-[N-(n-hexyl)-N-methyl-aminomethyl]-nitrobenzene
(10) 4-(thiomorpholin-4-yl-methyl)-nitrobenzene
(11) 4-[(4-methyl-piperazine-1-yl)-methyl]-nitrobenzene
(12) 4-(imidazol-1-yl-methyl)-nitrobenzene
(13) 4-[2-(4-hydroxy-piperidin-1-yl)-ethyl-amino]-nitrobenzene
(14) 4-[(3-hydroxy-pyrrolidin-1-yl)-methyl]-nitrobenzene
(15) 4-(1,2,4-triazol-1-yl-methyl)-nitrobenzene
(16) 4-(1,2,3-triazol-2-yl-methyl)-nitrobenzene
(17) 4-(1,2,3-triazol-1-yl-methyl)-nitrobenzene
(18) 4-[(N-ethoxycarbonylmethyl-N-methyl-amino)-methyl]-nitrobenzene
(19) 4-[(N-aminocarbonytmethyl-N-methyl-amino)-methyl]-nitrobenzene
(20) 4-(azetidin-1-yl-methyl)-nitrobenzene
(21) 4-[(di-(2-methoxy-ethyl)-amino)-methyl]-nitrobenzene
(22) 4-[N-(N-tert.butoxycarbonyl-3-amino-propyl)-N-methyl-aminomethyl]-nitrobenzene
(23) 4-[(N-propyl-N-methyl-amino)-methyl]-nitrobenzene
(24) 4-[(N-(2-dimethylamino-ethyl)-N-methyl-amino)-methyl]-nitrobenzene
(25) 4-[(N-(3-dimethylamino-propyl)-N-methyl-amino)-methyl]-nitrobenzene
(26) 4-[(N-(2-methoxy-ethyl)-N-methyl-amino)-methyl]-nitrobenzene
(27) 4-[(N-(2-hydroxy-ethyl)-N-methyl-amino)-methyl]-nitrobenzene
(28) 4-[(N-(dioxolan-2-yl-methyl)-N-methyl-amino)-methyl]-nitrobenzene
(29) 4-(3-oxo-piperazine-1-yl-methyl)-nitrobenzene

EXAMPLE XIII

4-[(N-carboxymethyl-N-methyl-amino)-methyl]-nitrobenzene 7.33 g of 4-[(N-ethoxycarbonylmethyl-N-methyl-amino)-methyl]-nitrobenzene are dissolved in 140 ml of ethanol, 34.0 ml of 1N sodium hydroxide solution are added and the mixture is stirred for half an hour at room temperature. After this time the mixture is neutralised with 34 ml of 1N hydrochloric acid, the solvent removed, the residue taken up in methylene chloride and extracted with water. The aqueous phase is evaporated down and the residue is recrystallised from methylene chloride.

Yield: 5.43 g (84% of theory), $R_f$ value: 0.4 (silica gel, methylene chloride/methanol=2:1) $C_{10}OH_{12}N_2O_4$.

Mass spectrum: m/z=223 [M$^+$].

EXAMPLE XIV 4-(N-ethyl-aminomethyl)-nitrobenzene 6.0 g of 4-nitrobenzyl bromide are dissolved in 25 ml of ethanol, combined with 25 ml of 10% ethanolic ethylamine solution and refluxed for 2 hours. Then the solution is concentrated by rotary evaporation, the residue is taken up with methylene chloride and washed with dilute sodium hydroxide solution. Finally the organic phase is evaporated down.

Yield: 2.3 g (46% of theory), $R_f$ value: 0.2 (silica gel, methylene chloride/methanol=9:1) $C_9H_{12}N_2O_2$.

ESI mass spectrum: m/z=179 [M–H$^-$].

The following compounds are prepared analogously to Example XIV:

(1) 4-[N-(4-chlorobenzyl)-aminomethyl]-nitrobenzene
(2) 4-(N-cyclohexyl-aminomethyl)-nitrobenzene
(3) 4-(N-isopropyl-aminomethyl)-nitrobenzene
(4) 4-(N-propyl-aminomethyl)-nitrobenzene
(5) 4-(N-methyl-aminomethyl)-nitrobenzene
(6) 4-(N-butyl-aminomethyl)-nitrobenzene
(7) 4-(N-methoxycarbonylmethyl-aminomethyl)-nitrobenzene
(8) 4-(N-benzyt-aminomethyl)-nitrobenzene
(9) 4-(aminomethyl)-nitrobenzene
(10) 4-(pyrrolidin-1-yl-methyl)-nitrobenzene
(11) 4-(morpholin-4-yl-methyl)-nitrobenzene
(12) 4-(hexamethyleneiminomethyl)-nitrobenzene
(13) 4-(4-hydroxy-piperidin-1-yl-methyl)-nitrobenzene
(14) 4-(4-methoxy-piperidin-1-yl-methyl)-nitrobenzene
(15) 4-(4-methyl-piperidin-1-yl-methyl)-nitrobenzene
(16) 4-(4-ethyl-piperidin-1-yl-methyl)-nitrobenzene
(17) 4-(4-isopropyl-piperidin-1-yl-methyl)-nitrobenzene
(18) 4-(4-phenyl-piperidin-1-yl-methyl)-nitrobenzene
(19) 4-(4-benzyl-piperidin-1-yl-methyl)-nitrobenzene
(20) 4-(4-ethoxycarbonyl-piperidin-1-yl-methyl)-nitrobenzene
(21) 4-(N,N-dipropyl-aminomethyl)-nitrobenzenc
(22) 4-(4-tert.butoxycarbonyl-piperazin-1-yl-methyl)-nitrobenzene
(23) 4-(2-morpholin-4-yl-ethyl)-nitrobenzenc
(24) 4-(2-pyrrolidin-1-yl-ethyl)-nitrobenzene
(25) 4-(2-piperidin-1-yl-ethyl)-nitrobenzene
(26) 4-(N-ethyl-N-benzyl-aminomethyl)-nitrobenzene
(27) 4-(N-propyl-N-benzyl-aminomethyl)-nitrobenzene
(28) 4[N-methyl-N-(4-chlorobenzyl)-aminomethyl]-nitrobenzene
(29) 4-[N-methyl-N-(4-bromobenzyl)-aminomethyl]-nitrobenzene

(30) 4[N-methyl-N-(4-fluorobenzyl)-aminomethyl]-nitrobenzene
(31) 4-[N-methyl-N-(4-methylbenzyl)-aminomethyl]-nitrobenzene
(32) 4-[N-methyl-N-(3-chlorobenzyl)-aminomethyl]-nitrobenzene
(33) 4-[N-methyl-N-(3,4-dimethoxybenzyl)-aminomethyl]-nitrobenzene
(34) 4-[N-methyl-N-(4-methoxybenzyl)-aminomethyl]-nitrobenzene
(35) 4-(N-2,2,2-trifluoroethyl-N-benzyl-aminomethyl)-nitrobenzene
(36) 4-[N-2,2,2-trifluoroethyl-N4-chlorobenzyl)-aminomethyl]-nitrobenzene
(37) 4-(thiomorpholin-4-yl-methyl)-nitrobenzene
(38) 4-(azetidion-1-yl-methyl)-nitrobenzene
(39) 4-(3,4-dihydropyrrolidin-1-yl-methyl)-nitrobenzene
(40) 4-(3,4-dihydropiperidin-1-yl-methyl)-nitrobenzene
(41) 4-(2-methoxycarbonyl-pyrrolidin-1-yl-methyl)-nitrobenzene
(42) 4-(3,5-dimethyl-piperidin-1-yl-methyl)-nitrobenzene
(43) 4-(4-phenyl-piperazin-1-yl-methyl)-nitrobenzene
(44) 4-(4-phenyl-4-hydroxy-piperidin-1-yl-methyl)-nitrobenzene
(45) 4-[N-(3,4,5-trimethoxybenzyl-N-methyl-aminomethyl)-nitrobenzene
(46) 4-[N-(3,4-dimethoxybenzyl)-N-ethyl-aminomethyl]-nitrobenzene
(47) 4-[N-(2,6-dichlorobenzyl)-N-methyl)-aminomethyl]-nitrobenzene
(48) 4-[N-(4-trifluoromethylbenzyl)-N-methyl)-aminomethyl]-nitrobenzene
(49) 4-(N-benzyl-N-isopropyl-aminomethyl)-nitrobenzene
(50) 4-(N-benzyl-N-tert.butyl-aminomethyl)-nitrobenzene
(51) 4-(N,N-diisopropyl-aminomethyl)-nitrobenzene
(52) 4-(N,N-diisobutyl-aminomethyl)-nitrobenzene
(53) 4-(2,3,4,5-tetrahydro-benzo(d)azepin-3-yl-methyl)-nitrobenzene
(54) 4-(2,3-dihydro-isoindol-2-yl-methyl)-nitrobenzene
(55) 4-(6,7-dimethoxy-1,2,3,4-tetrahydro-isoquinolin-2-yl-methyl)-nitrobenzene
(56) 4-(1,2,3,4-tetrahydro-isoquinolin-2-yl-methyl)-nitrobenzene
(57) 4-[N-(2-hydroxyethyl)-N-benzyl-aminomethyl]-nitrobenzene
(58) 4-[N-(1-ethyl-pentyl)-N-(pyridin-2-yl-methyl)-aminomethyl]-nitrobenzene
(59) 4-(piperin-1-yl-methyl)-1,3-dinitrobenzene
(60) 4-(N-phenethyl-N-methyl-aminomethyl)-nitrobenzene
(61) 4-[N-(3,4-dihydroxy-phenethyl)-N-methyl-aminomethyl]-nitrobenzene
(62) 4-[N-(3,4,5-trimethoxy-phenethyl)-N-methyl-aminomethyl]-nitrobenzene
(63) 4-[N-(3,4-dimethoxy-phenethyl)-N-methyl-aminomethyl]-nitrobenzene
(64) 4-[N-(3,4-dimethoxy-benzyl)-N-methyl-aminomethyl]-nitrobenzene
(65) 4-[N-(4-chloro-benzyl)-N-methyl-aminomethyl]-nitrobenzene
(66) 4-[N-(4-bromo-benzyl)-N-methyl-aminomethyl]-nitrobenzene
(67) 4-[N-(4-fluoro-benzyl)-N-methyl-aminomethyl]-nitrobenzene
(68) 4-[N-(4-methyl-benzyl)-N-methyl-aminomethyl]-nitrobenzene
(69) 4-[N-(4-nitro-phenethyl)-N-methyl-aminomethyl]-nitrobenzene
(70) 4-(N-phenethyl-N-benzyl-aminomethyl)-nitrobenzene
(71) 4-(N-phenethyl-N-cyclohexyl-aminomethyl)-nitrobenzene
(72) 4-[N-(2-(pyridin-2-yl)-ethyl)-N-methyl-aminomethyl]-nitrobenzene
(73) 4-[N-(2-(pyridin-4-yl)-ethyl)-N-methyl-aminomethyl]-nitrobenzene
(74) 4-[N-(pyridin-4-yl-methyl)-N-methyl-aminomethyl]-nitrobenzene
(75) 4-(N,N-dibenzyl-aminomethyl)-nitrobenzene
(76) 4-[N-(4-nitro-phenethyl)-N-propyl-aminomethyl]-nitrobenzene
(77) 4-(N-benzyl-N-(3-cyano-propyl)-aminomethyl)-nitrobenzene
(78) 4-(N-benzyl-N-allyl-aminomethyl)-nitrobenzene
(79) 4-[N-benzyl-N-(2,2,2-trifluoroethyl)-aminomethyl]-nitrobenzene
(80) 4-[N-(2-benzo(1,3)dioxol-5-yl-methyl)-N-methyl-aminomethyl]-nitrobenzene
(81) 4-(7-chloro-2,3,4,5-tetrahydro-benzo(d)azepin-3-yl-methyl)-nitrobenzene
(82) 4-(7,8-dichloro-2,3,4,5-tetrahydro-benzo(d)azepin-3-yl-methyl)-nitrobenzene
(83) 4-(7-methoxy-2,3,4,5-tetrahydro-benzo(d)azepin-3-yl-methyl)-nitrobenzene
(84) 4-(7-methyl-2,3,4,5-tetrahydro-benzo(d)azepin-3-yl-methyl)-nitrobenzene
(85) 4-(7,8-dimethoxy-2,3,4,5-tetrahydro-benzo(d)azepin-3-yl-methyl)-nitrobenzene
(86) 4-(6,7-dichloro-1,2,3,4-tetrahydro-isoquinolin-2-yl-methyl)-nitrobenzene
(87) 4-(6,7-dimethyl-1,2,3,4-tetrahydro-isoquinolin-2-yl-methyl)-nitrobenzene
(88) 4-(6-chloro-1,2,3,4-tetrahydro-isoquinolin-2-yl-methyl)-nitrobenzene
(89) 4-(7-chloro-1,2,3,4-tetrahydro-isoquinolin-2-yl-methyl)-nitrobenzene
(90) 4-(6-methoxy-1,2,3,4-tetrahydro-isoquinolin-2-yl-methyl)-nitrobenzene
(91) 4-(7-methoxy-1,2,3,4-tetrahydro-isoquinolin-2-yl-methyl)-nitrobenzene
(92) 4-[(2,3,4,5-tetrahydro-azepino(4,5-b)pyrazin-3-yl)-methyl]-nitrobenzene
(93) 4-[(7-amino-2,3,4,5-tetrahydro-azepino(4,5-b)pyrazin-3-yl)-methyl]-nitrobenzene
(94) 4-[(2-amino-5,6,7,8-tetrahydro-azepino(4,5-d)thiazol-6-yl)-methyl]-nitrobenzene
(95) 4-[(5,6,7,8-tetrahydro-azepino(4,5-d)thiazol-6-yl)-methyl]-nitrobenzene

EXAMPLE XV 4-(1,1-dioxo-thiomorpholin-4-yl-methyl)-nitrobenzene 6.0 g of 4-(thiomorpholin-4-yl-methyl)-nitrobenzene are dissolved in 100 ml of methylene chloride and 10.3 g of meta-chloroperbenzoic acid are slowly added. After a further 3 hours stirring at room temperature the precipitate obtained is filtered off.

Yield: 6.2 g (91% of theory) $R_f$ value: 0.5 (silica gel, methylene chloride/methanol=1:1) $C_{11}H_{14}N_2O_4S$.

Mass spectrum: n/z=270 [M$^+$].

The following compound is prepared analogously to Example XV:

(1) 4-(1-oxo-thiomorpholin-4-yl-methyl)-nitrobenzene

EXAMPLE XVI

4-[N-(3-amino-propyl)-N-methylsulphonyl-amino]-nitrobenzene 9.5 g of 4-[N-(3-phthalimido-2-yl-propyl)-N-methylsulphonyl-amino]-nitrobenzene are dissolved in 200 ml of ethanol, 11.5 ml of hydrazine hydrate are added and the mixture is stirred for 1.5 hours at 50° C. After cooling the residue is largely evaporated down, water is added and the solution is extracted with methylene chloride. The organic phase is dried, evaporated down and purified over a silica gel column with methylene chloride/methanol/ammonia 9:1:0.1.

Yield: 2.5 g (39% of theory) $R_f$ value: 0.2 (silica gel, methylene chloride/methanol=9:1) $C_{10}H_{15}N_3O_4S$.

ESI mass spectrum: m/z=272 [M–H$^-$].

The following compound is prepared analogously to Example XVI:

(1) 6[N-(2-dimethylamino-ethyl)-N-methylsulphonyl-amino]-3-amino-nitrobenzene

Prepared from 6-[N-(2-dimethylamino-ethyl)-N-methylsulphonyl-amino]-3-phthalimido-2-yl-nitrobenzene

EXAMPLE XVII 4-(1-methyl-imidazol-2-yl)-nitrobenzene 7.5 g of 4-(imidazol-2-yl)-nitrobenzene are dissolved in 50 ml of dimethylsulphoxide and at 0° C. 5.0 g of potassium tert.butoxide are added. After one hour of stirring at room temperature 2.6 ml of methyl iodide are added dropwise and the mixture is stirred for one hour at room temperature. After this time the residue is poured onto ice water and the precipitate formed is suction filtered, washed with water and dried.

Yield: 6.1 g (76% of theory), $R_f$ value: 0.6 (silica gel, methylene chloride/methanol=10:1)

Melting point: 186–187° C.

The following compounds are prepared analogously to Example XVII:

(1) 4-(1-ethyl-imidazol-2-yl)-nitrobenzene

Prepared from 4-(imidazol-2-yl)-nitrobenzene and ethyl iodide (2) 4-(1-benzyl-imidazol-2-yl)-nitrobenzene Prepared from 4-(imidazol-2-yl)-nitrobenzene and benzyl bromide

EXAMPLE XVIII

4-[(N-(2-(2-methoxy-ethoxy)-ethyl)-N-methyl-amino)-methyl]-nitrobenzene 5.0 g of 4-methylaminomethyl-nitrobenzene are dissolved in 30 ml of dimethylformamide and 4.6 g of 2-(2-methoxy-ethoxy)-ethyl chloride are added. After six hours' stirring at 100° C. the solvent is removed and the residue is taken up in ethyl acetate. The organic phase is washed with water and dried over sodium sulphate. After the elimination of the solvent the residue is purified over an aluminium oxide column (activity 2-3) with toluene/ethyl acetate 5:1 as eluant.

Yield: 2.3 g (29% of theory) $R_f$ value: 0.5 (aluminium oxide, toluene/ethyl acetate 5:1) $C_{13}H_{20}N_2O_4$.

ESI mass spectrum: m/z=267 [M–H$^-$].

EXAMPLE XIX 4-(N-ethyl-N-tert.butoxycarbonyl-aminomethyl)-nitrobenzene 2.2 g of 4-(ethylaminomethyl)-nitrobenzene are dissolved in 50 ml of ethyl acetate and stirred with 2.6 g of di-tert-butyl. dicarbonate (tert.butoxycarbonyl-anhydride) for 30 minutes at room temperature. Then the solution is washed with water and evaporated down.

Yield: 3.4 g of theory $R_f$ value: 0.3 (silica gel, methylene chloride/methanol=50:1).

Melting point: 85° C.

The following compounds are prepared analogously to Example XIX:

(1) 4-[N-(4-chlorophenyl-methyl)-N-tert.butoxycarbonyl-aminomethyl]-nitrobenzene (2) 4-(N-tert.butoxycarbonyl-aminomethyl)-nitrobenzene (3) 4-(N-cyclohexyl-N-tert.butoxycarbonyl-aminomethyl)-nitrobenzene (4) 4-(N-isopropyl-N-tert.butoxycarbonyl-aminomethyl)-nitrobenzene (5) (N-methyl-N-tert.butoxycarbonyl-aminomethyl)-nitrobenzene (6) (4-(N-propyl-N-tert.butoxycarbonyl-aminomethyl)-nitrobenzene (7) (N-butyl-N-tert.butoxycarbonyl-aminomethyl)-nitrobenzenc (8) (N-methoxycarbonylmethyl-N-tert.butoxycarbonyl-aminomethyl)-nitrobenzene (9) 4-(N-benzyl-N-tert.butoxycarbonyl-aminomethyl)-nitrobenzene

(10) 4-[N-(3-trifluoroacetylamino-propyl)-N-methylsulphonyl-amino]-nitrobenzene

Prepared from 4-[N-(3-amino-propyl)-N-methylsulphonyl-amino]-nitrobenzene and trifluoroacetic acid anhydride

(11) 4-[(4-tert.butoxycarbonyl-piperazin-1-yl)-methyl]-nitrobenzene

EXAMPLE XX 4-(piperidin-1-yl-methyl)-aniline 37.0 g of 4-(piperidin-1-yl-methyl)-nitrobenzene are dissolved in 300 ml of methanol, 8.0 g of Raney nickel are added and the mixture is hydrogenated for 85 minutes with 3 bars of hydrogen at room temperature. The catalyst is filtered off and the filtrate is evaporated down.

Yield: 24.0 g (75% of theory), $R_f$ value: 0.4 (silica gel, methylene chloride/methanol=9:1) $C_{12}H_{18}N_2$.

ESI mass spectrum: m/z=191 [M+H$^+$].

The following compounds are prepared analogously to Example VIII:

(1) 4-[(2,6-dimethyl-piperidin-1-yl)-methyl]-aniline (2) N-(2-dimethylamino-ethyl)-N-methylsulphonyl-p-phenylenediamine (3) 3dimethylaminomethyl)-aniline (4) 4-(dimethylaminomethyl)-aniline (5) 4-(2-dimethylamino-ethyl)-aniline (6) 4-[N-(2-dimethylamino-ethyl)-N-acetyl-amino]-aniline (7) 4-[N-(3-dimethylamino-propyl)-N-acetyl-amino]-aniline (8) 4-[N-(2-dimethylamino-ethyl)-N-benzoyl-amino]-aniline (9) 4-[N-(2-dimethylamino-ethyl)-N-propionyl-amino]-aniline

(10) 4-[N-(2-dimethylamino-ethyl)-N-butyryl-amino]-aniline

(11) 4-[N-(2-dimethylamino-ethyl)-N-isobutyryl-amino]-aniline

(12) 4-(N-tert.butoxycarbonyl-aminomethyl)-aniline

(13) 4-(N-ethyl-N-tert.butoxycarbonyl-aminomethyl)-aniline

(14) 4-[N-(4-chlorophenyl-methyl)-N-tert.butoxycarbonyl-aminomethyl]-aniline

(15) 4-(N-cyclohexyl-N-tert.butoxycarbonyl-aminomethyl)-aniline

(16) 4-(N-isopropyl-N-tert.butoxycarbonyl-aminomethyl)-aniline

(17) 4-(N-propyl-N-tert.butoxycarbonyl-aminomethyl)-aniline

(18) 4-(N-methyl-N-tert.butoxycarbonyl-aminomethyl)-aniline

(19) 4-(N-butyl-N-tert.butoxycarbonyl-aminomethyl)-aniline

(20) 4-(N-methoxycarbonyl-methyl-N-tert.butoxycarbonyl-aminomethyl)-aniline

(21) 4-(N-benzyl-N-tert.butoxycarbonyl-aminomethyl)-aniline

(22) 4-(pyrrolidin-1-yl-methyl)-aniline

(23) 4-(morpholin-4-yl-methyl)-aniline

(24) 4-(hexamethyleneiminomethyl)-aniline

(25) 4-(4-hydroxy-piperidin-1-yl-methyl)-aniline

(26) 4-(4-methoxy-piperidin-1-yl-methyl)-aniline

(27) 4-(4-methyl-piperidin-1-yl-methyl)-aniline

(28) 4-(4-ethyl-piperidin-1-yl-methyl)-aniline

(29) 4-(4-isopropyl-piperidin-1-yl-methyl)-aniline

(30) 4-(4-phenyl-piperidin-1-yl-methyl)-aniline

(31) 4-(4-benzyl-piperidin-1-yl-methyl)-aniline

(32) 4-(4-ethoxycarbonyl-piperidin-1-yl-methyl)-aniline

(33) 4-(N,N-dipropyl-aminomethyl)-aniline

(34) 4-(4-tert.butoxycarbonyl-piperazin-1-yl-methyl)-aniline

(35) 4-(2-morpholin-4-yl-ethyl)-aniline

(36) 4-(2-pyrrolidin-1-yl-ethyl)-aniline

(37) 4-(2-piperidin-1-yl-ethyl)-aniline

(38) 4-(N-propyl-N-benzyl-aminomethyl)-aniline

(39) 4-[N-(n-bexyl)-N-methyl-aminomethyl]-aniline

(40) 4-[N-methyl-N-(4-chlorobenzyl)-aminomethyl]-aniline

(41) 4-[N-methyl-N-(4-bromobenzyl)-aminomethyl]-aniline

(42) 4-[N-methyl-N-(4-methylbenzyl)-aminomethyl]-aniline

(43) 4-[N-methyl-N-(4-fluorobenzyl)-aminomethyl]-aniline

(44) 4-[N-methyl-N-(3-chlorobenzyl)-aminomethyl]-aniline

(45) 4-[N-methyl-N-(3,4-dimethoxybenzyl)-aminomethyl]-aniline

(46) 4-[N-methyl-N-(4-methoxybenzyl)-aminomethyl]-aniline

(47) 4-(N-2,2,2-trifluoroethyl-N-benzyl-aminomethyl)aniline

(48) 4-[N-2,2,2-trifluoroethyl-N-(4-chlorobenzyl)-aminomethyl]-aniline

(49) 4-(thiomorpholin-4-yl-methyl)-aniline

(50) 4-(1-oxo-thiomorpholin-4-yl-methyl)-aniline

(51) 4-(1,1-dioxo-thiomorpholin-4-yl-methyl)-aniline

(52) 4-(azetidion-1-yl-methyl)-aniline

(53) 4-(3,4-dihydropyrrolidin-1-yl-methyl)-aniline

(54) 4-(3,4-dihydropiperidin-1-yl-methyl)-aniline

(55) 4-(2-methoxycarbonyl-pyrrolidin-1-yl-methyl)-aniline

(56) 4-(3,5-dimethyl-piperidin-1-yl-methyl)-aniline

(57) 4-(4-phenyl-piperazin-1-yl-methyl)aniline

(58) 4-(4-phenyl-4-hydroxy-piperidin-1-yl-methyl)-aniline

(59) 4-[N-(3,4,5-trimethoxy-benzyl)-N-methyl-aminomethyl]-aniline

(60) 4-[N-(3,4-dimethoxy-benzyl)-N-ethyl-aminomethyl]-aniline

(61) 4-(N-benzyl-N-ethyl-aminomethyl)-aniline

(62) 4-[N-(2,6-dichlorobenzyl)-N-methyl-aminomethyl]-aniline

(63) 4-[N-(4-trifluoromethylbenzyl)-N-methyl-aminomethyl]-aniline

(64) 4N-benzyl-N-isopropyl-aminomethyl)-aniline

(65) 4N-benzyl-N-tert.butyl-aminomethyl)-aniline

(66) 4diethylamino-methyl)-aniline

(67) 4-(2-diethylamino-ethyl)-aniline

(68) 4-(N,N-diisopropyl-aminomethyl)-aniline

(69) 4-(N,N-diisobutyl-aminomethyl)-aniline

(70) 4-(2,3,4,5-tetrahydro-benzo(d)azepin-3-yl-methyl)-aniline

(71) 4-(2,3-dihydro-isoindol-2-yl-methyl)-aniline

(72) 4-(6,7-dimethoxy-1,2,3,4-tetrahydro-isoquinolin-2-yl-methyl)-aniline

(73) 4-(1,2,3,4-tetrahydro-isoquinolin-2-yl-methyl)-aniline

(74) 4-[N-(2-hydroxy-ethyl)-N-benzyl-aminomethyl]-aniline

(75) 4-[N-(1-ethyl-pentyl)-N-(pyridin-2-yl-methyl)-aminomethyl]-aniline

(76) 4-(piperidin-1-yl-methyl)-3-nitro-aniline

(77) 4-(piperidin-1-yl-methyl)-3-amino-aniline

(78) 4-(N-benzyl-N-methyl-aminomethyl)-aniline

(79) 4-(N-ethyl-N-methyl-aminomethyl)-aniline

(80) 4-(N-phenethyl-N-methyl-aminomethyl)-aniline

(81) 4-[N-(3,4-dihydroxy-phenethyl)-N-methyl-aminomethyl]-aniline

(82) 4-[N-(3,4,5-trimethoxy-phenethyl)-N-methyl-aminomethyl]-aniline

(83) 4-[N-(3,4-dimethoxy-phenethyl)-N-methyl-aminomethyl]-aniline

(84) 4-[N-(3,4-dimethoxy-benzyl)-N-methyl-aminomethyl]-aniline

(85) 4-[N-(4-chloro-benzyl)-N-methyl-aminomethyl]-aniline

(86) 4-[N-(4-bromo-benzyl)-N-methyl-aminomethyl]-aniline

(87) 4-[N-(4-fluoro-benzyl)-N-methyl-aminomethyl]-aniline

(88) 4-[N-(4-methyl-benzyl)-N-methyl-aminomethyl]-aniline

(89) 4-[N-(4-nitro-phenethyl)-N-methyl-aminomethyl]-aniline

(90) 4-(N-phenethyl-N-benzyl-aminomethyl)-aniline

(91) 4-(N-phenethyl-N-cyclohexyl-aminomethyl)-aniline

(92) 4-[N-(2-(pyridin-2-yl)-ethyl)-N-methyl-aminomethyl]-aniline

(93) 4-[N-(2-(pyridin-4-yl)-ethyl)-N-methyl-aminomethyl]-aniline

(94) 4-[N-(pyridin-4-yl-methyl)-N-methyl-aminomethyl]-aniline

(95) 4-(N,N-dibenzylaminomethyl)-aniline

(96) 4-[N-(4-nitro-benzyl)-N-propyl-aminomethyl]-aniline

(97) 4-[N-benzyl-N-(3-cyano-propyl)-aminomethyl]-aniline

(98) 4-(N-benzyl-N-allyl-aminomethyl)-aniline

(99) 4-[N-benzyl-N-(2,2,2-trifluoroethyl)-aminomethyl]-aniline (100) 4-[(benzo(1,3)dioxol-5-yl-methyl)-methyl-aminomethyl]-aniline (101) 4-(7-chloro-2,3,4,5-tetrahydro-benzo(d)azepin-3-yl-methyl)-aniline (102) 4-(7,8-dichloro-2,3,4,5-tetrahydro-benzo(d)azepin-3-yl-methyl)-aniline (103) 4-(7-methoxy-2,3,4,5-tetrahydro-benzo(d)azepin-3-yl-methyl)-aniline (104) 4-(7-methyl-2,3,4,5-tetrahydro-benzo(d)azepin-3-yl-methyl)-aniline (105) 4-(7,8-dimethoxy-2,3,4,5-tetrahydro-benzo(d)azepin-3-yl-methyl)-aniline (106) 4-(6,7-dichloro-1,2,3,4-tetrahydro-isoquinolin-2-yl-methyl)-aniline (107) 4-(6,7-dimethyl-1,2,3,4-tetrahydro-isoquinolin-2-yl-methyl)-aniline (108) 4-(6-chloro-1,2,3,4-tetrahydro-isoquinolin-2-yl-methyl)-aniline (109) 4-(7-chloro-1,2,3,4-tetrahydro-isoquinolin-2-yl-methyl)-aniline (110) 4-(6-methoxy-1,2,3,4-tetrahydro-isoquinolin-2-yl-methyl)-aniline (111) 4-(7-methoxy-1,2,3,4-tetrahydro-isoquinolin-2-yl-methyl)-aniline (112) 4-(2,3,4,5-tetrahydro-azepino(4,5-b)pyrazin-3-yl-methyl)-aniline (113) 4-(7-amino-2,3,4,5-tetrahydro-azepino(4,5-b)pyrazin-3-yl-methyl)-aniline (114) 4-(2-amino-5,6,7,8-tetrahydro-azepino(4,5-d)thiazol-6-yl-methyl)-aniline (115) 4-(5,6,7,8-tetrahydro-azepino(4,5-d)thiazol-6-yl-methyl)-aniline (116) 4-(4-methyl-piperazin-1-yl)-aniline (117) 4-[N-(2-dimethylamino-ethyl)-N-methyl-amino]-aniline (118) 4-[N-(3-dimethylamino-propyl)-N-methyl-amino]-aniline (119) N-(3-dimethylamino-propyl)-N-methylsulphonyl-p-phenylenediamine (120) 4-[(N-dimethylaminocarbonylmethyl-N-methylsulphonyl)-amino]-aniline (121) N-(4-aminophenyl)-N-methyl-methanesulphonamide (122) 4-(imidazol-4-yl)-aniline (123) 4-(tetrazol-5-yl)-aniline (124) 4-[N-(2-dimethylamino-ethyl)-N-propionyl-amino]-aniline (125) N-(dimethylaminomethylcarbonyl)-N-methyl-p-phenylenediamine (126) N-[(2-dimethylamino-ethyl)-carbonyl]-N-methyl-p-phenylenediamine (127) 4-(N-acetyl-N-dimethylaminocarbonylmethyl)-amino)-aniline (128) N-methylaminocarbonylmethyl-N-methylsulphonyl-p-phenylenediamine (129) N-aminocarbonylmethyl-N-methylsulphonyl-p-phenylenediamine (130) 4-(imidazolidin-2,4-dion-5-ylidene-methyl)-aniline (131) 4-(imidazolidin-2,4-dion-5-yl-methyl)-aniline (132) 4-(2-oxo-pyrrolidin-1-yl-methyl)-aniline (133) N-cyanomethyl-N-methylsulphonyl-p-phenylenediamine (134) 4-[2-(imidazol-4-yl)-ethyl]-aniline (135) 4-[(4-methyl-piperazin-1-yl)-methyl]-aniline (136) 4-[N-(2-(N-benzyl-N-methyl-amino)-ethyl)-N-methylsulphonyl-amino]-aniline (137) 4-[N-(3-(N-benzyl-N-methyl-amino)-propyl)-N-methylsulphonyl-amino]-aniline (138) N-cyclohexyl-p-phenylenediamine (139) 4-(pyridin-4-yl-methyl)-aniline (140) 4-(imidazol-1-yl-methyl)-aniline (141) 4-benzyl-aniline (142) N-(3-trifluoroacetylamino-propyl)-N-methylsulphonyl-p-phenylenediamine (143) tert.butyl 4-amino-phenylacetate (144) 4-(imidazol-2-yl)-aniline (145) 4-(1-methyl-imidazol-2-yl)-aniline (146) 4-(1-ethyl-imidazol-2-yl)-aniline (147) 4-(1-benzyl-imidazol-2-yl)-aniline (148) 4-[N-(2-dimethylamino-ethyl)-N-methylsulphonyl-amino]-3-amino-aniline (149) 4-[N-(2dimethylamino-ethyl)-N-methylsulphonyl-amino]-3-chloro-aniline (150) 4-[N-(2-dimethylamino-ethyl)-N-acetyl-amino]-3-amino-aniline (151) 4-[N-(2-dimethylamino-ethyl)-N-acetyl-amino]-3-bromo-aniline (152) 4-[2-(4-hydroxy-piperidin-1-yl)-ethyl-amino]-aniline (153) N-(2-dimethylamino-ethyl)-N-ethylsulphonyl-p-phenylenediamine (154) N-(2-dimethylamino-ethyl)-N-propylsulphonyl-p-phenylenediamine (155) N-(2-dimethylamino-ethyl)-N-isopropylsulphonyl-p-phenylenediamine (156) N-(2-dimethylamino-ethyl)-N-butylsulphonyl-p-phenylenediamine (157) N-(2-dimethylamino-ethyl)-N-benzylsulphonyl-p-phenylenediamine (158) N-(2-dimethylamino-ethyl)-N-phenylsulphonyl-p-phenylenediamine (159) 4-((3-hydroxy-pyrrolidin-1-yl)-methyl)-aniline (160) 4-[N-(2-dimethylamino-ethyl)-N-(furan-2-carbonyl)-amino]-aniline (161) 4-[N-(2-dimethylamino-ethyl)-N-(2-methoxy-benzoyl)-amino]-aniline (162) 4-[N-(2-dimethylamino-ethyl)-N-(pyridine-3-carbonyl)-amino]-aniline (163) 4-[N-(2-dimethylamino-ethyl)-N-(phenyl-acetyl)-amino]-aniline (164) N-(piperidin-1-yl-methylcarbonyl)-N-methyl-p-phenylenediamine (165) N-(morpholin-4-yl-methylcarbonyl)-N-methyl-p-phenylenediamine (166) N-[(4-benzyl-piperazin-1-yl)-methylcarbonyl]-N-methyl-p-phenylenediamine (167) N-(pyrrolidin-1-yl-methylcarbonyl)-N-methyl-p-phenylenediamine (168) 4-(5-methyl-imidazol-4-yl)-aniline (169) N-[(2-dimethylamino-ethyl)-carbonyl]-N-isopropyl-p-phenylenediamine (170) N-[(2-dimethylamino-ethyl)-carbonyl]-N-benzyl-p-phenylenediamine (171) N-(N-aminocarbonylmethyl-N-methyl-amino)-methylcarbonyl)-N-methyl-p-phenylenediamine (172) N-[(N-benzyl-N-methyl-amino)-methylcarbonyl]-N-methyl-p-phenylenediamine (173) N-[di-(2-methoxyethyl)-amino-methylcarbonyl]-N-methyl-p-phenylenediamine (174) N-[(2-(4-tert.butoxycarbonyl-piperazin-1-yl)-ethyl)-carbonyl]-N-methyl-p-phenylenediamine (175) N-[(2-(piperidin-1-yl)-ethyl)-carbonyl]-N-methyl-p-phenylenediamine (176) N-[(2-(N-benzyl-N-methyl-amino)-ethyl)-carbonyl]-N-methyl-p-phenylenediamine (177) N-(dimethylaminomethylcarbonyl)-N-isopropyl-p-phenylenediamine (178) N-(piperidin-1-yl-methylcarbonyl)-N-isopropyl-p-phenylenediamine (179) N-[(4-tert.butoxycarbonyl-piperazin-1-yl)-methylcaronyl]-N-isopropyl-p-phenylenediamine (180) N-[(N-benzyl-N-methyl-amino)-methylcarbonyl]-N-benzyl-p-phenylenediamine (181) N-(dimethylaminomethylcarbonyl)-N-benzyl-p-phenylenediamine (182) N-(piperidin-1-yl-methylcarbonyl)-N-benzyl-p-phenylenediamine (183) 4-(1,2,4-triazol-1-yl-methyl)-aniline (184) 4-(1,2,3-triazol-2-yl-methyl)-aniline (185) 4-(1,2,3-triazol-1-yl-methyl)-aniline (186) 4-[(N-ethoxycarbonylmethyl-N-methyl-amino)-methyl]-aniline (187) 4-[(N-aminocarbonylmethyl-N-methyl-amino)-methyl]-aniline (188) 4-(azetidin-1-yl-methyl)-aniline (189) 4-[(di-(2-methoxy-ethyl)-amino)-methyl]-aniline (190) 4-[(N-(2-(2-methoxy-ethoxy)-ethyl)-N-methyl-amino)-methyl]-aniline (191) [-(N-tert.butoxycarbonyl-3-amino-propyl)-N-methyl-aminomethyl]-aniline (192) 4-[(N-(methylcabamoyl-methyl)-N-methyl-amino)-methyl]-aniline (193) 4-[(N-(dimethylcarbamoyl-methyl)-N-methyl-amino)-methyl]-aniline (194) 4-[(N-propyl-N-methyl-amino)-methyl]-aniline (195) 4-[(N-(2-dimethylamino-ethyl)-N-methyl-amino)-methyl]-aniline (196) 4-[(N-(3-dimethylamino-propyl)-N-methyl-amino)-methyl]-aniline (197) 4-[(N-(2-methoxy-ethyl)-N-methyl-amino)-methyl]-aniline (198) 4-[(N-(2-hydroxy-ethyl)-N-methyl-amino)-methyl]-aniline (199) 4-[(N-(dioxolan-2-yl-methyl)-N-methyl-amino)-methyl]-aniline (200) 4-(3-oxo-piperazin-1-yl-methyl)-aniline (201) N-[di-(2-hydroxyethyl)-amino-methylcarbonyl]-N-methyl-p-phenylenediamine (202) N-[(N-(2-methoxyethyl)-N-methyl-amino)-methylcarbonyl]-N-methyl-p-phenylenediamine (203) N-[(N-(2-dimethylamino-ethyl)-N-methyl-amino)-methylcarbonyl]-N-methyl-p-phenylenediamine (204) N-[(4-methyl-piperazin-1-yl)-methylcarbonyl]-N-methyl-p-phenylenediamine (205) N-[(imidazol-1-yl)-methylcarbonyl]-N-methyl-p-phenylenediamine (206) N-[(phthalimido-2-yl)-methylcarbonyl]-N-methyl-p-phenylenediamine

EXAMPLE XXI 4-(4-hydroxymethyl-piperidin-1-yl-methyl-amino)-aniline 1.1 g of 4-(4-ethoxycarbonyl-piperidin-1-yl-methyl-amino)-aniline are suspended in 15 ml of tetrahydrofuran. 175 mg of lithium borohydride are added at room temperature, stirred for 24 h, another 175 mg of lithium borohydride are added and after a further 7.5 hours 15 ml of water are added and the mixture is stirred for 10 minutes. It is extracted three times with 15 ml of ethyl acetate. The combined organic phases are washed with water and saturated saline solution, dried over sodium sulphate and concentrated by rotary evaporation. The residue is purified over a silica gel column with methylene chloride/methanol/ammonia 4:1:0.01 as eluant.

Yield: 200 mg (27% of theory) $R_f$ value: 0.4 (silica gel, methylene chloride/methanol/ammonia 4:1:0.01)

Melting point: 157° C.

EXAMPLE XXII methyl 4-methoxycarbonylmethyl-3-nitro-benzoate 54.3 g of methyl 3-nitro-benzoate and 29.0 g of methyl chloroacetate are dissolved in 100 ml of dimethylformamide and this solution is added dropwise at −10° C. to a solution of 78.5 g of potassium-tert. butoxide in 500 ml of dimethylformamide. The mixture is stirred for another 10 minutes at room temperature and after this time the solution is poured onto 350 ml of concentrated hydrochloric acid in 2 l of ice water. The solution is stirred for 0.5 hours, the precipitate obtained is suction filtered and washed with water. The product is recrystallised from 150 ml of methanol and dried at 40° C. in vacuo.

Yield: 48.3 g of (51% of theory), contains about 20% of methyl 6-methoxycarbonylmethyl-3-nitro-benzoate. $R_f$ value: 0.7 (silica gel, petroleum ether/ethyl acetate=1:1).

Melting point: 65–73° C.

The following compound is prepared analogously to Example XXII:

(1) ethyl 4-methoxycarbonylmethyl-3-nitro-benzoate

Prepared from ethyl 4-thoxycarbonylmethyl-3-nitro-benzoate

EXAMPLE XXIII methyl 2-indolinone-6-carboxylate 48.3 g of methyl 4-methoxycarbonylmethyl-3-nitro-benzoate are dissolved in 800 ml of concentrated acetic acid, 5.0 g of palladium on carbon (10%) are added and the solution is hydrogenated for 2.5 hours at room temperature and 50 psi. The catalyst is filtered off and the filtrate is evaporated down. The residue is taken up in 150 ml of tert.-butylmethyl ether, filtered again and dried in vacuo at 100° C.

Yield: 28.6 g (98% of theory), $R_f$ value: 0.4 (silica gel, methylene chloride/methanol=10:1).

Melting point: 208–211° C.

The following compound is prepared analogously to Example XXIII:

(1) ethyl 2-indolinone-6-carboxylate

Prepared from ethyl 4-methoxycarbonylmethyl-3-nitro-benzoate

EXAMPLE XXIV 1-acetyl-3-(1-ethoxy-1-phenylmethylene)-6-ethoxycarbonyl-2-indolinone 15.0 g of ethyl 2-indolinone-6-carboxylate, 49.6 ml of triethyl orthobenzoate and 150 ml of acetic anhydride are stirred for 4 hours at 110° C. After this time the solvent is removed, the residue is recrystallised from petroleum ether and dried in vacuo at 50° C.

Yield: 16.9 g (61% of theory), $R_f$ value: 0.5 (silica gel, petroleum ether/methylene chloride/ethyl acetate=5:4:1).

Melting point: 98–100° C. $C_{22}H_{21}NO_5$.

The following compounds are prepared analogously to Example XXIV:

(1) 1-acetyl-3-(1-ethoxy-1-phenylmethylene)-6-methoxycarbonyl-2-indolinone

Prepared from methyl 2-indolinone-6-carboxylate, triethyl orthobenzoate and acetic anhydride (2) 1-acetyl-3-(1-ethoxy-1-ethyl-methylene)-6-ethoxycarbonyl-2-indolinone Prepared from ethyl 2-indolinone-6-carboxylate, triethyl orthopropionate and acetic anhydride Preparation of the final compounds:

EXAMPLE 1

3-Z-[1-(4-(piperidin-1-yl-methyl)-anilino)-1-phenyl-methylene]-6-carbamoyl-2-indolinone-trifluoroacetate 300 mg of resin obtained according to Example II are suspended in 3 ml of dimethylformamide and shaken with 0.2 g of 4-(piperidin-1-yl-methyl)-aniline for 22 hours at 70° C. Then it is filtered off and the resin is washed several times with methylene chloride, methanol and dimethylformamide. Then 1 ml of methanolic ammonia is added for 2 hours in order to eliminate the acetyl group. Then after further washing 4 ml of 10% trifluoroacetic acid in methylene chloride are added during another 60 minutes, the resin is separated off and the solution is evaporated down.

Yield: 69 mg. $R_f$ value: 0.1 (silica gel, methylene chloride/methanol=9:1) $C_{28}H_{28}N_4O_2$.

Mass spectrum: m/z=452 ($m^+$).

The following compounds are prepared analogously to Example 1:

(1) 3-Z-(1-Anilino-1-phenyl-methylene)-6-carbamoyl-2-indolinone

Prepared from the resin obtained according to Example II and aniline $C_{22}H_{17}N_3O_2$.

Mass spectrum: m/z=355 ($m^+$).

(2) 3-Z-[1-(4-dimethylaminomethyl-anilino)-1-phenyl-methylene]-6-carbamoyl-2-indolinone-trifluoroacetate Prepared from the resin obtained according to Example II and 4-dimethylaminomethyl-aniline $C_{25}H_{24}N_4O_2$ Mass spectrum: m/z=412 ($m^+$).

(3) 3-Z-[1-(4-(2-dimethylamino-ethyl)-anilino)-1-phenyl-methylene]-6-carbamoyl-2-indolinone-trifluoroacetate Prepared from the resin obtained according to Example II and 4-(2-diethylamino-ethyl)-aniline $C_{28}H_{30}N_4O_2$ Mass spectrum: m/z=454 ($m^+$).

(4) 3-Z-[1-(4-(morpholin-4-yl-methyl)-anilino)-1-phenyl-methylene]-6-carbamoyl-2-indolinone-trifluoroacetate Prepared from the resin obtained according to Example II and 4-(morpholin-4-yl-methyl)-aniline $R_f$ value: 0.50 (silica gel, methylene chloride/methanol=4:1) $C_{27}H_{26}N_4O_3$ Mass spectrum: m/z=454 ($m^+$).

(5) 3-Z-[1-(4-(1-oxo-thiomorpholin-4-yl-methyl)-anilino)-1-phenyl-methylene]-6-carbamoyl-2-indolinone-trifluoroacetate Prepared from the resin obtained according to Example II and 4-(1-oxo-thiomorpholin-4-yl-methyl)-aniline $R_f$ value: 0.30 (silica gel, methylene chloride/methanol=9:1) $C_{27}H_{26}N_4O_3S$ Mass spectrum: m/z=486 ($m^+$)

(6) 3-Z-[1-(4-(1,1-dioxo-thiomorpholin-4-yl-methyl)-anilino)-1-phenyl-methylene]-6-carbamoyl-2-indolinone-trifluoroacetate Prepared from the resin obtained according to Example II and 4-(1,1-dioxo-thiomorpholin-4-yl-methyl)-aniline $R_f$ value: 0.30 (silica gel, methylene chloride/methanol=9:1) $C_{27}H_{26}N_4O_4S$ Mass spectrum: m/z=502 ($m^+$).

(7) 3-Z-[1-(4-(benzylaminomethyl)-anilino)-1-phenyl-methylene]-6-carbamoyl-2-indolinone-trifluoroacetate Prepared from the resin obtained according to Example II and 4-[N-(phenyl-methyl)-N-tert.butoxycarbonyl-aminomethyl]-aniline $R_f$ value: 0.40 (silica gel, methylene chloride/methanol=4:1) $C_{30}H_{26}N_4O_2$ Mass spectrum: m/z=474 ($m^+$).

(8) 3-Z-[1-(4-(amino-methyl)-anilino)-1-phenyl-methylene-6-carbamoyl-2-indolinone-trifluoroacetate Prepared from the resin obtained according to Example II and 4-(N-tert.butoxycarbonyl-aminomethyl)-aniline $R_f$ value: 0.10 (silica gel, methylene chloride/methanol=4:1) $C_{23}H_{20}N_4O_2$ Mass spectrum: m/z=384 ($m^+$).

(9) 3-Z-[1-(4-(2,6-dimethylpiperidin-1-yl-methyl)-anilino)-1-phenyl-methylene]-6-carbamoyl-2-indolinone-trifluoroacetate Prepared from the resin obtained according to Example II and 4-(2,6-dimethylpiperidin-1-yl-methyl)-aniline $R_f$ value: 0.45 (silica gel, methylene chloride/methanol=4:1) $C_{30}H_{32}N_4O_2$ Mass spectrum: m/z=480 (m$^+$).

(10) 3-Z-[1-(4-(pyrrolidin-1-yl-methyl)-anilino)-1-phenyl-methylene]-6-carbamoyl-2-indolinone-trifluoroacetate Prepared from the resin obtained according to Example II and 4-(pyrrolidin-1-yl-methyl)-aniline $R_f$ value: 0.15 (silica gel, methylene chloride/methanol=4:1) $C_{27}H_{26}N_4O_2$ Mass spectrum: m/z=438 (m$^+$).

(11) 3-Z-[1-(3-(dimethylaminomethyl)-anilino)-1-phenyl-methylene]-6-carbamoyl-2-indolinone-trifluoroacetate Prepared from the resin obtained according to Example II and 3-dimethylaminomethyl-aniline $R_f$ value: 0.23 (silica gel, methylene chloride/methanol=4:1) $C_{25}H_{24}N_4O_2$ Mass spectrum: m/z=412 (m$^+$).

(12) 3-Z-[1-(3-(N-methyl-N-ethyl-aminomethyl)-anilino)-1-phenyl-methylene]-6-carbamoyl-2-indolinone-trifluoroacetate Prepared from the resin obtained according to Example II and 3-(N-methyl-N-ethyl-aminomethyl)-aniline $R_f$ value: 0.23 (silica gel, methylene chloride/methanol=4:1). $C_{26}H_{26}N_4O_2$ Mass spectrum: m/z=426 (m$^+$).

(13) 3-Z-[1-(3-(methylaminomethyl)-anilino)-1-phenyl-methylene]-6-carbamoyl-2-indolinone-trifluoroacetate Prepared from the resin obtained according to Example II and 4-(N-tert.butoxycarbonyl-N-methyl-aminomethyl)-aniline $R_f$ value: 0.06 (silica gel, methylene chloride/methanol=4:1) $C_{24}H_{22}N_4O_2$ Mass spectrum: m/z=399 (m+H$^+$).

(14) 3-Z-[1-(3-hydroxymethyl-anilino)-1-phenyl-methylene]-6-carbamoyl-2-indolinone Prepared from the resin obtained according to Example II and 3-amino-benzyl alcohol $R_f$ value: 0.7 (silica gel, methylene chloride/methanol=4:1) $C_{23}H_{19}N_3O_3$ Mass spectrum: m/z=385 (m$^+$).

(15) 3-Z-[1-(4-methoxycarbonylmethyl-aminomethyl)-anilino)-1-phenyl-methylene]-6-carbamoyl-2-indolinone-trifluoroacetate Prepared from the resin obtained according to Example II and 4-(N-methoxycarbonylmethyl-N-tert.butoxycarbonyl-aminomethyl)-aniline $R_f$ value: 0.40 (silica gel, methylene chloride/methanol=9:1) $C_{26}H_{24}N_4O_4$ Mass spectrum: m/z=457 (m+H$^+$).

(16) 3-Z-[1-(4-(N-methylsulphonyl-N-(dimethylaminocarbonyl-methyl)-amino)-anilino)-1-phenyl-methylene]-6-carbamoyl-2-indolinone Prepared from the resin obtained according to Example II and 4-(N-methylsulphonyl-N-(dimethylaminocarbonylmethyl)-amino)-aniline $R_f$ value: 0.40 (silica gel, methylene chloride/methanol=9:1) $C_{27}H_{27}N_5O_5S$ Mass spectrum: m/z=533 (m$^+$).

(17) 3-Z-[1-(4-(N-acetyl-aminomethyl)-anilino)-1-phenyl-methylene]-6-carbamoyl-2-indolinone Prepared from the resin obtained according to Example II and 4-(N-acetyl-aminomethyl)-aniline $R_f$ value: 0.70 (silica gel, methylene chloride/methanol=4:1) $C_{25}H_{22}N_4O_3$ Mass spectrum: m/z=426 (m$^+$).

(18) 3-Z-[1-(3,4-dimethoxy-anilino)-1-phenyl-methylene]-6-carbamoyl-2-indolinone Prepared from the resin obtained according to Example II and 3,4-dimethoxy-aniline $R_f$ value: 0.40 (silica gel, methylene chloride/methanol=9:1) $C_{24}H_{21}N_3O_4$ Mass spectrum: m/z=415 (m$^+$).

(19) 3-Z-[1-(4-(morpholin-4-yl)-anilino)-1-phenyl-methylene]-6-carbamoyl-2-indolinone-trifluoroacetate Prepared from the resin obtained according to Example II and 4-morpholin-4-yl-aniline $R_f$ value: 0.20 (silica gel, methylene chloride/methanol=9:1) $C_{26}H_{24}N_4O_3$ Mass spectrum: m/z=440 (m$^+$).

(20) 3-Z-[1-(4-acetylamino-anilino)-1-phenyl-methylene]-6-carbamoyl-2-indolinone Prepared from the resin obtained according to Example II and 4-acetylamino-aniline $R_f$ value: 0.25 (silica gel, methylene chloride/methanol=9;1) $C_{24}H_{20}N_4O_3$ Mass spectrum: m/z=412 (m$^+$).

(21) 3-Z-[1-(4-amino-anilino)-1-phenyl-methylene]-6-carbamoyl-2-indolinone

Prepared from the resin obtained according to Example II and 4-amino-aniline $R_f$ value: 0.40 (silica gel, methylene chloride/methanol=9:1) $C_{22}H_{18}N_4O_2$ Mass spectrum: m/z=370 (m$^+$).

(22) 3-Z-[1-(4-N-methyl-N-acetyl-amino-anilino)-1-phenyl-methylene]-6-carbamoyl-2-indolinone Prepared from the resin obtained according to Example II and 4-(N-methyl-N-acetyl-amino)-aniline $C_{25}H_{22}N_4O_3$ Mass spectrum: m/z=426 (m$^+$).

(23) 3-Z-[1-(4-ethoxycarbonyl-anilino)-1-phenyl-methylene]-6-carbamoyl-2-indolinone Prepared from the resin obtained according to Example II and ethyl 4amino-benzoate $C_{25}H_{21}N_3O_4$ Mass spectrum: m/z=427 (m$^+$).

(24) 3-Z-[1-(4-carboxy-anilino)-1-phenyl-methylene]-6-carbamoyl-2-indolinone

Prepared from the resin obtained according to Example II and 4-amino-benzoic acid $R_f$ value: 0.11 (silica gel, methylene chloride/methanol=9:1) $C_{23}H_{17}N_3O_4$ Mass spectrum: m/z=398 (m–H$^+$).

(25) 3-Z-[1-(4-benzylcarbamoyl-anilino)-1-phenyl-methylene]-6-carbamoyl-2-indolinone Prepared from the resin obtained according to Example II and 4-amino-benzoic acid-benzylamide $R_f$ value: 0.21 (silica gel, methylene chloride/methanol=9:1) $C_{30}H_{24}N_4O_3$ Mass spectrum: m/z=488 (m$^+$).

(26) 3-Z-[1-(cyclohexyl-amino)-1-phenyl-methylene]-6-carbamoyl-2-indolinone

Prepared from the resin obtained according to Example II and cyclohexylamine $R_f$ value: 0.60 (silica gel, methylene chloride/methanol=9:1) $C_{22}H_{23}N_3O_2$ Mass spectrum: m/z=361 (m$^+$).

(27) 3-Z-[1-(4-amino-cyclohexyl-amino)-1-phenyl-methylene]-6-carbamoyl-2-indolinone-trifluoroacetate Prepared from the resin obtained according to Example II and 4-amino-cyclohexylamine $C_{22}H_{24}N_4O_2$ Mass spectrum: m/z=376 (m$^+$).

(28) 3-Z-[1-(N-methyl-piperidine-4-yl-amino)-1-phenyl-methylene]-6-carbamoyl-2-indolinone-trifluoroacetate Prepared from the resin obtained according to Example II and 4-amino-1-methyl-piperidine $R_f$ value: 0.15 (silica gel, methylene chloride/methanol=4:1) $C_{22}H_{24}N_4O_2$ Mass spectrum: m/z=376 (m$^+$).

(29) 3-Z-[1-(4-(piperidin-1-yl-methyl)-anilino)-1-methyl-methylene]-6-carbamoyl-2-indolinone-trifluoroacetate Prepared from the resin obtained according to Example II(2) and 4-(piperidin-1-yl-methyl)-aniline $R_f$ value: 0.30 (silica gel, methylene chloride/methanol=4:1) $C_{23}H_{26}N_4O_2$ Mass spectrum: m/z=390 (m$^+$).

(30) 3-Z-f 1-(3-dimethylaminomethyl-anilino)-1-methyl-methylene]-6-carbamoyl-2-indolinone-trifluoroacetate Prepared from the resin obtained according to Example II(2) and 3-dimethylaminomethyl-aniline $R_f$ value: 0.51 (silica gel, methylene chloride/methanol=4:1) $C_{20}H_{22}N_4O_2$ Mass spectrum: m/z=351 (m+H$^+$).

(31) 3-Z-[1-(4-(N-methyl-N-benzyl-aminomethyl)-anilino)-1-methyl-methylene]-6-carbamoyl-2-indolinone-trifluoroacetate Prepared from the resin obtained according to Example II(2) and 4-(N-methyl-N-benzyl-aminomethyl)-aniline $R_f$ value: 0.73 (silica gel, methylene chloride/methanol=4:1) $C_{26}H_{26}N_4O_2$ Mass spectrum: m/z=426 (m$^+$).

(32) 3-Z-[1-(4-(N-methylsulphonyl-N-(2-dimethylamino-ethyl)-amino)-anilino)-1-methyl-methylene]-6-carbamoyl-2-indolinone-trifluoroacetate Prepared from the resin obtained according to Example II(2) and 4-(N-methylsulphonyl-N-(2-dimethylamino-ethyl)-amino)-aniline $C_{22}H_{27}N_5O_4S$ Mass spectrum: m/z=458 (m+H$^+$).

(33) 3-Z-[1-(4-chloro-anilino)-1-methyl-methylene]-6-carbamoyl-2-indolinone

Prepared from the resin obtained according to Example II(2) and 4-chloro-aniline $R_f$ value: 0.10 (silica gel, methylene chloride/methanol=9:1) $C_{17}H_{14}ClN_3O_2$ Mass spectrum: m/z=327/329 (m$^+$).

(34) 3-Z-[1-(3-chloro-anilino)-1-methyl-methylene]-6-carbamoyl-2-indolinone

Prepared from the resin obtained according to Example II(2) and 3-chloro-aniline $R_f$ value: 0.11 (silica gel, methylene chloride/methanol=9:1) $C_{17}H_{14}ClN_3O_2$ Mass spectrum: m/z=327/329 (m$^+$).

(35) 3-Z-[1-(4-methoxycarbonyl-anilino)-1-methyl-methylene]-6-carbamoyl-2-indolinone Prepared from the resin obtained according to Example II(2) and methyl 4-amino-benzoate $R_f$ value: 0.11 (silica gel, methylene chloride/methanol=9:1) $C_{19}H_{17}N_3O_4$ Mass spectrum: m/z=351 (m$^+$).

(36) 3-Z-[1-(4-carboxy-anilino)-1-methyl-methylene]-6-carbamoyl-2-indolinone

Prepared from the resin obtained according to Example II(2) and 4-amino-benzoic acid $C_{18}H_{15}N_3O_4$ Mass spectrum: m/z=336 (m–H$^+$).

(37) 3-Z-[1-(4-methyl-3-nitro-anilino)-1-methyl-methylene]-6-carbamoyl-2-indolinone Prepared from the resin obtained according to Example II(2) and 4-methyl-3-nitro-aniline $R_f$ value: 0.82 (silica gel, methylene chloride/methanol=4:1) $C_{18}H_{16}N_4O_4$ Mass spectrum: m/z=352 (m$^+$).

(38) 3-Z-[1-(4-(piperidin-1-yl-methyl)-anilino)-1-propyl-methylene]-6-carbamoyl-2-indolinone-trifluoroacetate Prepared from the resin obtained according to Example II(4) and 4-(piperidin-1-yl-methyl)-aniline $R_f$ value: 0.37 (silica gel, methylene chloride/methanol=4:1) $C_{25}H_{30}N_4O_2$ Mass spectrum: m/z=418 (m$^+$).

(39) 3-Z-[1-(3-dimethylaminomethyl-anilino)-1-propyl-methylene]-6-carbamoyl-2-indolinone-trifluoroacetate Prepared from the resin obtained according to Example II(4) and 3-dimethylaminomethyl-aniline $R_f$ value: 0.42 (silica gel, methylene chloride/methanol=4:1) $C_{22}H_{26}N_4O_2$ Mass spectrum: m/z=378 (m$^+$).

(40) 3-Z-[1-(4-(N-methyl-N-benzyl-aminomethyl)-anilino)-1-propyl-methylene]-6-carbamoyl-2-indolinone-trifluoroacetate Prepared from the resin obtained according to Example II(4) and 4-(N-methyl-N-benzyl-aminomethyl)-aniline $R_f$ value: 0.81 (silica gel, methylene chloride/methanol=4:1) $C_{28}H_{30}N_4O_2$ Mass spectrum: m/z=454 (m$^+$).

(41) 3-Z-[1-(4-(N-methylsulphonyl-N-(2-dimethylamino-ethyl)-amino)-anilino)-1-propyl-methylene]-6-carbamoyl-2-indolinone-trifluoroacetate Prepared from the resin obtained according to Example II(4) and 4-(N-methylsulphonyl-N-(2-dimethylamino-ethyl)-amino)-aniline $R_f$ value: 0.59 (silica gel, methylene chloride/methanol=4:1) $C_{24}H_{31}N_5O_4S$ Mass spectrum: m/z=486 (m+H$^+$).

(42) 3-Z-[1-(4-chloro-anilino)-1-propyl-methylene]-6-carbamoyl-2-indolinone

Prepared from the resin obtained according to Example II(4) and 4-chloro-aniline $R_f$ value: 0.17 (silica gel, methylene chloride/methanol=9:1) $C_{19}H_{18}ClN_3O_2$ Mass spectrum: m/z=355/357 (m$^+$).

(43) 3-Z-[1-(3-chloro-anilino)-1-propyl-methylene]-6-carbamoyl-2-indolinone

Prepared from the resin obtained according to Example II(4) and 3-chloro-aniline $R_f$ value: 0.12 (silica gel, methylene chloride/methanol=9:1).

$C_{19}H_{18}ClN_3O_2$

Mass spectrum: m/z=355/357 (m$^+$).

(44) 3-Z-[1-(4-methoxycarbonyl-anilino)-1-propyl-methylene]-6-carbamoyl-2-indolinone Prepared from the resin obtained according to Example II(4) and methyl 4-amino-benzoate $R_f$ value: 0.8 (silica gel, methylene chloride/methanol=4:1) $C_{21}H_{21}N_3O_4$ Mass spectrum: m/z=379 (m$^+$).

(45) 3-Z-[1-(4-carboxy-anilino)-1-propyl-methylene]-6-carbamoyl-2-indolinone

Prepared from the resin obtained according to Example II(4) and 4-amino-benzoic acid $C_{20}H_{19}N_3O_4$ Mass spectrum: m/z=364 (m–H$^+$).

(46) 3-Z-[1-(4-methyl-3-nitro-anilino)-1-propyl-methylene]-6-carbamoyl-2-indolinone Prepared from the resin obtained according to Example II(4) and 4-methyl-3-nitro-aniline $R_f$ value: 0.86 (silica gel, methylene chloride/methanol=4:1) $C_{20}H_{20}N_4O_4$ Mass spectrum: m/z=380 (m$^+$).

EXAMPLE 2

3-Z-[1-(3-(piperidin-1-yl-methyl)-anilino)-1-phenyl-methylene]-6-carbamoyl-2-indolinone-trifluoroacetate 2.0 g of resin obtained according to Example II are reacted analogously to Example 1 with 2.0 g of 3-aminobenzyl alcohol in 20 ml of dimethylformamide for 22 hours at 70° C. Then the solvent is suction filtered and the resin is washed several times with dimethylformamide and methylene chloride. Then 200 mg of the moist charged resin are suspended in 2 ml of methylene chloride and left to stand with 0.2 ml of methanesulphonic acid chloride and 0.1 ml of triethylamine for 2 hours at room temperature. Then the resin is washed several times with methylene chloride, suspended in 2 ml of methylene chloride and combined with 0.2 ml of piperidine. After 1 hour the resin is washed with methylene chloride and dimethylformamide and then treated with trifluoroacetic acid analogously to Example 1.

Yield: 15 mg. $R_f$ value: 0.30 (silica gel, methylene chloride/methanol=4:1) $C_{28}H_{28}N_4O_2$ Mass spectrum: m/z=452 (m$^+$).

The following compounds are prepared analogously to Example 2:

(1) 3-Z-[1-(3-diethylaminomethyl)-anilino)-1-phenyl-methylene]-6-carbamoyl-2-indolinone-trifluoroacetate Prepared from the resin obtained according to Example II and diethylamine $R_f$ value: 0.80 (silica gel, methylene chloride/methanol 4:1) $C_{27}H_{28}N_4O_2$ Mass spectrum: m/z=440 (m$^+$).

(2) 3-Z-[1-(3-(benzylaminomethyl)-anilino)-1-phenyl-methylene]-6-carbamoyl-2-indolinone-trifluoroacetate Prepared from the resin obtained according to Example II and benzylamine $R_f$ value: 0.80 (silica gel, methylene chloride/methanol=4:1) $C_{30}H_{26}N_4O_2$ Mass spectrum: m/z=474 (m$^+$).

(3) 3-Z-[1-(3-(N-methyl-N-benzyl-aminomethyl)-anilino)-1-phenyl-methylene]-6-carbamoyl-2-indolinone-trifluoroacetate Prepared from the resin obtained according to Example II and N-methyl-benzylamine $R_f$ value: 0.80 (silica gel, methylene chloride/methanol=4:1) $C_{31}H_{28}N_4O_2$ Mass spectrum: m/z=488 (m$^+$).

(4) 3-Z-[1-(3-(butylaminomethyl)-anilino)-1-phenyl-methylene]-6-carbamoyl-2-indolinone-trifluoroacetate Prepared from the resin obtained according to Example II and butylamine $R_f$ value: 0.40 (silica gel, methylene chloride/methanol=4:1) $C_{27}H_{28}N_4O_2$ Mass spectrum: m/z=440 (m$^+$).

(5) 3-Z-[1-(3-(aminomethyl)-anilino)-1-phenyl-methylene]-6-carbamoyl-2-indolinone-trifluoroacetate Prepared from the resin obtained according to Example II and ammonia $C_{23}H_{20}N_4O_2$ Mass spectrum: m/z=385 (m+H$^+$).

(6) 3-Z-[1-(3-(N-(3-dimethylaminopropyl)-N-methyl-amino-methyl)-anilino)-1-phenyl-methylene]-6-carbamoyl-2-indolinone-trifluoroacetate Prepared from the resin obtained according to Example II and 1-dimethylamino-3-methylaminopropane $R_f$ value: 0.67 (silica gel, methylene chloride/methanol=4:1) $C_{29}H_{33}N_5O_2$ Mass spectrum: m/z=484 (m+H$^+$).

(7) 3-Z-[1-(3N-(2-dimethylaminoethyl)-N-methyl-aminomethyl)-anilino)-1-phenyl-methylene]-6-carbamoyl-2-indolinone-trifluoroacetate Prepared from the resin obtained according to Example II and 1-dimethylamino-2-methylaminoethane $R_f$ value: 0.40 (silica gel, methylene chloride/methanol=4:1) $C_{28}H_{31}N_5O_2$ Mass spectrum: m/z=470 (m+H$^+$).

EXAMPLE 3

3-Z-[1-(4-(piperidin-1-yl-methyl)-anilino)-1-phenyl-methylene]-6-ethoxycarbonyl-2-indolinone 1.5 g of 1-acetyl-3-(1-ethoxy-1-phenylmethylene)-6-ethoxycarbonyl-2-indolinone and 1.1 g of 4-(piperidin-1-yl-methyl)-aniline are dissolved in 15 ml of dimethylformamide and stirred for 45 minutes at 100° C. After cooling 5.0 ml of piperidine are added and the mixture is stirred for another 3 hours at room temperature. The solvent is removed and the residue purified over an aluminium oxide column (activity: 2–3) with methylene chloride/ethanol (100:3) as eluant.

Yield: 1.1 g (58% of theory), $R_f$ value: 0.5 (aluminium oxide, methylene chloride/ethanol=100:3) $C_{30}H_{31}N_3O_3$ Mass spectrum: m/z=481 [M$^+$].

The following compounds are prepared analogously to Example 3:

(1) 3-Z-[1-(4-bromo-anilino)-1-phenyl-methylene]-6-ethoxy-carbonyl-2-indolinone

Prepared from 1-acetyl-3-(1-ethoxy-1-phenylmethylene)-6-ethoxycarbonyl-2-indolinone and 4-bromoaniline $R_f$ value: 0.4 (silica gel, toluene/ethyl acetate=5:1) $C_{24}H_{19}BrN_2O_3$ Mass spectrum: m/z=462/464 [M$^+$].

(2) 3-Z-[1-(3-(dimethylaminomethyl)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 3-(dimethylaminomethyl)-aniline $R_f$ value: 0.5 (aluminium oxide, methylene chloride/ethanol=30:1) $C_{27}H_{27}N_3O_3$ ESI mass spectrum: m/z=442 [M+H$^+$].

(3) 3-Z-[1-(4-(dimethylaminomethyl)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-(dimethylaminomethyl)-aniline $R_f$ value: 0.7 (aluminium oxide, ethyl acetate/ethanol=20:1) $C_{27}H_{27}N_3O_3$ ESI mass spectrum: m/z=442 [M+H$^+$].

(4) 3-Z-[1-(4-[(2,6-dimethyl-piperidin-1-yl)-methyl]-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-[(2,6-dimethyl-piperidin-1-yl)-methyl]-aniline $R_f$ value: 0.6 (silica gel, methylene chloride/ethanol=5:1) $C_{32}H_{35}N_3O_3$ Mass spectrum: m/z=509 [M$^+$].

(5) 3-Z-[1-(4-(2-dimethylamino-ethyl)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-(2-dimethylamino-ethyl)-aniline $R_f$ value: 0.2 (silica gel, methylene chloride/ethanol=5:1) $C_{28}H_{29}N_3O_3$ Mass spectrum: m/z=455 [M$^+$].

(6) 3-Z-[1-(4-(2-dimethylamino-ethyl)-N-acetyl-amino)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-(N-(2-dimethylamino-ethyl)-N-acetyl-amino)-aniline $R_f$ value: 0.4 (aluminium oxide, methylene chloride/ethanol=20:1) $C_{30}H_{32}N_4O_4$ Mass spectrum: m/z=512 [M$^+$].

(7) 3-Z-[1-(4-tert.butyloxycarbonyl-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-tert.butyloxycarbonyl-aniline $R_f$ value: 0.4 (aluminium oxide, methylene chloride/ethanol=40:1) $C_{29}H_{28}N_2O_5$ Mass spectrum: m/z=484 [M$^+$].

(8) 3-Z-[1-(4-(N-(3-dimethylamino-propyl)-N-acetyl-amino)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-(N-(3-dimethylamino-propyl)-N-acetyl-amino)-aniline $R_f$ value: 0.2 (aluminium oxide, methylene chloride/ethanol=40:1) $C_{31}H_{34}N_4O_4$ Mass spectrum: m/z=526 [M$^+$].

(9) 3-Z-[1-(4-(N-(2-dimethylamino-ethyl)-N-methylsulphonyl-amino)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and N-(2-dimethylamino-ethyl)-N-methylsulphonyl-p-phenylenediamine $R_f$ value: 0.3 (aluminium oxide, methylene chloride/ethanol=40:1) $C_{29}H_{32}N_4O_5S$ Mass spectrum: m/z=548 [M$^+$].

(10) 3-Z-[1-(4-(4-methyl-piperazin-1-yl)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-(4-methyl-piperazin-1-yl)-aniline $R_f$ value: 0.3 (aluminium oxide, ethyl acetate) $C_{29}H_{30}N_4O_3$ ESI mass spectrum: m/z=483 [M+H$^+$].

(11) 3-Z-[1-(4-(N-(2-dimethylamino-ethyl)-N-methyl-amino)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-(N-(2-dimethylamino-ethyl)-N-methyl-amino)-aniline $R_f$ value: 0.5 (aluminium oxide, methylene chloride/ethanol=20:1) $C_{29}H_{32}N_4O_3$ ESI mass spectrum: m/z=485 [M+H$^+$].

(12) 3-Z-[1-(4-(N-(3-dimethylamino-propyl)-N-methyl-amino)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-(N-(3-dimethylamino-propyl)-N-methyl-amino)-aniline $R_f$ value: 0.5 (aluminium oxide, ethyl acetate) $C_{30}H_{34}N_4O_3$ ESI mass spectrum: m/z=499 [M+H$^+$].

(13) 3-Z-[1-(4-(N-methyl-acetylamino)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-amino-N-methyl-acetanilide $R_f$ value: 0.3 (silica gel, methylene chloride/ethanol=15:1) $C_{27}H_{25}N_3O_4$ Mass spectrum: m/z=455 [M$^+$].

(14) 3-Z-[1-(4-(N-methyl-methylsulphonylamino)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and N-(4-aminophenyl)-N-methyl-methanesulphonamide $R_f$ value: 0.8 (aluminium oxide, ethyl acetate) $C_{26}H_{25}N_3O_5S$ Mass spectrum: m/z=491 [M$^+$].

(15) 3-Z-[1-(4-(N-(3-dimethylamino-propyl)-N-methylsulphonyl-amino)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and N-(3-dimethylamino-propyl)-N-methylsulphonyl-p-phenylenediamine $R_f$ value: 0.6 (silica gel, methylene chloride/ethanol/ammonia=5:2:0.01) $C_{30}H_{34}N_4O_5S$ ESI mass spectrum: m/z=563 [M+H$^+$].

(16) 3-Z-[1-(4-(N-dimethylaminocarbonylmethyl-N-methylsulphonyl-amino)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-(N-dimethylaminocarbonylmethyl-N-methylsulphonyl)-amino)-aniline $R_f$ value: 0.6 (silica gel, methylene chloride/ethanol=10:1) $C_{29}H_{30}N_4O_6S$ ESI mass spectrum: m/z=561 [M−H$^-$].

(17) 3-Z-[1-(4-(imidazol-4-yl)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-(imidazol-4-yl)-aniline $R_f$ value: 0.5 (silica gel, methylene chloride/ethanol/ammonia=10:1:0.01) $C_{27}H_{22}N_4O_3$ Mass spectrum: m/z=450 [M$^+$].

(18) 3-Z-[1-(4-(tetrazol-5-yl)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-(tetrazol-5-yl)-aniline $R_f$ value: 0.5 (silica gel, methylene chloride/ethanol=5:1) $C_{25}H_{20}N_6O_3$ ESI mass spectrum: m/z=451 [M−H$^-$].

(19) 3-Z-[1-(4-(N-benzyl-N-methyl-aminomethyl)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-(N-benzyl-N-methyl-aminomethyl)-aniline $R_f$ value: 0.4 (silica gel, methylene chloride/ethanol=10:1) $C_{33}H_{31}N_3O_3$ ESI mass spectrum: m/z=516 [M−H$^-$].

(20) 3-Z-[1-(4-(N-(2-dimethylamino-ethyl)-N-propionyl-amino)-aniline)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-[N-(2-dimethylamino-ethyl)-N-propionyl-amino]-aniline $R_f$ value: 0.2 (silica gel, methylene chloride/ethanol=5:1) $C_{31}H_{34}N_4O_4$ ESI mass spectrum: m/z=525 [M−H$^-$].

(21) 3-Z-[1-(4-(pyrrolidin-1-yl-methyl)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-(pyrrolidin-1-yl-methyl)-aniline $R_f$ value: 0.1 (silica gel, methylene chloride/ethanol=5:1) $C_{29}H_{29}N_3O_3$ ESI mass spectrum: m/z=466 [M−H$^-$].

(22) 3-Z-[1-(4-(N-methyl-N-phenethyl-aminomethyl)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and (N-phenethyl-N-methyl-aminomethyl)-aniline $R_f$ value: 0.4 (silica gel, methylene chloride/ethanol=10:1) $C_{34}H_{33}N_3O_3$ ESI mass spectrum: m/z=530 [M−H$^-$].

(23) 3-Z-[1-(4-(N-dimethylaminomethylcarbonyl-N-methyl-amino)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and N-dimethylaminomethylcarbonyl-N-methyl-p-phenylenediamine $R_f$ value: 0.1 (silica gel, methylene chloride/ethanol=10:1) $C_{29}H_{30}N_4O_4$ ESI mass spectrum: m/z=497 [M–H⁻].

(24) 3-Z-[1-(4-(N-2-dimethylamino-ethyl)-N-ethylsulphonyl-amino)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and N-(2-dimethylamino-ethyl)-N-ethylsulphonyl-p-phenylenediamine $R_f$ value: 0.6 (silica gel, methylene chloride/ethanol=5:1) $C_{30}H_{34}N_4O_5S$ ESI mass spectrum: m/z=561 [M–H⁻].

(25) 3-Z-[1-(4-(N-tert.butoxycarbonyl-N-ethyl-aminomethyl)-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and 4-(N-tert.butoxycarbonyl-N-ethyl-aminomethyl)-aniline $R_f$ value: 0.5 (silica gel, methylene chloride/methanol=10:1) $C_{32}H_{35}N_3O_5$ ESI mass spectrum: m/z=540 [M–H⁻].

(26) 3-Z-[1-(4-(piperidin-1-yl-methyl)-anilino)-1-ethyl-methylene]-6-ethoxycarbonyl-2-indolinone Prepared from 1-acetyl-3-(1-ethoxy-1-ethyl-methylene)-6-ethoxycarbonyl-2-indolinone and 4-(piperidin-1-yl-methyl)-aniline $R_f$ value: 0.9 (silica gel, methylene chloride/ethanol=5:1) $C_{26}H_{31}N_3O_3$ ESI mass spectrum: m/z=432 [M–H⁻].

(27) 3-Z-[1-(4-(N-(2-dimethylamino-ethyl)-N-methylsulphonyl-amino)-anilino)-1-ethyl-methylene]-6-ethoxycarbonyl-2-indolinone Prepared from 1-acetyl-3-(1-ethoxy-1-ethyl-methylene)-6-ethoxycarbonyl-2-indolinone and N-(2-dimethylamino-ethyl)-N-methylsulphonyl-p-phenylenediamine $R_f$ value: 0.3 (silica gel, methylene chloride/ethanol=5:1) $C_{25}H_{32}N_4O_5S$ ESI mass spectrum: m/z=499 [M–H⁻].

(28) 3-Z-[1-(4-(dimethylaminomethyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(dimethylaminomethyl)-aniline $R_f$ value: 0.6 (silica gel, methylene chloride/methanol=5:1) $C_{26}H_{25}N_3O_3$ ESI mass spectrum: m/z=428 [M+H⁺].

(29) 3-Z-[1-(4-[(2,6-dimethyl-piperidin-1-yl)-methyl]-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-[(2,6-dimethyl-piperidin-1-yl)-methyl]-aniline $R_f$ value: 0.5 (RP 8, methanol/five percent saline solution=4:1) $C_{31}H_{33}N_3O_3$ ESI mass spectrum: m/z=496 [M+H⁺].

(30) 3-Z-[1-(4-(N-(2-dimethylamino-ethyl)-N-methylsulphonyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(2-dimethylamino-ethyl)-N-methylsulphonyl-p-phenylenediamine $R_f$ value: 0.6 (silica gel, methylene chloride/ethanol=5:1) $C_{28}H_{30}N_4O_5S$ ESI mass spectrum: m/z=533 [M–H⁻].

(31) 3-Z-[1-(4-(N-(3-dimethylamino-propyl)-N-methylsulphonyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(3-dimethylamino-propyl)-N-methylsulphonyl-p-phenylenediamine $R_f$ value: 0.5 (aluminium oxide, methylene chloride/methanol=30:1) $C_{29}H_{32}N_4O_5S$ ESI mass spectrum: m/z=547 [M–H⁻].

(32) 3-Z-[1-(4-(N-dimethylaminocarbonylmethyl-N-methylsulphonyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-dimethylaminocarbonyl-methyl-N-methylsulphonyl)-amino)-aniline $R_f$ value: 0.5 (aluminium oxide, methylene chloride/methanol=20:1) $C_{28}H_{28}N_4O_6S$ ESI mass spectrum: m/z=547 [M–H⁻].

(33) 3-Z-[1-(4-(N-acetyl-N-dimethylaminocarbonylmethyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-acetyl-N-dimethylaminocarbonylmethyl)-amino)-aniline $R_f$ value: 0.6 (silica gel, methylene chloride/methanol=10:1) $C_{29}H_{28}N_4O_5$ ESI mass spectrum: m/z=511 [M–H⁻].

(34) 3-Z-[1-(4-(N-dimethylaminocarbonylmethyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-dimethylaminocarbonyl-methyl)-amino)-aniline $R_f$ value: 0.6 (aluminium oxide, methylene chloride/methanol=30:1) $C_{27}H_{26}N_4O_4$ ESI mass spectrum: m/z=469 [M–H⁻].

(35) 3-Z-[1-(4-(N-(3-dimethylamino-propyl)-N-acetyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(3-dimethylamino-propyl)-N-acetyl-p-phenylenediamine $R_f$ value: 0.5 (aluminium oxide, methylene chloride/methanol=20:1) $C_{30}H_{32}N_4O_4$ ESI mass spectrum: m/z=511 [M–H⁻].

(36) 3-Z-[1-(4-(N-methylaminocarbonylmethyl-N-methylsulphonyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-methylaminocarbonylmethyl-N-methylsulphonyl-p-phenylenediamine $R_f$ value: 0.5 (silica gel, methylene chloride/methanol=10:1) $C_{27}H_{26}N_4O_6S$ ESI mass spectrum: m/z=533 [M–H⁻].

(37) 3-Z-[1-(4-((imidazolidin-2,4-dion-5-ylidene)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((imidazolidin-2,4-dion-5-ylidene)-methyl)-aniline $R_f$ value: 0.4 (silica gel, methylene chloride/methanol=10:1) $C_{27}H_{20}N_4O_5$ ESI mass spectrum: m/z=479 [M–H⁻].

(38) 3-Z-[1-(4-(N-((2-dimethylamino-ethyl)-carbonyl)-N-methyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-((2- dimethylamino-ethyl)-carbonyl)-N-methyl-p-phenylenediamine $R_f$ value: 0.5 (aluminium oxide, methylene chloride/methanol=20:1) $C_{29}H_{30}N_4O_4$ ESI mass spectrum: m/z=497 [M–H⁻].

(39) 3-Z-[1-(4-(N-tert.butoxycarbonyl-aminomethyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-tert.butoxycarbonyl-aminomethyl)-aniline $R_f$ value: 0.3 (aluminium oxide, methylene chloride/methanol=20:1) $C_{29}H_{29}N_3O_5$ ESI mass spectrum: m/z=498 [M–H⁻].

(40) 3-Z-[1-(4-(2-oxo-pyrrolidin-1-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(2-oxo-pyrrolidin-1-yl-methyl)-aniline $R_f$ value: 0.3 (silica gel, methylene chloride/methanol=20:1) $C_{28}H_{25}N_3O_4$ ESI mass spectrum: m/z=466 [M–H⁻].

(41) 3-Z-[1-(4-(N-aminocarbonylmethyl-N-methylsulphonyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-aminocarbonylmethyl-N-methylsulphonyl-p-phenylenediamine $R_f$ value: 0.7 (silica gel, methylene chloride/methanol=5:1) $C_{26}H_{24}N_4O_6S$ ESI mass spectrum: m/z=519 [M–H⁻].

(42) 3-Z-[1-(4-(thiomorpholin-4-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(thiomorpholin-4-yl-methyl)-aniline $R_f$ value: 0.4 (silica gel, methylene chloride/methanol=15:1) $C_{28}H_{27}N_3O_3S$ ESI mass spectrum: m/z=484 [M–H⁻].

(43) 3-Z-[1-(4-(1,1-dioxo-thiomorpholin-4-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(1,1-dioxo-thiomorpholin-4-yl-methyl)-aniline $R_f$ value: 0.5 (silica gel, methylene chloride/methanol=10:1) $C_{28}H_{27}N_3O_5S$ ESI mass spectrum: m/z=516 [M–H⁻].

(44) 3-Z-[1-(4-(N-cyanomethyl-N-methylsulphonyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-cyanomethyl-N-methyl-sulphonyl-p-phenylenediamine $R_f$ value: 0.6 (silica gel, methylene chloride/methanol=10:1) $C_{26}H_{22}N_4O_5S$ ESI mass spectrum: m/z=501 [M–H⁻].

(45) 3-Z-[1-(4-(N-tert.butoxycarbonyl-ethylaminomethyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-ethyl-N-tert.butoxycarbonyl-aminomethyl)-aniline $R_f$ value: 0.6 (silica gel, methylene chloride/methanol=10:1) $C_{31}H_{33}N_3O_5$ ESI mass spectrum: m/z=526 [M–H⁻].

(46) 3-Z-[1-(4-(N-benzyl-N-methyl-aminomethyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-benzyl-N-methyl-aminomethyl)-aniline $R_f$ value: 0.5 (silica gel, methylene chloride/methanol=10:1) $C_{32}H_{29}N_3O_3$ ESI mass spectrum: m/z=502 [M–H⁻].

(47) 3-Z-[1-(4-(1-oxo-thiomorpholin-4-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(1-oxo-thiomorpholin-4-yl-methyl)-aniline $R_f$ value: 0.7 (silica gel, methylene chloride/methanol=10:1) $C_{28}H_{27}N_3O_4S$ ESI mass spectrum: m/z=500 [M–H⁻].

(48) 3-Z-[1-(4-(2-(imidazol-4-yl)-ethyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(2-(imidazol-4-yl)-ethyl)-aniline $R_f$ value: 0.4 (silica gel, methylene chloride/methanol=5:1) $C_{28}H_{24}N_4O_3$ ESI mass spectrum: m/z=463 [M–H⁻].

(49) 3-Z-[1-(4-(morpholin-4-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(morpholin-4-yl-methyl)-aniline $R_f$ value: 0.5 (silica gel, methylene chloride/methanol=10:1) $C_{28}H_{27}N_3O_4$ ESI mass spectrum: m/z=468 [M–H⁻].

(50) 3-Z-[1-(4-((4-methyl-piperazin-1-yl)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((4-methyl-piperazin-1-yl)-methyl)-aniline $R_f$ value: 0.4 (silica gel, methylene chloride/methanol 5:1) $C_{29}H_{30}N_4O_3$ ESI mass spectrum: m/z=481 [M–H⁻].

(51) 3-Z-[1-(4-((2-(N-benzyl-N-methyl-amino)-ethyl)-N-methylsulphonyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(2(N-benzyl-N-methyl-amino)-ethyl)-N-methylsulphonyl-amino)-aniline $R_f$ value: 0.7 (silica gel, methylene chloride/methanol=10:1) $C_{34}H_{34}N_4O_5S$ ESI mass spectrum: m/z=609 [M–H⁻].

(52) 3-Z-[1-(4-cyclohexylamino-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-cyclohexyl-p-phenylenediamine $R_f$ value: 0.8 (silica gel, methylene chloride/methanol=10:1) $C_{29}H_{28}N_2O_3$ ESI mass spectrum: m/z=451 [M–H⁻].

(53) 3-Z-[1-(4-(pyridin-4-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(pyridin-4-yl-methyl)-aniline $R_f$ value: 0.6 (silica gel, methylene chloride/methanol/ammonia=5:1:0.01) $C_{29}H_{23}N_3O_3$ ESI mass spectrum: m/z=460 [M–H⁻].

(54) 3-Z-[1-(4-(imidazol-1-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(imidazol-1-yl-methyl)-aniline $R_f$ value: 0.4 (silica gel, methylene chloride/methanol/ammonia=10:1:0.01) $C_{27}H_{22}N_4O_3$ ESI mass spectrum: m/z=449 [M–H⁻].

(55) 3-Z-[1-(4-(imidazol-1-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(imidazol-1-yl-methyl)-aniline $R_f$ value: 0.4 (silica gel, methylene chloride/methanol/ammonia=10:1:0.01) $C_{27}H_{22}N_4O_3$ ESI mass spectrum: m/z=449 [M–H$^-$].

(56) 3-Z-[1-(N-methyl-piperidine-4-yl-amino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-amino-1-methyl-piperidine $R_f$ value: 0.3 (silica gel, methylene chloride/methanol=5:1) $C_{23}H_{25}N_3O_3$ ESI mass spectrum: m/z=390 [M–H$^-$].

(57) 3-Z-[1-(4-(imidazol-4-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(imidazol-4-yl-methyl)-aniline $R_f$ value: 0.2 (silica gel, methylene chloride/methanol=5:1) $C_{27}H_{22}N_4O_3$ ESI mass spectrum: m/z=449 [M–H$^-$].

(58) 3-Z-[1-(4-((4-hydroxy-piperidin-1-yl)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((4-hydroxy-piperidin-1-yl)-methyl)-aniline $R_f$ value: 0.1 (silica gel, methylene chloride/methanol=10:1) $C_{29}H_{29}N_3O_3$ ESI mass spectrum: m/z=482 [M–H$^-$].

(59) 3-Z-[1-(4-((4-methoxy-piperidin-1-yl)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((4-methoxy-piperidin-1-yl)-methyl)-aniline $R_f$ value: 0.4 (silica gel, methylene chloride/methanol=10:1) $C_{30}H_{31}N_3O_4$ ESI mass spectrum: m/z=496 [M–H$^-$].

(60) 3-Z-[1-(4-benzyl-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-benzyl-aniline $R_f$ value: 0.6 (silica gel, methylene chloride/methanol=10:1) $C_{30}H_{24}N_2O_3$ Melting point: 224° C.

(61) 3-Z-[1-(4-(N-(3-trifluoroacetylamino-propyl)-N-methylsulphonyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(3-trifluoroacetylamino-propyl)-N-methylsulphonyl-p-phenylenediamine $R_f$ value: 0.5 (aluminium oxide, methylene chloride/methanol=20:1) $C_{29}H_{27}F_3N_4O_6S$ ESI mass spectrum: m/z=615 [M–H$^-$].

(62) 3-Z-[1-(4-tert.butoxycarbonylmethyl-anilino)-1-phenyl-methylene]-6-ethoxycarbonyl-2-indolinone Prepared from 1-acetyl-3-(1-ethoxy-1-phenylmethylene)-6-ethoxycarbonyl-2-indolinone and tert.butyl 4-aminophenylacetate $R_f$ value: 0.5 (aluminium oxide, ethyl acetate) $C_{30}H_{30}N_2O_5$ ESI mass spectrum: m/z=497 [M–H$^-$].

(63) 3-Z-[1-(4-tert.butoxycarbonyl-anilino)-1-ethyl-methylene]-6-ethoxycarbonyl-2-indolinone Prepared from 1-acetyl-3-(1-ethoxy-1-ethylmethylen)-6-ethoxycarbonyl-2-indolinone and 4-tert.butoxycarbonyl-aniline $R_f$ value: 0.4 (aluminium oxide, methylene chloride/ethanol=20:1) $C_{25}H_{28}N_2O_5$ ESI mass spectrum: m/z=435 [M–H$^-$].

(64) 3-Z-[1-(4-(4-tert.butoxycarbonyl-piperazin-1-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(4-tert.butoxycarbonyl-piperazin-1-yl-methyl)-aniline $R_f$ value: 0.5 (silica gel, methylene chloride/methanol=10:1) $C_{33}H_{36}N_4O_5$ ESI mass spectrum: m/z=567 [M–H$^-$].

(65) 3-Z-[1-(4-(1-methyl-imidazol-2-yl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(1-methyl-imidazol-2-yl)-aniline $R_f$ value: 0.6 (silica gel, methylene chloride/methanol=5:1) $C_{27}H_{22}N_4O_3$ ESI mass spectrum: m/z=449 [M–H$^-$].

(66) 3-Z-[1-(4-(N-(2-dimethylamino-ethyl)-N-methylsulphonyl-amino)-3-nitro-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 6-(N-(2-dimethylamino-ethyl)-N-methylsulphonyl-amino)-3-amino-nitrobenzene $R_f$ value: 0.6 (silica gel, methylene chloride/methanol=5:1) $C_{28}H_{29}N_5O_7S$.

ESI mass spectrum: m/z=578 [M–H$^-$].

(67) 3-Z-[1-(4-(N-(2-dimethylamino-ethyl)-N-methylsulphonyl-amino)-3-amino-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(2-dimethylamino-ethyl)-N-methylsulphonyl-amino)-3-amino-aniline $R_f$ value: 0.5 (aluminium oxide, methylene chloride/methanol=20:1) $C_{28}H_{31}N_5O_5S$ ESI mass spectrum: m/z=548 [M–H$^-$]. (68) 3-Z-[1-(4-((3-(N-benzyl-N-methyl-amino)-propyl)-N-methylsulphonyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(3-(N-benzyl-N-methyl-amino)-propyl)-N-methylsulphonyl-amino)-aniline $R_f$ value: 0.6 (silica gel, methylene chloride/methanol=10:1) $C_{35}H_{36}N_4O_5S$ ESI mass spectrum: m/z=623 [M–H$^-$].

(69) 3-Z-[1-(4N-(2-dimethylamino-ethyl)-N-methylsulphonyl-amino)-3-chloro-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(2-dimethylamino-ethyl)-N-methylsulphonyl-amino)-3-chloro-aniline $R_f$ value: 0.5 (silica gel, methylene chloride/methanol=10:1) $C_{28}H_{29}ClN_4O_5S$ ESI mass spectrum: m/z=567/569 [M–H$^-$].

(70) 3-Z-[1-(4-(N-dimethylaminomethylcarbonyl-N-methyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-dimethylaminomethylcarbonyl-N-methyl-p-phenylenediamine $R_f$ value: 0.5 (silica gel, methylene chloride/methanol=9:1) $C_{28}H_{28}N_4O_4$ ESI mass spectrum: m/z=483 [M–H$^-$].

(71) 3-Z-[1-(4N-(2-dimethylamino-ethyl)-N-acetyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(2-dimethylamino-ethyl)-N-acetyl-amino)-aniline $R_f$ value: 0.5 (silica gel, methylene chloride/methanol=9:1) $C_{29}H_{30}N_4O_4$ ESI mass spectrum: m/z=497 [M−H⁻].

(72) 3-Z-[1-(4-(N-(2-dimethylamino-ethyl)-N-propionyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(2-dimethylamino-ethyl)-N-propionyl-amino)-aniline $R_f$ value: 0.5 (silica gel, methylene chloride/methanol=9:1) $C_{30}H_{32}N_4O_4$ ESI mass spectrum: m/z=511 [M−H⁻].

(73) 3-Z-[1-(4-(N-(2-dimethylamino-ethyl)-N-butyryl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(2-dimethylamino-ethyl)-N-butyryl-amino)-aniline $R_f$ value: 0.5 (silica gel, methylene chloride/methanol=9:1) $C_{31}H_{34}N_4O_4$ ESI mass spectrum: m/z=525 [M−H⁻].

(74) 3-Z-[1-(4-(N-(2-dimethylamino-ethyl)-N-isobutyryl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(2-dimethylamino-ethyl)-N-isobutyryl-amino)-aniline $R_f$ value: 0.5 (silica gel, methylene chloride/methanol=9:1) $C_{31}H_{34}N_4O_4$ ESI mass spectrum: m/z=525 [M−H⁻].

(75) 3-Z-[1-(4-(N-(2-dimethylamino-ethyl)-N-benzoyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(2-dimethylamino-ethyl)-N-benzoyl-amino)-aniline $R_f$ value: 0.5 (silica gel, methylene chloride/methanol=9:1) $C_{34}H_{32}N_4O_4$ ESI mass spectrum: m/z=559 [M−H⁻].

(76) 3-Z-[1-(4-(N-(2-dimethylamino-ethyl)-N-acetyl-amino)-3-amino-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(2-dimethylamino-ethyl)-N-acetyl-amino)-3-amino-aniline $R_f$ value: 0.5 (aluminium oxide, methylene chloride/methanol=20:1) $C_{29}H_{31}N_5O_4$ ESI mass spectrum: m/z=512 [M−H⁻].

(77) 3-Z-[1-(4-(4-hydroxymethyl-piperidin-1-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(4-hydroxymethyl-piperidin-1-yl-methyl-amino)-aniline $R_f$ value: 0.3 (silica gel, methylene chloride/methanol=5:1) $C_{30}H_{31}N_3O_4$ ESI mass spectrum: m/z=496 [M−H⁻].

(78) 3-Z-[1-(4-(2-(4-hydroxy-piperidin-1-yl)-ethyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(2-(4-hydroxy-piperidin-1-yl)-ethyl-amino)-aniline $R_f$ value: 0.3 (silica gel, methylene chloride/methanol=5:1) $C_{30}H_{31}N_3O_4$ ESI mass spectrum: m/z=496 [M−H⁻].

(79) 3-Z-[1-(4-(N-(2-dimethylamino-ethyl)-N-propylsulphonyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(2-dimethylamino-ethyl)-N-propylsulphonyl-p-phenylenediamine $R_f$ value: 0.5 (silica gel, methylene chloride/methanol=9:1) $C_{30}H_{34}N_4O_5S$ ESI mass spectrum: m/z=561 [M−H⁻].

(80) 3-Z-[1-(4-(N-(2-dimethylamino-ethyl)-N-butylsulphonyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(2-dimethylamino-ethyl)-N-butylsulphonyl-p-phenylenediamine $R_f$ value: 0.5 (silica gel, methylene chloride/methanol=9:1) $C_{31}H_{36}N_4O_5S$ ESI mass spectrum: m/z=575 [M−H⁻].

(81) 3-Z-[1-(4-(N-(2-dimethylamino-ethyl)-N-phenylsulphonyl-amino)-anilino)-1-phenyl-9-methylene]-6-methoxycarbonyl-2-indolinone Prepared from 1-acetyl-3-(1-ethoxy-1-phenylmethylene)-6-methoxycarbonyl-2-indolinone and N-(2-dimethylamino-ethyl)-N-phenylsulphonyl-p-phenylenediamine $R_f$ value: 0.5 (silica gel, methylene chloride/methanol=9:1) $C_{33}H_{32}N_4O_5S$ ESI mass spectrum: m/z=595 [M−H⁻].

(82) 3-Z-[1-(4-(N-(2-dimethylamino-ethyl)-N-benzylsulphonyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(2-dimethylamino-ethyl)-N-benzylsulphonyl-p-phenylenediamine $R_f$ value: 0.5 (silica gel, methylene chloride/methanol=9:1) $C_{34}H_{34}N_4O_5S$ ESI mass spectrum: m/z=609 [M−H⁻].

(83) 3-Z-[1-(4-(N-(2-dimethylamino-ethyl)-N-ethylsulphonyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(2-dimethylamino-ethyl)-N-ethylsulphonyl-p-phenylenediamine $R_f$ value: 0.5 (silica gel, methylene chloride/methanol=9:1) $C_{29}H_{32}N_4O_5S$ ESI mass spectrum: m/z=547 [M−H⁻].

(84) 3-Z-[1-(4-((imidazolidin-2,4-dion-5-yl)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((imidazolidin-2,4-dion-5-yl)-methyl)-aniline $R_f$ value: 0.6 (silica gel, methylene chloride/methanol=5:1) $C_{27}H_{22}N_4O_5$ ESI mass spectrum: m/z=481 [M−H⁻].

(85) 3-Z-[1-(4-((3-hydroxy-pyrrolidin-1-yl)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((3-hydroxypyrrolidin-1-yl)-methyl)-aniline R$_f$ value: 0.1 (silica gel, methylene chloride/methanol=10:1) C$_{28}$H$_{27}$N$_3$O$_4$ ESI mass spectrum: m/z=468 [M–H$^-$].

(86) 3-Z-[1-(4-(cyclohexylyl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(cyclohexyl-methyl)-aniline (Eur. J. Med. Chem. Chim. Ther. 1992, 27, 537-544) R$_f$ value: 0.6 (silica gel, methylene chloride/methanol=10:1) C$_{30}$H$_{30}$N$_2$O$_3$ ESI mass spectrum: m/z=465 [M–H$^-$].

(87) 3-Z-[1-(4-(cyclohexyl-carbonyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4cyclohexyl-carbonyl)-aniline R$_f$ value: 0.5 (silica gel, methylene chloride/methanol=10:1) C$_{30}$H$_{28}$N$_2$O$_4$ ESI mass spectrum: m/z=479 [M–H$^-$].

(88) 3-Z-[1-(4-diethylaminomethyl-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(diethylamino-methyl)-aniline R$_f$ value: 0.4 (silica gel, methylene chloride/methanol=10:1) C$_{28}$H$_{29}$N$_3$O$_3$ ESI mass spectrum: m/z 454 [M–H$^-$].

(89) 3-Z-[1-(4-(N-(n-hexyl)-N-methyl-aminomethyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(n-hexyl)-N-methyl-aminomethyl)-aniline R$_f$ value: 0.6 (silica gel, methylene chloride/methanol=10:1) C$_{31}$H$_{35}$N$_3$O$_3$ ESI mass spectrum: m/z=496 [M–H$^-$].

(90) 3-Z-[1-(4-(N-(2-dimethylamino-ethyl)-N-(furan-2-carbonyl)-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(2-dimethylamino-ethyl)-N-(furan-2-carbonyl)-amino)-aniline R$_f$ value: 0.5 (silica gel, methylene chloride/methanol=9:1) C$_{32}$H$_{30}$N$_4$O$_5$ ESI mass spectrum: m/z=549 [M–H$^-$].

(91) 3-Z-[1-(4-(N-(2-dimethylamino-ethyl)-N-(2-methoxy-benzoyl)-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(2-dimethylamino-ethyl)-N-(2-methoxy-benzoyl)-amino)-aniline R$_f$ value: 0.5 (silica gel, methylene chloride/methanol=9:1) C$_{35}$H$_{34}$N$_4$O$_5$ ESI mass spectrum: m/z=589 [M–H$^-$].

(92) 3-Z-[1-(4-(N-(2-dimethylamino-ethyl)-N-(pyridine-3-carbonyl)-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(2-dimethylamino-ethyl)-N-(pyridine-3-carbonyl)-amino)-aniline R$_f$ value: 0.5 (silica gel, methylene chloride/methanol=9:1) C$_{33}$H$_{31}$N$_5$O$_4$ ESI mass spectrum: m/z 560 [M–H$^-$].

(93) 3-Z-[1-(4-(N-(2-dimethylaminoethyl)-N-(phenyl-acetyl)-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(2-dimethylamino-ethyl)-N-(phenyl-acetyl)-amino)-aniline R$_f$ value: 0.5 (silica gel, methylene chloride/methanol=9:1) C$_{35}$H$_{34}$N$_4$O$_4$ ESI mass spectrum: m/z=573 [M–H$^-$].

(94) 3-Z-[1-(4-(N-ethyl-N-methyl-aminomethyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-ethyl-N-methyl-aminomethyl)-aniline R$_f$ value: 0.3 (silica gel, methylene chloride/methanol=10:1) C$_{27}$H$_{27}$N$_3$O$_3$ ESI mass spectrum: m/z=440 [M–H$^-$].

(95) 3-Z-[1-(4-(imidazol-2-yl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(imidazol-2-yl)-aniline R$_f$ value: 0.5 (silica gel, methylene chloride/methanol=10:1) C$_{26}$H$_{20}$N$_4$O$_3$ ESI mass spectrum: m/z=435 [M–H$^-$].

(96) 3-Z-[1-(4-(1-ethyl-imidazol-2-yl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(1-ethyl-imidazol-2-yl)-aniline R$_f$ value: 0.4 (silica gel, methylene chloride/methanol=10:1) C$_{28}$H$_{24}$N$_4$O$_3$ ESI mass spectrum: m/z=463 [M–H$^-$].

(97) 3-Z-[1-(4-(1-benzyl-imidazol-2-yl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(1-benzyl-imidazol-2-yl)-aniline R$_f$ value: 0.3 (silica gel, methylene chloride/methanol=20:1) C$_{33}$H$_{26}$N$_4$O$_3$ ESI mass spectrum: m/z=525 [M–H$^-$].

(98) 3-Z-[1-(4-(N-(2-dimethylamino-ethyl)-N-isopropylsulphonyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(2-dimethylamino-ethyl)-N-isopropylsulphonyl-p-phenylenediamine R$_f$ value: 0.5 (silica gel, methylene chloride/methanol=9:1) C$_{30}$H$_{34}$N$_4$O$_5$S ESI mass spectrum: m/z=561 [M–H$^-$].

(99) 3-Z-[1-(4-(N-(piperidin-1-yl-methylcarbonyl)-N-methyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(piperidin-1-yl-methylcarbonyl)-N-methyl-p-phenylenediamine R$_f$ value: 0.5 (silica gel, methylene chloride/methanol=9:1) C$_{31}$H$_{32}$N$_4$O$_4$ ESI mass spectrum: m/z=523 [M–H$^-$].

(100) 3-Z-[1-(4-(N-(morpholin-4-yl-methylcarbonyl)-N-methyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(morpholinyl-methylcarbonyl)-N-methyl-p-phenylenediamine R$_f$ value: 0.5 (silica gel, methylene chloride/methanol=9:1) C$_{30}$H$_{30}$N$_4$O$_5$ ESI mass spectrum: m/z=525 [M–H$^-$].

(101) 3-Z-[1-(4-(N-((4-benzyl-piperazin-1-yl)-methylcarbonyl)-N-methyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-((4-benzyl-piperazin-1-yl)-methylcarbonyl)-N-methyl-p-phenylenediamine $R_f$ value: 0.5 (silica gel, methylene chloride/methanol=9:1) $C_{37}H_{37}N_5O_4$ ESI mass spectrum: m/z=614 [M–H⁻].

(102) 3-Z-[1-(4-(N-(pyrrolidin-1-yl-methylcarbony)-N-methyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(pyrrolidin-1-yl-methylcarbonyl)-N-methyl-p-phenylenediamine $R_f$ value: 0.5 (silica gel, methylene chloride/methanol=9:1) $C_{30}H_{30}N_4O_4$ ESI mass spectrum: m/z=509 [M–H⁻].

(103) 3-Z-[1-(4-(N-(2-dimethylamino-ethyl)-N-acetyl-amino)-3-bromo-anilino)-1-phenyl-methylene]6-methoxycarbonyl-2-indolinone Prepared from 1-acetyl-3-(1-ethoxy-1-phenylmethylene)-6-methoxycarbonyl-2-indolinone and 4-(N-(2-dimethylamino-ethyl)-N-acetyl-amino)-3-bromo-aniline $R_f$ value: 0.6 (silica gel, methylene chloride/methanol=5:1) $C_{29}H_{29}BrN_4O_4$ ESI mass spectrum: m/z=575/577 [M–H⁻].

(104) 3-Z-[1-(4-(5-methyl-imidazol-4-yl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(5-methyl-imidazol-4-yl)-aniline $R_f$ value: 0.5 (silica gel, methylene chloride/methanol/ammonia=10:1:0.01) $C_{27}H_{22}N_4O_3$ ESI mass spectrum: m/z=449 [M–H⁻].

(105) 3-Z-[1-(4-(N-((2-dimethylamino-ethyl)-carbonyl)-N-isopropyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-((2-dimethylamino-ethyl)-carbonyl)-N-isopropyl-p-phenylenediamine $R_f$ value: 0.1 (silica gel, methylene chloride/methanol=10:1) $C_{31}H_{34}N_4O_4$ ESI mass spectrum: m/z=525 [M–H⁻].

(106) 3-Z-[1-(4-(N-((2-dimethylamino-ethyl)-carbonyl)-N-benzyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-((2-dimethylamino-ethyl)-carbonyl)-N-benzyl-p-phenylenediamine $R_f$ value: 0.1 (silica gel, methylene chloride/methanol=10:1) $C_{31}H_{34}N_4O_4$ ESI mass spectrum: m/z=525 [M–H⁻].

(107) 3-Z-[1-(4-(N-butyl-N-tert.butoxycarbonyl-aminomethyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-butyl-N-tert.butoxycarbonyl-aminomethyl)-aniline $R_f$ value: 0.5 (silica gel, methylene chloride/methanol=9:1) $C_{33}H_{37}N_3O_5$ ESI mass spectrum: m/z=554 [M–H⁻].

(108) 3-Z-[1-(4-(N-((N-aminocarbonylmethyl-N-methyl-amino)-methylcarbonyl)-N-methyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(N-aminocarbonylmethyl-N-methyl-amino)-methylcarbonyl)-N-methyl-p-phenylenediamine $R_f$ value: 0.5 (silica gel, methylene chloride/methanol=9:1) $C_{29}H_{29}N_5O_5$ ESI mass spectrum: m/z=526 [M–H⁻].

(109) 3-Z-[1-(4-(4-((N-benzyl-N-methyl-amino)-methylcarbonyl)-N-methyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-((N-benzyl-N-methyl-amino)-methylcarbonyl)-N-methyl-p-phenylenediamine $R_f$ value: 0.5 (silica gel, methylene chloride/methanol=9:1) $C_{34}H_{32}N_4O_4$ ESI mass spectrum: m/z=559 [M–H⁻].

(110) 3-Z-[1-(4-(N-(di-(2-methoxyethyl)-amino-methylcarbonyl)-N-methyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(di-(2-methoxyethyl)-amino-methylcarbonyl)-N-methyl-p-phenylenediamine $R_f$ value: 0.5 (silica gel, methylene chloride/methanol=9:1) $C_{32}H_{36}N_4O_6$ ESI mass spectrum: m/z=571 [M–H⁻].

(111) 3-Z-[1-(4-(N-((2-(4-tert.butoxycarbonyl-piperazin-1-yl)-ethyl)-carbonyl)-N-methyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-((2-(4-tert.butoxycarbonyl-piperazin-1-yl)-ethyl)-carbonyl)-N-methyl-p-phenylenediamine $R_f$ value: 0.8 (silica gel, methylene chloride/methanol=5:1) $C_{36}H_{41}N_5O_6$ ESI mass spectrum: m/z=638 [M–H⁻].

(112) 3-Z-[1-(4-(N-((2-(piperidin-1-yl)-ethyl)-carbonyl)-N-methyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-((2-(piperidin-1-yl)-ethyl)-carbonyl)-N-methyl-p-phenylenediamine $R_f$ value: 0.5 (silica gel, methylene chloride/methanol=5:1) $C_{32}H_{34}N_4O_4$ ESI mass spectrum: m/z=537 [M–H⁻].

(113) 3-Z-[1-(4-(N-((2-(N-benzyl-N-methyl-amino)-ethyl)-carbonyl)-N-methyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-((2-(N-benzyl-N-methyl-amino)-ethyl)-carbonyl)-N-methyl-p-phenylenediamine $R_f$ value: 0.4 (silica gel, methylene chloride/methanol=10:1) $C_{35}H_{34}N_4O_4$ ESI mass spectrum: m/z=573 [M–H⁻].

(114) 3-Z-[1-(4-(N-dimethylaminomethylcarbonyl-N-isopropyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(dimethylaminomethylcarbonyl)-N-isopropyl-p-phenylenediamine $R_f$ value: 0.5 (silica gel, methylene chloride/methanol=9:1) $C_{30}H_{32}N_4O_4$ ESI mass spectrum: m/z=511 [M–H⁻].

(115) 3-Z-[1-(4-(N-(piperidin-1-yl-methylcarbonyl)-N-isopropyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(piperidin-1-yl-methylcarbonyl)-N-isopropyl-p-phenylenediamine $R_f$ value: 0.5 (silica gel, methylene chloride/methanol=9:1) $C_{33}H_{36}N_4O_4$ ESI mass spectrum: m/z=551 [M–H⁻].

(116) 3-Z-[1-(4N-((4-tert.butoxycarbonyl-piperazin-1-yl)-methylcarbonyl)-N-isopropyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-((4-tert.butoxycarbonyl-piperazin-1-yl)-methylcarbonyl)-N-isopropyl-p-phenylenediamine $R_f$ value: 0.5 (silica gel, methylene chloride/methanol=9:1) $C_{37}H_{43}N_5O_6$ ESI mass spectrum: m/z=652 [M–H$^-$].

(117) 3-Z-[1-(4-(N-((N-benzyl-N-methyl-amino)-methylcarbonyl)-N-benzyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-((N-benzyl-N-methyl-amino)-methylcarbonyl)-N-benzyl-p-phenylenediamine $R_f$ value: 0.5 (silica gel, methylene chloride/methanol=9:1) $C_{40}H_{36}N_4O_4$ ESI mass spectrum: m/z=635 [M–H$^-$].

(118) 3-Z-[1-(4-(N-dimethylaminomethylcarbonyl-N-benzyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and N-(dimethylaminomethyl-carbonyl)-N-benzyl-p-phenylenediamine $R_f$ value: 0.5 (silica gel, methylene chloride/methanol=9:1) $C_{34}H_{32}N_4O_4$ ESI mass spectrum: m/z=559 [M–H$^-$].

(119) 3-Z-[1-(4-(N-(piperidin-1-yl-methylcarbonyl)-N-benzyl-amino)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(5-methyl-imidazol-4-yl)-aniline $R_f$ value: 0.5 (silica gel, methylene chloride/methanol=9:1) $C_{37}H_{36}N_4O_4$ ESI mass spectrum: m/z=559 [M–H$^-$].

(120) 3-Z-[1-(4-(1,2,4-triazol-2-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(1,2,4-triazol-1-yl-methyl)-aniline $R_f$ value: 0.5 (silica gel, methylene chloride/methanol=10:1) $C_{26}H_{21}N_5O_3$ ESI mass spectrum: m/z=450 [M–H$^-$].

(121) 3-Z-[1-(4-(1,2,3-triazol-2-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(1,2,3-triazol-2-yl-methyl)-aniline $R_f$ value: 0.5 (silica gel, methylene chloride/methanol=20:1) $C_{26}H_{21}N_5O_3$ ESI mass spectrum: m/z=450 [M–H$^-$].

(122) 3-Z-[1-(4-(1,2,3-triazol-1-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(1,2,3-triazol-1-yl-methyl)-aniline $R_f$ value: 0.4 (silica gel, methylene chloride/methanol=9:1) $C_{26}H_{21}N_5O_3$ ESI mass spectrum: m/z=450 [M–H$^-$].

(123) 3-Z-[1-(4-((N-aminocarbonylmethyl-N-methyl-amino)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((N-aminocarbonylmethyl-N-methyl-amino)-methyl)-aniline $R_f$ value: 0.5 (silica gel, methylene chloride/methanol=9:1) $C_{27}H_{26}N_4O_4$ ESI mass spectrum: m/z=469 [M–H$^-$].

(124) 3-Z-[1-(4-((di-(2-methoxy-ethyl)-amino)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((di2-methoxy-ethyl)-amino)-methyl)-aniline $R_f$ value: 0.5 (silica gel, methylene chloride/methanol=9:1) $C_{30}H_{33}N_3O_5$ ESI mass spectrum: m/z=514 [M–H$^-$].

(125) 3-Z-[1-(4-(pyrrolidin-1-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(pyrrolidin-1-yl-methyl)-aniline $R_f$ value: 0.5 (silica gel, methylene chloride/methanol=9:1) $C_{28}H_{27}N_3O_3$ ESI mass spectrum: m/z=452 [M–H$^-$].

(126) 3-Z-[1-(4-((di-(2-hydroxy-ethyl)-amino)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((di-(2-hydroxy-ethyl)-amino)-methyl)-aniline $R_f$ value: 0.5 (silica gel, methylene chloride/methanol=9:1) $C_{28}H_{29}N_3O_5$ ESI mass spectrum: m/z=486 [M–H$^-$].

(127) 3-Z-[1-(4-((N-ethoxycarbonylmethyl-N-methyl-amino)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((N-ethoxycarbonylmethyl-N-methyl-amino)-methyl)-aniline $R_f$ value: 0.5 (aluminium oxide, methylene chloride/ethanol=40:1) $C_{29}H_{29}N_3O_5$ ESI mass spectrum: m/z=498 [M–H$^-$].

(128) 3-Z-[1-(4-(azetidin-1-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(azetidin-1-yl-methyl)-aniline $R_f$ value: 0.5 (silica gel, methylene chloride/methanol/ammonia=9:1:0.5) $C_{27}H_{25}N_3O_3$ ESI mass spectrum: m/z=438 [M–H$^-$].

(129) 3-Z-[1-(4-(N-propyl-N-tert.butoxycarbonyl-aminomethyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-propyl-N-tert.butoxycarbonyl-aminomethyl)-aniline $R_f$ value: 0.5 (silica gel, methylene chloride/methanol=9:1) $C_{32}H_{35}N_3O_5$ ESI mass spectrum: m/z=540 [M–H$^-$].

(130) 3-Z-[1-(4-((N-(2-(2-methoxy-ethoxy)-ethyl)-N-methyl-amino)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((N-(2-(2-methoxy-ethoxy)-ethyl)-N-methyl-amino)-methyl)-aniline $R_f$ value: 0.4 (silica gel, methylene chloride/methanol=9:1) $C_{30}H_{33}N_3O_5$ ESI mass spectrum: m/z=514 [M–H$^-$].

(131) 3-Z-[1-(4-((N-(tert.butoxycarbonyl-3-amino-propyl)-N-methyl-amino)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(N-tert.butoxycarbonyl-3-amino-propyl)-N-methylaminomethyl)-aniline $R_f$ value: 0.5 (silica gel, methylene chloride/methanol=9:1) $C_{33}H_{38}N_4O_5$ ESI mass spectrum: m/z=571 [M+H$^+$].

(132) 3-Z-[1-(4-((N-(methylcarbamoyl-methyl)-N-methyl-amino)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((N-(methylcarbamoyl-methyl)-N-methyl-amino)-methyl)-aniline $R_f$ value: 0.5 (silica gel, methylene chloride/methanol=9:1) $C_{28}H_{28}N_4O_4$ ESI mass spectrum: m/z=483 [M−H$^-$].

(133) 3-Z-[1-(4-((N-(dimethylcarbamoyl-methyl)-N-methyl-amino)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((N-(dimethylcarbamoyl-methyl)-N-methyl-amino)-methyl)-aniline $R_f$ value: 0.3 (silica gel, methylene chloride/methanol=10:1) $C_{29}H_{30}N_4O_4$ ESI mass spectrum: m/z=497 [M−H$^-$].

(134) 3-Z-[1-(4-methyl-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-methyl-aniline $R_f$ value: 0.4 (silica gel, methylene chloride/methanol=9:1) $C_{24}H_{20}N_2O_3$ ESI mass spectrum: m/z=383 [M−H$^-$].

(135) 3-Z-[1-(4-((N-propyl-N-methyl-amino)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((N-propyl-N-methyl-amino)-methyl)-aniline $R_f$ value: 0.5 (silica gel, methylene chloride/methanol 9:1) $C_{28}H_{29}N_3O_3$ ESI mass spectrum: m/z=454 [M−H$^-$].

(136) 3-Z-[1-(4-((N-(2-hydroxy-ethyl)-N-methyl-amino)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((N-(2-hydroxy-ethyl)-N-methyl-amino)-methyl)-aniline $R_f$ value: 0.5 (aluminium oxide, methylene chloride/ethanol=40:1) $C_{27}H_{27}N_3O_4$ ESI mass spectrum: m/z=456 [M−H$^-$].

(137) 3-Z-[1-(4-((N-(2-dimethylaminoethyl)-N-methyl-amino)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(N-(2-dimethylamino-ethyl)-N-methyl-amino)-methyl)-aniline $R_f$ value: 0.5 (silica gel, methylene chloride/methanol=9:1) $C_{29}H_{32}N_4O_3$ ESI mass spectrum: m/z=483 [M−H$^-$].

(138) 3-Z-[1-(4-((N-(3-dimethylamino-propyl)-N-methyl-amino)-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-((N-(3-dimethylamino-propyl)-N-methyl-amino)-methyl)-aniline $R_f$ value: 0.5 (silica gel, methylene chloride/methanol=9:1) $C_{30}H_{34}N_4O_3$ ESI mass spectrum: m/z=497 [M−H$^-$].

(139) 3-Z-[1-(4-(3-oxo-piperazin-1-yl-methyl)-anilino)-1-phenyl-methylene]-6-methoxycarbonyl-2-indolinone Prepared from 1-acetyl-3-(1-ethoxy-1-phenylmethylene)-6-methoxycarbonyl-2-indolinone and 4-(3-oxo-piperazin-1-yl-methyl)-aniline aniline $R_f$ value: 0.46 (silica gel, methylene chloride/methanol=9:1) $C_{28}H_{26}N_4O_4$ ESI mass spectrum: m/z=481 [M−H$^-$].

EXAMPLE 4

3-Z-[1-(4-carboxy-anilino)-1-phenyl-methylene]-6-ethoxy-carbonyl-2-indolinone 485 mg of 3-Z-[1-(4-tert.butoxycarbonyl-anilino)-1-phenyl-methylene]-6-ethoxycarbonyl-2-indolinone are dissolved in 15 ml of methylene chloride and 6.0 ml of trifluoroacetic acid are added. The mixture is stirred for 2 hours at room temperature. Then the solvent is removed and the residue recrystallised from ether.

Yield: 375 mg (87% of theory), $R_f$ value: 0.3 (silica gel, methylene chloride/methanol=10:1) $C_{25}H_{20}N_2O_5$ Mass spectrum: m/z=428 [M$^+$].

The following compounds are prepared analogously to Example 4:

(1) 3-Z-[1-(4-aminomethyl-anilino)-1-phenyl-methylene]-6-methoxycarbonyl-2-indolinone Prepared from 3-Z-[1-(4-(N-tert.butoxycarbonyl-aminomethyl)-anilino)-1-phenyl-methylene]-6-methoxycarbonyl-2-indolinone $R_f$ value: 0.5 (silica gel, methylene chloride/methanol/ammonia=5:1:0.01) $C_{24}H_{21}N_3O_3$ ESI mass spectrum: m/z=398 [M−H$^-$].

(2) 3-Z-[1-(4-ethylaminomethyl-anilino)-1-phenyl-methylene]-6-methoxycarbonyl-2-indolinone Prepared from 3-Z-[1-(4-(N-tert.butoxycarbonyl-ethylaminomethyl)-anilino)-1-phenyl-methylene]-6-methoxycarbonyl-2-indolinone $R_f$ value: 0.4 (silica gel, methylene chloride/methanol/ammonia=10:1:0.01) $C_{26}H_{25}N_3O_3$ ESI mass spectrum: m/z=426 [M−H$^-$].

(3) 3-Z-[1-(4-carboxymethyl-anilino)-1-phenyl-methylene]-6-ethoxycarbonyl-2-indolinone Prepared from 3-Z-[1-(4-tert.butoxycarbonylmethyl-anilino)-1-phenyl-methylene]-6-ethoxycarbonyl-2-indolinone $R_f$ value: 0.1 (aluminium oxide, methylene chloride/ethanol/ammonia=5:1:0.01) $C_{26}H_{22}N_2O_5$ ESI mass spectrum: m/z=441 [M−H$^-$].

(4) 3-Z-[1-(4-carboxy-anilino)-1-ethyl-methylene)-6-ethoxycarbonyl-2-indolinone

Prepared from 3-Z-[1-(4-tert.butoxycarbonyl-anilino)-1-ethyl-methylene]-6-ethoxycarbonyl-2-indolinone $R_f$ value: 0.1 (aluminium oxide, methylene chloride/ethanol=20:1) $C_{21}H_{20}N_2O_5$ ESI mass spectrum: m/z=379 [M−H$^-$].

(5) 3-Z-[1-(4-(piperazin-1-yl-methyl)-anilino)-1-phenyl-methylene]-6-methoxycarbonyl-2-indolinone Prepared from 3-Z-[1-(4-(4-tert.butoxycarbonyl-piperazin-1-yl-methyl)-anilino)-1-phenyl-methylene]-6-methoxycarbonyl-2-indolinone $R_f$ value: 0.1 (silica gel, methylene chloride/methanol/ammonia=10:1:0.01) $C_{28}H_{28}N_4O_3$ ESI mass spectrum: m/z=469 [M+H$^+$].

(6) 3-Z-[1-(4-butylaminomethyl-anilino)-1-phenyl-methylene]-6-methoxycarbonyl-2-indolinone Prepared from 3-Z-[1-(4-(N-butyl-N-tert.butoxycarbonyl-aminomethyl)-anilino)-1-phenyl-methylene]-6-methoxycarbonyl-2-indolinone $R_f$ value: 0.5 (silica gel, methylene chloride/methanol=9:1) $C_{28}H_{29}N_3O_3$ ESI mass spectrum: m/z=454 [M−H⁻].

(7) 3-Z-[1-(4-ethylaminomethyl-anilino)-1-phenyl-methylene]6-ethoxycarbonyl-2-indolinone Prepared from 3-Z-[1-(4-(N-tert.butoxycarbonyl-N-ethyl-aminomethyl)-anilino)-1-phenyl-methylene]-6-ethoxycarbonyl-2-indolinone $R_f$ value: 0.3 (silica gel, methylene chloride/methanol/ammonia=10:1:0.01) $C_{27}H_{27}N_3O_3$ ESI mass spectrum: m/z=442 [M+H⁺].

(8) 3-Z-[1-(4-ethylaminomethyl-anilino)-1-phenyl-methylene]-6-carbamoyl-2-indolinone Prepared from 3-Z-[1-(4-(N-tert.butoxycarbonyl-ethylaminomethyl)-anilino)-1-phenyl-methylene]-6-carbamoyl-2-indolinone $R_f$ value: 0.2 (silica gel, methylene chloride/methanol/ammonia=5:1:0.01) $C_{25}H_{24}N_4O_2$ ESI mass spectrum: m/z=411 [M−H⁻].

(9) 3-Z-[1-(4-(N-(piperazin-1-yl-methylcarbonyl)-N-isopropyl-amino)-anilino)-1-phenyl-methylene]-6-methoxycarbonyl-2-indolinone Prepared from 3-Z-[1-(4-(N-(4-tert.butoxycarbonyl-piperazin-1-yl)-methylcarbonyl)-N-isopropyl-amino)-anilino)-1-phenyl-methylene]-6-methoxycarbonyl-2-indolinone $R_f$ value: 0.35 (silica gel, methylene chloride/methanol=9:1) $C_{32}H_{35}N_5O_4$ ESI mass spectrum: m/z=552 [M−H⁻].

(10) 3-Z-[1-(4-(N-((2-(piperazin-1-yl)-ethyl)-carbonyl)-N-methyl-amino)-anilino)-1-phenyl-methylene]-6-methoxycarbonyl-2-indolinone Prepared from 3-Z-[1-(4-(N-((2-(4-tert.butoxycarbonyl-piperazin-1-yl)-ethyl)-carbonyl)-N-methyl-amino)-anilino)-1-phenyl-methylene]-6-methoxycarbonyl-2-indolinone $R_f$ value: 0.4 (silica gel, methylene chloride/methanol/ammonia=5:1:0.01) $C_{31}H_{33}N_5O_4$ ESI mass spectrum: m/z=540 [M+H⁺].

(11) 3-Z-[1-(4-(N-propyl-aminomethyl)-anilino)-1-phenyl-methylene]-6-methoxycarbonyl-2-indolinone Prepared from 3-Z-[1-(4-(N-propyl-N-tert.butoxycarbonyl-aminomethyl)-anilino)-1-phenyl-methylene]-6-methoxycarbonyl-2-indolinone $R_f$ value: 0.35 (silica gel, methylene chloride/methanol=9:1) $C_{27}H_{27}N_3O_3$ ESI mass spectrum: m/z=440 [M−H⁻].

(12) 3-Z-[1-(4-((N-(3-amino-propyl)-N-methyl-amino)-methyl)-anilino)-1-phenyl-methylene]-6-methoxycarbonyl-2-indolinone Prepared from 3-Z-[1-(4-((N-(tert.butoxycarbonyl-3-amino-propyl)-N-methyl-amino)-methyl)-anilino)-1-phenyl-methylene]-6-methoxycarbonyl-2-indolinone $R_f$ value: 0.35 (silica gel, methylene chloride/methanol=9:1) $C_{28}H_{30}N_4O_3$ ESI mass spectrum: m/z=471 [M+H⁺].

EXAMPLE 5

3-Z-[1-(4-methylaminomethyl-anilino)-1-phenyl-methylene]-6-ethoxycarbonyl-2-indolinone 100 mg of 3-Z-[1-(4-(N-benzyl-N-methyl-aminomethyl)-anilino)-1-phenyl-methylene]-6-ethoxycarbonyl-2-indolinone are dissolved in 20 ml of ethanol, 0.2 ml of 1N hydrochloric acid are added and the mixture is hydrogenated for 70 minutes at room temperature and 50 psi hydrogen pressure. The reaction solution is filtered and the filtrate concentrated by rotary evaporation. The residue is dried in vacuo at 100° C.

Yield: 50 mg (53% of theory), $R_f$ value: 0.3 (silica gel, methylene chloride/ethanol/ammonia=5:1:0.01) $C_{26}H_{25}N_3O_3$ ESI mass spectrum: m/z=426 [M−H⁻].

The following compounds are prepared analogously to Example 5:

(1) 3-Z-[1-(4-methylaminomethyl-anilino)-1-phenyl-methylene]-6-methoxycarbonyl-2-indolinone Prepared from 3-Z-[1-(4-(N-benzyl-N-methyl-aminomethyl)-anilino)-1-phenyl-methylene]-6-methoxycarbonyl-2-indolinone $R_f$ value: 0.2 (silica gel, methylene chloride/methanol/ammonia=10:1:0.01) $C_{25}H_{23}N_3O_3$ ESI mass spectrum: m/z=412 [M−H⁻].

(2) 3-Z-[1-(4-(N-(2-methylamino-ethyl)-N-methylsulphonyl-amino)-anilino)-1-phenyl-methylene]-6-methoxycarbonyl-2-indolinone Prepared from 3-Z-[1-(4-((2-(N-benzyl-N-methyl-amino)-ethyl)-N-methylsulphonyl-amino)-anilino)-1-phenyl-methylene]-6-methoxycarbonyl-2-indolinone $R_f$ Value: 0.3 (silica gel, methylene chloride/methanol/ammonia=10:1:0.01) $C_{27}H_{28}N_4O_5S$ ESI mass spectrum: m/z=519 [M−H⁻].

(3) 3-Z-[1-(4N-(2-amino-ethyl)-N-methylsulphonyl-amino)-anilino)-1-phenyl-methylene]-6-methoxycarbonyl-2-indolinone Prepared from 3-Z-[1-(4-(N-cyanomethyl-N-methylsulphonyl-amino)-anilino)-1-phenyl-methylene]-6-methoxycarbonyl-2-indolinone $R_f$ value: 0.5 (silica gel, methylene chloride/methanol/ammonia=5:1:0.01) $C_{26}H_{26}N_4O_5S$ ESI mass spectrum: m/z=505 [M−H⁻].

(4) 3-Z-[1-(4-(N-(3-methylamino-propyl)-N-methylsulphonyl-amino)-anilino)-1-phenyl-methylene]-6-methoxycarbonyl-2-indolinone Prepared from 3-Z-[1-(4-(N-(3-N-benzyl-N-methyl-amino)-propyl)-N-methylsulphonyl-amino)-anilino)-1-phenyl-methylene]-6-methoxycarbonyl-2-indolinone $R_f$ value: 0.3 (silica gel, methylene chloride/methanol/ammonia=5:1:0.01) $C_{28}H_{30}N_4O_5S$ ESI mass spectrum: m/z=533 [M−H⁻].

(5) 3-Z-[1-(4-(N-(piperazin-1-yl-methylcarbonyl)-N-methyl-amino)-anilino)-1-phenyl-methylene]-6-methoxycarbonyl-2-indolinone Prepared from 3-Z-[1-(4-(N-((4-benzyl-piperazin-1-yl)-methylcarbonyl)-N-methyl-amino)-anilino)-1-phenyl-methylene]-6-methoxycarbonyl-2-indolinone $R_f$ value: 0.5 (silica gel, methylene chloride/methanol=9:1) $C_{30}H_{31}N_5O_4$ ESI mass spectrum: m/z=524 [M−H⁻].

(6) 3-Z-[1-(4-(N-(methylamino-methylcarbonyl)-N-methyl-amino)-anilino)-1-phenyl-methylene]-6-methoxycarbonyl-2-indolinone Prepared from 3-Z-[1-(4-(N-((N-benzyl-N-methyl-amino)-methylcarbonyl)-N-methyl-amino)-anilino)-1-phenyl-methylene]-6-methoxycarbonyl-2-indolinone $R_f$ value: 0.3 (silica gel, methylene chloride/methanol=9:1) $C_{27}H_{26}N_4O_4$ ESI mass spectrum: m/z=469 [M−H⁻].

(7) 3-Z-[1-(4-(N-((2-methylamino-ethyl)-carbonyl)-N-methyl-amino)-anilino)-1-phenyl-methylene]-6-methoxycarbonyl-2-indolinone Prepared from 3-Z-[1-(4-(N-((2-(N-benzyl-N-methyl-amino)-ethyl)-carbonyl)-N-methyl-amino)-anilino)-1-phenyl-methylene]-6-methoxycarbonyl-2-indolinone $R_f$ value: 0.3 (silica gel, methylene chloride/methanol/ammonia=5:1:0.01) $C_{28}H_{28}N_4O_4$ ESI mass spectrum: m/z=483 [M–H$^-$].

EXAMPLE 6

3-Z-[1-(4-ureidomethyl-anilino)-1-phenyl-methylene]-6-methoxycarbonyl-2-indolinone 300 mg of 3-Z-[1-(4-aminomethyl-anilino)-1-phenyl-methylene]-6-methoxycarbonyl-2-indolinone are dissolved in 15 ml of methanol and 200 ml of triethylamine are added. Then 400 mg of potassium cyanate in 5 ml of water are added. After 2 days of stirring at room temperature the reaction solution is concentrated by rotary evaporation, the residue taken up in methylene chloride and washed once with water and once with saturated sodium chloride solution. The organic phase is dried over sodium sulphate and concentrated by rotary evaporation. The residue is dried in vacuo at 100° C.

Yield: 100 mg of (21% of theory), $R_f$ value: 0.7 (silica gel, methylene chloride/methanol=5;1) $C_{25}H_{22}N_4O_4$ ESI mass spectrum: m/z=441 [M–H$^-$].

EXAMPLE 7

3-Z-[1-(4-guanidinomethyl-anilino)-1-phenyl-methylene]-6-methoxycarbonyl-2-indolinone 300 mg of 3-Z-[1-(4-aminomethyl-anilino)-1-phenyl-methylene]-6-methoxycarbonyl-2-indolinone are dissolved in 5 ml of dimethylformamide and 300 ml of triethylamine are added. Then 700 mg of 3,5-dimethylpyrazol-1-carboxylic acid amidine in 5 ml of dimethylformamide are added. After one day of stirring at room temperature the reaction solution is concentrated by rotary evaporation. The residue is dried at 100° C. in vacuo.

Yield: 200 mg (87% of theory), $R_f$ value: 0.1 (Reversed phase RP 8, methanol/five percent saline solution=6:4) $C_{25}H_{23}N_5O_3$ Mass spectrum: m/z=441 [M$^+$].

EXAMPLE 8

3-Z-[1-(4-acetylaminomethyl-anilino)-1-phenyl-methylene]-6-methoxycarbonyl-2-indolinone 100 mg of 3-Z-[1-(4-aminomethyl-anilino)-1-phenyl-methylene]-6-methoxycarbonyl-2-indolinone are dissolved in 5 ml of glacial acetic acid, 0.1 ml of acetic anhydride is added and the mixture is stirred for 10 minutes at room temperature. After this time the reaction solution is poured onto saturated soda solution and extracted four times with methylene chloride. The combined organic phases are washed with saturated saline solution, dried over sodium sulphate and concentrated by rotary evaporation. The residue is dried at 100° C. in vacuo.

Yield: 20 mg (23% of theory), $R_f$ value: 0.4 (silica gel, methylene chloride/methanol=10:1) $C_{26}H_{23}N_3O_4$ ESI mass spectrum: m/z 440 [M–H$^-$].

The following compounds are prepared analogously to Example 8:

(1) 3-Z-[1-(4-(N-methylsulphonyl-aminomethyl)-anilino)-1-phenyl-methylene]-6-methoxycarbonyl-2-indolinone Prepared from 3-Z-[1-(4-aminomethyl-anilino)-1-phenyl-methylene]-6-methoxycarbonyl-2-indolinone and methanesulphonyl chloride/triethylamine $R_f$ value: 0.7 (silica gel, methylene chloride/methanol=5:1) $C_{25}H_{23}N_3O_5S$ ESI mass spectrum: m/z=476 [M–H$^-$].

(2) 3-Z-[1-(4-(4-benzoyl-piperazin-1-yl-methyl)-anilino)-1-phenyl-methylene]-6-methoxycarbonyl-2-indolinone Prepared from 3-Z-[1-(4-(piperazin-1-yl-methyl)-anilino)-1-phenyl-methylene]-6-methoxycarbonyl-2-indolinone and benzoyl chloride $R_f$ value: 0.7 (silica gel, methylene chloride/methanol=10:1) $C_{35}H_{32}N_4O_4$ ESI mass spectrum: m/z=571 [M–H$^-$].

(3) 3-Z-[1-(4-((N-(3-acetylamino-propyl)-N-methyl-amino)-methyl)-anilino)-1-phenyl-methylene]-6-methoxycarbonyl-2-indolinone Prepared from 3-Z-[1-(4-((N-(3-amino-propyl)-N-methyl-amino)-methyl)-anilino)-1-phenyl-methylene]-6-methoxycarbonyl-2-indolinone $R_f$ value: 0.3 (silica gel, methylene chloride/methanol=9:1) $C_{30}H_{32}N_4O_4$ ESI mass spectrum: m/z=511 [M–H$^-$].

EXAMPLE 9

3-Z-(1-(4-(piperidin-1-yl-methyl)-anilino)-1-phenyl-methylene]-6-carboxy-2-indolinone 0.8 g of 3-Z-[1-(4-(piperidin-1-yl-methyl)-anilino)-1-phenyl-methylene]-6-ethoxycarbonyl-2-indolinone are dissolved in 30 ml of ethanol, 8.3 ml of 1N sodium hydroxide solution are added and the mixture is stirred for 1 hour at 80° C. After cooling, it is neutralised with 8.3 ml of 1N hydrochloric acid. The precipitate formed is suction filtered, washed with water, ethanol and ether and dried in vacuo at 100° C.

Yield: 0.7 g of (89% of theory), $R_f$ value: 0.2 (silica gel, methylene chloride/methanol=5:2) $C_{28}H_{27}N_3O_3$ Mass spectrum: m/z=453 [M$^+$].

The following compounds are prepared analogously to Example 9:

(1) 3-Z-[1-(4-bromo-anilino)-1-phenyl-methylene]-6-carboxy-2-indolinone

Prepared from 3-Z-[1-(4-bromo-anilino)-1-phenyl-methylene]-6-ethoxycarbonyl-2-indolinone $R_f$ value: 0.4 (silica gel, toluene/ethyl acetate=5:1) $C_{22}H_{15}BrN_2O_3$ ESI mass spectrum: m/z=435/437 [M+H$^+$].

(2) 3-Z-[1-(3-(dimethylaminomethyl)-anilino)-1-phenyl-methylene]-6-carboxy-2-indolinone Prepared from 3-Z-[1-(3-(dimethylaminomethyl)-anilino)-1-phenyl-methylene]-6-ethoxycarbonyl-2-indolinone $R_f$ value: 0.7 (Reversed phase RP 8, methanol/five percent saline solution=4:1) $C_{25}H_{23}N_3O_3$ ESI mass spectrum: m/z=414 [M+H$^+$].

(3) 3-Z-[1-(4-(dimethylaminomethyl)-anilino)-1-phenyl-methylene]-6-carboxy-2-indolinone Prepared from 3-Z-[1-(4-(dimethylaminomethyl)-anilino)-1-phenyl-methylene]-6-ethoxycarbonyl-2-indolinone $R_f$ value: 0.7 (Reversed phase RP 8, methanol/five percent saline solution=4:1) $C_{25}H_{23}N_3O_3$ ESI mass spectrum: m/z=412 [M–H$^-$].

(4) 3-Z-[1-(4-[(2,6-dimethyl-piperidin-1-yl)-methyl]-anilino)-1-phenyl-methylene]-6-carboxy-2-indolinone Prepared from 3-Z-[1-(4-[(2,6-dimethyl-piperidin-1-yl)-methyl]-anilino)-1-phenyl-methylene]-6-ethoxycarbonyl-2- indolinone $R_f$ value: 0.6 (Reversed phase RP 8, methanol/five percent saline solution=4:1) $C_{30}H_{31}N_3O_3$ ESI mass spectrum: m/z=482 [M+H$^+$].

(5) 3-Z-[1-(4-(1-methyl-imidazol-2-yl)-anilino)-1-phenyl-methylene]-6-carboxy-2-indolinone Prepared from 3-Z-[1-(4-(1-methyl-imidazol-2-yl)-anilino)-1-phenyl-methylene]-6-methoxycarbonyl-2-indolinone $R_f$ value: 0.6 (Reversed phase RP 8, methanol/five percent saline solution=4:1) $C_{26}H_{20}N_4O_3$ ESI mass spectrum: m/z=435 [M−H$^-$].

(6) 3-Z-[1-(4-(N-acetyl-N-dimethylaminocarbonylmethyl-amino)-anilino)-1-phenyl-methylene]-6-carboxy-2-indolinone Prepared from 3-Z-[1-(4-(N-acetyl-N-dimethylaminocarbonylmethyl-amino)-anilino)-1-phenyl-methylene]-6-methoxycarbonyl-2-indolinone $R_f$ value: 0.3 (silica gel, methylene chloride/methanol=10:1) $C_{28}H_{26}N_4O_5$ ESI mass spectrum: m/z=497 [M−H$^-$].

(7) 3-Z-[1-(4-ethylaminomethyl-anilino)-1-phenyl-methylene]-6-carboxy-2-indolinone Prepared from 3-Z-[1-(4-ethylaminomethyl-anilino)-1-phenyl-methylene]-6-methoxycarbonyl-2-indolinone $R_f$ value: 0.6 (Reversed phase RP 8, methanol/five percent saline solution=4:1) $C_{25}H_{23}N_3O_3$ ESI mass spectrum: m/z=412 [M−H$^-$].

(8) 3-Z-[1-(4-(N-dimethylaminomethylcarbonyl-N-methyl-amino)-anilino)-1-phenyl-methylene]-6-carboxy-2-indolinone Prepared from 3-Z-[1-(4-(N-dimethylaminomethylcarbonyl-N-methyl-amino)-anilino)-1-phenyl-methylene]-6-methoxycarbonyl-2-indolinone $R_f$ value: 0.6 (Reversed phase RP 8, methanol/five percent saline solution=4:1) $C_{27}H_{26}N_4O_4$ ESI mass spectrum: m/z=469 [M−H$^-$].

(9) 3-Z-[1-(4-(N-tert.butoxycarbonyl-ethylaminomethyl)-anilino)-1-phenyl-methylene]-6-carboxy-2-indolinone Prepared from 3-Z-[1-(4-(N-tert.butoxycarbonyl-ethylaminomethyl)-anilino)-1-phenyl-methylene]-6-ethoxycarbonyl-2-indolinone $R_f$ value: 0.4 (silica gel, methylene chloride/methanol=10:1) $C_{30}H_{31}N_3O_5$ ESI mass spectrum: m/z=512 [M−H$^-$].

(10) 3-Z-[1-(4-((N-carboxymethyl-N-methyl-amino)-methyl)-anilino)-1-phenyl-methylene]-6-methoxycarbonyl-2-indolinone Prepared from 3-Z-[1-(4-((N-ethoxycarbonylmethyl-N-methyl-amino)-methyl)-anilino)-1-phenyl-methylene]-6-methoxycarbonyl -2-indolinone $R_f$ value: 0.4 (silica gel, methylene chloride/methanol=6:1) $C_{27}H_{25}N_3O_5$ ESI mass spectrum: m/z=470 [M−H$^-$].

EXAMPLE 10

3-Z-[1-(4-(piperidin-1-yl-methyl)-anilino)-1-phenyl-methylene]-6-methoxycarbonyl-2-indolinone 0.9 g of 3-Z-[1-(4-(piperidin-1-yl-methyl)-anilino)-1-phenyl-methylene]-6-carboxy-2-indolinone are suspended in 35 ml of dimethylformamide and 0.4 g of carbonyldiimidazole are added. The mixture is stirred for 14 hours at 80° C. After this time 20 ml of methanol are added and the mixture is stirred for another 3 hours at 50° C. The solvent is removed and the residue is purified over a silica gel column with methylene chloride/methanol (3:1) as eluant.

Yield: 0.5 g of (49% of theory), $R_f$ value: 0.5 (aluminium oxide, methylene chloride/methanol=30:1) $C_{29}H_{29}N_3O_3$ ESI mass spectrum: m/z=468 [M+H$^+$].

The following compounds are prepared analogously to Example 10:

(1) 3-Z-[1-(4-(piperidin-1-yl-methyl)-anilino)-1-phenyl-methylene]-6-benzyloxycarbonyl-2-indolinone Prepared from 3-Z-[1-(4-(piperidin-1-yl-methyl)-anilino)-1-phenyl-methylene]-6-carboxy-2-indolinone and benzyl alcohol $R_f$ value: 0.6 (aluminium oxide, methylene chloride/methanol=30:1) $C_{35}H_{33}N_3O_3$ Mass spectrum: m/z=543 [M$^+$].

(2) 3-Z-[1-(4-(piperidin-1-yl-methyl)-anilino)-1-phenyl-methylene]-6-isopropyloxycarbonyl-2-indolinone Prepared from 3-Z-[1-(4-(piperidin-1-yl-methyl)-anilino)-1-phenyl-methylene]-6-carboxy-2-indolinone and isopropanol $R_f$ value: 0.4 (aluminium oxide, methylene chloride/isopropanol=30:1) $C_{31}H_{33}N_3O_3$ Mass spectrum: m/z=495 [M$^+$].

(3) 3-Z-[1-(4-(piperidin-1-yl-methyl)-anilino)-1-phenyl-methylene]-6-propyloxycarbonyl-2-indolinone Prepared from 3-Z-[1-(4-(piperidin-1-yl-methyl)-anilino)-1-phenyl-methylene]-6-carboxy-2-indolinone and n-propanol $R_f$ value: 0.7 (silica gel, methylene chloride/methanol=5:1) $C_{31}H_{33}N_3O_3$ Mass spectrum: m/z=495 [M$^+$].

(4) 3-Z-[1-(4-(piperidin-1-yl-methyl)-anilino)-1-phenyl-methylene]-6-butyloxycarbonyl-2-indolinone Prepared from 3-Z-[1-(4-(piperidin-1-yl-methyl)-anilino)-1-phenyl-methylene]-6-carboxy-2-indolinone and n-butanol $R_f$ value: 0.5 (silica gel, methylene chloride/methanol=10:1) $C_{32}H_{35}N_3O_3$ Mass spectrum: m/z=509 [M$^+$].

(5) 3-Z-[1-(4-bromo-anilino)-1-phenyl-methylene]-6-carbamoyl-2-indolinone

Prepared from 3-Z-[1-(4-bromo-anilino)-1-phenyl-methylene]-6-carboxy-2-indolinone and ammonia $R_f$ value: 0.5 (silica gel, methylene chloride/methanol=10:1) $C_{22}H_{16}BrN_2O_3$ Mass spectrum: m/z=432/434 [M−H$^-$].

(6) 3-Z-[1-(4-(piperidin-1-yl-methyl)-anilino)-1-phenyl-methylene]-6-ethylcarbamoyl-2-indolinone Prepared from 3-Z-[1-(4-(piperidin-1-yl-methyl)-anilino)-1-phenyl-methylene]-6-carboxy-2-indolinone and ethylamine gas $R_f$ value: 0.6 (silica gel, methylene chloride/methanol=5:1) $C_{30}H_{32}N_4O_2$ Mass spectrum: m/z=480 [M$^+$].

(7) 3-Z-[1-(4-(dimethylaminomethyl)-anilino)-1-phenyl-methylene]-6-[(2-methoxy-ethoxy)-carbonyl]-2-indolinone Prepared from 3-Z-[1-(4-(dimethylaminomethyl)-anilino)-1-phenyl-methylene]-6-carboxy-2-indolinone and methylglycol $R_f$ value: 0.8 (silica gel, methylene chloride/methanol=4:1) $C_{25}H_{23}N_3O_3$ ESI mass spectrum: m/z=470 [M−H$^-$].

(8) 3-Z-[1-(4-(dimethylaminomethyl)-anilino)-1-phenyl-methylene]-6-[(2-dimethylamino-ethoxy)-carbonyl]-2-indolinone Prepared from 3-Z-[1-(4-(dimethylaminomethyl)-anilino)-1-phenyl-methylene]-6-carboxy-2-indolinone and 2-dimethylaminoethanol aniline $R_f$ value: 0.5 (silica gel, methylene chloride/methanol=5:2) $C_{29}H_{32}N_4O_3$ ESI mass spectrum: m/z=483 [M−H$^-$].

(9) 3-Z-[1-(4-(dimethylaminomethyl)-anilino)-1-phenyl-methylene]-6-[(2-N-tert.butoxycarbonyl-amino-ethoxy)-carbonyl]-2-indolinone Prepared from 3-Z-[1-(4-(dimethylaminomethyl)-anilino)-1-phenyl-methylene]-6-carboxy-2-indolinone and 2-N-tert.butoxycarbonyl-amino-ethanol aniline $R_f$ value: 0.8 (silica gel, methylene chloride/methanol=5:2) $C_{32}H_{36}N_4O_5$ ESI mass spectrum: m/z=412 [M–H$^-$].

(10) 3-Z-[1-(4-(dimethylaminomethyl)-anilino)-1-phenyl-methylene]-6-[(2,2,2-trifluoroethoxy)-carbonyl]-2-indolinone Prepared from 3-Z-[1-(4-(dimethylaminomethyl)-anilino)-1-phenyl-methylene]-6-carboxy-2-indolinone and 2,2,2-trifluoroethanol aniline $R_f$ value: 0.5 (silica gel, methylene chloride/methanol=5:1) $C_{27}H_{24}F_3N_3O_3$ ESI mass spectrum: m/z=494 [M–H$^-$].

EXAMPLE 11

3-Z-[1-(4-(piperidin-1-yl-methyl)-anilino)-1-phenyl-methylene]-6-carbamoyl-2-indolinone 0.9 g of 3-Z-[1-(4-(piperidin-1-yl-methyl)-anilino)-1-phenyl-methylene]-6-carboxy-2-indolinone, 0.8 g of TBTU and 0.4 g of HOBT are suspended in 25 ml of dimethylformamide and 1.0 ml of triethylamine are added. The mixture is stirred for 15 minutes at room temperature. After this time ammonia gas is introduced at 10–15° C. over a period of 15 minutes and the mixture is stirred for 1.5 hours at room temperature. The precipitate formed is suction filtered, washed with water, ethanol and ether and dried at 100° C. in vacuo.

Yield: 0.6 g (64% of theory), $R_f$ value: 0.4 (Reversed phase RP 8, methanol/five percent saline solution=6:4) $C_{28}H_{28}N_4O_2$ ESI mass spectrum: m/z=453 [M+H$^+$].

The following compounds are prepared analogously to Example 11:

(1) 3-Z-[1-(4-(piperidin-1-yl-methyl)-anilino)-1-phenyl-methylene]-6-dimethylcarbamoyl-2-indolinone Prepared from 3-Z-[1-(4-(piperidin-1-yl-methyl)-anilino)-1-phenyl-methylene]-6-carboxy-2-indolinone and dimethylamine hydrochloride/diisopropylethylamine $R_f$ value: 0.5 (silica gel, methylene chloride/methanol=5:1) $C_{30}H_{32}N_4O_2$ ESI mass spectrum: m/z=481 [M+H$^-$].

(2) 3-Z-[1-(4-(piperidin-1-yl-methyl)-anilino)-1-phenyl-methylene]-6-(N-ethyl-N-methyl-carbamoyl)-2-indolinone Prepared from 3-Z-[1-(4-(piperidin-1-yl-methyl)-anilino)-1-phenyl-methylene]-6-carboxy-2-indolinone and N-ethyl-N-methyl-amine $R_f$ value: 0.5 (aluminium oxide, methylene chloride/ethanol=20:1) $C_{31}H_{34}N_4O_2$ ESI mass spectrum: m/z=495 [M+H$^+$].

(3) 3-Z-[1-(4-(piperidin-1-yl-methyl)-anilino)-1-phenyl-methylene]-6-methylcarbamoyl-2-indolinone Prepared from 3-Z-[1-(4-(piperidin-1-yl-methyl)-anilino)-1-phenyl-methylene]-6-carboxy-2-indolinone and methylamine hydrochloride/diisopropylethylamine $R_f$ value: 0.3 (aluminium oxide, methylene chloride/ethanol=20:1) $C_{29}H_{30}N_4O_2$ ESI mass spectrum: m/z=467 [M+H$^+$].

(4) 3-Z-[1-(3-(dimethylaminomethyl)-anilino)-1-phenyl-methylene]-6-methylcarbamoyl-2-indolinone Prepared from 3-Z-[1-(3-(dimethylaminomethyl)-anilino)-1-phenyl-methylene]-6-carboxyl-2-indolinone and methylamine hydrochloride/triethylamine $R_f$ value: 0.3 (silica gel, methylene chloride/ethanol=2:1) $C_{26}H_{26}N_4O_2$ Mass spectrum: m/z=426 [M$^+$].

(5) 3-Z-[1-(4-(piperidin-1-yl-methyl)-anilino)-1-phenyl-methylene]-6-(2-hydroxyethyl-carbamoyl)-2-indolinone Prepared from 3-Z-[1-(4-(piperidin-1-yl-methyl)-anilino)-1-phenyl-methylene]-6-carboxy-2-indolinone and ethanolamine/diisopropylethylamine $R_f$ value: 0.5 (aluminium oxide, methylene chloride/methanol=20:1) $C_{30}H_{32}N_4O_3$ ESI mass spectrum: m/z=495 [M–H$^-$].

(6) 3-Z-[1-(4-(piperidin-1-yl-methyl)-anilino)-1-phenyl-methylene]-6-diethylcarbamoyl-2-indolinone Prepared from 3-Z-[1-(4-(piperidin-1-yl-methyl)-anilino)-1-phenyl-methylene]-6-carboxy-2-indolinone and diethylamine hydrochloride/diisopropylethylamine $R_f$ value: 0.8 (aluminium oxide, methylene chloride/methanol=10:1) $C_{32}H_{36}N_4O_2$ ESI mass spectrum: m/z=509 [M+H$^+$].

(7) 3-Z-[1-(4-(N-tert.butoxycarbonyl-ethylaminomethyl)-anilino)-1-phenyl-methylene]-6-carbamoyl-2-indolinone Prepared from 3-Z-[1-(4-(N-tert.butoxycarbonyl-ethylaminomethyl)-anilino)-1-phenyl-methylene]-6-carboxy-2-indolinone $R_f$ value: 0.3 (silica gel, toluene/ethyl acetate/ethanol=4:2:1) $C_{30}H_{32}N_4O_4$ ESI mass spectrum: m/z=511 [M–H$^-$].

(8) 3-Z-[1-(4-(N-dimethylaminomethylcarbonyl-N-methyl-amino)-anilino)-1-phenyl-methylene]-6-carbamoyl-2-indolinone Prepared from 3-Z-[1-(4-(N-dimethylaminomethylcarbonyl-N-methyl-amino)-anilino)-1-phenyl-methylene]-6-carboxy-2-indolinone $R_f$ value: 0.5 (silica gel, methylene chloride/methanol/ammonia=5:1:0.01) $C_{27}H_{27}N_5O_3$ ESI mass spectrum: m/z=468 [M–H$^-$].

EXAMPLE 12

3-Z-[1-(4-(N-dimethylaminomethylcarbonyl-N-methyl-amino)-anilino)-1-phenyl-methylene]-6-methoxycarbonyl-2-indolinone x citric acid 3.25 g of citric acid monohydrate are placed in 50 ml of methanol and 5.0g of 3-Z-[1-(4-(N-dimethylaminomethyl-carbonyl-N-methyl-amino)-anilino)-1-phenyl-methylene]-6-methoxycarbonyl-2-indolinone are added at room temperature. The solution formed is evaporated down, the residue is washed with ether and recrystallised from ethyl acetate.

Yield: 6.3 g (90% of theory), $R_f$ value: 0.6 (silica gel, methylene chloride/methanol/ammonia=5:1:0.01)

Melting point: 198° C. $C_{28}H_{28}N_4O_5$x$C_6H_8O_7$.

ESI mass spectrum: m/z=483 [M–H$^-$].

Elemental analysis: calc.: C 60.34 H 5.37 N 8.28; found: 59.98 5.25 8.13.

The following compound is prepared analogously to Example 12:

(1) 3-Z-[1-(4-(dimethylaminomethyl)-anilino)-1-phenyl-methylene]-6-methoxycarbonyl-2-indolinone x methanesulphonic acid Prepared from 3-Z-[1-(4-(dimethylaminomethyl)-anilino)-1-phenyl-methylene]-6-methoxycarbonyl-2-indolinone and methanesulphonic acid $R_f$ value: 0.6 (silica gel, methylene chloride/methanol/ammonia=5:1:0.01)

Melting point: 275° C. $C_{26}H_{25}N_3O_3$x$CH_4O_3S$

ESI mass spectrum: m/z=426 [M–H$^-$].

Elemental analysis: calc.: C 61.92 H 5.59 N 8.03 S 6.12; found: 61.43 5.87 7.85 5.39.

The following compounds may be prepared analogously to the foregoing Examples:

(1) 3-Z-(1-anilino-1-phenyl-methylene)-6-ethoxycarbonyl-2-indolinone
(2) 3-Z-[1-(4-nitro-anilino)-1-phenyl-methylene]-6-ethoxycarbonyl-2-indolinone
(3) 3-Z-[1-(4-fluoro-anilino)-1-phenyl-methylene]-6-ethoxy-carbonyl-2-indolinone
(4) 3-Z-[1-(4-chloro-anilino)-1-phenyl-methylene]-6-ethoxy-carbonyl-2-indolinone
(5) 3-Z-[1-(4-iodo-anilino)-1-phenyl-methylene]-6-ethoxycarbonyl-2-indolinone
(6) 3-Z-[1-(4-cyano-anilino)-1-phenyl-methylene]-6-ethoxy-carbonyl-2-indolinone
(7) 3-Z-[1-(4-methoxy-anilino)-1-phenyl-methylene]-6-ethoxycarbonyl-2-indolinone
(8) 3-Z-[1-(4-ethoxy-anilino)-1-phenyl-methylene]-6-ethoxycarbonyl-2-indolinone
(9) 3-Z-[1-(4-trifluoromethyl-anilino)-1-phenyl-methylene]-6-ethoxycarbonyl-2-indolinone
(10) 3-Z-[1-(4-methyl-anilino)-1-phenyl-methylene]-6-ethoxycarbonyl-2-indolinone
(11) 3-Z-[1-(4-methylmercapto-anilino)-1-phenyl-methylene]-6-ethoxycarbonyl-2-indolinone
(12) 3-Z-[1-(4-aminomethyl-anilino)-1-phenyl-methylene]-6-ethoxycarbonyl-2-indolinone
(13) 3-Z-[1-(4-isopropylaminomethyl)-anilino)-1-phenyl-methylene]-6-ethoxycarbonyl-2-indolinone
(14) 3-Z-[1-(4-(anilinomethyl)-anilino)-1-phenyl-methylene]-6-ethoxycarbonyl-2-indolinone
(15) 3-Z-[1-(4-(propylaminomethyl)-anilino)-1-phenyl-methylene]-6-ethoxycarbonyl-2-indolinone
(16) 3-Z-[1-(4-(butylaminomethyl)-anilino)-1-phenyl-methylene]-6-ethoxycarbonyl-2-indolinone
(17) 3-Z-[1-(4-(isobutylaminomethyl)-anilino)-1-phenyl-methylene]-6-ethoxycarbonyl-2-indolinone
(18) 3-Z-[1-(4-(cyclohexylaminomethyl)-anilino)-1-phenyl-methylene]-6-ethoxycarbonyl-2-indolinone
(19) 3-Z-[1-(4-(benzylaminomethyl)-anilino)-1-phenyl-methylene]-6-ethoxycarbonyl-2-indolinone
(20) 3-Z-[1-(4-((N-ethyl-N-methyl-amino)-methyl)-anilino)-1-phenyl-methylene]-6-ethoxycarbonyl-2-indolinone
(21) 3-Z-[1-(4-((N-methyl-N-propyl-amino)-methyl)-anilino)-1-phenyl-methylene]-6-ethoxycarbonyl-2-indolinone
(22) 3-Z-[1-(4-((N-isopropyl-N-methyl-amino)-methyl)-anilino)-1-phenyl-methylene]-6-ethoxycarbonyl-2-indolinone
(23) 3-Z-[1-(4-((N-ethyl-N-propyl-amino)-methyl)-anilino)-1-phenyl-methylene]-6-ethoxycarbonyl-2-indolinone
(24) 3-Z-[1-(4-((N-ethyl-N-isopropyl-amino)-methyl)-anilino)-1-phenyl-methylene]-6-ethoxycarbonyl-2-indolinone
(25) 3-Z-[1-(4-(dipropylaminomethyl)-anilino)-1-phenyl-methylene]-6-ethoxycarbonyl-2-indolinone
(26) 3-Z-[1-(4-(diisopropylaminomethyl)-anilino)-1-phenyl-methylene]-6-ethoxycarbonyl-2-indolinone
(27) 3-Z-[1-(4-((N-benzyl-N-ethyl-amino)-methyl)-anilino)-1-phenyl-methylene]-6-ethoxycarbonyl-2-indolinone
(28) 3-Z-[1-(4-(dibenzylaminomethyl)-anilino)-1-phenyl-methylene]-6-ethoxycarbonyl-2-indolinone
(29) 3-Z-[1-(4-(3,6-dihydro-2H-pyridin-1-yl-methyl)-anilino)-1-phenyl-methylene]-6-ethoxycarbonyl-2-indolinone
(30) 3-Z-[1-(4-(3,5-dimethyl-piperidin-1-y-methyl)-anilino)-1-phenyl-methylene]-6-ethoxycarbonyl-2-indolinone
(31) 3-Z-[1-(4-(azepan-1-yl-methyl)-anilino)-1-phenyl-methylene]-6-ethoxycarbonyl-2-indolinone
(32) 3-Z-[1-(4-(piperazin-1-yl-methyl)-anilino)-1-phenyl-methylene]-6-ethoxycarbonyl-2-indolinone
(33) 3-Z-[1-(4-(morpholin-4-yl-methyl)-anilino)-1-phenyl-methylene]-6-ethoxycarbonyl-2-indolinone
(34) 3-Z-[1-(4-(thiomorpholin-4-yl-methyl)-anilino)-1-phenyl-methylene]-6-ethoxycarbonyl-2-indolinone
(35) 3-Z-[1-(4-(1-oxo-thiomorpholin-4-yl-methyl)-anilino)-1-phenyl-methylene]-6-ethoxycarbonyl-2-indolinone
(36) 3-Z-[1-(4-(1,1-dioxo-thiomorpholin-4-yl-methyl)-anilino)-1-phenyl-methylene]-6-ethoxycarbonyl-2-indolinone
(37) 3-Z-[1-(4-(acetylamino-methyl)-anilino)-1-phenyl-methylene]-6-ethoxycarbonyl-2-indolinone
(38) 3-Z-[1-(4-(2-amino-ethyl)-anilino)-1-phenyl-methylene]-6-ethoxycarbonyl-2-indolinone
(39) 3-Z-[1-(4-(2-methylamino-ethyl)-anilino)-1-phenyl-methylene]-6-ethoxycarbonyl-2-indolinone
(40) 3-Z-[1-(4-(2-ethylamino-ethyl)-anilino)-1-phenyl-methylene]-6-ethoxycarbonyl-2-indolinone
(41) 3-Z-[1-(4-(2-diethylamino-ethyl)-anilino)-1-phenyl-methylene]-6-ethoxycarbonyl-2-indolinone
(42) 3-Z-[1-(4-(2-piperidin-1-yl-ethyl)-anilino)-1-phenyl-methylene]-6-ethoxycarbonyl-2-indolinone
(43) 3-Z-[1-(4-(2-acetylamino-ethyl)-anilino)-1-phenyl-methylene]-6-ethoxycarbonyl-2-indolinone
(44) 3-Z-[1-(4-(3-amino-propyl)-anilino)-1-phenyl-methylene]-6-ethoxycarbonyl-2-indolinone
(45) 3-Z-[1-(4-(3-dimethylamino-propyl)-anilino)-1-phenyl-methylene]-6-ethoxycarbonyl-2-indolinone
(46) 3-Z-[1-(4-(N-aminomethylcarbonyl-N-methyl-amino)-anilino)-1-phenyl-methylene]-6-ethoxycarbonyl-2-indolinone
(47) 3-Z-[1-(4-(N-methylaminomethylcarbonyl-N-methyl-amino)-anilino)-1-phenyl-methylene]-6-ethoxycarbonyl-2-indolinone
(48) 3-Z-[1-(4-(N-ethylaminomethylcarbonyl-N-methyl-amino)-anilino)-1-phenyl-methylene]-6-ethoxycarbonyl-2-indolinone
(49) 3-Z-[1-(4-(N-diethylaminomethylcarbonyl-N-methyl-amino)-anilino)-1-phenyl-methylene]-6-ethoxycarbonyl-2-indolinone
(50) 3-Z-[1-(4-(N-(piperidin-1-yl-methylcarbonyl)-N-methyl-amino)-anilino)-1-phenyl-methylene]-6-ethoxycarbonyl-2-indolinone
(51) 3-Z-[1-(4-(N-(morpholin-4-yl-methylcarbonyl)-N-methyl-amino)-anilino)-1-phenyl-methylene]-6-ethoxycarbonyl-2-indolinone
(52) 3-Z-[1-(4-(N-(piperazin-1-yl-methylcarbonyl)-N-methyl-amino]-anilino)-1-phenyl-methylene]-6-ethoxycarbonyl-2-indolinone
(53) 3-Z-[1-(4-(N-(2-amino-ethylcarbonyl)-N-methyl-amino)-anilino)-1-phenyl-methylene]-6-ethoxycarbonyl-2-indolinone
(54) 3-Z-[1-(40-(2-methylamino-ethylcarbonyl)-N-methyl-amino)-anilino)-1-phenyl-methylene]-6-ethoxycarbonyl-2-indolinone
(55) 3-Z-[1-(4-(N-(2-diethylamino-ethylcarbonyl)-N-methyl-amino)-anilino)-1-phenyl-methylene]-6-ethoxycarbonyl-2-indolinone
(56) 3-Z-[1-(4-(N-acetyl-N-(2-aminoethyl)-amino)-anilino)-1-phenyl-methylene]6-ethoxycarbonyl-2-indolinone

(57) 3-Z-[1-(4-(N-acetyl-N-(2-methylamino-ethyl)-amino)-anilino)-1-phenyl-methylene]-6-ethoxycarbonyl-2-indolinone
(58) 3-Z-[1-(4-(N-acetyl-N-(2-methylamino-propyl)-amino)-anilino)-1-phenyl-methylene]-6-ethoxycarbonyl-2-indolinone
(59) 3-Z-[1-(4-(N-acetyl-N-(2-piperidin-1-yl-ethyl)-amino)-anilino)-1-phenyl-methylene]-6-ethoxycarbonyl-2-indolinone
(60) 3-Z-[1-(4-(N-acetyl-N-(aminocarbonylmethyl)-amino)-anilino)-1-phenyl-methylene]-6-ethoxycarbonyl-2-indolinone
(61) 3-Z-[1-(4-(N-acetyl-N-(dimethylaminocarbonylmethyl)-amino)-anilino)-1-phenyl-methylene]-6-ethoxycarbonyl-2-indolinone
(62) 3-Z-[1-(4-(N-acetyl-N-(piperidin-1-yl-carbonylmethyl)-amino)-anilino)-1-phenyl-methylene]-6-ethoxycarbonyl-2-indolinone
(63) 3-Z-[1-(4-(N-methyl-N-(aminocarbonyl)-amino)-anilino)-1-phenyl-methylene]-6-ethoxycarbonyl-2-indolinone
(64) 3-Z-[1-(4-(N-methyl-N-methylaminocarbonyl)-amino)-anilino)-1-phenyl-methylene]-6-ethoxycarbonyl-2-indolinone
(65) 3-Z-[1-(4-(N-methyl-N-(dimethylaminocarbonyl)-amino)-anilino)-1-phenyl-methylene]-6-ethoxycarbonyl-2-indolinone
(66) 3-Z-[1-(4-(N-methyl-N-(piperidin-1-yl-carbonyl)-amino)-anilino)-1-phenyl-3-methylene]-6-ethoxycarbonyl-2-indolinone
(67) 3-Z-[1-(4-(N-(2-aminoethyl)-N-methlysulphonyl-amino)-anilino)-1-phenyl-methylene]-6-ethoxycarbonyl-2-indolinone
(68) 3-Z-[1-(4-(N-(2-methylamino-ethyl)-N-methylsulphonyl-amino)-anilino)-1-phenyl-methylene]-6-ethoxycarbonyl-2-indolinone
(69) 3-Z-[1-(4-(N-(2-thylamino-ethyl)-N-methylsulphonyln-amino)-anilino)-1-phenyl-methylene]-6-ethoxycarbonyl-2-indolinone
(70) 3-Z-[1-(4-(N-(2-diethylamino-ethyl)-N-methylsulphonyl-amino)-anilino)-1-phenyl-methylene]-6-ethoxycarbonyl-2-indolinone
(71) 3-Z-[1-(4-(N-(2-pyrrolidin-1-yl-ethyl)-N-methylsulphonyl-amino)-anilino)-1-phenyl-methylene]-6-ethoxycarbonyl-2-indolinone
(72) 3-Z-[1-(4-(N-(2-piperidin-1-yl-ethyl)-N-methylsulphonyl-amino)-anilino)-1-phenyl-methylene]-6-ethoxycarbonyl-2-indolinone
(73) 3-Z-[1-(4-(N-(2-piperazin-1-yl-ethyl)-N-methylsulphonyl-amino)-anilino)-1-phenyl-methylene]-6-ethoxycarbonyl-2-indolinone
(74) 3-Z-[1-(4-(N-(2-(morpholin-4-yl)-ethyl)-N-methylsulphonyl-amino)-anilino)-1-phenyl-methylene]-6-ethoxycarbonyl-2-indolinone
(75) 3-Z-[1-(4-(N-(aminocarbonylmethyl)-N-methylsulphonyl-amino)-anilino)-1-phenyl-methylene]-6-ethoxycarbonyl-2-indolinone
(76) 3-Z-[1-(4-(N-(methylaminocarbonylmethyl)-N-methylsulphonyl-amino)-anilino)-1-phenyl-methylene]-6-ethoxycarbonyl-2-indolinone
(77) 3-Z-[1-(4-(N-(ethylaminocarbonylmethyl)-N-methylsulphonyl-amino)-anilino)-1-phenyl-methylene]-6-ethoxycarbonyl-2-indolinone
(78) 3-Z-[1-(4-(N-(N-(2-dimethylamino-ethyl)-N-methyl-amino)-carbonylmethyl)-N-methylsulphonyl-amino)-anilino)-1-phenyl-methylene]-6-ethoxycarbonyl-2-indolinone
(79) 3-Z-[1-(4-(N-(diethylaminocarbonylmethyl)-N-methylsulphonyl-amino)-anilino)-1-phenyl-methylene]-6-ethoxycarbonyl-2-indolinone
(80) 3-Z-[1-(4-(N-(pyrrolidin-1-yl-carbonylmethyl)-N-methylsulphonyl-amino)-anilino)-1-phenyl-methylene]-6-ethoxycarbonyl-2-indolinone
(81) 3-Z-[1-(4-(N-(piperidin-1-yl-carbonylmethyl)-N-methylsulphonyl-amino)-anilino)-1-phenyl-methylene]-6-ethoxycarbonyl-2-indolinone
(82) 3-Z-[1-(4-(N-(piperazin-1-yl-carbonylmethyl)-N-methylsulphonyl-amino)-anilino)-1-phenyl-methylene]-6-ethoxycarbonyl-2-indolinone
(83) 3-Z-[1-(4-(N-((morpholin-4-yl)-carbonylmethyl)-N-methylsulphonyl-amino)-anilino)-1-phenyl-methylene]-6-ethoxycarbonyl-2-indolinone
(84) 3-Z-[1-(4-(2-dimethylamino-ethoxy)-anilino)-1-phenyl-methylene]-6-ethoxycarbonyl-2-indolinone
(85) 3-Z-[1-(4-(3-dimethylamino-propoxy)-anilino)-1-phenyl-methylene]-6-ethoxycarbonyl-2-indolinone
(86) 3-Z-[1-(4-(aminocarbonylmethyl)-anilino)-1-phenyl-methylene]-6-ethoxycarbonyl-2-indolinone
(87) 3-Z-[1-(4-(2-aminocarbonyl-ethyl)-anilino)-1-phenyl-methylene]-6-ethoxycarbonyl-2-indolinone
(88) 3-Z-[1-(4-(pyridin-2-yl)-anilino)-1-phenyl-methylene]-6-ethoxycarbonyl-2-indolinone
(89) 3-Z-[1-(4-(pyridine-3-yl)-anilino)-1-phenyl-methylene]-6-ethoxycarbonyl-2-indolinone
(90) 3-Z-[1-(4-pyridin-4-yl)-anilino)-1-phenyl-methylene]-6-ethoxycarbonyl-2-indolinone
(91) 3-Z-[1-(4-(N-acetyl-N-methyl-amino)-anilino)-1-phenyl-methylene]-6-ethoxycarbonyl-2-indolinone
(92) 3-Z-[1-(4-(N-ethylcarbonyl-N-(dimethylaminocarbonyl-methyl)-amino)-anilino)-1-phenyl-methylene]-6-ethoxycarbonyl-2-indolinone
(93) 3-Z-[1-(carbamoylmethyl-anilino)-1-phenyl-methylene]-6-ethoxycarbonyl-2-indolinone
(94) 3-Z-[1-(4-dimethylcarbamoylmethyl-anilino)-1-phenyl-methylene]-6-ethoxycarbonyl-2-indolinone
(95) 3-Z-[1-(4-(piperidin-1-yl-methyl)-anilino)-methylene]-6-ethoxycarbonyl-2-indolinone
(96) 3-Z-[1-(4-(piperidin-1-yl-methyl)-anilino)-propylidene]-6-ethoxycarbonyl-2-indolinone
(97) 3-Z-[1-(4-(piperidin-1-yl-methyl)-anilino)-butylidene]-6-ethoxycarbonyl-2-indolinone
(98) 3-Z-[1-(4-(N-(3-dimethylamino-propyl)-N-acetyl-amino)-anilino)-methylene]-6-ethoxycarbonyl-2-indolinone
(99) 3-Z-[1-(4-(N-(3-dimethylamino-propyl)-N-acetyl-amino)-anilino)-ethylidene]-6-ethoxycarbonyl-2-indolinone
(100) 3-Z-[1-(4-(N-(3-dimethylamino-propyl)-N-acetyl-amino)-anilino)-propylidene]-6-ethoxycarbonyl-2-indolinone
(101) 3-Z-[1-(4-(N-(3-dimethylamino-propyl)-N-acetyl-amino)-anilino)-butylidene]-6-ethoxycarbonyl-2-indolinone
(102) 3-Z-[1-(4-(N-(2-dimethylamino-ethyl)-N-methylsulphonyl-amino)-anilino)-methylene]-6-ethoxycarbonyl-2-indolinone
(103) 3-Z-[1-(4-(N-(2-dimethylamino-ethyl)-N-methylsulphonyl-amino)-anilino)-propylidene]-6-ethoxycarbonyl-2-indolinone
(104) 3-Z-[1-(4-(N-(2-dimethylamino-ethyl)-N-methylsulphonyl-amino)-anilino)-butylidene]-6-ethoxycarbonyl-2-indolinone
(105) 3-Z-[1-(4-tetrazol-5-yl-anilino)-methylene]-6-ethoxycarbonyl-2-indolinone (106) 3-Z-[1-(4-tetrazol-5-yl-anilino)-ethylidene]-6-ethoxycarbonyl-2-indolinone
(107) 3-Z-[1-(4-tetrazol-5-yl-anilino)-propylidene]-6-ethoxycarbonyl-2-indolinone
(108) 3-Z-[1-(4-tetrazol-5-yl-anilino)-butylidene]-6-ethoxycarbonyl-2-indolinone
(109) 3-Z-[1-(4-carboxy-anilino)-methylene]-6-ethoxycarbonyl-2-indolinone
(110) 3-Z-[1-(4-carboxy-anilino)-propylidene]-6-ethoxycarbonyl-2-indolinone
(111) 3-Z-[1-(4-carboxy-anilino)-butylidene]-6-ethoxycarbonyl-2-indolinon
(112) 3-Z-[1-(4-(N-(3-dimethylamino-propionyl)-N-dimethylaminocarbonylmethyl-amino)-anilino)-1-phenyl-methylene]-6-ethoxycarbonyl-2-indolinone
(113) 3-Z-[1-(4-(N-(4-dimethylamino-butyryl)-N-dimethylaminocarbonylmethyl-amino)-anilino)-1-phenyl-methylene]-6-ethoxycarbonyl-2-indolinone
(114) 3-Z-[1-(4-(N-dimethylaminocarbonylmethyl-N-(2-dimethylamino-ethylsulphonyl)-amino)-anilino)-1-phenyl-methylene]-6-ethoxycarbonyl-2-indolinone
(115) 3-Z-[1-(4-(N-dimethylaminocarbonylmethyl-N-(3-dimethylamino-propylsulphonyl)-amino)-anilino)-1-phenyl-methylene]-6-ethoxycarbonyl-2-indolinone
(116) 3-Z-[1-(4-((2-hydroxy-ethyl)-amino-methyl)-anilino)-1-phenyl-methylene]-6-ethoxycarbonyl-2-indolinone
(117) 3-Z-[1-(4-((2-methoxy-ethyl)-amino-methyl)-anilino)-1-phenyl-methylene]-6-ethoxycarbonyl-2-indolinone
(118) 3-Z-[1-(4-((2-dimethylamino-ethyl)-amino-methyl)-anilino)-1-phenyl-methylene]-6-ethoxycarbonyl-2-indolinone
(119) 3-Z-[1-(4-((3-dimethylamino-propyl)-amino-methyl)-anilino)-1-phenyl-methylene]-6-ethoxycarbonyl-2-indolinone
(120) 3-Z-[1-(4-((N-tert.butoxycarbonyl-2-amino-ethyl)-amino-methyl)-anilino)-1-phenyl-methylene]-6-ethoxycarbonyl-2-indolinone
(121) 3-Z-[1-(4-((N-tert.butoxycarbonyl-3-amino-propyl)-amino-methyl)-anilino)-1-phenyl-methylene]-6-ethoxycarbonyl-2-indolinone
(122) 3-Z-[1-(4-((2-amino-ethyl)-amino-methyl)-anilino)-1-phenyl-methylene]-6-ethoxycarbonyl-2-indolinone
(123) 3-Z-[1-(4-((3-amino-propyl)-amino-methyl)-anilino)-1-phenyl-methylene]-6-ethoxycarbonyl-2-indolinone
(124) 3-Z-[1-(4-((2-acetylamino-ethyl)-amino-methyl)-anilino)-1-phenyl-methylene]-6-ethoxycarbonyl-2-indolinone
(125) 3-Z-[1-(4-((3-acetylamino-propyl)-amino-methyl)-anilino)-1-phenyl-methylene]-6-ethoxycarbonyl-2-indolinone
(126) 3-Z-[1-(4-((2-methylsulphonylamino-ethyl)-amino-methyl)-anilino)-1-phenyl-methylene]-6-ethoxycarbonyl-2-indolinone
(127) 3-Z-[1-(4-((3-methylsulphonylamino-propyl)-amino-methyl)-anilino)-1-phenyl-methylene]-6-ethoxycarbonyl-2-indolinone
(128) 3-Z-[1-(4-(N-(N-tert.butoxycarbonyl-2-amino-ethyl)-N-methyl-amino-methyl)-anilino)-1-phenyl-methylene]-6-ethoxycarbonyl-2-indolinone
(129) 3-Z-[1-(4-(N-(2-amino-ethyl)-N-methyl-amino-methyl)-anilino)-1-phenyl-methylene]-6-ethoxycarbonyl-2-indolinone
(130) 3-Z-[1-(4-(N-(2-acetylamino-ethyl)-N-methyl-amino-methyl)-anilino)-1-phenyl-methylene]-6-ethoxycarbonyl-2-indolinone
(131) 3-Z-[1-(4-(N-(2-methylsulphonylamino-ethyl)-N-methyl-amino-methyl)-anilino)-1-phenyl-methylene]-6-ethoxycarbonyl-2-indolinone
(132) 3-Z-[1-(4-(carboxymethyl-amino-methyl)-anilino)-1-phenyl-methylene]-6-ethoxycarbonyl-2-indolinone
(133) 3-Z-[1-(4-(ethoxycarbonylmethyl-amino-methyl)-anilino)-1-phenyl-methylene]-6-ethoxycarbonyl-2-indolinone
(134) 3-Z-[1-(4-(carbamoylmethyl-amino-methyl)-anilino)-1-phenyl-methylene]-6-ethoxycarbonyl-2-indolinone
(135) 3-Z-[1-(4-(dimethylcarbamoyl-methyl-amino-methyl)-anilino)-1-phenyl-methylene]-6-ethoxycarbonyl-2-indolinone
(136) 3-Z-[1-(4-(methylcarbamoyl-methyl-amino-methyl)-anilino)-1-phenyl-methylene]-6-ethoxycarbonyl-2-indolinone
(137) 3-Z-[1-(4-(N-dimethylaminomethylcarbonyl-N-methyl-amino)-3-amino-anilino)-1-phenyl-methylene]-6-ethoxycarbonyl-2-indolinone
(138) 3-Z-[1-(4-(N-dimethylaminomethylcarbonyl-N-methyl-amino)-3-nitro-anilino)-1-phenyl-methylene]-6-ethoxycarbonyl-2-indolinone
(139) 3-Z-[1-(4-(N-dimethylaminomethylcarbonyl-N-methyl-amino)-3-acetylamino-anilino)-1-phenyl-methylene]-6-ethoxycarbonyl-2-indolinone
(140) 3-Z-[1-(4-(N-dimethylaminomethylcarbonyl-N-methyl-amino)-3-methylsulphonylamino-anilino)-1-phenyl-methylene]-6-ethoxycarbonyl-2-indolinone
(141) 3-Z-[1-(4-(N-dimethylaminomethylcarbonyl-N-methyl-amino)-3-cyano-anilino)-1-phenyl-methylene]-6-ethoxycarbonyl-2-indolinone
(142) 3-Z-[1-(4-(N-dimethylaminomethylcarbonyl-N-methyl-amino)-3-hydroxy-anilino)-1-phenyl-methylene]-6-ethoxycarbonyl-2-indolinone
(143) 3-Z-[1-(4-(N-dimethylaminomethylcarbonyl-N-methyl-amino)-3-methoxy-anilino)-1-phenyl-methylene]-6-ethoxycarbonyl-2-indolinone
(144) 3-Z-[1-(4-(N-dimethylaminomethylcarbonyl-N-methyl-amino)-3-ethoxycarbonyl-anilino)-1-phenyl-methylene]-6-ethoxycarbonyl-2-indolinone
(145) 3-Z-[1-(4-(N-dimethylaminomethylcarbonyl-N-methyl-amino)-3-carboxy-anilino)-1-phenyl-methylene]-6-ethoxycarbonyl-2-indolinone
(146) 3-Z-[1-(4-(N-dimethylaminomethylcarbonyl-N-methyl-amino)-3-carbamoyl-anilino)-1-phenyl-methylene]-6-ethoxycarbonyl-2-indolinone
(147) 3-Z-[1-(4-(N-dimethylaminomethylcarbonyl-N-methyl-amino)-3-chloro-anilino)-1-phenyl-methylene]-6-ethoxycarbonyl-2-indolinone
(148) 3-Z-[1-(4-(N-dimethylaminomethylcarbonyl-N-methyl-amino)-3-fluoro-anilino)-1-phenyl-methylene]-6-ethoxycarbonyl-2-indolinone
(149) 3-Z-[1-(4-(N-dimethylaminomethylcarbonyl-N-methyl-amino)-3-bromo-anilino)-1-phenyl-methylene]-6-ethoxycarbonyl-2-indolinone
(150) 3-Z-[1-(4-(N-dimethylaminomethylcarbonyl-N-methyl-amino)-3-methyl-anilino)-1-phenyl-methylene]-6-ethoxycarbonyl-2-indolinone
(151) 3-Z-[1-(4-(N-dimethylaminomethylcarbonyl-N-methyl-amino)-3-trifluoromethyl-anilino)-1-phenyl-methylene]-6-ethoxycarbonyl-2-indolinone
(152) 3-Z-[1-(4-(N-dimethylaminomethylcarbonyl-N-methyl-amino)-3,5-dibromo-anilino)-1-phenyl-methylene]-6-ethoxycarbonyl-2-indolinone
(153) 3-Z-[1-(4-(N-dimethylaminomethylcarbonyl-N-methyl-amino)-3,5-dichloro-anilino)-1-phenyl-methylene]-6-ethoxycarbonyl-2-indolinone
(154) 3-Z-[1-(4-(dimethylaminomethyl)-3-amino-anilino)-1-phenyl-methylene]-6-ethoxycarbonyl-2-indolinone
(155) 3-Z-[1-(4-(dimethylaminomethyl)-3-nitro-anilino)-1-phenyl-methylene]-6-ethoxycarbonyl-2-indolinone (156) 3-Z-[1-(4-(dimethylaminomethyl)-3-acetylamino-anilino)-1-phenyl-methylene]-6-ethoxycarbonyl-2-indolinone
(157) 3-Z-[1-(4-(dimethylaminomethyl)-3-(methylsulphonylamino)-anilino)-1-phenyl-methylene]-6-ethoxycarbonyl-2-indolinone
(158) 3-Z-[1-(4-(dimethylaminomethyl)-3-cyano-anilino)-1-phenyl-methylene]-6-ethoxycarbonyl-2-indolinone
(159) 3-Z-[1-(4-(dimethylaminomethyl)-3-hydroxy-anilino)-1-phenyl-methylene]-6-ethoxycarbonyl-2-indolinone
(160) 3-Z-[1-(4-(dimethylaminomethyl)-3-methoxy-anilino)-1-phenyl-methylene]-6-ethoxycarbonyl-2-indolinone
(161) 3-Z-[1-(4-(dimethylaminomethyl)-3-(ethoxycarbonyl)-anilino)-1-phenyl-methylene]-6-ethoxycarbonyl-2-indolinone
(162) 3-Z-[1-(4-(dimethylaminomethyl)-3-carboxy-anilino)-1-phenyl-methylene]-6-ethoxycarbonyl-2-indolinone
(163) 3-Z-[1-(4-(dimethylaminomethyl)-3-carbamoyl-anilino)-1-phenyl-methylene]-6-ethoxycarbonyl-2-indolinone
(164) 3-Z-[1-(4-(dimethylaminomethyl)-3-chloro-anilino)-1-phenyl-methylene]-6-ethoxycarbonyl-2-indolinone
(165) 3-Z-[1-(4-(dimethylaminomethyl)-3-fluoro-anilino)-1-phenyl-methylene]-6-ethoxycarbonyl-2-indolinone
(166) 3-Z-[1-(4-(dimethylaminomethyl)-3-bromo-anilino)-1-phenyl-methylene]-6-ethoxycarbonyl-2-indolinone
(167) 3-Z-[1-(4-(dimethylaminomethyl)-3-methyl-anilino)-1-phenyl-methylene]-6-ethoxycarbonyl-2-indolinone
(168) 3-Z-[1-(4-(dimethylaminomethyl)-3-trifluoromethyl-anilino)-1-phenyl-methylene]-6-ethoxycarbonyl-2-indolinone
(169) 3-Z-[1-(4-(dimethylaminomethyl)-3,5-dibromo-anilino)-1-phenyl-methylene]-6-ethoxycarbonyl-2-indolinone
(170) 3-Z-[1-(4-(dimethylaminomethyl)-3,5-dichloro-anilino)-1-phenyl-methylene]-6-ethoxycarbonyl-2-indolinone
(171) 3-Z-[1-(4-(N-((4-methyl-piperazin-1-yl)-methylcarbonyl)-N-methyl-amino)-anilino)-1-phenyl-methylene]-6-ethoxycarbonyl-2-indolinone
(172) 3-Z-[1-(4-(N-(imidazo-1-yl-methylcarbonyl)-N-methyl-amino)-anilino)-1-phenyl-methylene]-6-ethoxycarbonyl-2-indolinone
(173) 3-Z-[1-(4-(N-(phthalimido-2-yl-methylcarbonyl)-N-methyl-amino)-anilino)-1-phenyl-methylene]-6-ethoxycarbonyl-2-indolinone
(174) 3-Z-[1-(4-(N-aminomethylcarbonyl-N-methyl-amino)-anilino)-1-phenyl-methylene]-6-ethoxycarbonyl-2-indolinone
(175) 3-Z-[1-(4-(N-acetylaminomethylcarbonyl-N-methyl-amino)-anilino)-1-phenyl-methylene]-6-ethoxycarbonyl-2-indolinone
(176) 3-Z-[1-(4-(N-methylsulphonylaminomethylcarbonyl-N-methyl-amino)-anilino)-1-phenyl-methylene]-6-ethoxycarbonyl-2-indolinone
(177) 3-Z-[1-(4-(N-((N-(2-methoxyethyl)-N-methyl-amino)-methylcarbonyl)-N-methyl-amino)-anilino)-1-phenyl-methylene]-6-ethoxycarbonyl-2-indolinone
(178) 3-Z-[1-(4-(N-((N-(2-dimethylaminoethyl)-N-methyl-amino)-methylcarbonyl)-N-methyl-amino)-anilino)-1-phenyl-methylene]-6-ethoxycarbonyl-2-indolinone
(179) 3-Z-[1-(4-(N-((di-(2-hydroxyethyl)-amino)-methylcarbonyl)-N-methyl-amino)-anilino)-1-phenyl-methylene]-6-ethoxycarbonyl-2-indolinone
(180) 3-Z-[1-(4-(N-dimethylaminomethylcarbonyl-N-methyl-amino)-anilino)-methylene]-6-ethoxycarbonyl-2-indolinone
(181) 3-Z-[1-(4-(N-dimethylaminomethylcarbonyl-N-methyl-amino)-anilino)-ethylidene]-6-ethoxycarbonyl-2-indolinone
(182) 3-Z-[1-(4-(N-dimethylaminomethylcarbonyl-N-methyl-amino)-anilino)-propylidene]-6-ethoxycarbonyl-2-indolinone
(183) 3-Z-[1-(4-(N-dimethylaminomethylcarbonyl-N-methyl-amino)-anilino)-butylidene]-6-ethoxycarbonyl-2-indolinone
(184) 3-Z-[1-(4-(dimethylaminomethyl)-anilino)-methylene]-6-ethoxycarbonyl-2-indolinone
(185) 3-Z-[1-(4-(dimethylaminomethyl)-anilino)-ethylidene]-6-ethoxycarbonyl-2-indolinone
(186) 3-Z-[1-(4-(dimethylaminomethyl)-anilino)-propylidene]-6-ethoxycarbonyl-2-indolinone
(187) 3-Z-[1-(4-(dimethylaminomethyl)-anilino)-butylidene]-6-ethoxycarbonyl-2-indolinone
(188) 3-Z-[1-(4-(N-dimethylaminocarbonylmethyl-amino)-anilino)-1-phenyl-methylene]-6-ethoxycarbonyl-2-indolinone
(189) 3-Z-[1-(4-(N-(3-dimethylamino-propyl)-N-acetyl-amino)-anilino)-1-phenyl-methylene]-6-ethoxycarbonyl-2-indolinone
(190) 3-Z-[1-(4-((imidazolidin-2,4-dion-5-ylidene)-methyl)-anilino)-1-phenyl-methylene]-6-ethoxycarbonyl-2-indolinone
(191) 3-Z-[1-(4-((2-dimethylamino-ethyl)-carbonyl)-N-methyl-amino)-anilino)-1-phenyl-methylene]-6-ethoxycarbonyl-2-indolinone
(192) 3-Z-[1-(4-(N-tert.butoxycarbonyl-aminomethyl)-anilino)-1-phenyl-methylene]-6-ethoxycarbonyl-2-indolinone
(193) 3-Z-[1-(4-(2-oxo-pyrrolidin-1-yl-methyl)-anilino)-1-phenyl-methylene]-6-ethoxycarbonyl-2-indolinone
(194) 3-Z-[1-(4-(N-aminocarbonylmethyl-N-methylsulphonyl-amino)-anilino)-1-phenyl-methylene]-6-ethoxycarbonyl-2-indolinone
(195) 3-Z-[1-(4-(N-cyanomethyl-N-methylsulphonyl-amino)-anilino)-1-phenyl-methylene]-6-ethoxycarbonyl-2-indolinone
(196) 3-Z-[1-(4-(2-(imidazol-4-yl)-ethyl)-anilino)-1-phenyl-methylene]-6-ethoxycarbonyl-2-indolinone
(197) 3-Z-[1-(4-((2-(N-benzyl-N-methyl-amino)-ethyl)-N-methylsulphonyl-amino)-anilino)-1-phenyl-methylene]-6-ethoxycarbonyl-2-indolinone
(198) 3-Z-[1-(4-cyclohexylamino-anilino)-1-phenyl-methylene]-6-ethoxycarbonyl-2-indolinone
(199) 3-Z-[1-(4-(imidazol-1-yl-methyl)-anilino)-1-phenyl-methylene]-6-ethoxycarbonyl-2-indolinone
(200) 3-Z-[1-(4-(imidazol-1-yl-methyl)-anilino)-1-phenyl-methylene]-6-ethoxycarbonyl-2-indolinone
(201) 3-Z-[1-(N-methyl-piperidine-4-yl-amino)-1-phenyl-methylene]-6-ethoxycarbonyl-2-indolinone
(202) 3-Z-[1-(4-(imidazol-4-yl-methyl)-anilino)-1-phenyl-methylene]-6-ethoxycarbonyl-2-indolinone
(203) 3-Z-[1-(4-(4-hydroxy-piperidin-1-yl)-methyl)-anilino)-1-phenyl-methylene]-6-ethoxycarbonyl-2-indolinone
(204) 3-Z-[1-(4-(4-methoxy-piperidin-1-yl)-methyl)-anilino)-1-phenyl-methylene]-6-ethoxycarbonyl-2-indolinone
(205) 3-Z-[1-(4-benzyl-anilino)-1-phenyl-methylene]-6-ethoxycarbonyl-2-indolinone
(206) 3-Z-[1-(4-(N-(3-trifluoroacetylamino-propyl)-N-methylsulphonyl-amino)-anilino)-1-phenyl-methylene]-6-ethoxycarbonyl-2-indolinone (207) 3-Z-[1-(4-(4-tert.butoxycarbonyl-piperazin-1-yl-methyl)-anilino)-1-phenyl-methylene]-6-ethoxycarbonyl-2-indolinone
(208) 3-Z-[1-(4-(1-methyl-imidazol-2-yl)-anilino)-1-phenyl-methylene]-6-ethoxycarbonyl-2-indolinone
(209) 3-Z-[1-(4-(1-methyl-imidazol-2-yl)-anilino)-1-phenyl-methylene]-6-ethoxycarbonyl-2-indolinone
(210) 3-Z-[1-(4-(N-(2-dimethylamino-ethyl)-N-methylsulphonyl-amino)-3-amino-anilino)-1-phenyl-methylene]-6-ethoxycarbonyl-2-indolinone
(211) 3-Z-[1-(4-((3-(N-benzyl-N-methyl-amino)-propyl)-N-methylsulphonyl-amino)-anilino)-1-phenyl-methylene]-6-ethoxycarbonyl-2-indolinone
(212) 3-Z-[1-(4-(N-(2-dimethylamino-ethyl)-N-acetyl-amino)-anilino)-1-phenyl-methylene]-6-ethoxycarbonyl-2-indolinone
(213) 3-Z-[1-(4-(N-(2-dimethylamino-ethyl)-N-butyryl-amino)-anilino)-1-phenyl-methylene]-6-ethoxycarbonyl-2-indolinone
(214) 3-Z-[1-(4-(N-(2-dimethylamino-ethyl)-N-isobutyryl-amino)-anilino)-1-phenyl-methylene]-6-ethoxycarbonyl-2-indolinone
(215) 3-Z-[1-(4-(N-(2-dimethylamino-ethyl)-N-benzoyl-amino)-anilino)-1-phenyl-methylene]-6-ethoxycarbonyl-2-indolinone
(216) 3-Z-[1-(4-(N-(2-dimethylamino-ethyl)-N-acetyl-amino)-3-amino-anilino)-1-phenyl-methylene]-6-ethoxycarbonyl-2-indolinone
(217) 3-Z-[1-(4-(4-hydroxymethyl-piperidin-1-yl-methyl)-anilino)-1-phenyl-methylene]-6-ethoxycarbonyl-2-indolinone
(218) 3-Z-[1-(4-(2-(4-hydroxy-piperidin-1-yl)-ethyl)-anilino)-1-phenyl-methylene)-6-ethoxycarbonyl-2-indolinone
(219) 3-Z-[1-(4-(N-(2-dimethylamino-ethyl)-N-propylsulphonyl-amino)-anilino)-1-phenyl-methylene]-6-ethoxycarbonyl-2-indolinone
(220) 3-Z-[1-(4-(N-(2-dimethylamino-ethyl)-N-butylsulphonyl-amino)-anilino)-1-phenyl-methylene]-6-ethoxycarbonyl-2-indolinone
(221) 3-Z-[1-(4-(N-(2-dimethylamino-ethyl)-N-phenylsulphonyl-amino)-anilino)-1-phenyl-methylene]-6-ethoxycarbonyl-2-indolinone
(222) 3-Z-[1-(4-(N-(2-dimethylamino-ethyl)-N-benzylsulphonyl-amino)-anilino)-1-phenyl-methylene]-6-ethoxycarbonyl-2-indolinone
(223) 3-Z-[1-(4-((imidazolidin-2,4-dion-5-yl)-methyl)-anilino)-1-phenyl-methylene]-6-ethoxycarbonyl-2-indolinone
(224) 3-Z-[1-(4-((3-hydroxy-pyrrolidin-1-yl)-methyl)-anilino)-1-phenyl-methylene]-6-ethoxycarbonyl-2-indolinone
(225) 3-Z-[1-(4-(cyclohexylyl-methyl)-anilino)-1-phenyl-methylene]-6-ethoxycarbonyl-2-indolinone
(226) 3-Z-[1-(4-(cyclohexyl-carbonyl)-anilino)-1-phenyl-methylene]-6-ethoxycarbonyl-2-indolinone
(227) 3-Z-[1-(4-diethylaminomethyl-anilino)-1-phenyl-methylene]-6-ethoxycarbonyl-2-indolinone
(228) 3-Z-[1-(4-(N-(n-hexyl)-N-methyl-aminomethyl)-anilino)-1-phenyl-methylene]-6-ethoxycarbonyl-2-indolinone
(229) 3-Z-[1-(4-(N-(2-dimethylamino-ethyl)-N-(furan-2-carbonyl)-amino)-anilino)-1-phenyl-methylene]-6-ethoxycarbonyl-2-indolinone
(230) 3-Z-[1-(4-(N-(2-dimethylamino-ethyl)-N-(2-methoxy-benzoyl)-amino)-anilino)-1-phenyl-methylene]-6-ethoxycarbonyl-2-indolinone
(231) 3-Z-[1-(4-(N-(2-dimethylamino-ethyl)-N-(pyridine-3-carbonyl)-amino)-anilino)-1-phenyl-methylene]-6-ethoxycarbonyl-2-indolinone
(232) 3-Z-[1-(4-(N-(2-dimethylamino-ethyl)-N-(phenyl-acetyl)-amino)-anilino)-1-phenyl-methylene]-ethoxycarbonyl-2-indolinone
(233) 3-Z-[1-(4-(imidazol-2-yl)-anilino)-1-phenyl-methylene]-6-ethoxycarbonyl-2-indolinone
(234) 3-Z-[1-(4-(1-ethyl-imidazol-2-yl)-anilino)-1-phenyl-methylene]-6-ethoxycarbonyl-2-indolinone
(235) 3-Z-[1-(4-(1-benzyl-imidazol-2-yl)-anilino)-1-phenyl-methylene]-6-ethoxycarbonyl-2-indolinone
(236) 3-Z-[1-(4-(N-(2-dimethylamino-ethyl)-N-isopropylsulphonyl-amino)-anilino)-1-phenyl-methylene]-6-ethoxycarbonyl-2-indolinone
(237) 3-Z-[1-(4-(N-((4-benzyl-piperazin-1-yl)-methylcarbonyl)-N-methyl-amino)-anilino)-1-phenyl-methylene]-6-ethoxycarbonyl-2-indolinone
(238) 3-Z-[1-(4-(N-(pyrrolidin-1-yl-methylcarbonyl)-N-methyl-amino)-anilino)-1-phenyl-methylene]-6-ethoxycarbonyl-2-indolinone
(239) 3-Z-[1-(4-(N-(2-dimethylamino-ethyl)-N-acetyl-amino)-3-bromo-anilino)-1-phenyl-methylene]-6-ethoxycarbonyl-2-indolinone
(240) 3-Z-[1-(4-(5-methyl-imidazol-4-yl)-anilino)-1-phenyl-methylene]-6-ethoxycarbonyl-2-indolinone
(241) 3-Z-[1-(4-(N-((2-dimethylamino-ethyl)-carbonyl)-N-isopropyl-amino)-anilino)-1-phenyl-methylene]-6-ethoxycarbonyl-2-indolinone
(242) 3-Z-[1-(4-(N-((2-dimethylamino-ethyl)-carbonyl)-N-benzyl-amino)-anilino)-1-phenyl-methylene]-6-ethoxycarbonyl-2-indolinone
(243) 3-Z-[1-(4-(N-butyl-N-tert.butoxycarbonyl-aminomethyl)-anilino)-1-phenyl-methylene]-6-ethoxycarbonyl-2-indolinone
(244) 3-Z-[1-(4-(N-((N-aminocarbonylmethyl-N-methyl-amino)-methylcarbonyl)-N-methyl-amino)-anilino)-1-phenyl-methylene]-6-ethoxycarbonyl-2-indolinone
(245) 3-Z-[1-(4N-((N-benzyl-N-methyl-amino)-methylcarbonyl)-N-methyl-amino)-anilino)-1-phenyl-methylene]-6-ethoxycarbonyl-2-indolinone
(246) 3-Z-[1-(4-(N-(di-(2-methoxyethyl)-amino-methylcarbonyl)-N-methyl-amino)-anilino)-1-phenyl-methylene]-6-ethoxycarbonyl-2-indolinone
(247) 3-Z-[1-(4-(N-((2-(4-tert.butoxycarbonyl-piperazin-1-yl)-ethyl)-carbonyl)-N-methyl-amino)-anilino)-1-phenyl-methylene]-6-ethoxycarbonyl-2-indolinone
(248) 3-Z-[1-(4-(N-((2-(piperidin-1-yl)-ethyl)-carbonyl)-N-methyl-amino)-anilino)-1-phenyl-methylene]-6-ethoxycarbonyl-2-indolinone
(249) 3-Z-[1-(4-(N-((2-(N-benzyl-N-methyl-amino)-ethyl)-carbonyl)-N-methyl-amino)-anilino)-1-phenyl-methylene]-6-ethoxycarbonyl-2-indolinone
(250) 3-Z-[1-(4-(N-dimethylaminomethylcarbonyl-N-isopropyl-amino)-anilino)-1-phenyl-methylene]-6-ethoxycarbonyl-2-indolinone
(251) 3-Z-[1-(4-(N-(piperidin-1-yl-methylcarbonyl)-N-isopropyl-amino)-anilino)-1-phenyl-methylene]-6-ethoxycarbonyl-2-indolinone
(252) 3-Z-[1-(4-(N-((4-tert.butoxycarbonyl-piperazin-1-yl)-methylcarbonyl)-N-isopropyl-amino)-anilino)-1-phenyl-methylene]-6-ethoxycarbonyl-2-indolinone
(253) 3-Z-[1-(4-(N-((N-benzyl-N-methyl-amino)-methylcarbonyl)-N-benzyl-amino)-anilino)-1-phenyl-methylene]-6-ethoxycarbonyl-2-indolinone
(254) 3-Z-[1-(4-(N-dimethylaminomethylcarbonyl-N-benzyl-amino)-anilino)-1-phenyl-methylene]-6-ethoxycarbonyl-2-indolinone (255) 3-Z-[1-(4-(N-(piperidin-1-yl-methylcarbonyl)-N-benzyl-amino)-anilino)-1-phenyl-methylene]-6-ethoxycarbonyl-2-indolinone
(256) 3-Z-[1-(4-(1,2,4-triazol-2-yl-methyl)-anilino)-1-phenyl-methylene]-6-ethoxycarbonyl-2-indolinone
(257) 3-Z-[1-(4-(1,2,3-triazol-2-yl-methyl)-anilino)-1-phenyl-methylene]-6-ethoxycarbonyl-2-indolinone
(258) 3-Z-[1-(4-(1,2,3-triazol-1-yl-methyl)-anilino)-1-phenyl-methylene]-6-ethoxycarbonyl-2-indolinone
(259) 3-Z-[1-(4-((N-aminocarbonylmethyl-N-methyl-amino)-methyl)-anilino)-1-phenyl-methylene]-6-ethoxycarbonyl-2-indolinone
(260) 3-Z-[1-(4-((di-(2-methoxy-ethyl)-amino)-methyl)-anilino)-1-phenyl-methylene]-6-ethoxycarbonyl-2-indolinone
(261) 3-Z-[1-(4-((di-(2-hydroxy-ethyl)-amino)-methyl)-anilino)-1-phenyl-methylene]-6-ethoxycarbonyl-2-indolinone
(262) 3-Z-[1-(4-((N-ethoxycarbonylmethyl-N-methyl-amino)-methyl)-anilino)-1-phenyl-methylene]-6-ethoxycarbonyl-2-indolinone
(263) 3-Z-[1-(4-(azetidin-1-yl-methyl)-anilino)-1-phenyl-methylene]-6-ethoxycarbonyl-2-indolinone
(264) 3-Z-[1-(4-(N-propyl-N-tert.butoxycarbonyl-aminomethyl)-anilino)-1-phenyl-methylene]-6-ethoxycarbonyl-2-indolinone
(265) 3-Z-[1-(4-((N-(2-(2-methoxy-ethoxy)-ethyl)-N-methyl-amino)-methyl)-anilino)-1-phenyl-methylene]-6-ethoxycarbonyl-2-indolinone
(266) 3-Z-[1-(4-((N-(tert.butoxycarbonyl-3-amino-propyl)-N-methyl-amino)-methyl)-anilino)-1-phenyl-methylene]-6-ethoxycarbonyl-2-indolinone
(267) 3-Z-[1-(4-((N-(methylcarbamoyl-methyl)-N-methyl-amino)-methyl)-anilino)-1-phenyl-methylene]-6-ethoxycarbonyl-2-indolinone
(268) 3-Z-[1-(4-((N-(dimethylcarbamoyl-methyl)-N-methyl-amino)-methyl)-anilino)-1-phenyl-methylene)]-6-ethoxycarbonyl-2-indolinone
(269) 3-Z-[1-(4-((N-propyl-N-methyl-amino)-methyl)-anilino)-1-phenyl-methylene]-6-ethoxycarbonyl-2-indolinone
(270) 3-Z-[1-(4-((N-(2-dimethylamino-ethyl)-N-methyl-amino)-methyl)-anilino)-1-phenyl-methylene]-6-ethoxycarbonyl-2-indolinone
(271) 3-Z-[1-(4-((N-(3-dimethylamino-propyl)-N-methyl-amino)-methyl)-anilino)-1-phenyl-methylene]-6-ethoxycarbonyl-2-indolinone
(272) 3-Z-[1-(4-((N-(2-methoxy-ethyl)-N-methyl-amino)-methyl)-anilino)-1-phenyl-methylene]-6-ethoxycarbonyl-2-indolinone
(273) 3-Z-[1-(4-((N-(2-hydroxy-ethyl)-N-methyl-amino)-methyl)-anilino)-1-phenyl-methylene]-6-ethoxycarbonyl-2-indolinone
(274) 3-Z-[1-(4-((N-(dioxolan-2-yl-methyl)-N-methyl-amino)-methyl)-anilino)-1-phenyl-methylene]-6-ethoxycarbonyl-2-indolinone
(275) 3-Z-[1-(4-(3-oxo-piperazin-1-yl-methyl)-anilino)-1-phenyl-methylene]-6-ethoxycarbonyl-2-indolinone
(276) 3-Z-[1-(4-(piperazin-1-y-methylcarbonyl)-N-isopropyl-amino)-anilino)-1-phenyl-methylene]-6-ethoxycarbonyl-2-indolinone
(277) 3-Z-[1-(4-(N-((2-(piperazin-1-yl)-ethyl)-carbonyl)-N-methyl-amino)-anilino)-1-phenyl-methylene]-6-ethoxycarbonyl-2-indolinone
(278) 3-Z-[1-(4-((N-(3-amino-propyl)-N-methyl-amino)-methyl)-anilino)-1-phenyl-methylene]-6-ethoxycarbonyl-2-indolinone
(279) 3-Z-[1-(4-(N-(3-methylamino-propyl)-N-methylsulphonyl-amino)-anilino)-1-phenyl-methylene]-6-ethoxycarbonyl-2-indolinone
(280) 3-Z-[1-(4-Ureidomethyl-anilino)-1-phenyl-methylene]-6-ethoxycarbonyl-2-indolinone
(281) 3-Z-[1-(4-guanidinomethyl-anilino)-1-phenyl-methylene]-6-ethoxycarbonyl-2-indolinone
(282) 3-Z-[1-(4-(N-methlysulphonyl-aminomethyl)-anilino)-1-phenyl-methylene]-6-ethoxycarbonyl-2-indolinone
(283) 3-Z-[1-(4-(4-benzoyl-piperazin-1-yl-methyl)-anilino)-1-phenyl-methylene]-6-ethoxycarbonyl-2-indolinone
(284) 3-Z-[1-(4-((N-(3-acetylamino-propyl)-N-methyl-amino)-methyl)-anilino)-1-phenyl-methylene]-6-ethoxycarbonyl-2-indolinone
(285) 3-Z-[1-(4-((N-(3-methylsulphonylamino-propyl)-N-methyl-amino)-methyl)-anilino)-1-phenyl-methylene]-6-ethoxycarbonyl-2-indolinone
(286) 3-Z-[1-(4-((N-carboxymetyl-N-methyl-amino)-methyl)-anilino)-1-phenyl-methylene]-6-ethoxycarbonyl-2-indolinone
(287) 3-Z-(1-anilino-1-phenyl-methylene)-6-methoxycarbonyl-2-indolinone
(288) 3-Z-[1-(4-nitro-anilino)-1-phenyl-methylene]-6-methoxy carbonyl-2-indolinone
(289) 3-Z-[1-(4-fluoro-anilino)-1-phenyl-methylene]-6-methoxycarbonyl-2-indolinone
(290) 3-Z-[1-(4-chloro-anilino)-1-phenyl-methylene]-6-methoxycarbonyl-2-indolinone
(291) 3-Z-[1-(4-bromo-anilino)-1-phenyl-methylene]-6-methoxycarbonyl-2-indolinone
(292) 3-Z-[1-(4-iodo-anilino)-1-phenyl-methylene]-6-methoxycarbonyl-2-indolinone
(293) 3-Z-[1-(4-cyano-anilino)-1-phenyl-methylene]-6-methoxycarbonyl-2-indolinone
(294) 3-Z-[1-(4-carboxy-anilino)-1-phenyl-methylene]-6-methoxycarbonyl-2-indolinone
(295) 3-Z-[1-(4-methoxy-anilino)-1-phenyl-methylene]-6-methoxycarbonyl-2-indolinone
(296) 3-Z-[1-(4-ethoxy-anilino)-1-phenyl-methylene]-6-methoxycarbonyl-2-indolinone
(297) 3-Z-[1-(4-trifluoromethyl-anilino)-1-phenyl-methylene]-6-methoxycarbonyl-2-indolinone
(298) 3-Z-[1-(4-methylmercapto-anilino)-1-phenyl-methylene]-6-methoxycarbonyl-2-indolinone
(299) 3-Z-[1-(4-(isopropylaminomethyl)-anilino)-1-phenyl-methylene]-6-methoxycarbonyl-2-indolinone
(300) 3-Z-[1-(4-(anilinomethyl)-anilino)-1-phenyl-methylene]-6-methoxycarbonyl-2-indolinone
(301) 3-Z-[1-(4-(isobutylaminomethyl)-anilino)-1-phenyl-methylene]-6-methoxycarbonyl-2-indolinone
(302) 3-Z-[1-(4-(cyclohexylaminomethyl)-anilino)-1-phenyl-methylene]-6-methoxycarbonyl-2-indolinone
(303) 3-Z-[1-(4-(benzylaminomethyl)-anilino)-1-phenyl-methylene]-6-methoxycarbonyl-2-indolinone
(304) 3-Z-[1-(4-((N-methyl-N-propyl-amino)-methyl)-anilino)-1-phenyl-methylene]-6-methoxycarbonyl-2-indolinone
(305) 3-Z-[1-(4-((N-isopropyl-N-methyl-amino)-methyl)-anilino)-1-phenyl-methylene]-6-methoxycarbonyl-2-indolinone
(306) 3-Z-[1-(4-((N-ethyl-N-propyl-amino)-methyl)-anilino)-1-phenyl-methylene]-6-methoxycarbonyl-2-indolinone
(307) 3-Z-[1-(4-((N-ethyl-N-isopropyl-amino)-methyl)-anilino)-1-phenyl-methylene]-6-methoxycarbonyl-2-indolinone (308) 3-Z-[1-(4-(dipropylaminomethyl)-anilino)-1-phenyl-methylene]-6-methoxycarbonyl-2-indolinone
(309) 3-Z-[1-(4-(diisopropylaminomethyl)-anilino)-1-phenyl-methylene]-6-methoxycarbonyl-2-indolinone
(310) 3-Z-[1-(4-((N-benzyl-N-ethyl-amino)-methyl)-anilino)-1-phenyl-methylene]-6-methoxycarbonyl-2-indolinone
(311) 3-Z-[1-(4-(dibenzylaminomethyl)-anilino)-1-phenyl-methylene]-6-methoxycarbonyl-2-indolinone
(312) 3-Z-[1-(4-(3,6-dihydro-2H-pyridin-1-yl-methyl)-anilino)-1-phenyl-methylene]-6-methoxycarbonyl-2-indolinone
(313) 3-Z-[1-(4-(3,5-dimethyl-piperidin-1-yl-methyl)-anilino)-1-phenyl-methylene]-6-methoxycarbonyl-2-indolinone
(314) 3-Z-[1-(4-(azepan-1-yl-methyl)-anilino)-1-phenyl-methylene]-6-methoxycarbonyl-2-indolinone
(315) 3-Z-[1-(4-(2-amino-ethyl)-anilino)-1-phenyl-methylene]-6-methoxycarbonyl-2-indolinone
(316) 3-Z-[1-(4-(2-methylamino-ethyl)-anilino)-1-phenyl-methylene]-6-methoxycarbonyl-2-indolinone
(317) 3-Z-[1-(4-(2-ethylamino-ethyl)-anilino)-1-phenyl-methylene]-6-methoxycarbonyl-2-indolinone
(318) 3-Z-[1-(4-(2-dimethylamino-ethyl)-anilino)-1-phenyl-methylene]-6-methoxycarbonyl-2-indolinone
(319) 3-Z-[1-(4-(2-diethylamino-ethyl)-anilino)-1-phenyl-methylene]-6-methoxycarbonyl-2-indolinone
(320) 3-Z-[1-(4-(2-piperidin-1-yl-ethyl)-anilino)-1-phenyl-methylene]-6-methoxycarbonyl-2-indolinone
(321) 3-Z-[1-(4-(2-acetylamino-ethyl)-anilino)-1-phenyl-methylene]-6-methoxycarbonyl-2-indolinone
(322) 3-Z-[1-(4-(3-amino-propyl)-anilino)-1-phenyl-methylene]-6-methoxycarbonyl-2-indolinone
(323) 3-Z-[1-(4-(3-dimethylamino-propyl)-anilino)-1-phenyl-methylene]-6-methoxycarbonyl-2-indolinone
(324) 3-Z-[1-(4-(N-aminomethylcarbonyl-N-methyl-amino)-anilino)-1-phenyl-methylene]-6-methoxycarbonyl-2-indolinone
(325) 3-Z-[1-(4-(N-ethylaminomethylcarbonyl-N-methyl-amino)-anilino)-1-phenyl-methylene]-6-methoxycarbonyl-2-indolinone
(326) 3-Z-[1-(4-(N-diethylaminomethylcarbonyl-N-methyl-amino)-anilino)-1-phenyl-methylene]-6-methoxycarbonyl-2-indolinone
(327) 3-Z-[1-(4-(N-dipropylaminomethylcarbonyl-N-methyl-amino)-anilino)-1-phenyl-methylene]-6-methoxycarbonyl-2-indolinone
(328) 3-Z-[1-(4-(N-((N-ethyl-N-methyl-amino)-methylcarbonyl)-N-methyl-amino)-anilino)-1-phenyl-methylene]-6-methoxycarbonyl-2-indolinone
(329) 3-Z-[1-(4-(N-((N-ethyl-N-propyl-amino)-methylcarbonyl)-N-methyl-amino)-anilino)-1-phenyl-methylene]-6-methoxycarbonyl-2-indolinone
(330) 3-Z-[1-(4-(N-((N-methyl-N-propyl-amino)-methylcarbonyl)-N-methyl-amino)-anilino)-1-phenyl-methylene]-6-methoxycarbonyl-2-indolinone
(331) 3-Z-[1-(4-(N-dimethylaminomethylcarbonyl-N-ethyl-amino)-anilino)-1-phenyl-methylene]-6-methoxycarbonyl-2-indolinone
(332) 3-Z-[1-(4-(N-dimethylaminomethylcarbonyl-N-propyl-amino)-anilino)-1-phenyl-methylene]-6-methoxycarbonyl-2-indolinone
(333) 3-Z-[1-(4-(N-dimethylaminomethylcarbonyl-N-butyl-amino)-anilino)-1-phenyl-methylene]-6-methoxycarbonyl-2-indolinone
(334) 3-Z-[1-(4-(N-(2-amino-ethylcarbonyl)-N-methyl-amino)-anilino)-1-phenyl-methylene]-6-methoxycarbonyl-2-indolinone
(335) 3-Z-[1-(4-(N-(2-diethylamino-ethylcarbonyl)-N-methyl-amino)-anilino)-1-phenyl-methylene]-6-methoxycarbonyl-2-indolinone
(336) 3-Z-[1-(4-(N-acetyl-N-(2-aminoethyl)-amino)-anilino)-1-phenyl-methylene]-6-methoxycarbonyl-2-indolinone
(337) 3-Z-[1-(4-(N-acetyl-N-(2-methylamino-ethyl)-amino)-anilino)-1-phenyl-methylene]-6-methoxycarbonyl-2-indolinone
(338) 3-Z-[-(4-(N-acetyl-N-(3-methylamino-propyl)-amino)-anilino)-1-phenyl-methylene]-6-methoxycarbonyl-2-indolinone
(339) 3-Z-[1-(4-(N-acetyl-N-(2-piperidin-1-yl-ethyl)-amino)-anilino)-1-phenyl-methylene]-6-methoxycarbonyl-2-indolinone
(340) 3-Z-[1-(4-(N-acetyl-N-(aminocarbonylmethyl)-amino)-anilino)-1-phenyl-methylene]-6-methoxycarbonyl-2-indolinone
(341) 3-Z-[1-(4-(N-acetyl-N-(piperidin-1-yl-carbonylmethyl)-amino)-anilino)-1-phenyl-methylene]-6-methoxycarbonyl-2-indolinone
(342) 3-Z-[1-(4-(N-methyl-N-(aminocarbonyl)-amino)-anilino)-1-phenyl-methylene]-6-methoxycarbonyl-2-indolinone
(343) 3-Z-[1-(4-(N-methyl-N-(methylaminocarbonyl)-amino)-anilino)-1-phenyl-methylene]-6-methoxycarbonyl-2-indolinone
(344) 3-Z-[1-(4-(N-methyl-N-(dimethylaminocarbonyl)-amino)-anilino)-1-phenyl-methylene]-6-methoxycarbonyl-2-indolinone
(345) 3-Z-[1-(4-(N-methyl-N-(piperidin-1-yl-carbonyl)-amino)-anilino)-1-phenyl-methylene]-6-methoxycarbonyl-2-indolinone
(346) 3-Z-[1-(4-(N-(2-ethylamino-ethyl)-N-methylsulphonyl-amino)-anilino)-1-phenyl-methylene]-6-methoxycarbonyl-2-indolinone
(347) 3-Z-[1-(4-(N-(2-diethylamino-ethyl)-N-methylsulphonyl-amino)-anilino)-1-phenyl-methylene]-6-methoxycarbonyl-2-indolinone
(348) 3-Z-[1-(4-(N-(2-pyrrolidin-1-yl-ethyl)-N-methylsulphonyl-amino)-anilino)-1-phenyl-methylene]-6-methoxycarbonyl-2-indolinone
(349) 3-Z-[1-(4-N-(2-piperidin-1-yl-ethyl)-N-methylsulphonyl-amino)-anilino)-1-phenyl-methylene]-6-methoxycarbonyl-2-indolinone
(350) 3-Z-[1-(4-(N-(2-piperazin-1-yl-ethyl)-N-methylsulphonyl-amino)-anilino)-1-phenyl-methylene]-6methoxycarbonyl-2-indolinone
(351) 3-Z-[1-(4-(N-(2-(4-morpholin-1-yl)-ethyl)-N-methylsulphonyl-amino)-anilino)-1-phenyl-methylene]-6-methoxycarbonyl-2-indolinone
(352) 3-Z-[1-(4-(N-(ethylaminocarbonylmethyl)-N-methylsulphonyl-amino)-anilino)-1-phenyl-methylene]-6-methoxycarbonyl-2-indolinone
(353) 3-Z-[1-(4-(N-(diethylaminocarbonylmethyl)-N-methylsulphonyl-amino)-anilino)-1-phenyl-methylene]-6-methoxycarbonyl-2-indolinone
(354) 3-Z-[1-(4-(N-(pyrrolidin-1-yl-carbonylmethyl)-N-methylsulphonyl-amino)-anilino)-1-phenyl-methylene]-6-methoxycarbonyl-2-indolinone
(355) 3-Z-[1-(4-(N-(piperidin-1-yl-carbonylmethyl)-N-methylsulphonyl-amino)-anilino)-1-phenyl-methylene]-6-methoxycarbonyl-2-indolinone
(356) 3-Z-[1-(4-(N-(piperazin-1-yl-carbonylmethyl)-N-methylsulphonyl-amino)-anilino)-1-phenyl-methylene]-6-methoxycarbonyl-2-indolinone
(357) 3-Z-[1-(4-(N-((morpholin-4-yl)-carbonylmethyl)-N-methylsulphonyl-amino)-anilino)-1-phenyl-methylene]-6-methoxycarbonyl-2-indolinone (358) 3-Z-[1-(4-(2-dimethylamino-ethoxy)-anilino)-1-phenyl-methylene]-6-methoxycarbonyl-2-indolinone
(359) 3-Z-[1-(4-(3-dimethylamino-propoxy)-anilino)-1-phenyl-methylene]-6-methoxycarbonyl-2-indolinone
(360) 3-Z-[1-(4-(aminocarbonylmethyl)-anilino)-1-phenyl-methylene]-6-methoxycarbonyl-2-indolinone
(361) 3-Z-[1-(4-(2-aminocarbonyl-ethyl)-anilino)-1-phenyl-methylene]-6-methoxycarbonyl-2-indolinone
(362) 3-Z-[1-(4-(pyridin-2-yl)-anilino)-1-phenyl-methylene]-6-methoxycarbonyl-2-indolinone
(363) 3-Z-[1-(4-(pyridine-3-yl)-anilino)-1-phenyl-methylene]-6-methoxycarbonyl-2-indolinone
(364) 3-Z-[1-(4((N-phenethyl-N-methyl-amino)-methyl)-anilino)-1-phenyl-methylene]-6-methoxycarbonyl-2-indolinone
(365) 3-Z-[1-(4-(N-acetyl-N-methyl-amino)-anilino)-1-phenyl-methylene]-6-methoxycarbonyl-2-indolinone
(366) 3-Z-[1-(4-(N-ethylcarbonyl-N-(dimethylaminocarbonyl-methyl)-amino)-anilino)-1-phenyl-methylene]-6-methoxycarbonyl-2-indolinone
(367) 3-Z-[1-(4-(N-methyl-N-methylsulphonyl-amino)-anilino)-1-phenyl-methylene]-6-methoxycarbonyl-2-indolinone
(368) 3-Z-[1-(4-carboxymethyl-anilino)-1-phenyl-methylene]-6-methoxycarbonyl-2-indolinone
(369) 3-Z-[1-(4-carbamoylmethyl-anilino)-1phenyl-methylene]-6-methoxycarbonyl-2-indolinone
(370) 3-Z-[1-(4-dimethylcarbamoylmethyl-anilino)-1-phenyl-methylene]-6-methoxycarbonyl-2-indolinone
(371) 3-Z-[1-(4-tetrazol-5-yl-anilino)-1-phenyl-methylene]-6-methoxycarbonyl-2-indolinone
(372) 3-Z-[1-(4-(piperidin-1-yl-methyl)-anilino)-methylene]-6-methoxycarbonyl-2-indolinone
(373) 3-Z-[1-(4-(piperidin-1-yl-methyl)-anilino)-ethylidene]-6-methoxycarbonyl-2-indolinone
(374) 3-Z-[1-(4-(piperidin-1-yl-methyl)-anilino)-propylidene]-6-methoxycarbonyl-2-indolinone
(375) 3-Z-[1-(4-(piperidin-1-yl-methyl)-anilino)-butylidene]-6-methoxycarbonyl-2-indolinone
(376) 3-Z-[1-(4-(N-(3-dimethylamino-propyl)-N-acetyl-amino)-anilino)-methylene]-6-methoxycarbonyl-2-indolinone
(377) 3-Z-[1-(4-(N-(3-dimethylamino-propyl)-N-acetyl-amino)-anilino)-ethylidene]-6-methoxycarbonyl-2-indolinone
(378) 3-Z-[1-(4-(N-(3-dimethylamino-propyl)-N-acetyl-amino)-anilino)-propylidede]-6-methoxycarbonyl-2-indolinone
(379) 3-Z-[1-(4-(N-(3-dimethylamino-propyl)-N-acetyl-amino)-anilino)-butylidene]-6-methoxycarbonyl-2-indolinone
(380) 3-Z-[1-(4-(N-(2-dimethylamino-ethyl)-N-methylsuphony-amino)-anilino)-methylene]-6-methoxycarbonyl-2-indolinone
(381) 3-Z-[1-(4-(N-(2-dimethylamino-ethyl)-N-methylsulphonyl-amino)-anilino)-ethylidene]-6-methoxycarbonyl-2-indolinone
(382) 3-Z-[1-(4-(N-(2-dimethylamino-ethyl)-N-methylsulphonyl-amino)-anilino)-propylidene]-6-methoxycarbonyl-2-indolinone
(383) 3-Z-[1-(4-(N-(2-dimethylamino-ethyl)-N-methylsulphonyl-amino)-anilino)-butylidene]-6-methoxycarbonyl-2-indolinone
(384) 3-Z-[1-(4-tetrazol-5-yl-anilino)-methylene]-6-methoxycarbonyl-2-indolinone
(385) 3-Z-[1-(4-tetrazol-5-yl-anilino)-ethylidene]-6-methoxycarbonyl-2-indolinone
(386) 3-Z-[1-(4-tetrazol-5-yl-anilino)-propylidene]-6-methoxycarbonyl-2-indolinone
(387) 3-Z-[1-(4-tetrazol-5-yl-anilino)-butylidene]-6-methoxycarbonyl-2-indolinone
(388) 3-Z-[1-(4-carboxy-anilino)-methylene]-6-methoxycarbonyl-2-indolinone
(389) 3-Z-[1-(4-carboxy-anilino)-ethylidene]-6-methoxycarbonyl-2-indolinone
(390) 3-Z-[1-(4carboxy-anilino)-propylidene]-6-methoxycarbonyl-2-indolinone
(391) 3-Z-[1-(4-carboxy-anilino)-butylidene]-6-methoxycarbonyl-2-indolinone
(392) 3-Z-[1-(4-(N-benzyl-N-methyl-aminomethyl)-anilino)-1-methyl-methylene]-6-methoxycarbonyl-2-indolinone
(393) 3-Z-[1-(4-(2,3,4,5-tetrahydro-benzo(d)azepin-3-yl-methyl)-anilino)-1-methyl-methylene]-6-methoxycarbonyl-2-indolinone
(394) 3-Z-[1-(4-((benzo(1,3)dioxol-5-yl-methyl)-methyl-amino-methyl)-anilino)-1-methyl-methylene]-6-methoxycarbonyl-2-indolinone
(395) 3-Z-[1-(4-(N-phenethyl-N-methyl-aminomethyl)-anilino)-1-methyl-methylene]-6-methoxycarbonyl-2-indolinone
(396) 3-Z-[1-(4-(N-(3,4-dimethoxy-benzyl)-N-methyl-amino-methyl)-anilino)-1-methyl-methylene]-6-methoxycarbonyl-2-indolinone
(397) 3-Z-[1-(4-(N-(4-Chloro-benzyl)-N-methyl-amino-methyl)-anilino)-1-methyl-methylene]-6-methoxycarbonyl-2-indolinone
(398) 3-Z-[1-(4-(N-(4-methylbenzyl)-N-methyl-amino-methyl)-anilino)-1-methyl-methylene]-6-methoxycarbonyl-2-indolinone
(399) 3-Z-[1-(4-(N-(4-fluoro-benzyl)-N-methyl-amino-methyl)-anilino)-1-methyl-methylene]-6-methoxycarbonyl-2-indolinone
(400) 3-Z-[1-(4-(N-(4-bromo-benzyl)-N-methyl-amino-methyl)-anilino)-1-methyl-methylene]-6-methoxycarbonyl-2-indolinone
(401) 3-Z-[1-(4-(N-(3-dimethylamino-propionyl)-N-dimethylaminocarbonylmethyl-amino)-anilino)-1-phenyl-methylene]-6-methoxycarbonyl-2-indolinone
(402) 3-Z-[1-(4-(N-(4-dimethylamino-butyryl)-N-dimethylaminocarbonylmethyl-amino)-anilino)-1-phenyl-methylene]-6-methoxycarbonyl-2-indolinone
(403) 3-Z-[1-(4-(N-dimethylaminocarbonylmethyl-N-(2-dimethylamino-ethylsulphonyl)-amino)-anilino)-1-phenyl-methylene]-6-methoxycarbonyl-2-indolinone
(404) 3-Z-[1-(4-(N-dimethylaminocarbonylmethyl-N-(3-dimethylamino-propylsulphonyl)-amino)-anilino)-1-phenyl-methylene]-6-methoxycarbonyl-2-indolinone
(405) 3-Z-[1-(4-((2-hydroxy-ethyl)-amino-methyl)-anilino)-1-phenyl-methylene]-6-methoxycarbonyl-2-indolinone
(406) 3-Z-[1-(4-((2-methoxy-ethyl)-amino-methyl)-anilino)-1-phenyl-methylene]-6-methoxycarbonyl-2-indolinone
(407) 3-Z-[1-(4-((2-dimethylamino-ethyl)-amino-methyl)-anilino)-1-phenyl-methylene]-6-methoxycarbonyl-2-indolinone
(408) 3-Z-[1-(4-((3-dimethylamino-propyl)-amino-methyl)-anilino)-1-phenyl-methylene]-6-methoxycarbonyl-2-indolinone
(409) 3-Z-[1-(4-((N-tert.butoxycarbonyl-2-amino-ethyl)-amino-methyl)-anilino)-1-phenyl-methylene]-6-methoxycarbonyl-2-indolinone
(410) 3-Z-[1-(4-((N-tert.butoxycarbonyl-3-amino-propyl)-amino-methyl)-anilino)-1-phenyl-methylene]-6-methoxycarbonyl-2-indolinone (411) 3-Z-[1-(4-((2-amino-ethyl)-amino-methyl)-anilino)-1-phenyl-methylene]-6-methoxycarbonyl-2-indolinone
(412) 3-Z-[1-(4-((3-amino-propyl)-amino-methyl)-anilino)-1-phenyl-methylene]-6-methoxycarbonyl-2-indolinone
(413) 3-Z-[1-(4-((2-acetylamino-ethyl)-amino-methyl)-anilino)-1-phenyl-methylene]-6-methoxycarbonyl-2-indolinone
(414) 3-Z-[1-(4-((3-acetylamino-propyl)-amino-methyl)-anilino)-1-phenyl-methylene]-6-methoxycarbonyl-2-indolinone
(415) 3-Z-[1-(4-((2-methylsulphonylamino-ethyl)-amino-methyl)-anilino)-1-phenyl-methylene]-6-methoxycarbonyl-2-indolinone
(416) 3-Z-[1-(4-((3-methylsulphonylamino-propyl)-amino-methyl)-anilino)-1-phenyl-methylene]-6-methoxycarbonyl-2-indolinone
(417) 3-Z-[1-(4-(N-(N-tert.butoxycarbonyl-2-amino-ethyl)-N-methyl-amino-methyl)-anilino-1-phenyl-methylene]-6-methoxycarbonyl-2-indolinone
(418) 3-Z-[1-(4-(N-(2-amino-ethyl)-N-methyl-amino-methyl)-anilino)-1-phenyl-methylene]-6-methoxycarbonyl-2-indolinone
(419) 3-Z-[1-(4-(N-(2-acetylamino-ethyl)-N-methyl-amino-methyl)-anilino)-1-phenyl-methylene]-6-methoxycarbonyl-2-indolinone
(420) 3-Z-[1-(4-(N-(2-methylsulphonylamino-ethyl)-N-methyl-amino-methyl)-anilino)-1-phenyl-methylene]-6-methoxycarbonyl-2-indolinone
(421) 3-Z-[1-(4-(carboxymethyl-amino-methyl)-anilino)-1-phenyl-methylene]-6-methoxycarbonyl-2-indolinone
(422) 3-Z-[1-(4-(ethoxycarbonylmethyl-amino-methyl)-anilino)-1-phenyl-methylene]-6-methoxycarbonyl-2-indolinone
(423) 3-Z-[1-(4-(carbamoylmethyl-amino-methyl)-anilino)-1-phenyl-methylene]-6-methoxycarbonyl-2-indolinone
(424) 3-Z-[1-(4-(dimethylcarbamoyl-methyl-amino-methyl)-anilino)-1-phenyl-methylene]-6-methoxycarbonyl-2-indolinone
(425) 3-Z-[1-(4-(methylcarbamoyl-methyl-amino-methyl)-anilino)-1-phenyl-methylene]-6-methoxycarbonyl-2-indolinone
(426) 3-Z-[1-(4-(N-dimethylaminomethylcarbonyl-N-methyl-amino)-3-amino-anilino)-1-phenyl-methylene]-6-methoxycarbonyl-2-indolinone
(427) 3-Z-[1-(4-(N-dimethylaminomethylcarbonyl-N-methyl-amino)-3-nitro-anilino)-1-phenyl-methylene]-6-methoxycarbonyl-2-indolinone
(428) 3-Z-[1-(4-(N-dimethylaminomethylcarbonyl-N-methyl-amino)-3-acetylamino-anilino)-1-phenyl-methylene]-6-methoxycarbonyl-2-indolinone
(429) 3-Z-[1-(4-(N-dimethylaminomethylcarbonyl-N-methyl-amino)-3-methylsulphonylamino-anilino)-1-phenyl-methylene]-6-methoxycarbonyl-2-indolinone
(430) 3-Z-[1-(4-(N-dimethylaminomethylcarbonyl-N-methyl-amino)-3-cyano-anilino)-1-phenyl-methylene]-6-methoxycarbonyl-2-indolinone
(431) 3-Z-[1-(4-(N-dimethylaminomethylcarbonyl-N-methyl-amino)-3-hydroxy-anilino)-1-phenyl-methylene]-6-methoxycarbonyl-2-indolinone
(432) 3-Z-[1-(4-(N-dimethylaminomethylcarbonyl-N-methyl-amino)-3-methoxy-anilino)-1-phenyl-methylene]-6-methoxycarbonyl-2-indolinone
(433) 3-Z-[1-(4-(N-dimethylaminomethylcarbonyl-N-methyl-amino)-3-ethoxycarbonyl-anilino)-1-phenyl-methylene]-6-methoxycarbonyl-2-indolinone
(434) 3-Z-[1-(4-(N-dimethylaminomethylcarbonyl-N-methyl-amino)-3-carboxy-anilino)-1-phenyl-methylene]-6-methoxycarbonyl-2-indolinone
(435) 3-Z-[1-(4-(N-dimethylaminomethylcarbonyl-N-methyl-amino)-3-carbamoyl-anilino)-1-phenyl-methylene]-6-methoxycarbonyl-2-indolinone
(436) 3-Z-[1-(4-(N-dimethylaminomethylcarbonyl-N-methyl-amino)-3-chloro-anilino)-1-phenyl-methylene]-6-methoxycarbonyl-2-indolinone
(437) 3-Z-[1-(4-(N-dimethylaminomethylcarbonyl-N-methyl-amino)-3-fluoro-anilino)-1-phenyl-methylene]-6-methoxycarbonyl-2-indolinone
(438) 3-Z-[1-(4-(N-dimethylaminomethylcarbonyl-N-methyl-amino)-3-bromo-anilino)-1-phenyl-methylene]-6-methoxycarbonyl-2-indolinone
(439) 3-Z-[1-(4-(N-dimethylaminomethylcarbonyl-N-methyl-amino)-3-methyl-anilino)-1-phenyl-methylene]-6-methoxycarbonyl-2-indolinone
(440) 3-Z-[1-(4-(N-dimethylaminomethylcarbonyl-N-methyl-amino)-3-trifluoromethyl-anilino)-1-phenyl-methylene]-6-methoxycarbonyl-2-indolinone
(441) 3-Z-[1-(4-(N-dimethylaminomethylcarbonyl-N-methyl-amino)-3,5-dibromo-anilino)-1-phenyl-methylene]-6-methoxycarbonyl-2-indolinone
(442) 3-Z-[1-(4-(N-dimethylaminomethylcarbonyl-N-methyl-amino)-3,5-dichloro-anilino)-1-phenyl-methylene]-6-methoxycarbonyl-2-indolinone
(443) 3-Z-[1-(4-(dimethylaminomethyl)-3-amino-anilino)-1-phenyl-methylene]-6-methoxycarbonyl-2-indolinone
(444) 3-Z-[1-(4-(dimethylaminomethyl)-3-nitro-anilino)-1-phenyl-methylene]-6-methoxycarbonyl-2-indolinone
(445) 3-Z-[1-(4-(dimethylaminomethyl)-3-acetylamino-anilino)-1-phenyl-methylene]-6-methoxycarbonyl-2-indolinone
(446) 3-Z-[1-(4-(dimethylaminomethyl)-3-methylsulphonylamino-anilino)-1-phenyl-methylene]-6-methoxycarbonyl-2-indolinone
(447) 3-Z-[1-(4-(dimethylaminomethyl)-3-cyano-anilino)-1-phenyl-methylene]-6-methoxycarbonyl-2-indolinone
(448) 3-Z-[1-(4-(dimethylaminomethyl)-3-hydroxy-anilino)-1-phenyl-methylene]-6-1methoxycarbonyl-2-indolinone
(449) 3-Z-[1-(4-(dimethylaminomethyl)-3-methoxy-anilino)-1-phenyl-methylene]-6-methoxycarbonyl-2-indolinone
(450) 3-Z-[1-(4-(dimethylaminomethyl)-3-ethoxycarbonyl-anilino)-1-phenyl-methylene]-6-methoxycarbonyl-2-indolinone
(451) 3-Z-[1-(4-(dimethylaminomethyl)-3-carboxy-anilino)-1-phenyl-methylene]-6-methoxycarbonyl-2-indolinone
(452) 3-Z-[1-(4-(dimethylaminomethyl)-3-carbaroyl-anilino)-1-phenyl-methylene]-6-methoxycarbonyl-2-indolinone
(453) 3-Z-[1-(4-(dimethylaminomethyl)-3-chloro-anilino)-1-phenyl-methylene]-6-methoxycarbonyl-2-indolinone
(454) 3-Z-[1-(4-(dimethylaminomethyl)-3-fluoro-anilino)-1-phenyl-methylene]-6-methoxycarbonyl-2-indolinone
(455) 3-Z-[1-(4-(dimethylaminomethyl)-3-bromo-anilino)-1-phenyl-methylene]-6-methoxycarbonyl-2-indolinone
(456) 3-Z-[1-(4-(dimethylaminomethyl)-3-methyl-anilino)-1-phenyl-methylene]-6-methoxycarbonyl-2-indolinone
(457) 3-Z-[1-(4-(dimethylaminomethyl)-3-trifluoromethyl-anilino)-1-phenyl-methylene]-6-methoxycarbonyl-2-indolinone
(458) 3-Z-[1-(4-dimethylaminomethyl-3,5-dibromo-anilino)-1-phenyl-methylene]-6-methoxycarbonyl-2-indolinone
(459) 3-Z-[1-(4-(dimethylaminomethyl)-3,5-dichloro-anilino)-1-phenyl-methylene]-6-methoxycarbonyl-2-indolinone (460) 3-Z-[1-(4-(dimethylaminomethyl)-anilino)-1-phenyl-methylene]-6-[(2-hydroxy-ethoxy)-carbonyl]-2-indolinone
(461) 3-Z-[1-(4-(dimethylaminomethyl)-anilino)-1-phenyl-methylene]-6-[(ethoxycarbonyl-methoxy)-carbonyl]-2-indolinone
(462) 3-Z-[1-(4-(dimethylaminomethyl)-anilino)-1-phenyl-methylene]-6-[(carboxy-methoxy)-carbonyl]-2-indolinone
(463) 3-Z-[1-(4-(dimethylaminomethyl)-anilino)-1-phenyl-methylene]-6-[(carbamoyl-methoxy)-carbonyl]-2-indolinone
(464) 3-Z-[1-(4-(N-dimethylaminomethylcarbonyl-N-methyl-amino)-anilino)-1-phenyl-methylene]-6-[(2-hydroxy-ethoxy)-carbonyl]-2-indolinone
(465) 3-Z-[1-(4-N-dimethylaminomethylcarbonyl-N-methyl-amino)-anilino)-1-phenyl-methylene]-6-[(ethoxycarbonyl-methoxy)-carbonyl]-2-indolinone
(466) 3-Z-[1-(4-(N-dimethylaminomethylcarbonyl-N-methyl-amino)-anilino)-1-phenyl-methylene]-6-[(carboxy-methoxy)-carbonyl]-2-indolinone
(467) 3-Z-[1-(4-(N-dimethylaminomethylcarbonyl-N-methyl-amino)-anilino)-1-phenyl-methylene]-6-[(carbamoyl-methoxy)-carbonyl]-2-indolinone
(468) 3-Z-[1-(4-(N-dimethylaminomethylcarbonyl-N-methyl-amino)-anilino)-1-phenyl-methylene]-6-[(2-methoxy-ethoxy)-carbonyl]-2-indolinone
(469) 3-Z-[1-(4-(N-dimethylaminomethylcarbonyl-N-methyl-amino)-anilino)-1-phenyl-methylene]-6-[(2-dimethylamino-ethoxy)-carbonyl]-2-indolinone
(470) 3-Z-[1-(4-(N-dimethylaminomethylcarbonyl-N-methyl-amino)-anilino)-1-phenyl-methylene]-6-[(2-(N-tert.butoxycarbonyl-amino)-ethoxy)-carbonyl]-2-indolinone
(471) 3-Z-[1-(4-(N-dimethylaminomethylcarbonyl-N-methyl-amino)-anilino)-1-phenyl-methylene]-6-[(2-amino-ethoxy)-carbonyl]-2-indolinone
(472) 3-Z-[1-(4-(N-dimethylaminomethylcarbonyl-N-methyl-amino)-anilino)-1-phenyl-methylene]-6-[(2,2,2-trifluoroethoxy)-carbonyl]-2-indolinone
(473) 3-Z-[1-(4-(N-((4-methyl-piperazin-1-yl)-methylcarbonyl)-N-methyl-amino)-anilino)-1-phenyl-methylene]-6-methoxycarbonyl-2-indolinone
(474) 3-Z-[1-(4-(N-(imidazo-1-yl-methylcarbonyl)-N-methyl-amino)-anilino)-1-phenyl-methylene]-6-methoxycarbonyl-2-indolinone
(475) 3-Z-[1-(4-(N-(phthalimido-2-yl-methylcarbonyl)-N-methyl-amino)-anilino)-1-phenyl-methylene]-6-methoxycarbonyl-2-indolinone
(476) 3-Z-[1-(4-(N-aminomethylcarbonyl-N-methyl-amino)-anilino)-1-phenyl-methylene]-6-methoxycarbonyl-2-indolinone
(477) 3-Z-[1-(4-(N-acetylaminomethylcarbonyl-N-methyl-amino)-anilino)-1-phenyl-methylene]-6-methoxycarbonyl-2-indolinone
(478) 3-Z-[1-(4-(N-methylsulphonylaminomethylcarbonyl-N-methyl-amino)-anilino)-1-phenyl-methylene]-6-methoxycarbonyl-2-indolinone
(479) 3-Z-[1-(4-(N-((N-(2-methoxyethyl)-N-methyl-amino)-methylcarbonyl)-N-methyl-amino)-anilino)-1-phenyl-methylene]-6-methoxycarbonyl-2-indolinone
(480) 3-Z-[1-(4-(N-((N-(2-dimethylaminoethyl)-N-methyl-amino)-methylcarbonyl)-N-methyl-amino)-anilino)-1-phenyl-methylene]-6-methoxycarbonyl-2-indolinone
(481) 3-Z-[1-(4-(N-((di-(2-hydroxyethyl)-amino)-methylcarbonyl)-N-methyl-amino)-anilino)-1-phenyl-methylene]-6-methoxycarbonyl-2-indolinone
(482) 3-Z-[1-(4-tert.butoxycarbonylmethyl-anilino)-1-phenyl-methylene]-6-methoxycarbonyl-2-indolinone
(483) 3-Z-[1-(4-(N-dimethylaminomethylcarbonyl-N-methyl-amino)-anilino)-methylene]-6-methoxycarbonyl-2-indolinone
(484) 3-Z-[1-(4-(N-dimethylaminomethylcarbonyl-N-Methyl-amino)-anilino)-ethylidene]-6-methoxycarbonyl-2-indolinone
(485) 3-Z-[1-(4-(N-dimethylaminomethylcarbonyl-N-methyl-amino)-anilino)-propylidene]-6-methoxycarbonyl-2-indolinone
(486) 3-Z-[1-(4-(N-dimethylaminomethylcarbonyl-N-methyl-amino)-anilino)-butylidene]-6-methoxycarbonyl-2-indolinone
(487) 3-Z-[1-(4-(dimethylaminomethyl)-anilino)-methylene]-6-methoxycarbonyl-2-indolinone
(488) 3-Z-[1-(4-(dimethylaminomethyl)-anilino)-ethylidene]-6-methoxycarbonyl-2-indolinone
(489) 3-Z-[1-(4-(dimethylaminomethyl)-anilino)-propylidene]-6-methoxycarbonyl-2-indolinone
(490) 3-Z-[1-(4-(dimethylaminomethyl)-anilino)-butylidene]-6-methoxycarbonyl-2-indolinone
(491) 3-Z-[1-(4-tert.butyloxycarbonyl-anilino)-1-phenyl-methylene]-6-methoxycarbonyl-2-indolinone
(492) 3-Z-[1-(4-(N-(2-dimethylaminoethyl)-N-methyl-amino)-anilino)-1-phenyl-methylene]-6-methoxycarbonyl-2-indolinone
(493) 3-Z-[1-(4-(N-(3-dimethylamino-propyl)-N-methyl-amino)-anilino)-1-phenyl-methylene]-6-methoxycarbonyl-2-indolinone
(494) 3-Z-[1-(4-(N-methyl-acetylamino)-anilino)-1-phenyl-methylene]-6-methoxycarbonyl-2-indolinone
(495) 3-Z-[1-(4-(imidazol-4-yl)-anilino)-1-phenyl-methylene]-6-methoxycarbonyl-2-indolinone
(496) 3-Z-[1-(4-((N-(dioxolan-2-yl-methyl)-N-methyl-amino)-methyl)-anilino)-1-phenyl-methylene]-6-methoxycarbonyl-2-indolinone
(497) 3-Z-[1-(4-(N-benzyl-N-methyl-amino-methyl)-anilino)-1-methyl-methylene]-6-carbamoyl-2-indolinone
(498) 3-Z-[1-(4-(2,3,4,5-tetrahydro-benzo(d)azepin-3-yl-methyl)-anilino)-1-methyl-methylene]-6-carbamoyl-2-indolinone
(499) 3-Z-[1-(4-((benzo(1,3)dioxol-5-yl-methyl)-methyl-amino-methyl)-anilino)-1-methyl-methylene]-6-carbamoyl-2-indolinone
(500) 3-Z-[-(4-(N-phenethyl-N-methyl-amino-methyl)-anilino)-1-methyl-methylene]-6-carbamoyl-2-indolinone
(501) 3-Z-[1-(4-(N-(3,4-dimethoxy-benzyl)-N-methyl-amino-methyl)-anilino)-1-methyl-methylene]-6-carbamoyl-2-indolinone
(502) 3-Z-[1-(4-(N-(4-Chloro-benzyl)-N-methyl-amino-methyl)-anilino)-1-methyl-methylene]-6-carbamoyl-2-indolinone
(503) 3-Z-[1-(4-(N-(4-methyl-benzyl)-N-methyl-amino-methyl)-anilino)-1-methyl-methylene]-6-carbamoyl-2-indolinone
(504) 3-Z-[1-(4-(N-(4-fluoro-benzyl)-N-methyl-amino-methyl)-anilino)-1-methyl-methylene]-6-carbamoyl-2-indolinone
(505) 3-Z-[1-(4-(N-(4-bromo-benzyl)-N-methyl-amino-methyl)-anilino)-1-methyl-methylene]-6-carbamoyl-2-indolinone
(506) 3-Z-[1-(4-((N-(2-methoxy-ethyl)-N-methyl-amino)-methyl)-anilino)-1-phenyl-methylene]-6-methoxycarbonyl-2-indolinone
(507) 3-Z-[1-(4-(dimethylaminomethyl)-anilino)-1-phenyl-methylene]-6-[(2-amino-ethoxy)-carbonyl]-2-indolinone (508) 3-Z-[1-(4-((N-(3-methylsulfonylamino-propyl)-N-methyl-amino)-methyl)-anilino)-1-phenyl-methylene]-6-methoxycarbonyl-2-indolinone

EXAMPLE 13

Dry Ampoule Containing 75 mg of Active Substance per 10 ml

Composition:

| Active substance | 75.0 mg |
|---|---|
| Mannitol | 50.0 mg |
| water for injection | ad 10.0 ml |

Preparation:

Active substance and mannitol are dissolved in water. After packaging the solution is freeze-dried. To produce the solution ready for use, the product is dissolved in water for injections.

EXAMPLE 14

Dry Ampoule Containing 35 mg of Active Substance per 2 ml

Composition:

| Active substance | 35.0 mg |
|---|---|
| Mannitol | 100.0 mg |
| water for injections | ad 2.0 ml |

Preparation:

Active substance and mannitol are dissolved in water. After packaging, the solution is freeze-dried.

To produce the solution ready for use, the product is dissolved in water for injections.

EXAMPLE 15

Tablet Containing 50 mg of Active Substance

Composition:

| (1) Active substance | 50.0 mg |
|---|---|
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 9 mm.

EXAMPLE 16

Tablet Containing 350 mg of Active Substance

Composition:

| (1) Active substance | 350.0 mg |
|---|---|
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side.

Diameter of the tablets: 12 mm.

EXAMPLE 17

Capsules Containing 50 mg of Active Substance

Composition:

| (1) Active substance | 50.0 mg |
|---|---|
| (2) Dried maize starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with vigorous mixing.

This powder mixture is packed into size 3 hard gelatine capsules in a capsule filling machine.

EXAMPLE 18

Capsules Containing 350 mg of Active Substance

Composition:

| (1) Active substance | 350.0 mg |
|---|---|
| (2) Dried maize starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with vigorous mixing.

This powder mixture is packed into size 0 hard gelatine capsules in a capsule filling machine.

EXAMPLE 19

Suppositories Containing 100 mg of Active Substance

1 Suppository Contains:

| | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylene sorbitan monostearate. At 40° C. the ground active substance is homogeneously dispersed in the melt. It is cooled to 38° C. and poured into slightly chilled suppository moulds.

What is claimed is:

1. A compound of the formula I

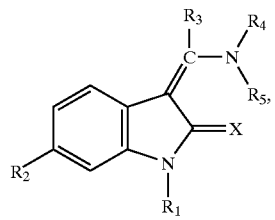

(I)

wherein:

X denotes an oxygen atom, $R_1$ denotes a hydrogen atom or a $C_{1-4}$-alkoxycarbonyl or $C_{2-4}$-alkanoyl group, $R_2$ denotes a carboxy group, a straight-chain or branched $C_{1-6}$-alkoxy-carbonyl group, a $C_{4-7}$-cycloalkoxycarbonyl or an aryloxycarbonyl group, a straight-chain or branched $C_{1-6}$-alkoxy-carbonyl group, which is terminally substituted in the alkyl moiety by a phenyl, heteroaryl, carboxy, $C_{1-3}$-alkoxy-carbonyl, aminocarbonyl, $C_{1-3}$-alkylamino carbonyl or di-($C_{1-3}$-alkyl)-aminocarbonyl group, a straight-chain or branched $C_{2-6}$-alkoxy-carbonyl group, which is terminally substituted in the alkyl moiety by a chlorine atom or a hydroxy, $C_{1-3}$-alkoxy, amino, $C_{1-3}$-alkylamino or di-($C_{1-3}$-alkyl)-amino group, an aminocarbonyl or methylaminocarbonyl group, an ethylaminocarbonyl group optionally substituted in the 2 position of the ethyl group by a hydroxy or $C_{1-3}$-alkoxy group, $R_3$ denotes a hydrogen atom, a $C_{1-6}$-alkyl, $C_{3-7}$-cycloalkyl, trifluoromethyl or heteroaryl group, a phenyl or naphthyl group, a phenyl or naphthyl group mono- or disubstituted by a fluorine, chlorine, bromine or iodine atom, by a trifluoromethyl, $C_{1-3}$-alkyl or $C_{1-3}$-alkoxy group, whilst in the event of disubstitution the substituents may be identical or different and wherein the abovementioned unsubstituted as well as the mono- and disubstituted phenyl and naphthyl groups may additionally be substituted by a hydroxy, hydroxy-$C_{1-3}$-alkyl or $C_{1-3}$-alkoxy-$C_{1-3}$-alkyl group, by a cyano, carboxy, carboxy-$C_{1-3}$-alkyl, $C_{1-3}$-alkoxycarbonyl, aminocarbonyl, $C_{1-3}$-alkylaminocarbonyl or di-($C_{1-3}$-alkyl)-aminocarbonyl group, by a nitro group, by an amino, $C_{1-3}$-alkylamino, di-($C_{1-3}$-alkyl)-amino or amino—$C_{1-3}$-alkyl group, by a $C_{1-3}$-alkylcarbonylamino, N—($C_{1-3}$-alkyl)—$C_{1-3}$-alkylcarbonylamino, $C_{1-3}$-alkylcarbonylamino-$C_{1-3}$-alkyl, N—($C_{1-3}$-alkyl)—$C_{1-3}$-alkylcarbonylamino-$C_{1-3}$-alkyl, $C_{1-3}$-alkyl-sulphonylamino, $C_{1-3}$-alkylsulphonylamino-$C_{1-3}$-alkyl, N—($C_{1-3}$-alkyl)—$C_{1-3}$-alkylsulphonylamino-$C_{1-3}$-alkyl or aryl-$C_{1-3}$-alkylsulphonylamino group, by a cycloalkylamino, cycloalkyleneimino, cycloalkyleneiminocarbonyl, cycloalkyleneimino-$C_{1-3}$-alkyl, cycloalkyleneiminocarbonyl-$C_{1-3}$-alkyl or cycloalkyleneiminosulphonyl-$C_{1-3}$-alkyl group having 4 to 7 ring members in each case, whilst in each case the methylene group in position 4 of a 6- or 7-membered cycloalkyleneimino group may be replaced by an oxygen or sulphur atom, by a sulphinyl, sulphonyl, —NH or —N($C_{1-3}$-alkyl) group, or by a heteroaryl or heteroaryl-$C_{1-3}$-alkyl group, $R_4$ denotes a $C_{3-7}$-cycloalkyl group, whilst the methylene group in the 4 position of a 6- or 7-membered cycloalkyl group may be substituted by an amino, $C_{1-3}$-alkylamino or di-($C_{1-3}$-alkyl)-amino group or replaced by an —NH or —N($C_{1-3}$-alkyl) group, or a phenyl group substituted by the group $R_6$, which may additionally be mono- or disubstituted by fluorine, chlorine, bromine or iodine atoms, by $C_{1-5}$-alkyl, trifluoromethyl, hydroxy, $C_{1-3}$-alkoxy, carboxy, $C_{1-3}$-alkoxycarbonyl, amino, acetylamino, $C_{1-3}$-alkylsulphonylamino, aminocarbonyl, $C_{1-3}$-alkyl-aminocarbonyl, di-($C_{1-3}$-alkyl)-aminocarbonyl, aminosulphonyl, $C_{1-3}$-alkyl-aminosulphonyl, di-($C_{1-3}$-alkyl)-aminosulphonyl, nitro or cyano groups, wherein the substituents may be identical or different and wherein $R_6$ denotes a hydrogen, fluorine, chlorine, bromine or iodine atom, a cyano, nitro, amino, $C_{1-5}$-alkyl, $C_{3-7}$-cycloalkyl, trifluoromethyl, phenyl, tetrazolyl or heteroaryl group, the group of formula

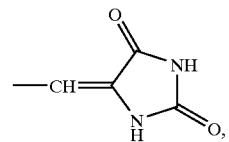

wherein the hydrogen atoms bound to a nitrogen atom may in each case be replaced independently of one another by a $C_{1-3}$-alkyl group, a $C_{1-3}$-alkoxy group, a $C_{1-3}$-alkoxy-$C_{1-3}$-alkoxy, phenyl-$C_{1-3}$-alkoxy, amino-$C_{2-3}$-alkoxy, $C_{1-3}$-alkylamino-$C_{2-3}$-alkoxy, di-($C_{1-3}$-alkyl-amino-$C_{2-3}$-alkoxy, phenyl-$C_{1-3}$- alkylamino-$C_{2-3}$-alkoxy, N—($C_{1-3}$-alkyl)-phenyl-$C_{1-3}$- alkylamino-$C_{2-3}$-alkoxy, $C_{5-7}$-cycloalkyleneimino-$C_{2-3}$-alkoxy or $C_{1-3}$-alkylmercapto group, a carboxy, $C_{1-4}$-alkoxycarbonyl, aminocarbonyl, $C_{1-3}$-alkylamino-carbonyl, N—($C_{1-5}$-alkyl)—$C_{1-3}$-alkylaminocarbonyl, phenyl-$C_{1-3}$-alkylaminocarbonyl, N—($C_{1-3}$-alkyl)-phenyl-$C_{1-3}$-alkylaminocarbonyl, piperazinocarbonyl or N—($C_{1-3}$-alkyl)-piperazinocarbonyl group, a $C_{1-3}$-alkylaminocarbonyl or N—($C_{1-5}$-alkyl)—$C_{1-3}$-alkylaminocarbonyl group wherein an alkyl moiety is substituted by a carboxy or $C_{1-3}$-alkoxycarbonyl group or in the 2 or 3 position by a di-($C_{1-3}$-alkyl)-amino, piperazino, N—($C_{1-3}$-alkyl)-piperazino or a 4- to 7-membered cycloalkyleneimino group, a $C_{3-7}$-cycloalkyl-carbonyl group,
  wherein the methylene group in the 4 position of the 6- or 7-membered cycloalkyl moiety may be substituted by an amino, $C_{1-3}$-alkylamino or di-($C_{1-3}$-alkyl)-amino group or replaced by an —NH or —N($C_{1-3}$-alkyl) group, a 4- to 7-membered cycloalkyleneimino group wherein
  a methylene group linked to the imino group may be replaced by a carbonyl or sulphonyl group or
  the cycloalkylene moiety may be fused to a phenyl ring or
  one or two hydrogen atoms may each be replaced by a $C_{1-3}$-alkyl group and/or
  in each case the methylene group in the 4 position of a 6- or 7-membered cycloalkyleneimino group may be substituted by a carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or
  may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, a $C_{1-4}$-alkyl group substituted by the group $R_7$, wherein $R_7$ denotes a $C_{3-7}$-cycloalkyl group,
  whilst the methylene group in the 4 position of a 6- or 7-membered cycloalkyl group may be substituted by an amino, $C_{1-3}$-alkylamino or di-($C_{1-3}$-alkyl)-amino group or replaced by an —NH or —N($C_{1-3}$-alkyl) group or
  in a 5- to 7-membered cycloalkyl group a —(CH$_2$)$_2$ group may be replaced by a —CO—NH group, a —(CH$_2$)$_3$ group may be replaced by a —NH—CO—NH or —CO—NH—CO group or a —(CH$_2$)$_4$ group may be replaced by a —NH—CO—NH—CO group, whilst in each case a hydrogen atom bound to a nitrogen atom may be replaced by a C1–3-alkyl group, an aryl or heteroaryl group, a hydroxy or $C_{1-3}$-alkoxy group, an amino, $C_{1-7}$-alkylamino, di-($C_{1-7}$-alkyl)-amino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group, an ω-hydroxy-$C_{2-3}$-alkyl-amino, N—($C_{1-3}$-alkyl)-ω-hydroxy-$C_{2-3}$-alkyl-amino, di-(ω-hydroxy-$C_{2-3}$-alkyl)-amino, di-(ω-($C_{1-3}$-alkoxy)—$C_{2-3}$-alkyl)-amino or N-(dioxolan-2-yl)—$C_{1-3}$-alkyl-amino group, a $C_{1-3}$-alkylcarbonylamino-$C_{2-3}$-alkyl-amino or $C_{1-3}$-alkylcarbonylamino-$C_{2-3}$-alkyl-N—($C_{1-3}$-alkyl)-amino group, a $C_{1-3}$-alkylsulphonylamino, N—($C_{1-3}$-alkyl)—$C_{1-3}$-alkylsulphonylamino, $C_{1-3}$-alkylsulphonylamino-$C_{2-3}$-alkyl-amino or $C_{1-3}$-alkylsulphonylamino-$C_{2-3}$-alkyl-N—($C_{1-3}$-alkyl)-amino group, a hydroxycarbonyl-$C_{1-3}$-alkylamino or N—($C_{1-3}$-alkyl)-hydroxycarbonyl-$C_{1-3}$-alkyl-amino group, a guanidino group wherein one or two hydrogen atoms may each be replaced by a $C_{1-3}$-alkyl group, a group of formula $$-N(R_8)-CO-(CH_2)_n-R_9 \qquad (II),$$

wherein
$R_8$ denotes a hydrogen atom or a $C_{1-3}$-alkyl group,
n denotes one of the numbers 0, 1, 2 or 3 and
$R_9$ denotes an amino, $C_{1-4}$-alkylamino, di-($C_{1-4}$-alkyl)-amino, phenylamino, N—($C_{1-4}$-alkyl)-phenylamino, benzylamino, N—($C_{1-4}$-alkyl)-benzylamino or $C_{1-4}$-alkoxy group, a 4- to 7-membered cycloalkyleneimino group, whilst in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, or, if n denotes one of the numbers 1, 2 or 3, it may also denote a hydrogen atom, a group of formula $$-N(R_{10})-(CH_2)_m-(CO)_o-R_{11} \qquad (III),$$

wherein
$R_{10}$ denotes a hydrogen atom, a $C_{1-3}$-alkyl group, a $C_{1-3}$-alkylcarbonyl, arylcarbonyl, phenyl-$C_{1-3}$-alkyl-carbonyl, $C_{1-3}$-alkylsulphonyl, arylsulphonyl or phenyl-$C_{1-3}$-alkylsulphonyl group,
m denotes one of the numbers 1, 2, 3 or 4,
o denotes the number 1 or, if m denotes one of the numbers 2, 3 or 4, o may also denote the number 0 and
$R_{11}$ denotes an amino, $C_{1-4}$-alkylamino, di-($C_{1-4}$-alkyl)-amino, phenylamino, N—($C_{1-4}$-alkyl)-phenylamino, benzylamino, N—($C_{1-4}$-alkyl)-benzylamino, $C_{1-4}$-alkoxy or $C_{1-3}$-alkoxy-$C_{1-3}$-alkoxy group, a di-($C_{1-4}$-alkyl)-amino-$C_{1-3}$-alkylamino group optionally substituted in the 1 position by a $C_{1-3}$-alkyl group or a 4- to 7-membered cycloalkyleneimino group, wherein the cycloalkylene moiety may be fused to a phenyl ring or in each case the methylene group in the 4 position of a 6- or 7-membered cycloalkyleneimino group may be replaced by an oxygen or sulphur atom, by a sulphinyl, sulphonyl, —NH, —N($C_{1-3}$-alkyl), —N(phenyl), —N($C_{1-3}$-alkyl-carbonyl) or —N(benzoyl) group, a $C_{4-7}$-cycloalkylamino, $C_{4-7}$-cycloalkyl-$C_{1-3}$-alkylamino or $C_{4-7}$-cycloalkenylamino group wherein position 1 of the ring is not involved in the double bond and wherein the abovementioned groups may each additionally be substituted at the amino-nitrogen atom by a $C_{5-7}$-cycloalkyl, $C_{2-4}$-alkenyl or $C_{1-4}$-alkyl group, a 4- to 7-membered cycloalkyleneimino group, wherein
  the cycloalkylene moiety may be fused to a phenyl group or to an oxazolo, imidazolo, thiazolo, pyridino, pyrazino or pyrimidino group optionally substituted by a fluorine, chlorine, bromine or iodine atom, by a nitro, $C_{1-3}$-alkyl, $C_{1-3}$-alkoxy or amino group, and/or
  one or two hydrogen atoms may each be replaced by a $C_{1-3}$-alkyl, $C_{5-7}$-cycloalkyl or phenyl group and/or
  the methylene group in the 3 position of a 5-membered cycloalkyleneimino group may be substituted by a hydroxy, hydroxy-$C_{1-3}$-alkyl, $C_{1-3}$-alkoxy or $C_{1-3}$-alkoxy-$C_{1-3}$-alkyl group,
  the methylene group in the 3 or 4 position of a 6- or 7-membered cycloalkyleneimino group may in each case be substituted by a hydroxy, hydroxy-$C_{1-3}$-alkyl, $C_{1-3}$-alkoxy, $C_{1-3}$-alkoxy-$C_{1-3}$-alkyl, carboxy, $C_{1-4}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkyl-amino group or may be replaced by an oxygen or sulphur atom, by a sulphinyl, sulphonyl, —NH, —N($C_{1-3}$-alkyl-), —N(phenyl), —N(phenyl-$C_{1-3}$-alkyl-), —N($C_{1-3}$-alkyl-carbonyl-), —N($C_{1-4}$-hydroxy-carbonyl-), —N($C_{1-4}$-alkoxy-carbonyl-), —N(benzoyl-) or —N(phenyl-$C_{1-3}$-alkyl-carbonyl-) group, wherein a methylene group linked to an imino-nitrogen atom of the cycloalkyleneimino group may be replaced by a carbonyl or sulphonyl group or in a 5- to 7-membered monocyclic cycloalkyleneimino group or a cycloalkyleneimino group fused to a phenyl group the two methylene groups linked to the imino-nitrogen atom may each be replaced by a carbonyl group, or $R_6$ denotes a $C_{1-4}$-alkyl group which is substituted by a carboxy, $C_{1-3}$-alkoxycarbonyl, aminocarbonyl, $C_{1-3}$-alkylaminocarbonyl or di-($C_{1-3}$-alkyl)-aminocarbonyl group or by a 4- to 7-membered cycloalkyleneiminocarbonyl group, an N—($C_{1-3}$-alkyl)—$C_{2-4}$-alkanoylamino group which is additionally substituted in the alkyl moiety by a carboxy or $C_{1-3}$-alkoxycarbonyl group, a group of formula

—N($R_{12}$)—CO—$(CH_2)_p$—$R_{13}$      (IV), wherein $R_{12}$ denotes a hydrogen atom, a $C_{1-6}$-alkyl or $C_{3-7}$-cycloalkyl group or a $C_{1-3}$-alkyl group terminally substituted by a phenyl, heteroaryl, trifluoromethyl, hydroxy, $C_{1-3}$-alkoxy, aminocarbonyl, $C_{1-4}$-alkylamino-carbonyl, di-($C_{1-4}$-alkyl)-aminocarbonyl, $C_{1-3}$-alkyl-carbonyl, $C_{1-3}$-alkyl-sulphonylamino, N—($C_{1-3}$-alkyl)—$C_{1-3}$-alkyl-sulphonylamino, $C_{1-3}$-alkyl-aminosulphonyl or di-($C_{1-3}$-alkyl)-aminosulphonyl group and p denotes one of the numbers 0, 1, 2 or 3 and $R_{13}$ assumes the meanings of the abovementioned group $R_7$, or, if p denotes one of the numbers 1, 2 or 3, it may also denote a hydrogen atom, a group of formula

—N($R_{14}$)—$(CH_2)_q$—$(CO)_r$—$R_{15}$      (V), wherein $R_{14}$ denotes a hydrogen atom, a $C_{1-4}$-alkyl group, a $C_{1-3}$-alkylcarbonyl, arylcarbonyl, phenyl-$C_{1-3}$-alkylcarbonyl, heteroarylcarbonyl, heteroaryl-$C_{1-3}$-alkylcarbonyl, $C_{1-4}$-alkylsulphonyl, arylsulphonyl, phenyl-$C_{1-3}$-alkylsulphonyl, heteroarylsulphonyl or heteroaryl-$C_{1-3}$-alkyl-sulphonyl group, q denotes one of the numbers 1, 2, 3 or 4, r denotes the number 1 or, if q is one of the numbers 2, 3 or 4, it may also denote the number 0 and $R_{15}$ assumes the meanings of the abovementioned group $R_7$, a group of formula

—N($R_{16}$)—$SO_2$—$R_{17}$      (VI), wherein $R_{16}$ denotes a hydrogen atom or a $C_{1-4}$-alkyl group optionally terminally substituted by a cyano, trifluoromethyl-carbonylamino or N—($C_{1-3}$-alkyl)-trifluoromethyl-carbonyl-amino group and $R_{17}$ denotes a $C_{1-3}$-alkyl group, an amino group substituted by a di-($C_{1-3}$-alkyl)-amino-$C_{1-3}$-alkyl-carbonyl or di-($C_{1-3}$-alkyl)-amino-$C_{1-3}$-alkyl-sulphonyl group and a di-($C_{1-3}$-alkyl)-aminocarbonyl-$C_{1-3}$-alkyl group, or an N—($C_{1-3}$-alkyl)—$C_{1-5}$-alkylsulphonylamino or N—($C_{1-3}$-alkyl)-phenylsulphonylamino group wherein the alkyl moiety is additionally substituted by a cyano or carboxy group, wherein all the single-bonded or fused phenyl groups contained in the groups mentioned under $R_6$ may be mono- or disubstituted by fluorine, chlorine, bromine or iodine atoms, by $C_{1-5}$-alkyl, trifluoromethyl, hydroxy, $C_{1-3}$-alkoxy, carboxy, $C_{1-3}$-alkoxycarbonyl, aminocarbonyl, $C_{1-4}$-alkylamino-carbonyl, di-($C_{1-4}$-alkyl)-amino-carbonyl, aminosulphonyl, $C_{1-3}$-alkyl-aminosulphonyl, di-($C_{1-3}$-alkyl)-aminosulphonyl, $C_{1-3}$-alkyl-sulphonylamino, nitro or cyano groups, wherein the substituents may be identical or different, or two adjacent hydrogen atoms of the phenyl groups may be replaced by a methylenedioxy group, and $R_5$ denotes a hydrogen atom or a $C_{1-3}$-alkyl group, wherein by an aryl group is meant a phenyl or naphthyl group optionally mono- or disubstituted by a fluorine, chlorine, bromine or iodine atom, by a cyano, trifluoromethyl, nitro, carboxy, aminocarbonyl, $C_{1-3}$-alkyl or $C_{1-3}$-alkoxy group and by a heteroaryl group is meant a monocyclic 5- or 6-membered heteroaryl group optionally substituted by a $C_{1-3}$-alkyl group in the carbon skeleton, wherein the 6-membered heteroaryl group contains one, two or three nitrogen atoms and the 5-membered heteroaryl group contains an imino group optionally substituted by a $C_{1-3}$-alkyl or phenyl-$C_{1-3}$-alkyl group, an oxygen or sulphur atom or an imino group optionally substituted by a $C_{1-3}$-alkyl or phenyl-$C_{1-3}$-alkyl group or an oxygen or sulphur atom and additionally a nitrogen atom or an imino group optionally substituted by a $C_{1-3}$-alkyl or phenyl-$C_{1-3}$-alkyl group and two nitrogen atoms, and moreover a phenyl ring may be fused to the abovementioned monocyclic heterocyclic groups via two adjacent carbon atoms and the bonding takes place via a nitrogen atom or via a carbon atom of the heterocyclic moiety or a fused phenyl ring, some or all of the hydrogen atoms in the abovementioned alkyl and alkoxy groups or in the alkyl moieties contained in the above-defined groups of formula I may be replaced by fluorine atoms, and wherein any carboxy group contained in the above-mentioned groups may be replaced by a tert.butoxy-carbonyl precursor group, and wherein a hydrogen atom bound to a nitrogen atom may each be replaced by hydroxyl, benzoyl, pyridinoyl, formyl, acetyl, propionyl, butanoyl, pentanoyl, hexanoyl, allyloxycarbonyl, methoxycarbonyl, ethoxycarbonyl, propoxycarbonyl, isopropoxycarbonyl, butoxycarbonyl, tert.butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl, hexadecyloxycarbonyl, benzyloxycarbonyl, phenylethoxycarbonyl, phenylpropoxycarbonyl, $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or an $R_eCO$—O—($R_fCR_g$)—O—CO group wherein $R_e$ denotes a $C_{1-8}$-alkyl, $C_{5-7}$-cycloalkyl, phenyl or phenyl-$C_{1-3}$-alkyl group, $R_f$ denotes a hydrogen atom, a $C_{1-3}$-alkyl, $C_{5-7}$-cycloalkyl or phenyl group and $R_g$ denotes a hydrogen atom, a $C_{1-3}$-alkyl or $R_eCO$—O—($R_fCR_g$)—O group wherein $R_e$ to $R_g$ are as hereinbefore defined, or wherein an amino nitrogen may form part of a phthalimido group, or a tautomer or salt thereof.

2. A compound of the formula I according to claim 1, wherein:

$R_1$ and $R_3$ are as defined in claim 1,

X denotes an oxygen atom, $R_2$ denotes a carboxy group, a straight-chain or branched $C_{1-6}$-alkoxy-carbonyl group, a $C_{5-7}$-cycloalkoxycarbonyl or a phenoxycarbonyl group, a straight-chain or branched $C_{1-3}$-alkoxy-carbonyl group, which is terminally substituted in the alkyl moiety by a phenyl, heteroaryl, carboxy, $C_{1-3}$-alkoxycarbonyl, aminocarbonyl, $C_{1-3}$-alkylaminocarbonyl or di-($C_{1-3}$-alkyl)-aminocarbonyl group, a straight-chain or branched $C_{2-3}$-alkoxy-carbonyl group, which is terminally substituted in the alkyl moiety by a chlorine atom, by a hydroxy, $C_{1-3}$-alkoxy, amino, $C_{1-3}$-alkylamino or di-($C_{1-3}$-alkyl)-amino group, an aminocarbonyl or methylaminocarbonyl group, an ethylaminocarbonyl group optionally substituted in the 2 position of the ethyl group by a hydroxy or $C_{1-3}$-alkoxy group, $R_4$ denotes a $C_{3-7}$-cycloalkyl group,
whilst the methylene group in the 4 position of a 6 or 7-membered cycloalkyl group may be substituted by an amino, $C_{1-3}$-alkylamino or di-($C_{1-3}$-alkyl)-amino group or replaced by an —NH or —N($C_{1-3}$-alkyl) group, or a phenyl group substituted by the group $R_6$, which may additionally be mono- or disubstituted by fluorine, chlorine or bromine atoms, by $C_{1-3}$-alkyl, trifluoromethyl, hydroxy, $C_{1-3}$-alkoxy, carboxy, $C_{1-3}$-alkoxycarbonyl, amino, acetylamino, aminocarbonyl, $C_{1-3}$-alkyl-aminocarbonyl, di-($C_{1-3}$-alkyl)-aminocarbonyl, nitro or cyano groups, wherein the substituents may be identical or different and wherein $R_6$ denotes a hydrogen, fluorine, chlorine, bromine or iodine atom, a cyano, nitro, amino, $C_{1-5}$-alkyl, $C_{3-7}$-cycloalkyl, trifluoromethyl, phenyl, tetrazolyl or heteroaryl group, the group of formula

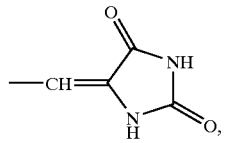

wherein a hydrogen atom bound to the nitrogen atom may be replaced by a $C_{1-3}$-alkyl group, a $C_{1-3}$-alkoxy group, an amino-$C_{2-3}$-alkoxy, $C_{1-3}$-alkylamino-$C_{2-3}$-alkoxy, di-($C_{1-3}$-alkyl)-amino-$C_{2-3}$-alkoxy, phenyl-$C_{1-3}$-alkylamino-$C_{2-3}$-alkoxy, N—($C_{1-3}$-alkyl)-phenyl-$C_{1-3}$-alkylamino-$C_{2-3}$-alkoxy, pyrrolidino-$C_{2-3}$-alkoxy, piperidino-$C_{2-3}$-alkoxy or $C_{1-3}$-alkylmercapto group, a carboxy, $C_{1-4}$-alkoxycarbonyl, aminocarbonyl, $C_{1-3}$-alkylamino-carbonyl, phenyl-$C_{1-3}$-alkylamino-carbonyl or N—($C_{1-3}$-alkyl)-phenyl-$C_{1-3}$-alkylamino-carbonyl group, a $C_{3-7}$-cycloalkyl-carbonyl group,
wherein the methylene group in the 4 position of the 6- or 7-membered cycloalkyl moiety may be replaced by an —NH or —N($C_{1-3}$-alkyl) group, a 4- to 7-membered cycloalkyleneimino group, wherein a methylene group linked to the imino group may be replaced by a carbonyl or sulphonyl group or one or two hydrogen atoms may each be replaced by a $C_{1-3}$-alkyl group and/or in each case the methylene group in the 4 position of a 6- or 7-membered cycloalkyleneimino group may be substituted by a carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or may be replaced by an oxygen or sulphur atom, by a sulphinyl, sulphonyl, —NH or —N($C_{1-3}$-alkyl) group, a $C_{1-4}$-alkyl group terminally substituted by the group $R_7$, wherein $R_7$ denotes a $C_{5-7}$-cycloalkyl group,
whilst the methylene group in the 4 position of a 6- or 7-membered cycloalkyl group may be replaced by an —NH or —N($C_{1-3}$-alkyl) group or in a 5- to 7-membered cycloalkyl group a —(CH$_2$)$_2$ group may be replaced by a —CO—NH group, a —(CH$_2$)$_3$ group may be replaced by a —NH—CO—NH— or a —(CH$_2$)$_4$ group may be replaced by a —NH—CO—NH—CO group, whilst in each case a hydrogen atom bound to a nitrogen atom may be replaced by a $C_{1-3}$-alkyl group, a phenyl or heteroaryl group, a hydroxy or $C_{1-3}$-alkoxy group, an amino, $C_{1-6}$-alkylamino, di-($C_{1-6}$-alkyl)-amino, phenylamino, N-phenyl-$C_{1-3}$-alkyl-amino, phenyl-$C_{1-3}$-alkylamino, N—($C_{1-3}$-alkyl)-phenyl-$C_{1-3}$-alkylamino or di-(phenyl-$C_{1-3}$-alkyl)-amino group, a ω-hydroxy-$C_{2-3}$-alkyl-amino, N—($C_{1-3}$-alkyl)ω-hydroxy-$C_{2-3}$-alkyl-amino, di-(ω-hydroxy-$C_{2-3}$-alkyl)-amino, di-(ω-($C_{1-3}$-alkoxy)—$C_{2-3}$-alkyl)-amino or N—(dioxolan-2-yl)—$C_{1-3}$-alkyl-amino group, a $C_{1-3}$-alkylcarbonylamino-$C_{2-3}$-alkyl-amino or $C_{1-3}$-alkylcarbonylamino-$C_{2-3}$-alkyl-N—($C_{1-3}$-alkyl)-amino group, a $C_{1-3}$-alkylsulphonylamino, N—($C_{1-3}$-alkyl)—$C_{1-3}$-alkylsulphonylamino, $C_{1-3}$-alkylsulphonylamino-$C_{2-3}$- alkyl-amino or $C_{1-3}$-alkylsulphonylamino-$C_{2-3}$-alkyl-N—($C_{1-3}$-alkyl)-amino group, a hydroxycarbonyl-$C_{1-3}$-alkylamino or N—($C_{1-3}$-alkyl)-hydroxycarbonyl-$C_{1-3}$-alkyl-amino group a guanidino group wherein a hydrogen atom may be replaced by a $C_{1-3}$-alkyl group, a group of formula

$$—N(R_8)—CO—(CH_2)_n-R_9 \quad (II),$$

wherein $R_8$ denotes a hydrogen atom or a $C_{1-3}$-alkyl group, n denotes one of the numbers 0, 1, 2 or 3 and $R_9$ denotes an amino, $C_{1-3}$-alkylamino, di-($C_{1-3}$-alkyl)-amino, phenylamino, benzylamino or $C_{1-4}$-alkoxy group, a 5- to 7-membered cycloalkyleneimino group, wherein the methylene group in position 4 of the piperidino group may be replaced by an oxygen or sulphur atom, by an —NH, —N($C_{1-3}$-alkyl), —N(phenyl), —N($C_{1-3}$-alkyl-carbonyl) or —N(benzoyl) group, or, if n denotes one of the numbers 1, 2 or 3, it may also denote a hydrogen atom, a group of formula

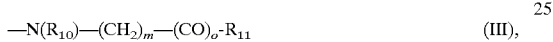

$$—N(R_{10})—(CH_2)_m—(CO)_o-R_{11} \quad (III),$$

wherein $R_{10}$ denotes a hydrogen atom, a $C_{1-3}$-alkyl group, a $C_{1-3}$-alkylcarbonyl or $C_{1-3}$-alkylsulphonyl group, m denotes one of the numbers 1, 2 or 3, o denotes the number 1 or, if m is one of the numbers 2 or 3, o may also denote the number 0 and $R_{11}$ denotes an amino, $C_{1-3}$-alkylamino, di-($C_{1-3}$-alkyl)-amino, $C_{1-4}$-alkoxy or $C_{1-3}$-alkoxy-$C_{1-3}$-alkoxy group or a 5- to 7-membered cycloalkyleneimino group, wherein the methylene group in position 4 of the piperidino group may be replaced by an oxygen or sulphur atom, by an —NH, —N($C_{1-3}$-alkyl), —N(phenyl), —N($C_{1-3}$-alkyl-carbonyl) or —N(benzoyl) group, a $C_{4-7}$-Cycloalkylamino or $C_{4-7}$-cycloalkenylamino group wherein position 1 of the ring is not involved in the double bond, a 4- to 7-membered cycloalkyleneimino group, wherein the cycloalkylene moiety may be fused to a phenyl group or one or two hydrogen atoms may each be replaced by a $C_{1-3}$-alkyl group and/or the methylene group in position 3 of the pyrrolidino group may be substituted by a hydroxy or $C_{1-3}$-alkoxy group, in each case the methylene group in the 4 position of a 6- or 7-membered cycloalkyleneimino group may be substituted by a hydroxy, hydroxy-$C_{1-3}$-alkyl, $C_{1-3}$-alkoxy, carboxy, $C_{1-3}$-alkoxycarbonyl, aminocarbonyl, $C_{1-3}$-alkylaminocarbonyl, di-($C_{1-3}$-alkyl)-aminocarbonyl, phenyl-$C_{1-3}$-alkylamino or N—($C_{1-3}$-alkyl)-phenyl-$C_{1-3}$-alkylamino group or may be replaced by an oxygen or sulphur atom, by a sulphinyl, sulphonyl, —NH, —N($C_{1-3}$-alkyl), —N(phenyl), —N(phenyl-$C_{1-3}$-alkyl), —N($C_{1-3}$-alkyl-carbonyl), —N($C_{1-4}$-alkoxycarbonyl), —N(benzoyl) or —N(phenyl-$C_{1-3}$-alkyl-carbonyl) group, wherein a methylene group linked to an imino-nitrogen atom of the cycloalkyleneimino group may be replaced by a carbonyl or sulphonyl group or in a 5- to 6-membered monocyclic cycloalkyleneimino group or a cycloalkyleneimino group fused to a phenyl group the two methylene groups linked to the imino-nitrogen atom may each be replaced by a carbonyl group, or $R_6$ denotes a $C_{1-4}$-alkyl group which is terminally substituted by a carboxy, $C_{1-3}$-alkoxycarbonyl, aminocarbonyl, $C_{1-3}$-alkylaminocarbonyl or di-($C_{1-3}$-alkyl)-aminocarbonyl group or by a 4- to 7-membered cycloalkyleneiminocarbonyl group, a group of formula

$$—N(R_{12})—CO—(CH_2)_p—R_{13} \quad (IV),$$

wherein $R_{12}$ denotes a hydrogen atom, a $C_{1-3}$-alkyl, $C_{5-7}$-cycloalkyl, phenyl-$C_{1-3}$-alkyl or heteroaryl-$C_{1-3}$-alkyl group and p denotes one of the numbers 0, 1, 2 or 3 and $R_{13}$ assumes the meanings of the abovementioned group $R_7$, or, if p denotes one of the numbers 1, 2 or 3, it may also denote a hydrogen atom, a group of formula

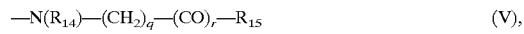

$$—N(R_{14})—(CH_2)_q—(CO)_r—R_{15} \quad (V),$$

wherein $R_{14}$ denotes a hydrogen atom, a $C_{1-4}$-alkyl group, a $C_{1-3}$-alkylcarbonyl, phenylcarbonyl, phenyl-$C_{1-3}$-alkylcarbonyl, heteroarylcarbonyl, heteroaryl-$C_{1-3}$-alkylcarbonyl, $C_{1-4}$-alkylsulphonyl, phenylsulphonyl, phenyl-$C_{1-3}$-alkylsulphonyl-heteroarylsulphonyl or heteroaryl-$C_{1-3}$-alkyl-sulphonyl group, q denotes one of the numbers 1, 2, 3 or 4, r denotes the number 1 or, if q is one of the numbers 2, 3 or 4, it may also denote the number 0 and $R_{15}$ assumes the meanings of the abovementioned group $R_7$, a group of formula

$$—N(R_{16})—SO_2—R_{17} \quad (VI),$$

wherein $R_{16}$ denotes a hydrogen atom or a $C_{1-4}$-alkyl group optionally terminally substituted by a cyano, trifluoromethyl-carbonylamino or N—($C_{1-3}$-alkyl)-trifluoromethyl-carbonyl-amino group and $R_{17}$ denotes a $C_{1-3}$-alkyl group, an amino group substituted by a di-($C_{1-3}$-alkyl)-amino-$C_{1-3}$-alkyl-carbonyl or di-($C_{1-3}$-alkyl)-amino-$C_{1-3}$-alkyl-sulphonyl group and a di-($C_{1-3}$-alkyl)-aminocarbonyl-$C_{1-3}$-alkyl group, wherein all the single-bonded or fused phenyl groups contained in the groups mentioned under $R_6$ may be mono- or disubstituted by fluorine, chlorine or bromine atoms, by $C_{1-3}$-alkyl, trifluoromethyl, hydroxy, $C_{1-3}$-alkoxy, carboxy, $C_{1-3}$-alkoxycarbonyl, aminocarbonyl, $C_{1-3}$-alkyl-aminocarbonyl, aminosulphonyl, $C_{1-3}$-alkyl-aminosulphonyl, nitro or cyano groups, wherein the substituents may be identical or different, or two adjacent hydrogen atoms of the phenyl groups may be replaced by a methylenedioxy group, and $R_5$ denotes a hydrogen atom or a $C_{1-3}$-alkyl group, whilst by a heteroaryl group as mentioned above is meant a pyridinyl, pyrazinyl, pyrimidinyl, pyridazinyl, pyrrolyl, furyl, thienyl, oxazolyl, thiazolyl, pyrazolyl, imidazolyl or triazolyl group optionally substituted in the carbon skeleton by a $C_{1-3}$-alkyl group wherein a hydrogen atom bound to a nitrogen atom may be replaced by a $C_{1-3}$-alkyl or phenyl-$C_{1-3}$-alkyl group and wherein the 5-membered heteroaryl groups containing at least one imino group are bound via a carbon or nitrogen atom, a hydrogen atom bound to a nitrogen atom in the above-mentioned groups may be replaced by hydroxyl, benzoyl, pyridinoyl, formyl, acetyl, propionyl, butanoyl, pentanoyl, hexanoyl, allyloxycarbonyl, methoxycarbonyl, ethoxycarbonyl, propoxycarbonyl, isopropoxycarbonyl, butoxycarbonyl, tert.butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl, hexadecyloxycarbonyl, benzyloxycarbonyl, phenylethoxycarbonyl, phenylpropoxycarbonyl, $C_{1-3}$-alkylsulphonyl-$C_{2-4}$-alkoxycarbonyl, $C_{1-3}$-alkoxy-$C_{2-4}$-alkoxy-$C_{2-4}$-alkoxycarbonyl or an $R_eCO$—O—($R_fCR_g$)—O—CO group wherein $R_e$ denotes a $C_{1-8}$-alkyl, $C_{5-7}$-cycloalkyl, phenyl or phenyl-$C_{1-3}$-alkyl group, $R_f$ denotes a hydrogen atom, a $C_{1-3}$-alkyl, $C_{5-7}$-cycloalkyl or phenyl group and $R_g$ denotes a hydrogen atom, a $C_{1-3}$-alkyl or $R_eCO$—O—($R_fCR_g$)—O group wherein $R_e$ to $R_g$ are as hereinbefore defined, or wherein an amino nitrogen may form part of a phthalimido group, and wherein any carboxy group contained in the abovementioned groups may be replaced by a tert.butoxycarbonyl precursor group, and wherein some or all of the hydrogen atoms in the abovementioned alkyl and alkoxy groups or in the alkyl moieties contained in the above-defined groups of formula I may be replaced by fluorine atoms, or a tautomer or salt thereof.

3. A compound of the formula I according to claim 1, wherein:

X denotes an oxygen atom, $R_1$ denotes a hydrogen atom, $R_2$ denotes a carboxy group, a straight-chain or branched $C_{1-4}$-alkoxycarbonyl group or a phenoxycarbonyl group, a straight-chain or branched $C_{1-3}$-alkoxy-carbonyl group, which is terminally substituted in the alkyl moiety by a phenyl, carboxy, $C_{1-3}$-alkoxycarbonyl, aminocarbonyl, $C_{1-3}$-alkylaminocarbonyl or di-($C_{1-3}$-alkyl)-aminocarbonyl group, a straight-chain or branched $C_{2-3}$-alkoxy-carbonyl group which is terminally substituted in the alkyl moiety by a hydroxy, $C_{1-3}$-alkoxy, amino, $C_{1-3}$-alkylamino or di-($C_{1-3}$-alkyl)-amino group, an aminocarbonyl or methylaminocarbonyl group, an ethylaminocarbonyl group optionally substituted in the 2 position of the ethyl group by a hydroxy or $C_{1-3}$-alkoxy group or, if $R_4$ does not denote an aminosulphonyl-phenyl or N—($C_{1-5}$-alkyl)—$C_{1-3}$-alkylaminocarbonyl-phenyl group, it may also denote a di-($C_{1-2}$-alkyl)-aminocarbonyl group, $R_3$ denotes a $C_{1-4}$-alkyl group or a phenyl group which may be substituted by a fluorine, chlorine or bromine atom, by a trifluoromethyl, $C_{1-3}$-alkyl, hydroxy or $C_{1-3}$-alkoxy group, $R_4$ denotes a $C_{5-6}$-cycloalkyl group,
wherein the methylene group in position 4 of the cyclohexyl group may be substituted by an amino, $C_{1-3}$-alkylamino or di-($C_{1-3}$-alkyl)-amino group or replaced by an —NH or —N($C_{1-3}$-alkyl) group, a phenyl group, a phenyl group disubstituted by $C_{1-3}$-alkyl, $C_{1-3}$-alkoxy or nitro groups, wherein the substituents may be identical or different, or a phenyl group substituted by the group $R_6$, which may additionally be substituted by a fluorine, chlorine or bromine atom or by an amino or nitro group, wherein $R_6$ denotes a fluorine, chlorine or bromine atom, a $C_{1-3}$-alkyl, $C_{1-3}$-alkoxy, nitro, amino or $C_{5-6}$-cycloalkyl group, a pyrrolyl, pyrazolyl, imidazolyl, triazolyl or tetrazolyl group bound via a carbon atom, wherein the abovementioned heteroaromatic groups in the carbon skeleton may be substituted by a $C_{1-3}$-alkyl group or a hydrogen atom bound to a nitrogen atom may be replaced by a $C_{1-3}$-alkyl or phenyl-$C_{1-3}$-alkyl group, the group of formula

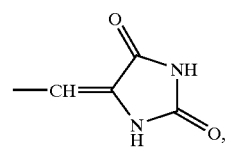

a carboxy, $C_{1-4}$-alkoxycarbonyl, phenyl-$C_{1-3}$-alkylaminocarbonyl or $C_{5-7}$-cycloalkyl-carbonyl group, a 5 or 6-membered cycloalkyleneimino group, wherein the methylene group in position 4 of the piperidino group may be replaced by an oxygen or sulphur atom, by an —NH or —N($C_{1-3}$-alkyl) group, an unbranched $C_{1-3}$-alkyl group terminally substituted by the group $R_7$, wherein $R_7$ denotes a $C_{5-7}$-cycloalkyl group,
wherein in a 5 or 6-membered cycloalkyl group a —(CH$_2$)$_2$ group may be replaced by a —CO—NH group, a —(CH$_2$)$_3$ group may be replaced by an —(NH—CO—NH— or a —(CH$_2$)$_4$ group may be replaced by an —NH—CO—NH—CO group, whilst in each case a hydrogen atom bound to a nitrogen atom may be replaced by a $C_{1-3}$-alkyl group, a phenyl or pyridinyl group or a pyrrolyl, pyrazolyl, imidazolyl or triazolyl group bound via a carbon or nitrogen atom, wherein the abovementioned heteroaromatic groups in the carbon skeleton may be substituted by a $C_{1-3}$-alkyl group or a hydrogen atom bound to a nitrogen atom may be replaced by a $C_{1-3}$-alkyl group, a hydroxy or $C_{1-3}$-alkoxy group, an amino, $C_{1-6}$-alkylamino, di-($C_{1-6}$-alkyl)-amino, phenylamino, N-phenyl-$C_{1-3}$-alkylamino, phenyl-$C_{1-3}$-alkylamino or N—($C_{1-3}$-alkyl)-phenyl-$C_{1-3}$-alkylamino group, a ω-hydroxy-$C_{2-3}$-alkyl-amino, N—($C_{1-3}$-alkyl)-ω-hydroxy-$C_{2-3}$-alkylamino, di-(ω-hydroxy-$C_{2-3}$-alkyl)-amino or di-(ω-($C_{1-3}$-alkoxy)—$C_{2-3}$-alkyl)-amino group, a $C_{1-3}$-alkylcarbonylamino-$C_{2-3}$-alkyl-amino or $C_{1-3}$-alkylcarbonylamino-$C_{2-3}$-alkyl-N—($C_{1-3}$-alkyl)-amino group, a $C_{1-3}$-alkylsulphonylamino, N—($C_{1-3}$-alkyl)—$C_{1-3}$-alkylsulphonylamino, $C_{1-3}$-alkylsulphonylamino-$C_{2-3}$-alkylamino or $C_{1-3}$-alkylsulphonylamino-$C_{2-3}$-alkyl-N—($C_{1-3}$-alkyl)-amino group, a hydroxycarbonyl-$C_{1-3}$-alkylamino or N—($C_{1-3}$-alkyl)-hydroxycarbonyl-$C_{1-3}$-alkyl-amino group, a guanidino group wherein a hydrogen atom may be replaced by a $C_{1-3}$-alkyl group, a group of formula

$$—N(R_8)—CO—(CH_2)_n—R_9 \qquad (II),$$

wherein
$R_8$ denotes a hydrogen atom or a $C_{1-3}$-alkyl group,
n denotes one of the numbers 0, 1, 2 or 3 and
$R_9$ denotes an amino, $C_{1-3}$-alkylamino, di-($C_{1-3}$-alkyl)-amino or $C_{1-4}$-alkoxy group, a 5- or 6-membered cycloalkyleneimino group, wherein the methylene group in position 4 of the piperidino group may be replaced by an —NH, —N($C_{1-3}$-alkyl) or —N($C_{1-3}$-alkyl-carbonyl) group, or, if n denotes one of the numbers 1, 2 or 3, $R_9$ may also denote a hydrogen atom, a group of formula

$$—N(R_{10})—(CH_2)_m—(CO)_o—R_{11} \qquad (III),$$

wherein
$R_{10}$ denotes a hydrogen atom or a $C_{1-3}$-alkyl group,
m denotes one of the numbers 1, 2 or 3,
o denotes the number 1 or, if m is one of the numbers 2 or 3, o may also denote the number 0 and
$R_{11}$ denotes an amino, $C_{1-3}$-alkylamino, di-($C_{1-3}$-alkyl)-amino, $C_{1-4}$-alkoxy or methoxy-$C_{1-3}$-alkoxy group or a 5- or 6-membered cycloalkyleneimino group, wherein the methylene group in position 4 of the piperidino group may be replaced by an —NH, —N($C_{1-3}$-alkyl) or —N($C_{1-3}$-alkyl-carbonyl) group, an azetidino, pyrrolidino, piperidino, 2,6-dimethyl-piperidino, 3,5-dimethyl-piperidino or azepino group, wherein
the methylene group in position 3 of the pyrrolidino group may be substituted by a hydroxy group,
the methylene group in position 4 of the piperidino group may be substituted by a hydroxy, hydroxy-$C_{1-3}$-alkyl or $C_{1-3}$-alkoxy group or
may be replaced by an oxygen or sulphur atom, by a sulphinyl, sulphonyl, —NH, —N($C_{1-3}$-alkyl), —N($C_{1-3}$-alkyl-carbonyl), —N(benzoyl) or —N(phenyl-$C_{1-3}$-alkyl-carbonyl) group,
wherein a methylene group linked to an imino-nitrogen atom of the pyrrolidino, piperidino or piperazino group may be replaced by a carbonyl group, or $R_6$ denotes a straight-chain $C_{1-3}$-alkyl group which is terminally substituted by a carboxy or $C_{1-3}$-alkoxycarbonyl group, a group of formula

$$—N(R_{12})—CO—(CH_2)_p—R_{13} \qquad (IV),$$

wherein
$R_{12}$ denotes a hydrogen atom, a $C_{1-3}$-alkyl or phenyl-$C_{1-3}$-alkyl group,
p denotes one of the numbers 0, 1 or 2 and
$R_{13}$ denotes an amino, $C_{1-4}$-alkylamino, di-($C_{1-4}$-alkyl)-amino, benzylamino, N—($C_{1-3}$-alkyl)-benzylamino, $C_{1-3}$-alkoxy-$C_{1-3}$-alkylamino, N—($C_{1-3}$-alkyl)-$C_{1-3}$-alkoxy-$C_{1-3}$-alkylamino, di-(2-methoxy-ethyl)-amino, di-(ω-hydroxy-$C_{2-3}$-alkyl)-amino or aminocarbonyl-methyl-N-(methyl)-amino group, a pyrrolyl, pyrazolyl or imidazolyl group bound via a nitrogen atom and optionally substituted by a $C_{1-3}$-alkyl group, a pyrrolidino, piperidino, morpholino, thiomorpholino or a piperazino group optionally substituted in the 4 position by a $C_{1-3}$-alkyl, phenyl-$C_{1-3}$-alkyl, $C_{1-3}$-alkylcarbonyl or $C_{1-4}$-alkoxycarbonyl group or, if n denotes the number 1 or 2, it may also denote a hydrogen atom, a group of formula

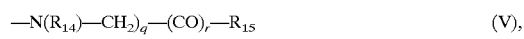
$$—N(R_{14})—(CH_2)_q—(CO)_r—R_{15} \qquad (V),$$

wherein
$R_{14}$ denotes a hydrogen atom, a $C_{1-4}$-alkyl, $C_{1-3}$-alkylcarbonyl, phenylcarbonyl, phenyl-$C_{1-3}$-alkylcarbonyl, furyl-carbonyl, pyridinyl-carbonyl, furyl-$C_{1-3}$-alkylcarbonyl, pyridinyl-$C_{1-3}$-alkylcarbonyl, $C_{1-4}$-alkylsulphonyl, phenylsulphonyl or phenyl-$C_{1-3}$-alkylsulphonyl group,
q denotes one of the numbers 1, 2 or 3,
r denotes the number 1 or, if q is one of the numbers 2 or 3, it may also denote the number 0 and
$R_{15}$ denotes an amino, $C_{1-4}$-alkylamino, di-($C_{1-4}$-alkyl)-amino, phenylamino, N—($C_{1-4}$-alkyl)-phenylamino, benzylamino or N—($C_{1-4}$-alkyl)-benzylamino group, or a group of formula

$$—N(R_{16})—SO_2—R_{17} \qquad (VI),$$

wherein
$R_{16}$ denotes a hydrogen atom or a $C_{1-3}$-alkyl group optionally terminally substituted by a cyano, trifluoromethyl-carbonylamino or N—($C_{1-3}$-alkyl)-trifluoromethyl-carbonyl-amino group and
$R_{17}$ denotes a $C_{1-3}$-alkyl group,
wherein all the single-bonded or fused phenyl groups contained in the groups mentioned under $R_6$ may be substituted by a fluorine, chlorine or bromine atom, by a methyl, trifluoromethyl, methoxy, nitro or cyano group and $R_5$ denotes a hydrogen atom, wherein a hydrogen atom bound to a nitrogen atom in the abovementioned groups may be replaced by an acetyl or tert.butoxycarbonyl group, the carboxy groups contained in the abovementioned groups may also be present in the form of the tert.butoxycarbonyl precursor group, or a tautomer or salt thereof.

4. A compound of the formula I according to claim 1, wherein:

X denotes an oxygen atom, $R_1$ and $R_5$ each denote a hydrogen atom, $R_2$ denotes a methoxycarbonyl, ethoxycarbonyl or aminocarbonyl group, $R_3$ denotes a phenyl group and $R_4$ denotes a phenyl group monosubstituted by the group $R_6$, wherein $R_6$ denotes an N-methyl-imidazol-2-yl group, an unbranched $C_{1-3}$-alkyl group which is terminally substituted by a $C_{1-4}$-alkylamino, di-($C_{1-4}$-alkyl)-amino, piperidino or 2,6-dimethyl-piperidino group, a group of formula

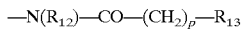   (IV), wherein $R_{12}$ denotes a $C_{1-3}$-alkyl group, p denotes one of the numbers 1 or 2 and $R_{13}$ denotes a di-($C_{1-3}$-alkyl)-amino group, or a group of formula

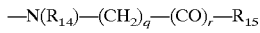   (V), wherein $R_{14}$ denotes a $C_{1-3}$-alkyl-carbonyl or $C_{1-3}$-alkylsulphonyl group, q denotes one of the numbers 1, 2 or 3, r denotes the number 1 or, if q is one of the numbers 2 or 3, r may also denote the number 0 and $R_{15}$ denotes a di-($C_{1-3}$-alkyl)-amino group, or a tautomer or salt thereof.

5. A compound selected from the group consisting of:
(a) 3-Z-[1-(4-(piperidin-1-yl-methyl)-anilino)-1-phenyl-methylene]-6-ethoxycarbonyl-2-indolinone,
(b) 3-Z-[(1-(4-(piperidin-1-yl-methyl)-anilino)-1-phenyl-methylene]-6-carbamoyl-2-indolinone,
(c) 3-Z-[1-(4-(piperidin-1-yl-methyl)-anilino)-1-phenyl-methylene]-6-methoxycarbonyl-2-indolinone,
(d) 3-Z-[1-(4-(dimethylaminomethyl)-anilino)-1-phenyl-methylene]-6-ethoxycarbonyl-2-indolinone,
(e) 3-Z-[1-(4-((2,6-dimethyl-piperidin-1-yl)-methyl)-anilino)-1-phenyl-methylene]-6-ethoxycarbonyl-2-indolinone,
(f) 3-Z-[1-(4-(N-(2-dimethylamino-ethyl)-N-acetyl-amino)-anilino)-1-phenyl-methylene]-6-ethoxycarbonyl-2-indolinone,
(g) 3-Z-[1-(4-(N-(3-dimethylamino-propyl)-N-acetyl-amino)-anilino)-1-phenyl-methylene]-6-ethoxycarbonyl-2-indolinone,
(h) 3-Z-[1-(4-(N-(2-dimethylamino-ethyl)-N-methylsulphonyl-amino)-anilino)-1-phenyl-methylene]-6-ethoxycarbonyl-2-indolinone,
(i) 3-Z-[1-(4-(dimethylaminomethyl)-anilino)-1-phenyl-methylene]-6-methoxycarbonyl-2-indolinone,
(j) 3-Z-[1-(4-(N-acetyl-N-dimethylaminocarbonylmethyl-amino)-anilino)-1-phenyl-methylene]-6-methoxycarbonyl-2-indolinone,
(k) 3-Z-[1-(4-ethylaminomethyl-anilino)-1-phenyl-methylene]-6-methoxycarbonyl-2-indolinone,
(l) 3-Z-[1-(4-(1-methyl-imidazol-2-yl)-anilino)-1-phenyl-methylene]-6-methoxycarbonyl-2-indolinone,
(m) 3-Z-[1-(4-(N-dimethylaminomethylcarbonyl-N-methyl-amino)-anilino)-1-phenyl-methylene]-6-methoxycarbonyl-2-indolinone,
(n) 3-Z-[1-(4-(N-(2-dimethylamino-ethyl)-N-methylsulphonyl-amino)-anilino)-1-phenyl-methylene]-6-methoxycarbonyl-2-indolinone,
(o) 3-Z-[1-(4-(N-(3-dimethylamino-propyl)-N-methylsulphonyl-amino)-anilino)-1-phenyl-methylene]-6-methoxycarbonyl-2-indolinone,
(p) 3-Z-[1-(4-(N-dimethylaminocarbonylmethyl-N-methylsulphonyl-amino)-anilino)-1-phenyl-methylene]-6-methoxycarbonyl-2-indolinone,
(q) 3-Z-[1-(4-(N-((2-dimethylamino-ethyl)-carbonyl)-N-methyl-amino)-anilino)-1-phenyl-methylene]-6-methoxycarbonyl-2-indolinone,
(r) 3-Z-[1-(4-(N-(2-dimethylamino-ethyl)-N-acetyl-amino)-anilino)-1-phenyl-methylene]-6-methoxycarbonyl-2-indolinone,
(s) 3-Z-[1-(4-methylaminomethyl-anilino)-1-phenyl-methylene]-6-methoxycarbonyl-2-indolinone and
(t) 3-Z-[1-(4-(N-((4-methyl-piperazin-1-yl)-methylcarbonyl)-N-methyl-amino)-anilino)-1-phenyl-methylene]-6-methoxycarbonyl-2-indolinone, or a tautomer or salt thereof.

6. A physiologically acceptable salt of a compound according to claims 1, 2, 3, 4 or 5.

7. A pharmaceutical composition containing a compound according to claims 1, 2, 3 or 4, or a physiologically acceptable salt thereof in accordance with claim 5, together with a pharmaceutically acceptable carrier.

8. 3-Z-[1-(4-(N-((4-methyl-piperazin-1-yl)-methylcarbonyl)-N-methyl-amino)-anilino)-1-phenyl-methylene]-6-methoxycarbonyl-2-indolinone or a pharmaceutically acceptable salt thereof.

* * * * *

Disclaimer

6,762,180 B1 — Gerald Juergen Roth, Biberach (DE); Armin Heckel, Biberach (DE); Rainer Walter, Biberach (DE); Jacobus Van Meel, Moedling (AT); Norbert Redemann, Biberach (DE); Ulrike Tontsch-Grunt, Baden (AT); Walter Spevak, Oberrohrbach (AT); Frank Hilberg, Vienna (AT). SUBSTITUTED INDOLINES WHICH INHIBIT RECEPTOR TYROSINE KINASES. Patent dated July 13, 2004. Disclaimer filed January 31, 2018, by the assignee, Boehringer Ingelheim Pharma GmbH & Co. KG.

Hereby disclaims the term of this patent which would extend beyond October 3, 2020.

*(Official Gazette, July 28, 2020)*